US010196386B2

United States Patent
Rancati et al.

(10) Patent No.: US 10,196,386 B2
(45) Date of Patent: Feb. 5, 2019

(54) COMPOUNDS HAVING MUSCARINIC RECEPTOR ANTAGONIST AND BETA2 ADRENERGIC RECEPTOR AGONIST ACTIVITY

(71) Applicant: CHIESI FARMACEUTICI S.P.A., Parma (IT)

(72) Inventors: Fabio Rancati, Parma (IT); Andrea Rizzi, Parma (IT); Laura Carzaniga, Parma (IT); Ian Linney, Saffron Walden (GB); Chris Knight, Saffron Walden (GB); Wolfgang Schmidt, Saffron Walden (GB)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

(21) Appl. No.: 15/647,901

(22) Filed: Jul. 12, 2017

(65) Prior Publication Data
US 2018/0016267 A1   Jan. 18, 2018

(30) Foreign Application Priority Data

Jul. 13, 2016   (EP) .................................. 16179236

(51) Int. Cl.
| | | |
|---|---|---|
| *C07D 409/14* | (2006.01) | |
| *A61K 31/4709* | (2006.01) | |
| *A61K 9/00* | (2006.01) | |
| *A61K 31/497* | (2006.01) | |
| *A61K 31/506* | (2006.01) | |
| *A61K 45/06* | (2006.01) | |
| *A61M 15/00* | (2006.01) | |
| *A61M 16/14* | (2006.01) | |
| *C07D 401/14* | (2006.01) | |
| *C07D 405/14* | (2006.01) | |
| *C07D 417/14* | (2006.01) | |
| *C07D 471/08* | (2006.01) | |
| *C07D 495/04* | (2006.01) | |

(52) U.S. Cl.
CPC .......... *C07D 409/14* (2013.01); *A61K 9/0073* (2013.01); *A61K 31/4709* (2013.01); *A61K 31/497* (2013.01); *A61K 31/506* (2013.01); *A61K 45/06* (2013.01); *A61M 15/009* (2013.01); *A61M 16/14* (2013.01); *C07D 401/14* (2013.01); *C07D 405/14* (2013.01); *C07D 417/14* (2013.01); *C07D 471/08* (2013.01); *C07D 495/04* (2013.01); *A61M 2202/064* (2013.01)

(58) Field of Classification Search
CPC .. C07D 409/14; C07D 401/14; C07D 405/14; C07D 417/14; C07D 471/08; C07D 495/04; A61K 31/4709; A61K 31/497; A61K 31/506; A61K 9/0073; A61K 45/06
See application file for complete search history.

(56) References Cited

U.S. PATENT DOCUMENTS

| | | | | |
|---|---|---|---|---|
| 8,178,679 | B2 * | 5/2012 | Matassa ................ | C07C 217/60 546/157 |
| 2006/0035933 | A1 | 2/2006 | Mammen et al. | |
| 2016/0015704 | A1 * | 1/2016 | Aparici Virgili ...... | A61K 31/56 514/171 |

FOREIGN PATENT DOCUMENTS

| | | |
|---|---|---|
| WO | 2012/168349 | 12/2012 |
| WO | 2016/128456 | 8/2016 |

OTHER PUBLICATIONS

European Search Report in Application No. 16179236.1 dated Sep. 22, 2016.
International Search Report in Application No. PCT/EP2017/067155 dated Aug. 21, 2017.

* cited by examiner

*Primary Examiner* — D Margaret M Seaman
(74) *Attorney, Agent, or Firm* — Oblon, McClelland, Maier & Neustadt, L.L.P.

(57) ABSTRACT

Compounds of formula I defined herein act both as muscarinic receptor antagonists and beta2 adrenergic receptor agonists and are useful for the prevention and/or treatment of broncho-obstructive or inflammatory diseases.

20 Claims, No Drawings

US 10,196,386 B2

COMPOUNDS HAVING MUSCARINIC RECEPTOR ANTAGONIST AND BETA2 ADRENERGIC RECEPTOR AGONIST ACTIVITY

CROSS REFERENCES TO RELATED APPLICATIONS

This application claims priority to European Patent Application No. 16179236.1, filed on Jul. 13, 2016, which is incorporated herein by reference in its entirety.

BACKGROUND OF THE INVENTION

Field of the Invention

The present invention relates to compounds, which act both as muscarinic receptor antagonists and beta2 adrenergic receptor agonists. The present invention also relates to processes for the preparation of such a compound, compositions which contain such a compound, therapeutic uses of such a compound, and combinations of such a compound with other pharmaceutical active ingredients.

Discussion of the Background

Pulmonary disorders, such as asthma and chronic obstructive pulmonary disease (COPD), are commonly treated with bronchodilators. A well-known class of bronchodilators consists of beta-2 adrenergic receptor agonists, such as salbutamol, fenoterol, formoterol and salmeterol. These compounds are generally administered by inhalation.

Another well-known class of bronchodilators consists of muscarinic receptor antagonists (anticholinergic compounds), such as ipratropium and tiotropium. These compounds are also typically administered by inhalation.

Inhaled formulations of both beta-2 agonists and muscarinic receptor antagonists are valuable agents in the treatment of asthma and COPD, with both classes of agents providing symptomatic relief due to their ability to relax constricted airways. Observations that the bronchodilator effects of the two classes of agents were additive, prompted studies with combinations of the two agents. In 1975, it was shown that beneficial effects could be achieved by combining two ingredients such as fenoterol and ipratropium bromide in a single aerosol. This prompted the development of fixed dose combinations of ipratropium bromide firstly with fenoterol (Berodual, introduced in 1980), and then with salbutamol (Combivent, introduced in 1994).

More recently the availability of both long-acting muscarinic antagonists and long-acting beta-2 agonists prompted to the development of combinations of these agents. For example, WO 00/69468, which is incorporated herein by reference in its entirety, discloses medicament compositions containing a muscarinic receptor antagonist, such as tiotropium bromide, and beta-2 adrenergic receptor agonists, such as formoterol fumarate or salmeterol, and WO 2005/115467, which is incorporated herein by reference in its entirety, discloses a combination which comprises a beta-2 agonist and an antagonist of M3 muscarinic receptors which is a salt of 3(R)-(2-hydroxy-2,2-dithien-2-ylacetoxy)-1-(3-phenoxypropyl)-1-azoniabicyclo[2.2.2]octane.

An alternative approach to the development of fixed dose combinations is the identification of molecules that combine both activities of muscarinic antagonism and beta-2 agonism. In fact compounds possessing both beta-2 adrenergic receptor agonist and muscarinic receptor antagonist activity are highly desirable since such bifunctional compounds would provide bronchodilation through two independent mechanisms of action while having a single molecule pharmacokinetics.

Such kind of compounds was described in some patent applications, such as WO 2004/074246, WO 2004/074812, WO 2005/051946, WO 2006/023457, WO 2006/023460, WO 2010/123766, WO 2011/048409 WO 2012/168349, WO 2012/168359, WO2014/086924, WO 2014/086927 and co-pending patent application PCT/EP2016/052812, all of which are incorporated herein by reference in their entireties.

It has now been found that some particular phenyl hydroxyacetic ester derivatives, besides possessing both beta-2 adrenergic receptor agonist and muscarinic receptor antagonist activity, possess elevated affinity for the M3 muscarinic receptors and long lasting bronchodilating activity.

However, there remains a need for compounds which act both as muscarinic receptor antagonists and beta2 adrenergic receptor agonists.

SUMMARY OF THE INVENTION

Accordingly, it is one object of the present invention to provide novel compounds which act both as muscarinic receptor antagonists and beta2 adrenergic receptor agonists.

It is another object of the present invention to provide novel processes for the preparation of such a compound.

It is another object of the present invention to provide novel compositions which contain such a compound.

It is another object of the present invention to provide novel therapeutic uses of such a compound.

It is another object of the present invention to provide novel combinations of such a compound with other pharmaceutical active ingredients.

These and other objects, which will become apparent during the following detailed description, have been achieved by the inventors' discovery that some particular phenyl hydroxyacetic ester derivatives, besides possessing both beta-2 adrenergic receptor agonist and muscarinic receptor antagonist activity, possess elevated affinity for the M3 muscarinic receptors and long lasting bronchodilating activity.

Thus, the present invention provides compounds of general formula I which, act both as muscarinic receptor antagonists and beta2 adrenergic receptor agonists, processes for the preparation of such a compound, compositions which contain such a compound, therapeutic uses of such a compound, and combinations of such a compound with other pharmaceutical active ingredients among which are, for instance, those currently used in the treatment of respiratory disorders, e.g. corticosteroids, P38 MAP kinase inhibitors, IKK2, HNE inhibitors, PDE4 inhibitors, leukotriene modulators, NSAIDs and mucus regulators.

DETAILED DESCRIPTION OF THE PREFERRED EMBODIMENTS

In particular, the present invention is directed to compounds of general formula I

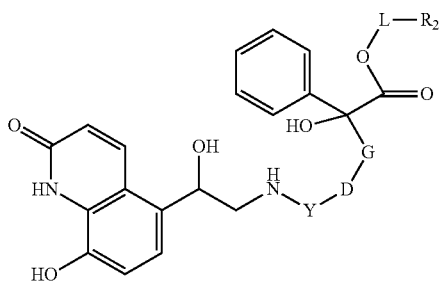

I wherein D is a cycloalkylene heterocycloalkylene or heteroarylene group selected from D0-D8

D0
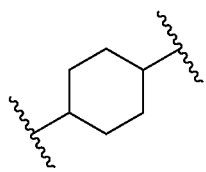

D1
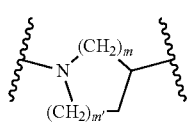

D2
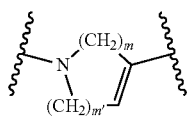

D3
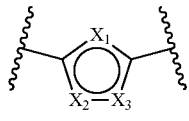

D4
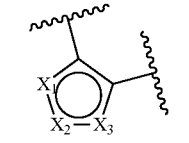

D5
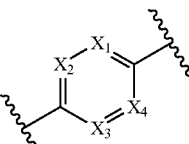

D6
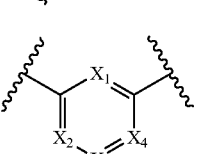

D7
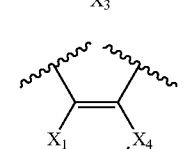

D8
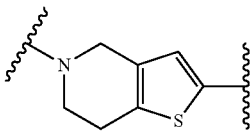

wherein at least one of X1, X2, X3, and X4 is at each occurrence independently selected from N, $NR_7$, O, and S and the others are CH groups;

Y is a divalent group of formula $$\{-A_1-B-A_2-C-(CH_2)_n-\}$$

wherein

A1 and A2 are independently absent or selected from $(C_1-C_{12})$alkylene, $(C_3-C_8)$cycloalkylene and $(C_3-C_8)$heterocycloalkylene optionally substituted by one or more substituents selected from $(C_1-C_6)$alkyl, aryl$(C_1-C_6)$alkyl and heteroaryl$(C_1-C_6)$alkyl;

B is absent or is selected from $(C_3-C_8)$cycloalkylene, $(C_3-C_8)$heterocycloalkylene, arylene or heteroarylene optionally substituted by one or more groups selected from —OH, halogens, —CN, $(C_1-C_6)$alkyl, $(C_1-C_6)$alkoxy, $(C_1-C_6)$haloalkyl, $(C_1-C_6)$haloalkoxy and aryl$(C_1-C_6)$alkyl;

C is absent or is selected from —O—, —C(O)—, —OC(O)—, —(O)CO—, —S—, —S(O)—, —S(O)$_2$— and —N($R_7$)—, or is one of the following groups C1-C5

C1
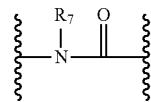

C2
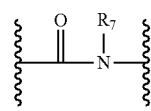

C3
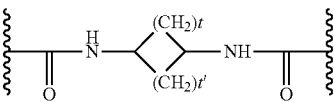

C4
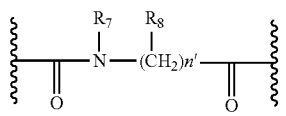

C5
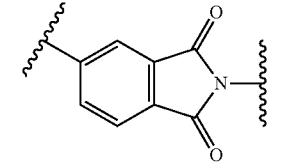

wherein $R_7$ is in each occurrence independently H or selected from linear or branched $(C_1-C_8)$alkyl, aryl$(C_1-C_6)$alkyl, arylsulfanyl, arylsulfinyl, arylsulfonyl, $(C_3-C_8)$cycloalkyl, $(C_3-C_8)$heterocycloalkyl, aryl and heteroaryl;

$R_8$ is in each occurrence independently H or $(C_1-C_8)$alkyl;

n and n' are at each occurrence independently 0 or an integer from 1 to 3;

m, m', t, t', v and v' are at each occurrence independently an integer from 1 to 3;

G is arylene optionally substituted by one or more substituents selected from halogen atoms, —OH, oxo (=O), —SH, —$NO_2$, —CN, —$CON(R_6)_2$, —$NH_2$, —$NHCOR_6$, —$CO_2R_6$, $(C_1-C_{10})$alkylsulfanyl, $(C_1-C_{10})$alkylsulfinyl, $(C_1-C_{10})$alkylsulfonyl, $(C_1-C_{10})$alkyl, aryl, haloaryl, heteroaryl and $(C_1-C_{10})$alkoxy;

L is a bond or $(C_1-C_8)$alkylene;

$R_2$ is a nitrogen containing group which may be selected from J1-J8

J1
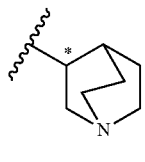

J2
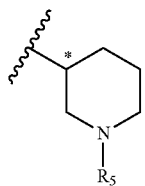

J3
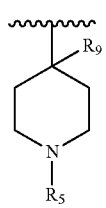

J4
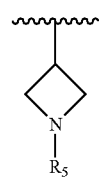

J5
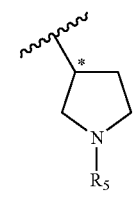

J6
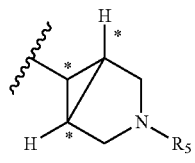

J7
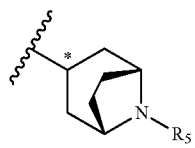

J8
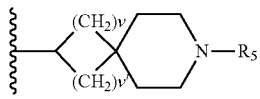

$R_5$ is a group of formula K

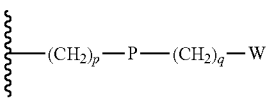
K wherein p is 0 or an integer from 1 to 4; q is 0 or an integer from 1 to 4;

P is absent or is selected from the divalent group consisting of O, S, SO, $SO_2$, CO, $NR_6$ CH=CH, $N(R_6)SO_2$, $N(R_6)COO$, $N(R_6)C(O)$, $SO_2N(R_6)$, $OC(O)N(R_6)$ and $C(O)N(R_6)$;

W is selected from H, $(C_1-C_6)$alkyl, $(C_3-C_8)$cycloalkyl, aryl and heteroaryl, optionally substituted by one or more substituents selected independently from halogen atoms, —OH, oxo (=O), —SH, —$NO_2$, —CN, —$CON(R_6)_2$, —$NH_2$, —$NHCOR_6$, —$CO_2R_6$, $(C_1-C_{10})$alkylsulfanyl, $(C_1-C_{10})$alkylsulfinyl, $(C_1-C_{10})$alkylsulfonyl, $(C_1-C_{10})$alkyl and $(C_1-C_{10})$alkoxy;

$R_6$ is at each occurrence independently H or selected from $(C_1-C_{10})$alkyl, $(C_1-C_6)$haloalkyl, $(C_2-C_6)$alkynyl, $(C_2-C_6)$alkenyl, $(C_3-C_8)$cycloalkyl, heteroaryl and aryl optionally substituted by one or more substituents selected from halogen atoms, —OH, oxo (=O), —SH, —$NO_2$, —CN, —$CONH_2$, —COOH, $(C_1-C_{10})$alkoxycarbonyl, $(C_1-C_{10})$alkylsulfanyl, $(C_1-C_{10})$alkylsulfinyl, $(C_1-C_{10})$alkylsulfonyl, $(C_1-C_{10})$alkyl and $(C_1-C_{10})$alkoxy; and $R_9$ is in each occurrence independently H or $(C_1-C_8)$alkyl; and pharmaceutically acceptable salts or solvates thereof.

The term "pharmaceutically acceptable salts", as used herein, refers to compounds according to the present invention obtained by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid, and citric acid.

Many organic compounds can form complexes with solvents in which they are reacted or from which they are precipitated or crystallized. These complexes are known as "solvates". Pharmaceutically acceptable solvates of compounds of the invention are within the scope of the invention.

The present invention also includes polymorphs and crystalline forms of compounds of formula (I), or of pharmaceutically acceptable salts, or solvates thereof.

The term "halogen", "halogens" or "halogen atoms" as used herein includes fluorine, chlorine, bromine, and iodine, preferably chlorine or fluorine, referring independently to one or more of these atoms.

The expression "$(C_1-C_x)$alkyl" refers to straight or branched chain alkyl groups wherein the number of carbon atoms is from 1 to x, preferably from 1 to 6 thus referring to $(C_1-C_6)$alkyl. Examples of groups are methyl, ethyl, n-propyl, isopropyl, t-butyl, pentyl, hexyl, octyl, nonyl, decyl, undecyl, dodecyl, and the like.

In an analogous manner, the expression "$(C_1-C_x)$alkylene" herewith refers to divalent groups wherein the number of carbon atoms is from 1 to x, preferably from 1 to 6 thus referring to $(C_1-C_6)$alkylene, such as methylene, ethylene, n-propylene, isopropylene, n-butylene, t-butylene, pentylene, hexylene, octylene, nonylene, decylene, undecylene, dodecylene, and the like. The above divalent groups can also be referred to as methanediyl, ethanediyl, n-propanediyl, propan1,2diyl, and the like.

The expression "$(C_1-C_6)$haloalkyl" refers to the above "$(C_1-C_6)$alkyl" group wherein one or more hydrogen atoms are replaced by one or more halogen atoms, which can be the same or different from each other.

Examples of said $(C_1-C_6)$haloalkyl groups include halogenated, poly-halogenated and fully halogenated alkyl groups wherein one or more of the hydrogen atoms are replaced by halogen atoms, e.g. trifluoromethyl group.

The expression "hydroxy$(C_1-C_6)$alkyl" likewise refers to -alkyl-OH groups.

The expressions "$(C_1-C_{10})$alkylsulfanyl", "$(C_1-C_{10})$alkylsulfinyl" or "$(C_1-C_{10})$alkylsulfonyl" refer, respectively, to alkyl-S—, alkyl-SO— or alkyl-SO$_2$— groups.

The expression "$(C_2-C_x)$alkenyl" refers to straight or branched carbon chains with one or more double bonds, wherein the number of carbon atoms is from 1 to x. Examples of said groups comprise ethenyl, propenyl, butenyl, pentenyl, hexenyl, heptenyl, octenyl, nonenyl, decenyl, undecenyl, dodecenyl, and the like.

In an analogous manner, the expression "$(C_2-C_x)$alkenylene" refers to divalent groups, such as ethenylene, propenylene, butenylene, pentenylene, hexenylene, heptenylene, octenylene, nonenylene, decenylene, undecenylene, dodecenylene, and the like.

The expression "$(C_2-C_x)$alkynyl" refers to straight or branched carbon chains with one or more triple bonds, wherein the number of carbon atoms is from 1 to x. Examples of said groups comprise ethynyl, propynyl, butynyl, pentynyl, hexynyl, and the like.

In an analogous manner, the expression "$(C_2-C_6)$alkynylene" refers to divalent groups, such as ethynylene, propynylene, butynylene, pentynylene, hexynylene, and the like; otherwise commonly referred to as ethynediyl, propynediyl, butyndiyl and the like.

The expression "$(C_1-C_x)$alkoxy" refers to alkyl-oxy (i.e. alkoxy) groups, being the alkyl portion as above defined, wherein the number of carbon atoms is from 1 to x. Examples of said groups comprise methoxy (i.e. CH$_3$O—), ethoxy, n-propoxy, isopropoxy, n-butoxy, isobutoxy, sec-butoxy, tert-butoxy, pentoxy, hexoxy and the like.

The expression "$(C_1-C_6)$haloalkoxy" refers to the above "$(C_1-C_6)$alkoxy" group wherein one or more hydrogen atoms are replaced by one or more halogen atoms, which can be the same or different from each other.

Examples of said $(C_1-C_6)$haloalkoxy groups include halogenated, poly-halogenated and fully halogenated alkoxy groups wherein one or more of the hydrogen atoms are replaced by halogen atoms, e.g. trifluoromethoxy group.

The expression "$(C_1-C_{10})$alkoxycarbonyl" refers to $(C_1-C_{10})$alkoxyC(O)— groups. No-limiting examples of $(C_1-C_{10})$alkoxycarbonyl may thus include methoxycarbonyl, ethoxycarbonyl, propoxycarbonyl, butoxycarbonyl, isopropoxycarbonyl, and the like.

The expression "cycloalkyl" refers to mono or bi-cycloaliphatic hydrocarbon groups with 5 to 20 ring atoms, preferably from 5 to 15. Specifically "$(C_3-C_8)$cycloalkyl" refers to such "cycloalkyl" groups having 3 to 8 carbon atoms. Examples include cyclopropyl, cyclobutyl, cyclopentyl, cyclohexyl, cycloheptyl, bicyclo[2.2.1]hept-2-yl and the like.

The expression "heterocycloalkyl" refers to saturated or partially saturated mono, bi- or tri-cyclic systems with 3 to 20 ring atoms, preferably from 5 to 15, in which at least one carbon ring atom is replaced by a heteroatom (e.g. N, NH, S, or O).

The expression "$(C_3-C_8)$heterocycloalkyl" refers to such "heterocycloalkyl" groups with 3 to 8 ring atoms. Examples include quinuclidinyl, pyrrolidinyl, piperidinyl, azabicyclo[3.2.1]octan-3-yl and azoniabicyclo[2.2.2]octanyl, [1.2.3.6]tetrahydropyridin-1yl, dihydropyrrolyl, and the like.

In an analogous manner, the term "cycloalkylene" refers to mono or bi-cyclic groups such as saturated cycloalkane-diyl and partially saturated cycloalkene-diyl. The term "heterocycloalkylene" refers to mono or bi-cyclic groups above defined in which at least one carbon ring atom is replaced by a heteroatom (e.g. N, NH, S or O). Thus, specifically expressions "$(C_3-C_8)$cycloalkylene" and "$(C_3-C_8)$heterocycloalkylene" herewith refer to such divalent groups with 3 to 8 ring atoms.

Examples of such $(C_3-C_8)$cycloalkylene and $(C_3-C_8)$heterocycloalkylene are divalent groups, such as, respectively, cyclopropylene, cyclobutylene, cyclopentylene, cyclohexylene, cycloheptylene, bicyclo[2.2.1]hept-2-ylene and quinuclidinylene, pyrrolidinylene, piperidinylene, azabicyclo[3.2.1]octan-3-ylene, azoniabicyclo[2.2.2]octanylene, [1.2.3.6]tetrahydropyridinylene, dihydropyrrolyl-ene 1 and the like. With alternative common name, deriving from the name of the corresponding alkanes or alkenes, the above divalent groups can be referred to also as cyclopropanediyl, cyclobutanediyl, cyclopentanediyl, cyclohexanediyl, cycloheptanediyl, bicyclo[2.2.1]heptanediyl and quinuclidinediyl, pyrrolidinediyl, piperidinediyl, azabicyclo[3.2.1]octandiyl, azoniabicyclo[2.2.2]octandiyl, [1.2.3.6]tetrahydropyridine-[1.4]diyl, dihydropyrrolediyl, and the like.

The expression "aryl" refers to mono, bi- or tricyclic ring systems having 5 to 20, preferably from 5 to 15, more preferably from 5 to 8 ring atoms, and wherein at least one ring is aromatic.

The expression "heteroaryl" refers to mono, bi- or tricyclic systems with 5 to 20 ring atoms, preferably from 5 to 15, in which at least one ring is aromatic and in which at least one carbon ring atom is replaced by a heteroatom (e.g. N, NH, S or O).

Examples of suitable aryl or heteroaryl monocyclic systems include, thiophene (thiophenyl), benzene (phenyl), pyrrole (pyrrolyl), pyrazole (pyrazolyl), imidazole (imidazolyL), isoxazole (isoxazolyl), oxazole (oxazolyl), isothiazole (isothiazolyl), thiazole (thiazolyl), pyridine (pyridinyl), imidazolidine (Imidazolidinyl), furan (furanyl) radicals, and the like.

Examples of suitable aryl or heteroaryl bicyclic systems include naphthalene (naphthalenyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, indane or dihydro-indene, dihydrobenzo dioxepin, benzo oxazine radicals, and the like.

Examples of suitable aryl or heteroaryl tricyclic systems include fluorine (fluorinyl) radicals as well as benzocondensed derivatives of the aforementioned heteroaryl bicyclic systems.

In an analogous manner, the expressions "arylene" and "heteroarylene" refer to divalent groups, such as phenylene, biphenylene and thienylene. Such groups are also referred to as "arenediyl" or "heteroarenediyl" groups. E.g. ortho-phenylene is also named benzene-1,2-diyl, para-phenylene is also named benzene-1,4-diyl, meta-phenylene is also named benzene-1,3-diyl. Thus, examples of suitable arylene or heteroarylene monocyclic systems include thiophenediyl, benzenediyl, pyrrolediyl, pyrazolediyl, imidazolediyl, isoxazolediyl, oxazolediyl, isothiazolediyl, thiazolediyl, pyridinediyl, imidazolidinediyl, furandiyl radicals, and the like.

Examples of suitable arylene or heteroarylene bicyclic systems include indanediyl (also named dihydroindenediyl), naphthalenediyl, biphenylenediyl, purinediyl, pteridinediyl, benzotriazolediyl, quinolinediyl, isoquinolinediyl, indolediyl, isoindolediyl, benzothiophenediyl, dihydrobenzo dioxindiyl, dihydro-indenediyl, dihydrobenzo dioxepindiyl, benzo oxazinediyl radicals and the like.

Examples of suitable arylene or heteroarylene tricyclic systems include fluorenediyl radicals as well as benzocondensed derivatives of the aforementioned heteroaryl bicyclic systems. The expressions "aryl($C_1$-$C_6$)alkyl", "heteroaryl ($C_1$-$C_6$)alkyl" and "($C_3$-$C_8$)cycloalkyl($C_1$-$C_6$)alkyl" refer to a "($C_1$-$C_6$)alkyl" respectively substituted by one or more aryl, heteroaryl or ($C_3$-$C_8$)cycloalkyl groups, as defined above. Examples of aryl($C_1$-$C_6$)alkyl include triphenylmethyl.

By way of analogy the expressions "arylsulfanyl", "arylsulfinyl" or "arylsulfonyl" refer, respectively, to aryl-S—, aryl-SO— or aryl-$SO_2$— groups. Preferred aryl groups are Examples are phenyl-S—, phenyl-SO— or phenyl-$SO_2$—.

Likewise the expression "haloaryl" refers to the above "aryl" group wherein one or more hydrogen atoms are replaced by one or more halogen atoms, which can be the same or different from each other.

As used herein an oxo moiety is represented by (O) as an alternative to other common representations, e.g. (═O). Thus, in terms of general formula, the carbonyl group is herein preferably represented as —C(O)— as an alternative to the other common representations such as —CO—, —(CO)—, C═O or —C(═O)—. In general the bracketed group is a lateral group, not included into the chain, and brackets are used, when deemed useful, to help disambiguating linear chemical formulas; e.g. the sulfonyl group —$SO_2$— might be also represented as —$S(O)_2$— to disambiguate e.g. with respect to the sulfinic group —S(O)O—.

Whenever basic amino or quaternary ammonium groups are present in the compounds of formula I, as above said, physiological acceptable anions, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate may be present. Likewise, in the presence of acidic groups such as —COOH groups, corresponding physiological cation salts may be present as well, for instance including alkaline or alkaline earth metal ions.

Compounds of general formula (I) contain at least two stereogenic centers. Therefore, the invention also includes any of the optical stereoisomers, diastereoisomers and mixtures thereof, in any proportion.

In particular, the carbon atom (2) linked to phenyl, —OH, G and C═O groups, and the carbon atom (1) linked to the carbostiryl moiety

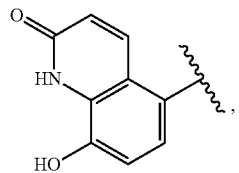 [SMILES: *c1ccc(O)c2[nH]c(=O)ccc12]

—OH and the rest of the molecule, are stereogenic centers.

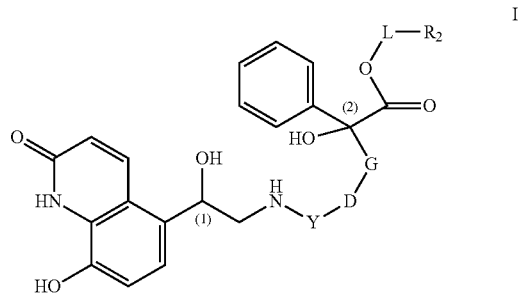

Thus, compounds of the invention, having at least two stereogenic centers, may accordingly exist as at least four diastereoisomers. Where the compounds of the present invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the invention is directed to compounds of formula (I)', which are compounds of formula (I) as above defined where the absolute configuration of carbon (1) is that shown herebelow:

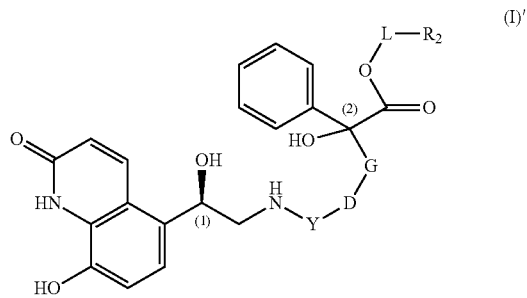

The absolute configuration for a chiral carbon is determined via X ray and assigned on the basis of Cahn-Ingold-Prelog nomenclature based on groups' priorities. Thus, in one preferred embodiment, for compounds of formula (I), absolute configuration at carbon (1) is (R).

As above said, compounds of formula (I) may exist as at least four diastereoisomers (Ia), (Ib), (Ic) and (Id) herebelow represented, which are comprised within the scope of the present invention; each diastereoisomer (Ia), (Ib), (Ic), (Id) may be constituted by a mixture of corresponding epimers when a third stereogenic center is present in the molecule.

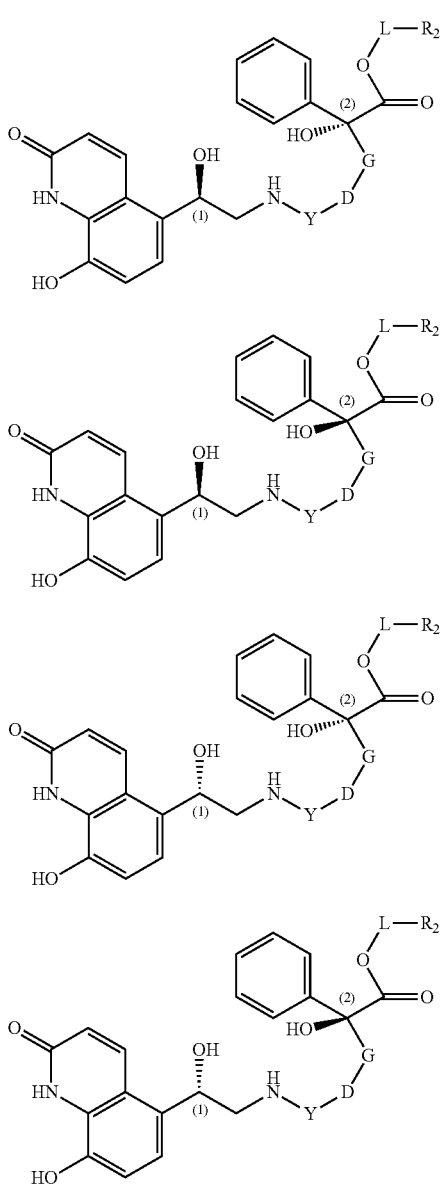

In a further preferred embodiment, the invention is directed to compounds of formula (Ia) or (Ib), which are respectively compounds of formula (I) as above defined wherein the absolute configuration at carbon (1) is (R) and at carbon (2) is (S); or wherein the absolute configuration at carbon (1) is (R) and at carbon (2) is (R).

Preferred are compounds of general formula (I), (Ia), or (Ib) wherein L is a $(C_1-C_8)$alkylene which is —$(CH_2)_s$—; wherein s is 0 or an integer from 1-3.

More preferred are compounds of general formula I″

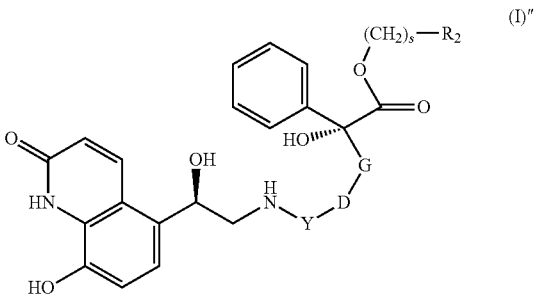

It is to be understood that all preferred groups or embodiments described herebelow and hereabove for compounds of formula (I) may be combined among each other and apply to compounds of formula (Ia), (Ib), (Ic), (Id) and (I)' as well mutatis mutandis.

In a first preferred embodiment the invention is directed to group of compounds of general formula I wherein $R_2$ is a group of formula J3:

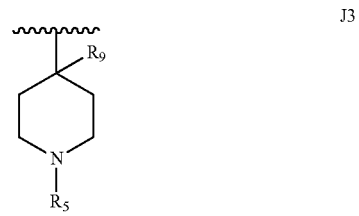

wherein $R_5$ is a group of formula K, wherein p is 0 or 1, P is absent or is CO, q is absent or is 1 and W is H or is selected from $(C_1-C_6)$alkyl and aryl, and all the other variables are as defined above.

In a more preferred embodiment, $R_2$ is a group of formula J3, $R_5$ is methyl or benzyl, $R_9$ is H or methyl and all the other variables are as defined above.

In another preferred embodiment, G is arylene.

In another further preferred embodiment, G is phenylene and particularly preferred are compounds wherein G is p-phenylene or m-phenylene.

In a second preferred embodiment A1 and A2 are independently absent or selected from methylene, ethylene, propylene, butylene, pentylene, hexylene, heptylene, octylene and nonylene, and all the other variables are as defined above.

Most preferred compounds in this other preferred embodiment are those compounds of formula (I) wherein A2 is absent or methylene and A1 is independently selected from $(C_1-C_{12})$alkylene which is methylene, ethylene, n-propylene, butylene, isobutylene, pentylene, hexylene, heptylene, octylene;

B is absent or is selected from $(C_3-C_8)$heterocycloalkylene which is piperidinylene or indanediyl, arylene which is phenylene and heteroarylene which is thiophenediyl or pyridine-diyl; B being optionally substituted by one or more groups selected independently from —OH, halogen which is fluorine, chlorine, bromine, $(C_1-C_6)$alkyl which is methyl, $(C_1-C_6)$alkoxy which is methoxy, ethoxy, isopropoxy, $(C_1-C_6)$haloalkyl which is trifluoromethyl and $(C_1-C_6)$haloalkoxy which is trifluoromethoxy;

C is absent or is selected from —C(O)—, or is one of the following groups C1, C2, C3, C4, C5; wherein $R_7$ is H or methyl and $R_8$ is H or methyl, t, t' and n' are 1;

D is absent or is selected from cycloalkylene D0 which is cyclohexanediyl, heterocycloalkylene selected from D1 which is piperidin-diyl, pyrrolidine-diyl, D2 which is tetrahydropyridin-diyl, 1H-dihydropyrrolediyl or heteroarylene selected from D3 which is furane-diyl, thiophene-diyl, pyrazolediyl, thiazole-diyl, oxazole-diyl, D4 which is pyrazolediyl D5 which is pyridinediyl, pyrimidinediyl, or pyrazinediyl, pyridazinediyl D6 which is pyridinediyl, pyrimidinediyl or pyrazinediyl, D7 which is pyridinediyl, pyrimidinediyl or pyrazinediyl, D8 which is tetrahydrothienopyridin-diyl n is 0 or 1;
v and v' are at each occurrence independently 1 or 2;
G is arylene which is meta-phenylene or para-phenylene;
L is a bond or $(C_1$-$C_8)$alkylene which is —CH(CH$_3$)— or —(CH$_2$)—;
$R_2$ is a group of formula J1, J2, J3, J4, J5, J6, J7 or J8
$R_5$ is a group of formula K

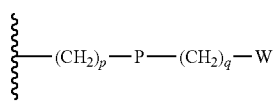

K wherein p is 0 or 1; q is 0;
P is absent
W is selected from $(C_1$-$C_6)$alkyl which is methyl, $(C_3$-$C_8)$cycloalkyl which is cyclobutyl or cyclopentyl, aryl which is phenyl optionally substituted by $(C_1$-$C_{10})$alkoxy which is methoxy;
$R_9$ is in each occurrence independently H or $(C_1$-$C_8)$alkyl which is methyl; and pharmaceutically acceptable salts or solvates thereof.

Particularly preferred compounds of the invention are those compounds of formula (I) wherein
A2 is absent and A1 is independently selected from $(C_1$-$C_{12})$alkylene which is methylene or ethylene;
B is arylene which is phenylene; B being optionally substituted by one or more groups selected independently from halogen which is fluorine, $(C_1$-$C_6)$alkoxy which is methoxy;
C is absent or is selected from —C(O)— and C4; wherein $R_7$ is H, $R_8$ is H or methyl; D is heterocycloalkylene D2 which is tetrahydropyridin-diyl, 1H-dihydropyrrolediyl or heteroarylene D5 which is pyridazinediyl
n is 0 and n' is 1;
G is arylene which is meta-phenylene;
L is-(CH$_2$)—;
$R_2$ is J3 wherein
$R_5$ is benzyl; $R_9$ is H;
and pharmaceutically acceptable salts or solvates thereof.

The present invention is also directed to a process for the preparation of the compounds of general formula I.

The present invention also provides pharmaceutical compositions of compounds of formula I alone or in combination with or in admixture with one or more pharmaceutically acceptable carriers and/or excipients.

The present invention also provides the use of compounds of formula I for preparing a medicament.

In a further aspect, the present invention provides the use of compounds of formula I for the prevention and/or treatment of any broncho-obstructive or inflammatory disease, preferably asthma or chronic bronchitis or chronic obstructive pulmonary disease (COPD).

In a further aspect, the present invention provides the use of compounds of formula I for the manufacture of a medicament for the prevention and/or treatment of any broncho-obstructive or inflammatory disease, preferably asthma or chronic bronchitis or chronic obstructive pulmonary disease (COPD).

The present invention further provides a method for prevention and/or treatment of any broncho-obstructive or inflammatory disease, preferably asthma or chronic bronchitis or chronic obstructive pulmonary disease (COPD), which comprises administering to a subject in need thereof a therapeutically effective amount of a compound of general formula I.

The present invention also provides pharmaceutical compositions suitable for administration by inhalation.

Inhalable preparations include inhalable powders, propellant-containing metering aerosols or propellant-free inhalable formulations.

The present invention is also directed to a device which may be a single- or multi-dose dry powder inhaler, a metered dose inhaler and a soft mist nebulizer comprising the compounds of formula I.

The present invention is also directed to a kit comprising the pharmaceutical compositions of compounds of formula I alone or in combination with or in admixture with one or more pharmaceutically acceptable carriers and/or excipients and a device which may be a single- or multi-dose dry powder inhaler, a metered dose inhaler and a soft mist nebulizer comprising the said combination or admixture.

According to specific embodiments, the present invention provides the compounds reported below:

| Cpd. | Structure |
|---|---|
| 1 | (1-Benzylpiperidin-4-yl)methyl (S)-2-(3-(5-((2-chloro-4-((((R)-2-hydroxy-2-(8-hydroxy-2-oxo-1,2-dihydroquinolin-5-yl)ethyl)amino)methyl)benzamido)-methyl)thiophen-2-yl)phenyl)-2-hydroxy-2-phenylacetate |
| 1A | (1-Benzylpiperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)benzamido)-methyl)thiophen-2-yl)phenyl)-2-phenylacetate |
| 1B | (1-Benzylpiperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)-3-methoxybenzamido)methyl)thiophen-2-yl)phenyl)-2-phenylacetate |
| 1C | (1-Benzylpiperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)-2-methoxybenzamido)methyl)thiophen-2-yl)phenyl)-2-phenylacetate |
| 1D | (1-Benzylpiperidin-4-yl)methyl (S)-2-(3-(5-((2-chloro-4-((((R)-2-hydroxy-2-(8-hydroxy-2-oxo-1,2-dihydroquinolin-5-yl)ethyl)amino)methyl)-5-methoxybenzamido)methyl)thiophen-2-yl)phenyl)-2-hydroxy-2-phenylacetate |

-continued

| Cpd. | Structure |
|---|---|
| 1E | (1-Benzylpiperidin-4-yl)methyl (S)-2-(3-(5-((2-fluoro-4-((((R)-2-hydroxy-2-(8-hydroxy-2-oxo-1,2-dihydroquinolin-5-yl)ethyl)amino)methyl)-5-methoxybenzamido)methyl)thiophen-2-yl)phenyl)-2-hydroxy-2-phenylacetate |
| 1F | (1-Benzylpiperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)-3-(trifluoromethyl)benzamido)methyl)thiophen-2-yl)phenyl)-2-phenylacetate |
| 1G | (1-Benzylpiperidin-4-yl)methyl (S)-2-(3-(5-((2-fluoro-4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-hydroxy-2-phenylacetate |
| 1H | (1-Benzylpiperidin-4-yl)methyl (S)-2-hydroxy-2-(3-(5-((4-(2-(((R)-2-hydroxy-2-(8-hydroxy-2-oxo-1,2-dihydroquinolin-5-yl)ethyl)amino)ethyl)-benzamido)methyl)thiophen-2-yl)phenyl)-2-phenylacetate |
| 1I | (1-Benzylpiperidin-4-yl)methyl (S)-2-(3-(5-((3-ethoxy-4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-hydroxy-2-phenylacetate |
| 1J | (1-Benzylpiperidin-4-yl)methyl (S)-2-(3-(5-((3-fluoro-4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-hydroxy-2-phenylacetate |
| 1K | (1-Benzylpiperidin-4-yl)methyl (S)-2-(3-(5-((2-fluoro-4-((((R)-2-hydroxy-2-(8-hydroxy-2-oxo-1,2-dihydroquinolin-5-yl)ethyl)amino)methyl)-3-methoxybenzamido)methyl)thiophen-2-yl)phenyl)-2-hydroxy-2-phenylacetate |
| 1L | (1-Benzylpiperidin-4-yl)methyl (S)-2-hydroxy-2-(3-(5-((6-((((R)-2-hydroxy-2-(8-hydroxy-2-oxo-1,2-dihydroquinolin-5-yl)ethyl)amino)methyl)-nicotinamido)methyl)thiophen-2-yl)phenyl)-2-phenylacetate |
| 1M | (1-Benzylpiperidin-4-yl)methyl (S)-2-hydroxy-2-(3-(5-((3-fluoro-4-((((R)-2-hydroxy-2-(8-hydroxy-2-oxo-1,2-dihydroquinolin-5-yl)ethyl)amino)methyl)-5-methoxybenzamido)methyl)thiophen-2-yl)phenyl)-2-hydroxy-2-phenylacetate |
| 1N | (1-Benzylpiperidin-4-yl)methyl (S)-2-hydroxy-2-(3-(5-((3-((((R)-2-hydroxy-2-(8-hydroxy-2-oxo-1,2-dihydroquinolin-5-yl)ethyl)amino)methyl)-benzamido)methyl)thiophen-2-yl)phenyl)-2-phenylacetate |
| 1O | (1-Benzylpiperidin-4-yl)methyl (S)-2-(3-(5-((2-fluoro-4-((((R)-2-hydroxy-2-(8-hydroxy-2-oxo-1,2-dihydroquinolin-5-yl)ethyl)amino)methyl)-5-methylbenzamido)methyl)thiophen-2-yl)phenyl)-2-hydroxy-2-phenylacetate |
| 1P | (1-Benzylpiperidin-4-yl)methyl (S)-2-hydroxy-2-(3-(5-((2-(4-((((R)-2-hydroxy-2-(8-hydroxy-2-oxo-1,2-dihydroquinolin-5-yl)ethyl)amino)methyl)-phenyl)acetamido)methyl)thiophen-2-yl)phenyl)-2-phenylacetate |
| 1Q | (1-Benzylpiperidin-4-yl)methyl (S)-2-hydroxy-2-(3-(5-((5-((((R)-2-hydroxy-2-(8-hydroxy-2-oxo-1,2-dihydroquinolin-5-yl)ethyl)amino)methyl)-picolinamido)methyl)thiophen-2-yl)phenyl)-2-phenylacetate |
| 1R | (1-Benzylpiperidin-4-yl)methyl (S)-2-(3-(5-((3-chloro-4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-hydroxy-2-phenylacetate |
| 1S | (1-Benzylpiperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)-3-methylbenzamido)methyl)thiophen-2-yl)phenyl)-2-phenylacetate |
| 1T | (1-Benzylpiperidin-4-yl)methyl (S)-2-hydroxy-2-(3-(5-((5-((((R)-2-hydroxy-2-(8-hydroxy-2-oxo-1,2-dihydroquinolin-5-yl)ethyl)amino)methyl)thiophene-2-carboxamido)methyl)thiophen-2-yl)phenyl)-2-phenylacetate |
| 1U | (1-Benzylpiperidin-4-yl)methyl (S)-2-(3-(5-((2,5-difluoro-4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-hydroxy-2-phenylacetate |
| 1V | (1-Benzylpiperidin-4-yl)methyl (S)-2-(3-(5-((2,3-difluoro-4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-hydroxy-2-phenylacetate |
| 1W | (1-Benzylpiperidin-4-yl)methyl (S)-2-(3-(5-((2-chloro-6-fluoro-4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-hydroxy-2-phenylacetate |
| 1X | (1-Benzylpiperidin-4-yl)methyl (S)-2-(3-(5-((2-fluoro-4-((((R)-2-hydroxy-2-(8-hydroxy-2-oxo-1,2-dihydroquinolin-5-yl)ethyl)amino)methyl)-6-methoxybenzamido)methyl)thiophen-2-yl)phenyl)-2-hydroxy-2-phenylacetate |
| 2 | 1-Methylpiperidin-4-yl (S)-2-hydroxy-2-(3-(5-((4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-phenylacetate |
| 2A | (1-(4-Methoxybenzyl)piperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)-methyl)benzamido)methyl)thiophen-2-yl)phenyl)-2-phenylacetate |
| 2B | (1-Methylpiperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-phenylacetate |
| 2C | ((S)-1-Benzylpiperidin-3-yl)methyl (S)-2-hydroxy-2-(3-(5-((4-((((R)-2-hydroxy-2-(8-hydroxy-2-oxo-1,2-dihydroquinolin-5-yl)ethyl)amino)-methyl)benzamido)methyl)thiophen-2-yl)phenyl)-2-phenylacetate |
| 2D | ((1R,5S,6r)-3-Benzyl-3-azabicyclo[3.1.0]hexan-6-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)thiophen-2-yl)phenyl)-2-phenylacetate |

| Cpd. | Structure |
|---|---|
| 2E | (1-(3-Methoxybenzyl)piperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)-methyl)benzamido)methyl)thiophen-2-yl)phenyl)-2-phenylacetate |
| 2F | 1-Benzylpiperidin-4-yl (S)-2-hydroxy-2-(3-(5-((((((R)-2-hydroxy-2-(8-hydroxy-2-oxo-1,2-dihydroquinolin-5-yl)ethyl)amino)methyl)-benzamido)methyl)thiophen-2-yl)phenyl)-2-phenylacetate |
| 2G | (R)-1-(1-Benzylpiperidin-4-yl)ethyl (S)-2-hydroxy-2-(3-(5-((4-((((((R)-2-hydroxy-2-(8-hydroxy-2-oxo-1,2-dihydroquinolin-5-yl)ethyl)amino)-methyl)benzamido)methyl)thiophen-2-yl)phenyl)-2-phenylacetate |
| 2H | 3-Benzyl-3-azaspiro[5.5]undecan-9-yl (S)-2-hydroxy-2-(3-(5-((4-((((R)-2-hydroxy-2-(8-hydroxy-2-oxo-1,2-dihydroquinolin-5-yl)ethyl)amino)-methyl)benzamido)methyl)thiophen-2-yl)phenyl)-2-phenylacetate |
| 3 | (1-Benzylpiperidin-4-yl)methyl (S)-2-hydroxy-2-(3-(1-(4-(2-(((R)-2-hydroxy-2-(8-hydroxy-2-oxo-1,2-dihydroquinolin-5-yl)ethyl)amino)ethyl)benzoyl)-1,2,3,6-tetrahydropyridin-4-yl)phenyl)-2-phenylacetate |
| 3A | (1-Benzylpiperidin-4-yl)methyl (S)-2-hydroxy-2-(3-(5-((4-(((((R)-2-hydroxy-2-(8-hydroxy-2-oxo-1,2-dihydroquinolin-5-yl)ethyl)amino)methyl)-benzamido)methyl)furan-2-yl)phenyl)-2-phenylacetate |
| 3B | (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)benzoyl)-1,2,3,6-tetrahydropyridin-4-yl)phenyl)-2-phenylacetate |
| 3C | (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)-3-methoxybenzoyl)-1,2,3,6-tetrahydropyridin-4-yl)phenyl)-2-phenylacetate |
| 3D | (1-Benzylpiperidin-4-yl)methyl (S)-2-(3-(1-(2-fluoro-4-((((R)-2-hydroxy-2-(8-hydroxy-2-oxo-1,2-dihydroquinolin-5-yl)ethyl)amino)methyl)-3-methoxybenzoyl)-1,2,3,6-tetrahydropyridin-4-yl)phenyl)-2-hydroxy-2-phenylacetate |
| 3E | (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)-2-methoxybenzoyl)-1,2,3,6-tetrahydropyridin-4-yl)phenyl)-2-phenylacetate |
| 3F | (1-Benzylpiperidin-4-yl)methyl (S)-2-hydroxy-2-(3-(1-(4-(2-(((R)-2-hydroxy-2-(8-hydroxy-2-oxo-1,2-dihydroquinolin-5-yl)ethyl)amino)ethyl)benzoyl)-2,5-dihydro-1H-pyrrol-3-yl)phenyl)-2-phenylacetate |
| 3G | (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)benzoyl)-2,5-dihydro-1H-pyrrol-3-yl)phenyl)-2-phenylacetate |
| 3H | (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)-3-methoxybenzoyl)-1,2,5,6-tetrahydropyridin-3-yl)phenyl)-2-phenylacetate |
| 3I | (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)benzoyl)-1,2,5,6-tetrahydropyridin-3-yl)phenyl)-2-phenylacetate |
| 3J | (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)-3-methoxybenzoyl)-2,5-dihydro-1H-pyrrol-3-yl)phenyl)-2-phenylacetate |
| 4 | (1-Benzylpiperidin-4-yl)methyl (S)-2-hydroxy-2-(3-(2-((4-(((((R)-2-hydroxy-2-(8-hydroxy-2-oxo-1,2-dihydroquinolin-5-yl)ethyl)amino)methyl)-benzamido)methyl)pyrimidin-5-yl)phenyl)-2-phenylacetate |
| 4A | (1-Benzylpiperidin-4-yl)methyl (S)-2-hydroxy-2-(3-(4-((4-((((R)-2-hydroxy-2-(8-hydroxy-2-oxo-1,2-dihydroquinolin-5-yl)ethyl)amino)methyl)-3-methoxybenzamido)methyl)pyrimidin-2-yl)phenyl)-2-phenylacetate |
| 4B | (1-Benzylpiperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)-benzamido)methyl)pyrazin-2-yl)phenyl)-2-phenylacetate |
| 4C | (1-Benzylpiperidin-4-yl)methyl (S)-2-hydroxy-2-(3-(6-((4-((((R)-2-hydroxy-2-(8-hydroxy-2-oxo-1,2-dihydroquinolin-5-yl)ethyl)amino)methyl)-3-methoxybenzamido)methyl)pyridazin-3-yl)phenyl)-2-phenylacetate |
| 4D | (1-Benzylpiperidin-4-yl)methyl (S)-2-hydroxy-2-(3-(4-((4-((((R)-2-hydroxy-2-(8-hydroxy-2-oxo-1,2-dihydroquinolin-5-yl)ethyl)amino)methyl)-benzamido)methyl)pyrimidin-2-yl)phenyl)-2-phenylacetate |
| 4E | (1-Benzylpiperidin-4-yl)methyl (S)-2-hydroxy-2-(3-(2-((4-((((R)-2-hydroxy-2-(8-hydroxy-2-oxo-1,2-dihydroquinolin-5-yl)ethyl)amino)methyl)-3-methoxybenzamido)methyl)pyrimidin-5-yl)phenyl)-2-phenylacetate |
| 4F | (1-Benzylpiperidin-4-yl)methyl (S)-2-hydroxy-2-(3-(3-((4-((((R)-2-hydroxy-2-(8-hydroxy-2-oxo-1,2-dihydroquinolin-5-yl)ethyl)amino)methyl)-3-methoxybenzamido)methyl)-1-methyl-1H-pyrazol-4-yl)phenyl)-2-phenylacetate |
| 4G | (1-Benzylpiperidin-4-yl)methyl (S)-2-hydroxy-2-(3-(6-((4-(((((R)-2-hydroxy-2-(8-hydroxy-2-oxo-1,2-dihydroquinolin-5-yl)ethyl)amino)methyl)-3-methoxybenzamido)methyl)pyrazin-2-yl)phenyl)-2-phenylacetate |
| 4H | (1-Benzylpiperidin-4-yl)methyl (S)-2-hydroxy-2-(3-(5-((4-(((((R)-2-hydroxy-2-(8-hydroxy-2-oxo-1,2-dihydroquinolin-5-yl)ethyl)amino)methyl)-3-methoxybenzamido)methyl)pyrazin-2-yl)phenyl)-2-phenylacetate |
| 5 | (1-Benzylpiperidin-4-yl)methyl (S)-2-hydroxy-2-(3-(5-((4-(((((R)-2-hydroxy-2-(8-hydroxy-2-oxo-1,2-dihydroquinolin-5-yl)ethyl)amino)methyl)-benzamido)methyl)thiophen-3-yl)phenyl)-2-phenylacetate |

-continued

| Cpd. | Structure |
|---|---|
| 5A | (1-Benzylpiperidin-4-yl)methyl (S)-2-hydroxy-2-(3-(4-((4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-phenylacetate |
| 5B | (1-Benzylpiperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)-benzamido)methyl)thiazol-2-yl)phenyl)-2-phenylacetate |
| 5C | (1-Benzylpiperidin-4-yl)methyl (S)-2-hydroxy-2-(3-(5-(4-((((R)-2-hydroxy-2-(8-hydroxy-2-oxo-1,2-dihydroquinolin-5-yl)ethyl)amino)methyl)benzoyl)-4,5,6,7-tetrahydrothieno[3,2-c]pyridin-2-yl)phenyl)-2-phenylacetate |
| 5D | (1-Benzylpiperidin-4-yl)methyl (S)-2-hydroxy-2-(3-(5-(2-(4-((((R)-2-hydroxy-2-(8-hydroxy-2-oxo-1,2-dihydroquinolin-5-yl)ethyl)amino)methyl)-benzamido)ethyl)thiophen-2-yl)phenyl)-2-phenylacetate |
| 5E | (1-Benzylpiperidin-4-yl)methyl (S)-2-hydroxy-2-(3-(3-((4-((((R)-2-hydroxy-2-(8-hydroxy-2-oxo-1,2-dihydroquinolin-5-yl)ethyl)amino)methyl)-3-methoxybenzamido)methyl)pyrazin-2-yl)phenyl)-2-phenylacetate |
| 6 | (1-Benzylpiperidin-4-yl)methyl (S)-2-hydroxy-2-(3-(4-(4-((((R)-2-hydroxy-2-(8-hydroxy-2-oxo-1,2-dihydroquinolin-5-yl)ethyl)amino)methyl)piperidine-1-carbonyl)pyridin-2-yl)phenyl)-2-phenylacetate |
| 6A | (1-Benzylpiperidin-4-yl)methyl (S)-2-hydroxy-2-(3-(6-(4-((((R)-2-hydroxy-2-(8-hydroxy-2-oxo-1,2-dihydroquinolin-5-yl)ethyl)amino)methyl)piperidine-1-carbonyl)pyrazin-2-yl)phenyl)-2-phenylacetate |
| 6B | (1-Benzylpiperidin-4-yl)methyl (S)-2-hydroxy-2-(3-(2-(4-((((R)-2-hydroxy-2-(8-hydroxy-2-oxo-1,2-dihydroquinolin-5-yl)ethyl)amino)methyl)piperidine-1-carbonyl)pyridin-4-yl)phenyl)-2-phenylacetate |
| 6C | (1-Benzylpiperidin-4-yl)methyl (S)-2-hydroxy-2-(3-(6-(4-((((R)-2-hydroxy-2-(8-hydroxy-2-oxo-1,2-dihydroquinolin-5-yl)ethyl)amino)methyl)piperidine-1-carbonyl)pyridin-3-yl)phenyl)-2-phenylacetate |
| 6D | (1-Benzylpiperidin-4-yl)methyl (S)-2-hydroxy-2-(3-(5-(4-((((R)-2-hydroxy-2-(8-hydroxy-2-oxo-1,2-dihydroquinolin-5-yl)ethyl)amino)methyl)piperidine-1-carbonyl)pyridin-2-yl)phenyl)-2-phenylacetate |
| 6E | (1-Benzylpiperidin-4-yl)methyl (S)-2-hydroxy-2-(3-(5-(4-((((R)-2-hydroxy-2-(8-hydroxy-2-oxo-1,2-dihydroquinolin-5-yl)ethyl)amino)methyl)piperidine-1-carbonyl)pyridin-3-yl)phenyl)-2-phenylacetate |
| 6F | (1-Benzylpiperidin-4-yl)methyl (S)-2-hydroxy-2-(3-(6-(4-((((R)-2-hydroxy-2-(8-hydroxy-2-oxo-1,2-dihydroquinolin-5-yl)ethyl)amino)methyl)piperidine-1-carbonyl)pyridin-2-yl)phenyl)-2-phenylacetate |
| 7 | (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)benzoyl)piperidin-4-yl)phenyl)-2-phenylacetate |
| 7A | (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)-3-methoxybenzoyl)piperidin-4-yl)phenyl)-2-phenylacetate |
| 7B | (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)-2-methoxybenzoyl)piperidin-4-yl)phenyl)-2-phenylacetate |
| 7C | (1-Benzylpiperidin-4-yl)methyl (S)-2-hydroxy-2-(3-(1-(4-(2-(((R)-2-hydroxy-2-(8-hydroxy-2-oxo-1,2-dihydroquinolin-5-yl)ethyl)amino)ethyl)benzoyl)piperidin-4-yl)phenyl)-2-phenylacetate |
| 7D | (1-Benzylpiperidin-4-yl)methyl (2S)-2-hydroxy-2-(3-(1-(2-(((R)-2-hydroxy-2-(8-hydroxy-2-oxo-1,2-dihydroquinolin-5-yl)ethyl)amino)-2,3-dihydro-1H-indene-5-carbonyl)piperidin-4-yl)phenyl)-2-phenylacetate |
| 8 | (1-Benzylpiperidin-4-yl)methyl (S)-2-hydroxy-2-(3-(1-((4-(2-(((R)-2-hydroxy-2-(8-hydroxy-2-oxo-1,2-dihydroquinolin-5-yl)ethyl)amino)ethyl)-benzoyl)glycyl)-1,2,3,6-tetrahydropyridin-4-yl)phenyl)-2-phenylacetate |
| 8A | (1-Benzylpiperidin-4-yl)methyl (S)-2-hydroxy-2-(3-(1-((4-((((R)-2-hydroxy-2-(8-hydroxy-2-oxo-1,2-dihydroquinolin-5-yl)ethyl)amino)methyl)-2-methoxybenzoyl)glycyl)-1,2,3,6-tetrahydropyridin-4-yl)phenyl)-2-phenylacetate |
| 8B | (1-Benzylpiperidin-4-yl)methyl (S)-2-hydroxy-2-(3-(1-((4-((((R)-2-hydroxy-2-(8-hydroxy-2-oxo-1,2-dihydroquinolin-5-yl)ethyl)amino)methyl)benzoyl)-D-alanyl)-1,2,3,6-tetrahydropyridin-4-yl)phenyl)-2-phenylacetate |
| 8C | (1-Benzylpiperidin-4-yl)methyl (S)-2-hydroxy-2-(3-(1-((4-((((R)-2-hydroxy-2-(8-hydroxy-2-oxo-1,2-dihydroquinolin-5-yl)ethyl)amino)methyl)benzoyl)-L-alanyl)-1,2,3,6-tetrahydropyridin-4-yl)phenyl)-2-phenylacetate |
| 8D | (1-Benzylpiperidin-4-yl)methyl (S)-2-hydroxy-2-(3-(1-((4-((((R)-2-hydroxy-2-(8-hydroxy-2-oxo-1,2-dihydroquinolin-5-yl)ethyl)amino)methyl)-benzoyl)glycyl)-1,2,3,6-tetrahydropyridin-4-yl)phenyl)-2-phenylacetate |
| 8E | (1-Benzylpiperidin-4-yl)methyl (S)-2-hydroxy-2-(3-(1-((4-((((R)-2-hydroxy-2-(8-hydroxy-2-oxo-1,2-dihydroquinolin-5-yl)ethyl)amino)methyl)-3-methoxybenzoyl)glycyl)-1,2,3,6-tetrahydropyridin-4-yl)phenyl)-2-phenylacetate |
| 8F | (1-Benzylpiperidin-4-yl)methyl (S)-2-hydroxy-2-(3-(1-(N-(4-((((R)-2-hydroxy-2-(8-hydroxy-2-oxo-1,2-dihydroquinolin-5-yl)ethyl)amino)-methyl)benzoyl)-N-methylglycyl)-1,2,3,6-tetrahydropyridin-4-yl)phenyl)-2-phenylacetate |
| 9 | (1-Benzylpiperidin-4-yl)methyl (S)-2-hydroxy-2-(3-(6-((((1R,3S)-3-(4-((((R)-2-hydroxy-2-(8-hydroxy-2-oxo-1,2-dihydroquinolin-5-yl)ethyl)amino)methyl)-benzamido)cyclobutyl)carbamoyl)pyrazin-2-yl)phenyl)-2-phenylacetate |

-continued

| Cpd. | Structure |
| --- | --- |
| 10 | (1-Benzylpiperidin-4-yl)methyl (S)-2-hydroxy-2-(3-(6-((3-(((R)-2-hydroxy-2-(8-hydroxy-2-oxo-1,2-dihydroquinolin-5-yl)ethyl)amino)propyl)carbamoyl)pyrazin-2-yl)phenyl)-2-phenylacetate |
| 11 | (1-Benzyl-4-methylpiperidin-4-yl)methyl (S)-2-(3-(5-((2-chloro-4-((((R)-2-hydroxy-2-(8-hydroxy-2-oxo-1,2-dihydroquinolin-5-yl)ethyl)amino)methyl)-5-methoxybenzamido)methyl)thiophen-2-yl)phenyl)-2-hydroxy-2-phenylacetate |
| 12 | (1-Benzylpiperidin-4-yl)methyl (S)-2-hydroxy-2-(3-(5-((5-((((R)-2-hydroxy-2-(8-hydroxy-2-oxo-1,2-dihydroquinolin-5-yl)ethyl)amino)methyl)-1,3-dioxoisoindolin-2-yl)methyl)thiophen-2-yl)phenyl)-2-phenylacetate |
| 13 | (1-Benzylpiperidin-4-yl)methyl (S)-2-hydroxy-2-(3-(1-((4-(2-(((R)-2-hydroxy-2-(8-hydroxy-2-oxo-1,2-dihydroquinolin-5-yl)ethyl)amino)ethyl)benzoyl)glycyl)piperidin-4-yl)phenyl)-2-phenylacetate |
| 14 | (1-Benzylpiperidin-4-yl)methyl (S)-2-hydroxy-2-(3-(3-((4-((((R)-2-hydroxy-2-(8-hydroxy-2-oxo-1,2-dihydroquinolin-5-yl)ethyl)amino)methyl)benzyl)carbamoyl)-1-methyl-1H-pyrazol-5-yl)phenyl)-2-phenylacetate |
| 15 | (1-benzylpiperidin-4-yl)methyl (S)-2-hydroxy-2-(4-(5-((4-((((R)-2-hydroxy-2-(8-hydroxy-2-oxo-1,2-dihydroquinolin-5-yl)ethyl)amino)methyl)benzamido)methyl)thiophen-2-yl)phenyl)-2-phenylacetate |
| 15A | (1-benzylpiperidin-4-yl)methyl (S)-2-hydroxy-2-(4-(5-((4-((((R)-2-hydroxy-2-(8-hydroxy-2-oxo-1,2-dihydroquinolin-5-yl)ethyl)amino)methyl)-3-methoxybenzamido)methyl)thiophen-2-yl)phenyl)-2-phenylacetate |
| 15B | (1-benzylpiperidin-4-yl)methyl (S)-2-hydroxy-2-(4-(5-((4-((((R)-2-hydroxy-2-(8-hydroxy-2-oxo-1,2-dihydroquinolin-5-yl)ethyl)amino)methyl)benzamido)methyl)thiophen-3-yl)phenyl)-2-phenylacetate |
| 15C | (1-benzylpiperidin-4-yl)methyl (S)-2-hydroxy-2-(4-(5-((4-((((R)-2-hydroxy-2-(8-hydroxy-2-oxo-1,2-dihydroquinolin-5-yl)ethyl)amino)methyl)benzamido)methyl)thiazol-2-yl)phenyl)-2-phenylacetate |
| 15D | (1-benzylpiperidin-4-yl)methyl (S)-2-hydroxy-2-(4-(6-((4-((((R)-2-hydroxy-2-(8-hydroxy-2-oxo-1,2-dihydroquinolin-5-yl)ethyl)amino)methyl)benzamido)methyl)pyridin-3-yl)phenyl)-2-phenylacetate |
| 15E | (1-benzylpiperidin-4-yl)methyl (S)-2-hydroxy-2-(4-(1-(4-((((R)-2-hydroxy-2-(8-hydroxy-2-oxo-1,2-dihydroquinolin-5-yl)ethyl)amino)methyl)benzoyl)-1,2,3,6-tetrahydropyridin-4-yl)phenyl)-2-phenylacetate |
| 15F | (1-benzylpiperidin-4-yl)methyl (S)-2-hydroxy-2-(4-(5-((4-((((R)-2-hydroxy-2-(8-hydroxy-2-oxo-1,2-dihydroquinolin-5-yl)ethyl)amino)methyl)-3-methoxybenzamido)methyl)thiophen-3-yl)phenyl)-2-phenylacetate |
| 16 | (1-benzylpiperidin-4-yl)methyl (S)-2-hydroxy-2-(4-(5-((4-(2-(((R)-2-hydroxy-2-(8-hydroxy-2-oxo-1,2-dihydroquinolin-5-yl)ethyl)amino)ethyl)benzyl)carbamoyl)thiophen-2-yl)phenyl)-2-phenylacetate |

The compounds of the present invention can be prepared from readily available starting materials using the following general methods and procedures or by using other information readily available to those of ordinary skill in the art. Although a particular embodiment of the present invention may be shown or described herein, those skilled in the art will recognize that all embodiments or aspects of the invention can be prepared using the methods described herein or by using other known methods, reagents and starting materials. When typical or preferred process conditions (i.e., reaction temperatures, times, mole ratios of reactants, solvents, pressures, etc.) are given, other process conditions can also be used unless stated otherwise. While the optimum reaction conditions may vary depending on the particular reactants or solvent used, such conditions can be readily determined by one skilled in the art by routine optimization procedures.

Compounds of general formula I may be prepared according to the following synthetic Scheme.

General Scheme 1A
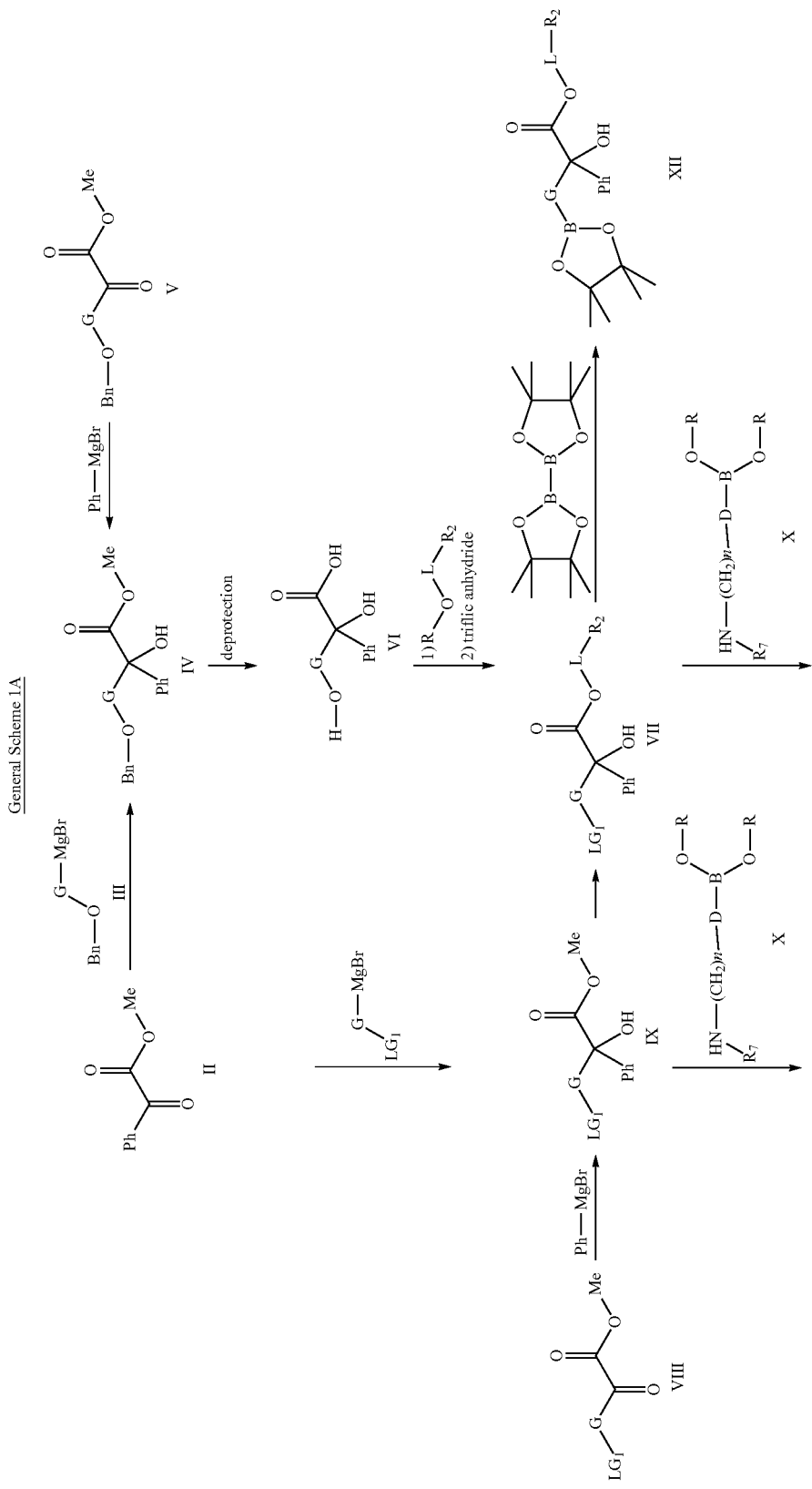

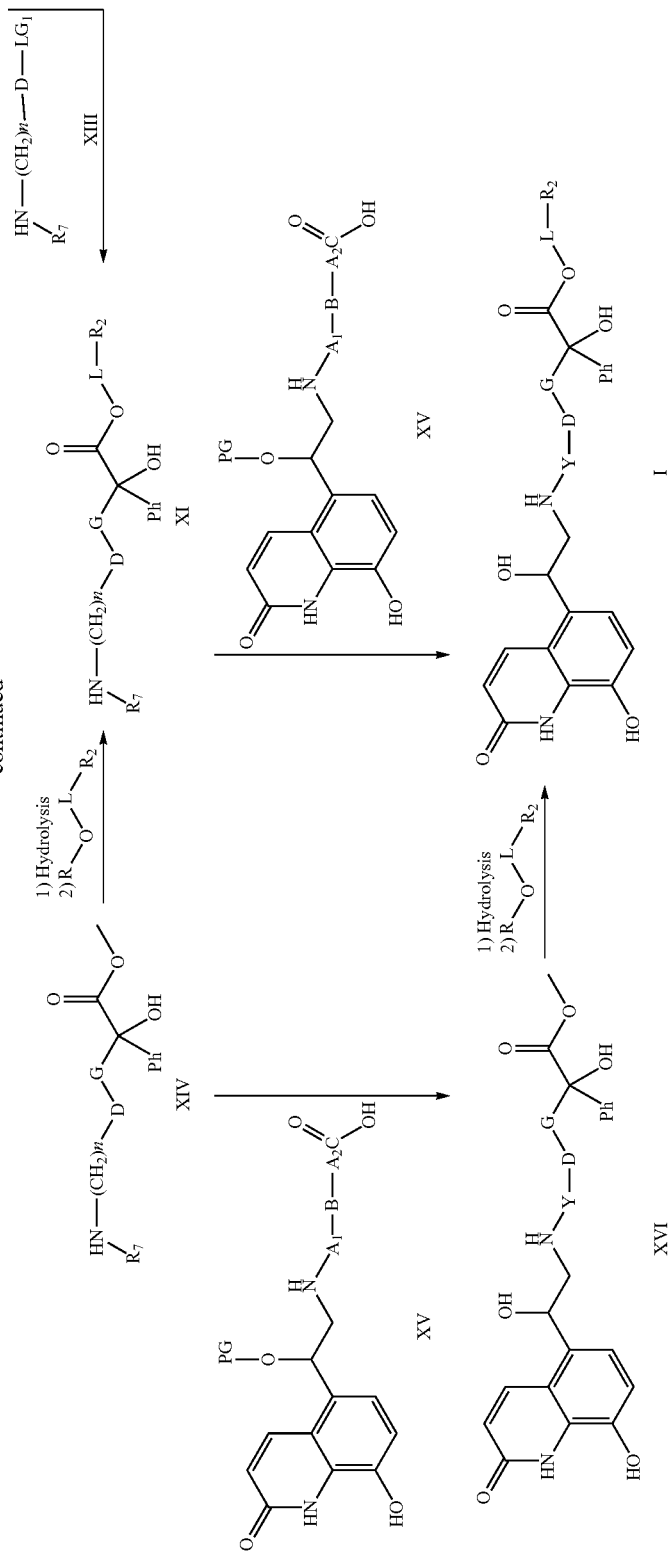

General Scheme 1B
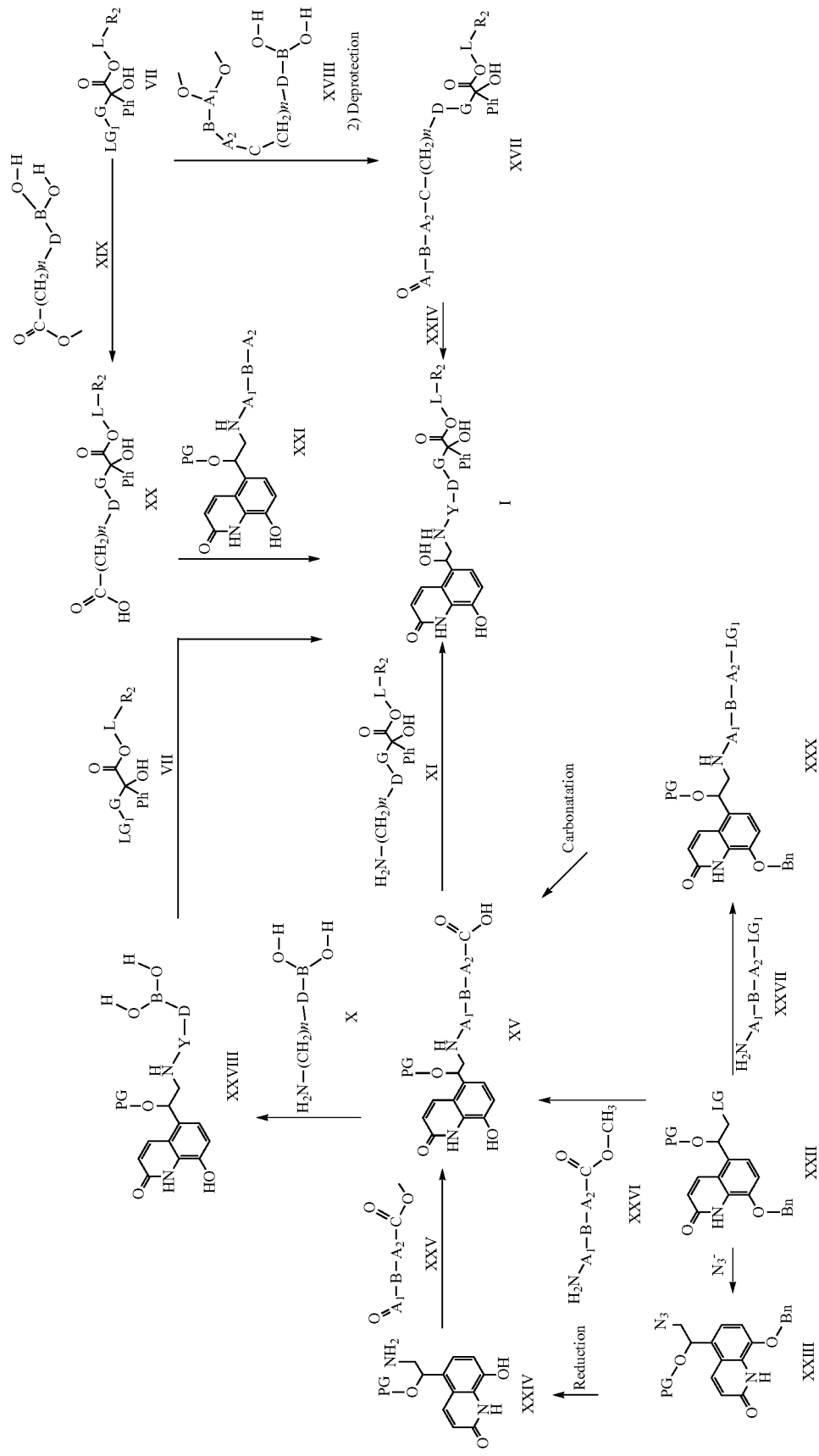

General Procedure for the Preparation of Compounds of Formula I

Compounds of formula I are compounds in which Y is a divalent group $-A_1-B-A_2-C-(CH_2)_n-$.

The synthesis of compounds of formula I may require the protection of potential reactive functionalities in addition to those methods herewith described. Examples of compatible protecting groups (PG) and their particular methods of protection and deprotection are described in "Protecting groups in organic Synthesis" by T. W. Green and P. Wutz (Wiley-Interscience publication, 1999), which is incorporated herein by reference in its entirety.

Compounds I can be prepared for example according to general Scheme 1B by reaction of a compound of general formula XVII with a compound of formula XXIV. This reductive amination reaction can be performed following several different protocols described in the literature. For example, it can be performed in solvents such as methanol, ethanol, tetrahydrofuran (THF) or dichloromethane (DCM) using a reducing agent such as $NaBH_4$, $NaCNBH_3$ or $NaB(AcO)_3H$. t could be useful to pre-form the imine before adding the reducing agent. The reaction proceeds smoothly at room temperature (RT) over 1 to 12 hours. The reaction can be done on XXIV wherein the protecting group PG is still present or already removed during its synthesis. In the first case, the reductive amination must be followed by an additional step for the removal of PG. Reaction conditions depend on the nature of PG.

The intermediate XVII can be easily prepared by reaction of a compound XVIII with a compound of formula VII under the well-known Suzuki cross-coupling reaction conditions. LG1 is a leaving group such as iodine, bromine, chlorine or triflate that reacts with a boronic acid or ester in the presence of a metal catalyst such as $Pd(PPh_3)_4$, $Pd(dppf)Cl_2$ or other Pd catalysts. The presence and the nature of organic phosphines is crucial to promote the reaction that occurs in solvents such as DMF, 1,4-dioxane or ACN at a temperature ranging from 80 to 120° C. The reaction completes in 1 to 12 hours. Compound XVIII represents a compound wherein $A_1$ is alkylene substituted with oxo, leading to an aldehyde or ketone, protected as acetal or cyclic acetal.

In few cases the reaction can be performed reacting compound VII and a compound XVIII wherein the group D is functionalized with a group like LG1. In this case, the cross-coupling reaction occurs in the presence of hypodiboric acid and a reactive catalytic system such as X-Phos-Pd-G2 and X-Phos. Both reaction described allow the formation of the C—C bond between generic group D and G.

A following step for the deprotection of the acetal on $A_1$ gives the compound of formula XVII.

A compound of formula VII can be used for the synthesis of a compound of formula XX by mean of a reaction with a compound of formula XIX under the same cross-coupling reaction conditions described above that, followed by the hydrolysis of the ester, lead to the compound of formula XX. Compound of formula XX can be reacted with a compound of formula XXI, wherein $A_2$ is absent and B is heterocycloalkyl-ene divalent group containing at least one nitrogen atom, under the known condensation conditions for the preparation of amides. The reaction occurs smoothly in an aprotic polar solvent such as DCM, THF or DMF at room or higher temperature in the presence of a condensing agent such as EDC, DCC, HATU. Alternatively the acid XX can be converted into the corresponding chloride (e.g. with $COCl_2$ in DMC) or imidazolide (with CDI in DCM or DMF) and then treated with XXI. A similar reaction can also be performed with a compound of formula XXI wherein the terminal $-A_1-B-A_2$ is functionalized with a pending amino group of formula $-NH-R_7$.

The presence of OH and NH moiety, for example in a compound of formula XXI, can affect the formation of the compound I as these functional groups can compete in the reaction of amide formation. For this reason, it is worth considering performing such described reaction, for the conversion of XX into I, using intermediate XXI in which the OH and NH are protected with suitable protecting group (PG). For the purpose silyl ethers for the OH and carbamates for the NH are well known protecting groups, whose selection should not be limited to them as it often depends on the complexity of the molecule and the presence of other functional groups in Y that can be not compatible with the reaction conditions required for introduction or removal of protecting groups. A similar consideration applies to the carbostiryl moiety that contains a phenolic OH. In this case, its reactivity can suggests protection to avoid any competitive reaction and formation of by-products. Benzyl is a suitable protecting group. The specific sequence of reaction for the preparation of I might be different from case to case, those skilled in the art will readily recognize the more appropriate sequence considering the structure of linker Y.

In another embodiment, the compound of the invention can be prepared reacting a compound of general formula XV with a compound of formula XI under the same reaction condition used for the amide formation described above, followed by deprotection of PG if required.

Compounds of formula XV can also be reacted under same reaction condition with a compound of formula X to generate a compound of formula XXVIII. This boronic acid, or alternatively an analogue boronic ester, like for example pinacolate, can be then reacted with a compound of formula VII to provide, in an alternative way, a compound of formula I under the same reaction condition described above for the Suzuki coupling of compound of formula XVIII with a compound of formula VII.

Reactions described above start from a compound of formula XVI that can be prepared in different ways. For example, it can be synthesized reacting a compound of formula XXIV with a compound of formula XXV under reductive amination conditions described for the reaction of compound XVII with a compound XXIV, followed by the hydrolysis of the ester. The latter well-known reaction can accomplished by using alkaline hydroxides in polar solvent, such as MeOH, EtOH or THF mixed with water in a suitable ratio. The reaction occurs at RT, but higher temperature can speed the reaction up that can complete in a time ranging from 30 minutes to overnight. Alternatively, compound of formula XV can be prepared reacting a compound of formula XXII, wherein LG is a leaving group such as chlorine or bromine, with a compound of formula XXVI under nucleophilic substitution (SN) condition. The reaction occurs in a polar solvent such as acetone, acetonitrile or DMF at a temperature ranging from 50 to 120° C. and can be accelerated by the presence of potassium iodide. The same reaction can be used to react a compound of formula XXII with a compound of formula XXVII wherein LG1 is a group such as iodine, bromine or triflate. The latter could be instable under the nucleophilic substitution reaction condition and for this reason the reaction can be performed using the phenol precursor of triflate that, after SN, can be easily obtained treating the phenol with trifluoromethanesulfonic anhydride or other triflating agent such as 2-[N,N-bis(trifluoromethanesulfonyl)amino]-5-chloropyridine, in polar solvent such as DCM or THF at low temperature in the presence of a base such as, but not limited to, DMAP or TEA. Compound XXX obtained can be then converted into compound XVI by mean of carbonatation. This reaction can be accomplished treating first compound XXX with an alkyl lithium in a polar solvent such as, but not limited to THF, at low temperature (typically −78° C.) and then with dry gaseous carbon dioxide. The same conversion can be accomplished using a palladium catalyzed reaction and phenyl formate. The most widely used catalytic system is formed by Palladium diacetate, an organic phosphine, such as but not limited to 4,5-bis(diphenylphosphino)-9,9-dimethylxanthene, and an organic base such as triethylamine. The reaction occurs in an aprotic solvent such as toluene or trifluoro-toluene at a temperature ranging from 80 to 120° C. and completes over a period of time ranging from 4 to 24 hours.

Compound of formula XXIV can be obtained by simple reduction of the azide XXIII. The reaction can be accomplished by mean of a catalytic hydrogenation in the presence Palladium catalyst. The reaction occurs, in polar solvent such as methanol or ethanol, under hydrogen atmosphere or under hydrogen transfer condition, using for example 1,4-cyclohexadiene or 1-methyl1,4-cyclohexadiene as source of hydrogen. The reaction proceeds at room temperature. In case it is performed under hydrogen transfer conditions higher temperature can be required. Alternatively, the conversion can be accomplished under Staudinger reaction conditions that does not cleave the benzyl group. The azide XXIII can be easily prepared from XXII by the well-known nucleophilic substitution of alkyl bromide with alkaline azide. The reaction proceeds at a temperature ranging from 50 to 80° C. and in a polar solvent such as DMF of NMP and can be accelerated by the presence of alkaline iodide.

In another embodiment the compounds of the invention can be prepared according to General Scheme 1A reacting a compound of formula XI with a compound of formula XV under the amide formation reaction condition described above for the reaction of a compound of formula XX with a compound of formula XXI.

The compounds of formula XI can be easily obtained from a compound of formula XIV that is first hydrolyzed to convert the ester into the corresponding carboxylic acid and then reacted with a compound of formula R—O-L-$R_2$. The structure of group R determines the reaction conditions. In case R is hydrogen, the reaction is the well-known condensation used for the preparation of esters. The reaction occurs smoothly in an aprotic polar solvent such as DCM, THF or DMF at room or higher temperature in the presence of a condensing agent such as EDC, DCC, HATU. Alternatively the acid XI can be converted into the corresponding chloride (e.g. with $COCl_2$ in DMC) or imidazolide (with CDI in DCM or DMF) and then treated with alcohol of formula HO-L-$R_2$. In case R is Tosyl or Mesyl the conversion of the carboxylic acid into XI is an alkylation of carboxylic acid and can be achieved in many different ways. For example, the group TosO in a compound of formula TosO-L-$R_2$ can be easily displaced reacting the two compounds in a polar solvent such as, but not limited to, ACN or DMF, for one or more hours at room or higher temperature in the presence of a base such as sodium, potassium or cesium carbonate.

In a slightly different approach, the same set of reactions can be used to convert a compound of formula XIV into compound of formula I. In this approach, compound of formula XIV is first reacted with a compound of formula XV to give compound XVI, then hydrolyzed and then reacted with a compound of formula R—O-L-$R_2$ as described above.

Compound of formula XI can be prepared reacting a compound of general formula VII with a compound of formula X under cross coupling reaction condition described for the reaction of compound VII with a compound XVIII. The same reaction can be used to prepare compounds of formula XIV reacting a compound of formula IX with a compound of formula X.

The compounds of formula VII can also be converted into a compound of formula XII by reaction with bispinacolate diboron in the presence of a palladium catalyst such as Pd(ddpf)2Cl2 and potassium acetate in polar solvent such as DMSO at 80-100° C. Compound XII can be then converted into a compound of formula XI, as described above, by mean of a cross coupling reaction. In few cases, it could be also possible react a compound VII with a compound XIII as described for the reaction of compound VII with compound XVIII wherein the group D is functionalized with a group like LG1 reactive under cross coupling reaction condition.

The compound of formula VII can be easily obtained from a compound of formula IX following the same approach used for the preparation of compound XI from compound XIV.

Compound of formula IX can be obtained using the addition of Grignard reagent (or other metal derivatives) to keto-containing compounds such as VIII or II. The selection of one of the two possible reactions depends on the availability of suitable Grignard's reagent or a precursor for its generation. The conversion of VIII to IX can be performed in a solvent such as $Et_2O$ or THF at a temperature below 0° C. The reaction is normally smooth and completes over a period ranging from one to overnight standing at room temperature. The same reaction conditions can be used for the reaction of II with LG1-G-MgBr to give IX, or with III to give IV. Compounds of formula IV can be obtained reacting compound V with Ph-MgBr under same conditions for Grignard addition.

Compounds of formula VII, wherein LG1 is triflate can be obtained from a compound of formula IV. The deprotection step includes the hydrogenation for the removal of the benzyl group protecting the phenol and then hydrolysis of the ester to give compound of formula VI. The obtained carboxylic acid VI can be first reacted with R—O-L-$R_2$, under ester formation reaction condition and then treated with a triflating agent, as described above for the preparation of compound of formula XXVII.

Compounds IV, VII and IX are all suitable intermediates for the preparation of single stereoisomers of compound of formula I. For example, the racemic mixtures or mixtures in any proportion of isomers of anyone of these three intermediates can be separated by mean of chiral chromatographic separation. In case, for example, R2 is enantiomerically pure J1, J2 or J5, a compound VII is a mixture of diastereoisomers that can be separated by mean of a normal chromatographic separation.

The absolute configuration of the stereogenic center present in VII is conserved unmodified within the synthetic pathway applied for the conversion of VII or IX into the final compound I.

Compounds of formula I wherein L is —$(CH_2)_s$—, s is 0 and $R_2$ is J1, J2 or J5 contain three stereogenic centers, as indicated below (wherein e.g. J=J2) with the symbol *. Therefore the structure of formula I is characterized by different stereoisomers.

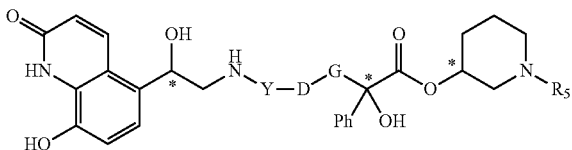

Each diastereoisomer can be obtained theoretically by chromatographic separation of the mixture obtained by reacting racemic mixtures of the required intermediates. It is clear that this approach it is not convenient and that it can be used only for the separation of mixtures containing few diastereoisomers.

In a more convenient approach, the synthesis of each single stereoisomer can be accomplished using, in the reactions described above, only enantiomerically pure intermediates.

The enantiomerically pure alcohol required for the preparation of compounds I wherein $R_2$ is J1, J2, J5 or J6 are commercially available.

The preparation of single enantiomerically pure compounds XXII wherein LG is bromine are described in WO 2005/092861, which is incorporated herein by reference in its entirety.

The present invention also provides pharmaceutical compositions of compounds of formula I in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds of the present invention are preferably administered by inhalation.

Inhalable preparations include inhalable powders, propellant-containing metering aerosols or propellant-free inhalable formulations.

For administration as a dry powder, known single- or multi-dose inhalers may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. corticosteroids, P38 MAP kinase inhibitors, IKK2, HNE inhibitors, PDE4 inhibitors, leukotriene modulators, NSAIDs, and mucus regulators.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula I can be administered for example, at a dosage of 0.001 to 1000 mg/day, preferably 0.1 to 500 mg/day.

When the compounds of formula I are administered by inhalation route, they are preferably given at a dosage of 0.001 to 500 mg/day, preferably 0.1 to 200 mg/day.

The compounds of formula I may be administered for the prevention and/or treatment of broncho-obstructive or inflammatory diseases, such as asthma, chronic bronchitis, chronic obstructive pulmonary disease (COPD), bronchial hyperreactivity, cough, emphysema or rhinitis; urological disorders such as urinary incontinence, pollakiuria, cystospasm, chronic cystitis and overactive bladder (OAB); gastrointestinal disorders such as bowel syndrome, spastic colitis, diverticulitis, peptic ulceration, gastrointestinal motility or gastric acid secretion; dry mouth; mydriasis, tachycardia; ophthalmic interventions cardiovascular disorders such as vagally induced sinus bradycardia.

Other features of the invention will become apparent in the course of the following descriptions of exemplary embodiments which are given for illustration of the invention and are not intended to be limiting thereof.

EXAMPLES

The intermediate compounds for the synthesis of final compounds of general formula (I) were obtained through the preparations herebelow described.

Preparation of Intermediates and Examples

All compounds were named with PerkinElmer Chem Draw Professional Version 15, where not differently specified.

Abbreviations
$Et_2O$=diethyl ether;
$Et_3N$=triethyl amine;
DCE=1,2-dichloroethane;
TEA=triethylamine;
DCC=N,N'-dicyclohexylcarbodiimide;
HOBt=hydroxybenzotriazole;
HATU=(dimethylamino)-N,N-dimethyl(3H-[1,2,3]triazolo[4,5-b]pyridin-3-yloxy)-methaniminium hexafluorophosphate;
EDC=1-ethyl-3-(3-dimethylaminopropyl) carbodiimide hydrochloride;
DMAP=4-dimethylaminopyridine;
DMF=dimethyl-formamide;
EtOAc=ethyl acetate;
RT=room temperature;
THF=tetrahydrofuran;
DCM=dichloromethane;
MeOH=methyl alcohol;
EtOH=ethylic alcohol;
LHMDS=lithium bis(trimethylsilyl)amide;
m-CPBA=meta-chloroperoxybenzoic acid;
TFA=trifluoroacetic acid;
LC-MS=liquid chromatography/mass spectrometry;
HPLC=high pressure liquid chromatography;
MPLC=medium pressure liquid chromatography;
SFC=supercritical fluid chromatography
General Experimental Details
Analytical Methods
Method 1
UPLC Setup
Solvents:—B Acetonitrile (Far UV grade) with 0.1% (V/V) formic acid
A Water (High purity via PureLab Option unit) with 0.1% formic acid
Column:—Acquity UPLC HSS C18 1.8 um 100×2.1 mm. (Plus guard cartridge)
Flow Rate:—0.5 ml/min
Gradient:

| Time (min) | % A | % B |
|---|---|---|
| 0.00 | 95 | 5 |
| 1.2 | 95 | 5 |
| 3.5 | 0 | 100 |
| 4.9 | 0 | 100 |
| 5 | 95 | 5 |
| 6 | 95 | 5 |

Injections 0.5-2 ul
UV detection via Waters DAD

| Start Range (nm) | 210 | End Range (nm) | 400 | Resolution (nm) | 1.2 |
|---|---|---|---|---|---|

MS detection: Waters SQD2, single quadrupole UPLC-MS
Scan range for MS Data (m/z)
Start (m/z)   100
End (m/z)   700 or 1500 when required
With +ve/−ve switching Ionisation is ESI.
ESI voltages and temperatures are:

| Source 150° C. | 3.5 KV capillary | 25 V cone |
|---|---|---|

Method 2
UPLC Setup

Solvents:- B Acetonitrile (Far UV grade)
A Water (High purity via PureLab Option unit) with 10 mM ammonium hydrogen carbonate
Column:- Acquity UPLC BEH Shield RP18 1.7 um 100 × 2.1 mm. (Plus guard cartridge)
Flow Rate:- 0.5 ml/min
Gradient:- A: Water/Basic B: MeCN/Basic

| Time | A % | B % |
|---|---|---|
| 0.00 | 95 | 5 |
| 1.20 | 95 | 5 |
| 3.5 | 0 | 100 |
| 4.90 | 0 | 100 |
| 5.00 | 95 | 5 |
| 6.00 | 95 | 5 |

Typical Injections 0.5-2 ul (concentration~0.2-1 mg/ml).
UV detection via Waters DAD

| Start Range (nm) | 210 | End Range (nm) | 400 | Resolution (nm) | 1.2 |
|---|---|---|---|---|---|

Other wavelength traces are extracted from the DAD data.

MS detection: Waters SQD2, single quadrupole UPLC-MS
Flow splitter gives approximately 300 ul/min to mass spec Scan range for MS Data (m/z)
Start (m/z)   100
End (m/z)   700 or 1500 when required With +ve/−ve switching Method 3:
UPLC Setup
Solvents:—B Acetonitrile/Water 95/5 with 0.05% (V/V) formic acid
A Water/Acetonitrile 95/5 with 0.05% formic acid
Column:—Acquity UPLC CSH C18 1.7 um 50×2.1 mm
Flow Rate:—1 mL/min
Gradient:

| Time (min) | % A | % B |
|---|---|---|
| 0.00 | 99 | 1 |
| 1.50 | 0.1 | 99.9 |
| 1.90 | 0.1 | 99.9 |
| 2.00 | 99 | 1 |

Injections 0.5-2 ul
LC-UV-MS instrument (Waters Aquity UPLC system) equipped with UV (PDA detector) and mass spectrometer (Aquity QDa Detector). UV acquisition range 210-400 nm. MS acquisition range 110-1200 amu.
MS instrument: Waters ZQ (or equivalent)
Polarity ES
Capillary (kV) 3.20
Cone (V) 25.00
Extractor (V) 3.00
RF Lens (V) 0.1
Polarity ES–
Capillary (kV) 3.40
Cone (V) 24.00
Extractor (V) 2.00
RF Lens (V) 0.2
Source Temperature (° C.) 130
Desolvation Temperature (° C.) 400
Cone Gas Flow (L/Hr) 80
Desolvation Gas Flow (L/Hr) 800
Mass range: 60 to 1200
Scan time (sec): 0.4
Method 4:
UPLC Setup
Solvents:—B Acetonitrile+0.1% formic acid
A Buffer Ammonium Formate 0.025M pH 3
Column:—Kinetex 1.7 u C8 100A 100×2.1 mm
Flow Rate:—0.5 mL/min
Gradient:

| Time (min) | % A | % B |
|---|---|---|
| 0.00 | 99 | 1 |
| 0.50 | 99 | 1 |
| 3 | 70 | 30 |
| 6.5 | 50 | 50 |
| 7.5 | 20 | 80 |
| 8 | 20 | 80 |
| 8.1 | 99 | 1 |
| 10 | 99 | 1 |

Injection volume (µl): 2
LC-UV-MS instrument (Waters Aquity UPLC system) equipped with UV (PDA detector) and mass spectrometer (Waters TQS Detector). UV acquisition range 210-400 nm. MS acquisition range 100-1000 amu ESI+ and ESI–.
Flow (ml/min) 0.5 mL/min
Stop time (mins) 10 min
Column Temperature 55° C.
UV acquisition range (nm): 254
Preparative reverse-phase HPLC conditions
Preparative HPLC
Waters Micromass ZQ/Sample manager 2767
Photodiode array detector 2996;
Column: XTerra Prep MS C18 Column (5 µm, 19×150 mm, Waters)
Flow rate: 20 ml/min with MS detection
UV wavelength: 254 nm.
Mobile phase: Solvent A (water:MeCN:HCOOH 95:5:0.05); Solvent B (water:MeCN:HCOOH 5:95:0.05)
Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

Where the preparation of starting materials is not described, these are commercially available, known in the literature, or readily obtainable by those skilled in the art using standard procedures.

Flash chromatography is carried out using an Isolera MPLC system (manufactured by Biotage) using pre-packed silica gel or reverse-phase cartridges (supplied by Biotage or Interchim).

NMR $^1$H-NMR spectra were performed on a Varian MR-400 spectrometer operating at 400 MHz (proton frequency), equipped with: a self-shielded z-gradient coil 5 mm 1H/nX broad band probehead for reverse detection, deuterium digital lock channel unit, quadrature digital detection unit with transmitter offset frequency shift.

Alternatively a Bruker instrument was used (either Bruker Avance 400 MHz or Bruker Avance III 400 MHz) operating at 400 MHz using the stated solvent at around room temperature unless stated otherwise, or on a Bruker AVANCE III HD 600 spectrometer operating at 600 MHz (proton frequency). The spectrometer is equipped with a 5 mm TCI INVERSE TRIPLE RESONACE CRYOPROBE H-C/N-D-0.5-Z ATMA. The probe is fitted with an actively shielded single axis Z-gradient and allows simultaneous decoupling on multiple X-nuclei such as $^{13}$C and $^{15}$N as well as automatic tuning and matching. Standard sample temperature range is comprised between 0° C. and 80° C.

In all cases, NMR data were consistent with the proposed structures. Chemical shift are reported as δ values in ppm relative to trimethyl silane (TMS) as an internal standard. Coupling constants (J values) if given are in hertz (Hz) and multiplicities are reported using the following abbreviation (s=singlet, d=doublet, t=triplet, q=quartet, m=multiplet, br=broad, nd=not determined).

Procedure A

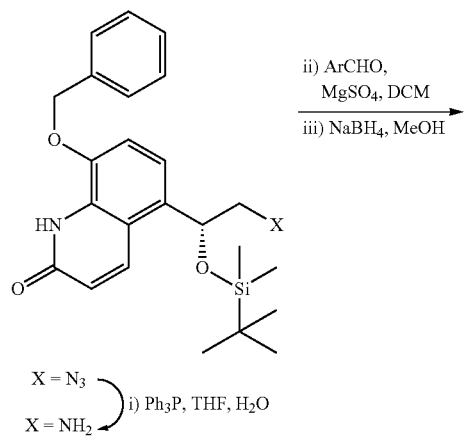

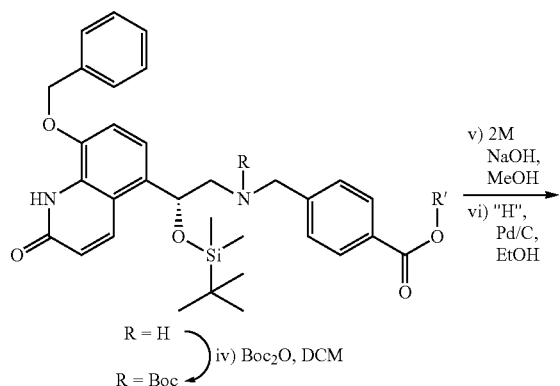

Preparation of (R)-4-(((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid

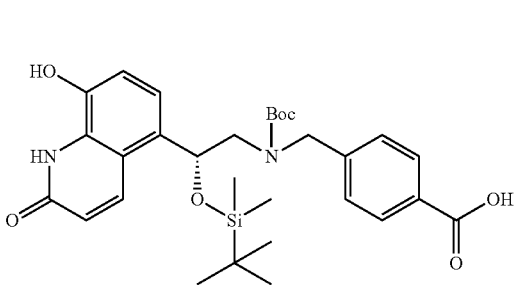

Step 1: (R)-5-(2-Amino-1-((tert-butyldimethylsilyl)oxy)ethyl)-8-(benzyloxy)quinolin-2(1H)-one

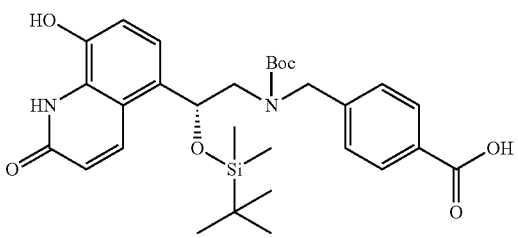

A solution of (R)-5-(2-azido-1-((tert-butyldimethylsilyl)oxy)ethyl)-8-(benzyloxy)quinolin-2(1H)-one (9.4 g, 21.0 mmol) in THF/water (80 mL/4 mL) was added with triphenylphosphine (6.03 g, 23.0 mmol). The reaction mixture was refluxed for 18 hours. The solvent was evaporated and residue was purified by flash column chromatography (eluent—100% DCM to 25:1 DCM/methanol) to afford the title compound (8.30 g, 93%).

$^1$H NMR (400 MHz, CDCl$_3$); δ 9.19-9.17 (m, 1H), 8.23 (d, J=9.9 Hz, 1H), 7.44-7.42 (m, 5H), 7.14 (d, J=8.3 Hz, 1H), 7.01 (d, J=8.2 Hz, 1H), 6.67 (d, J=9.9 Hz, 1H), 5.17 (s, 2H), 4.98 (dd, J=4.4, 7.2 Hz, 1H), 2.99-2.85 (m, 2H), 1.36-1.35 (m, 2H), 0.90 (s, 9H), 0.08 (s, 3H), −0.14 (s, 3H).

Step 2: (R)-Methyl 4-(((2-(8-(benzyloxy)-2-oxo-1,2-dihydroquinolin-5-yl)-2-((tert-butyldimethylsilyl)oxy)ethyl)amino)methyl)benzoate

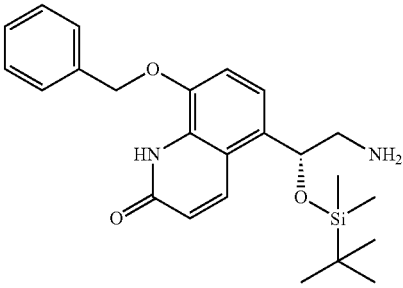 [SMILES: CC(C)(C)[Si](C)(C)O[C@@H](CN)c1ccc(OCc2ccccc2)c2[nH]c(=O)ccc12]

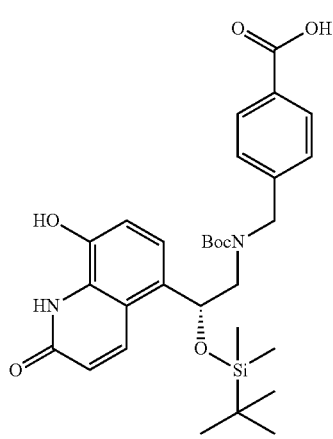

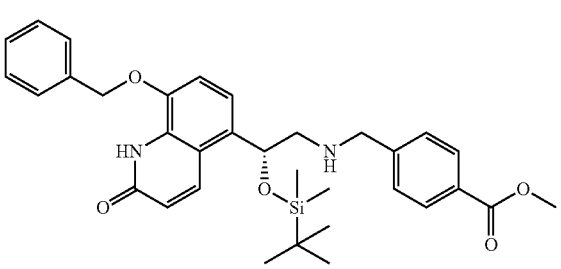 [SMILES: COC(=O)c1ccc(CNC[C@H](O[Si](C)(C)C(C)(C)C)c2ccc(OCc3ccccc3)c3[nH]c(=O)ccc23)cc1]

A stirred mixture of (R)-5-(2-amino-1-((tert-butyldimethylsilyl)oxy)ethyl)-8-(benzyloxy)quinolin-2(1H)-one (2.9 g, 6.83 mmol) and methyl 4-formylbenzoate (1.23 g, 7.49 mmol) in DCM (30 mL) was added with anhydrous magnesium sulfate and the mixture stirred at room temperature for 18 hours. The suspension was filtered through a plug of anhydrous magnesium sulfate, the filter cake was washed with further DCM and the filtrate was evaporated under reduced pressure. The residue was dissolved in methanol (30 mL) and the mixture cooled to 0° C. Sodium borohydride (0.517 g, 13.7 mmol) was added portion wise and the reaction mixture stirred at 0° C. for 30 minutes. The coolant was removed and the mixture stirred at room temperature for a further 2 hours. The mixture was quenched with 10% aqueous potassium carbonate and extracted with DCM (×2). The combined DCM extracts were washed with brine, dried over anhydrous magnesium sulfate and the filtrate was evaporated under reduced pressure. The residue was purified by flash column chromatography (eluent—100% DCM to 25:1 DCM/methanol) to afford the title compound (3.26 g, 83%).

$^1$H NMR (400 MHz, DMSO-$d_6$); δ 10.51 (s, 1H), 8.20 (d, J=9.9 Hz, 1H), 7.81 (d, J=8.3 Hz, 2H), 7.52 (d, J=7.2 Hz, 2H), 7.36-7.31 (m, 4H), 7.29-7.25 (m, 1H), 7.15 (d, J=8.3 Hz, 1H), 7.07 (d, J=8.4 Hz, 1H), 6.46 (d, J=9.9 Hz, 1H), 5.23 (s, 2H), 5.13 (dd, J=4.7, 7.2 Hz, 1H), 3.80-3.78 (m, 3H), 3.73 (s, 2H), 2.72 (dd, J=7.8, 12.0 Hz, 1H), 2.63-2.55 (m, 1H), 0.77 (s, 9H), 0.00 (s, 3H), −0.21 (s, 3H).

Step 3: (R)-Methyl 4-(((2-(8-(benzyloxy)-2-oxo-1,2-dihydroquinolin-5-yl)-2-((tert-butyldimethylsilyl)oxy)ethyl)(tert-butoxycarbonyl)amino)methyl)benzoate A stirred solution of (R)-methyl 4-(((2-(8-(benzyloxy)-2-oxo-1,2-dihydroquinolin-5-yl)-2-((tert-butyldimethylsilyl)oxy)ethyl)amino)methyl)benzoate (3.25 g, 5.67 mmol) in DCM (25 mL) was added with a solution of di-tert-butyl dicarbonate (1.49 g, 6.83 mmol) in DCM (5 mL). The reaction mixture was stirred at room temperature for 18 hours. The solvent was evaporated under reduced pressure and the residue purified by flash column chromatography (eluent—100% iso-hexane to 3:2 iso-hexane/ethyl acetate) to afford the title compound (2.84 g, 75%).

LCMS (Method 1); Rt 4.33 min; M+1 673.4

Step 4: (R)-4-(((2-(8-(Benzyloxy)-2-oxo-1,2-dihydroquinolin-5-yl)-2-((tert-butyldimethylsilyl)oxy)ethyl)(tert-butoxycarbonyl)amino)methyl)benzoic acid

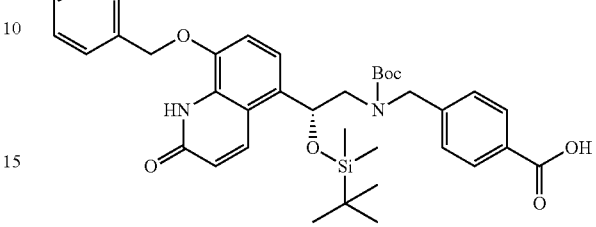

A stirred solution of (R)-methyl 4-(((2-(8-(benzyloxy)-2-oxo-1,2-dihydroquinolin-5-yl)-2-((tert-butyldimethylsilyl)oxy)ethyl)(tert-butoxycarbonyl)-amino)methyl)benzoate (2.84 g, 4.22 mmol) in methanol (10 mL) was added with aqueous 2M sodium hydroxide (10 mL). The reaction mixture was then stirred at room temperature for 18 hours. The solvent was evaporated under reduced pressure and the residue partitioned between DCM and 10% aqueous potassium hydrogen sulfate. The organic phase was removed and the aqueous phase extracted with further DCM. The combined DCM extracts were washed with brine, dried over anhydrous magnesium sulfate and the filtrate was evaporated under reduced pressure to afford the title compound (2.58 g, 93%).

LCMS (Method 1); Rt 4.05 min; M+1 659

Step 5: (R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)benzoic acid

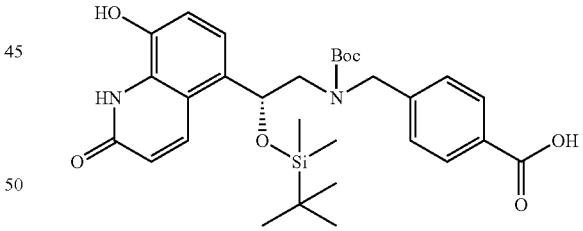

10% Palladium on carbon (2 g) was added to a stirred solution of (R)-4-(((2-(8-(benzyloxy)-2-oxo-1,2-dihydroquinolin-5-yl)-2-((tert-butyldimethylsilyl)oxy)ethyl)(tert-butoxycarbonyl)amino)methyl)benzoic acid (2.06 g, 3.12 mmol) in ethanol (25 mL) under an inert nitrogen atmosphere. 1-Methyl-1,4-cyclohexadiene (1.75 mL, 15.6 mmol) was added and the reaction mixture was carefully heated to reflux [Care—vigorous evolution of gas]. The reaction mixture was heated under reflux for 1 hour. The suspension was filtered, the filter cake washed with further ethanol and the filtrate was evaporated under reduced pressure to afford the title compound (1.66 g, 94%).

LCMS (Method 1); Rt 3.61 min; M+1 569.5.

Analogously prepared were:
| Structure | LCMS (Method 1 unless stated otherwise) | Starting material |
|---|---|---|
| 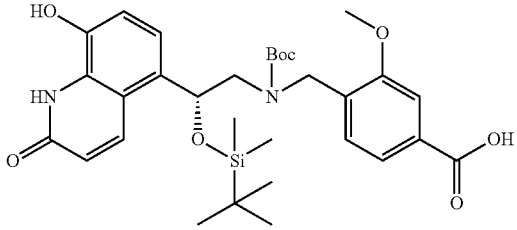 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] | Rt 3.75 min; ES+ 599.4 | methyl 4-formyl-3-methoxybenzoate |
| 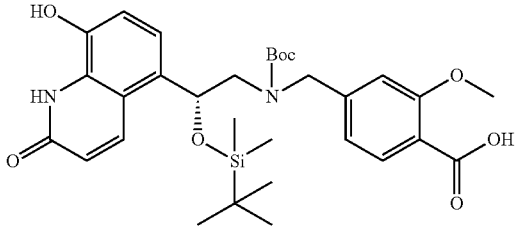 [SMILES: COc1cc(CN(C[C@H](O[Si](C)(C)C(C)(C)C)c2ccc(O)c3[nH]c(=O)ccc23)C(=O)OC(C)(C)C)ccc1C(=O)O] | Rt 3.61 min; ES+ 599.4 | methyl 4-formyl-2-methoxybenzoate |
| 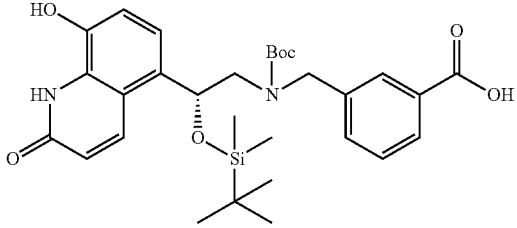 [SMILES: CC(C)(C)OC(=O)N(Cc1cccc(C(=O)O)c1)C[C@H](O[Si](C)(C)C(C)(C)C)c1ccc(O)c2[nH]c(=O)ccc12] | Rt 3.68 min; ES+ 569.4 | methyl 3-formylbenzoate |
| 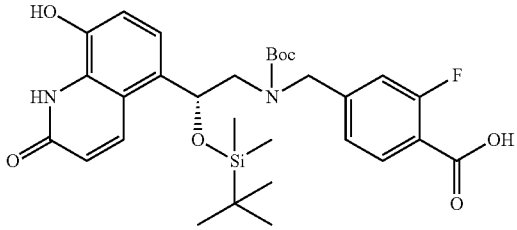 [SMILES: CC(C)(C)OC(=O)N(Cc1ccc(C(=O)O)c(F)c1)C[C@H](O[Si](C)(C)C(C)(C)C)c1ccc(O)c2[nH]c(=O)ccc12] | Rt 3.64 min; ES+ 587.3 | methyl 2-fluoro-4-formylbenzoate |
| 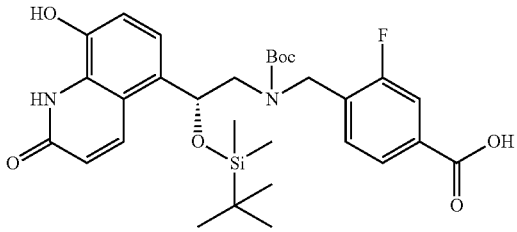 [SMILES: CC(C)(C)OC(=O)N(Cc1ccc(C(=O)O)cc1F)C[C@H](O[Si](C)(C)C(C)(C)C)c1ccc(O)c2[nH]c(=O)ccc12] | Rt 3.70 min; ES+ 587.4 | methyl 3-fluoro-4-formylbenzoate |
| 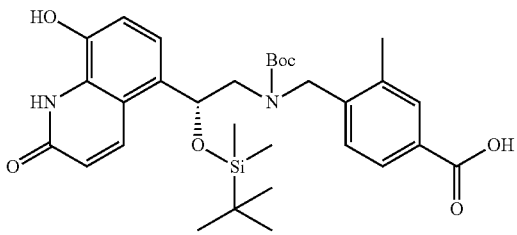 [SMILES: Cc1cc(C(=O)O)ccc1CN(C[C@H](O[Si](C)(C)C(C)(C)C)c1ccc(O)c2[nH]c(=O)ccc12)C(=O)OC(C)(C)C] | Rt 3.70 min; ES+ 587.4 | methyl 4-formyl-3-methylbenzoate |

| Structure | LCMS (Method 1 unless stated otherwise) | Starting material |
|---|---|---|
| (structure) | Rt 3.79 min; ES+ 637.3 | methyl 3-trifluoromethyl-4-formylbenzoate |
| (structure) | Rt 3.66 min; ES+ 605/607 | methyl 2,3-difluoro-4-formylbenzoate |
| (structure) | Rt 3.76 min; ES+ 613.7 | ethyl 3-ethoxy-4-formylbenzoate |
| (structure) | Rt 3.82 min; ES+ 627.6 | isopropoxy 3-isopropoxy-4-formylbenzoate |
| (structure) | Rt 2.83 min; ES+ 570.4 (Method 2) | methyl 6-formylnicotinate |
| (structure) | Rt 3.66 min; ES+ 617.6 | methyl 2-fluoro-4-formyl-5-methoxybenzoate |

| Structure | LCMS (Method 1 unless stated otherwise) | Starting material |
|---|---|---|
| [structure] | Rt 2.93 min; ES+ 583.4 | methyl 2-(4-formylphenyl)acetate |
| [structure] | Rt 3.69 min; ES+ 583 | methyl 4-formyl-3-methylbenzoate |
| [structure] | Rt 3.60 min; ES+ 575 | methyl 5-formylthiophene-2-carboxylate |
| [structure] | Rt 3.66 min; ES− 603 | methyl 2,3-difluoro-4-formylbenzoate |

Representative synthesis of the required substituted formylbenzoate esters are highlighted below.

Synthesis of methyl 3-trifluoromethyl-4-formylbenzoate

A solution of 4-methyl-3-trifluoromethylbenzoic acid (1.71 g, 8.37 mmol) in DMF (20 mL) was added with potassium carbonate (1.39 g, 10.1 mmol) and the reaction mixture was stirred at room temperature for five minutes. Iodomethane (0.78 mL, 12.5 mmol) was added and the reaction mixture stirred at room temperature for 18 hours. The reaction mixture was diluted with ethyl acetate and washed with water and brine (×2). The organic phase was dried over anhydrous magnesium sulfate, filtered and the filtrate evaporated at reduced pressure to afford methyl 4-methyl-3-trifluoromethylbenzoate. The material was dissolved in carbon tetrachloride (10 mL) and treated sequentially with N-bromosuccinimide (2.74 g, 15.4 mmol) and benzoyl peroxide (catalytic) and heated at 80° C. for 18 hours. The mixture was allowed to cool and diluted with water. The mixture was poured through a hydrophobic frit and the solvent evaporated at reduced pressure to afford methyl 4-(dibromomethyl)-3-trifluoromethylbenzoate. The material was dissolved in acetone/water (25 mL/5 mL) and silver nitrate (2.38 g, 14.0 mmol) added.

The reaction mixture was stirred at room temperature for 72 hours. The suspension was filtered through a pad of celite and the filtrate diluted with ethyl acetate. The solution was washed with water and brine. The organic phase was dried over anhydrous magnesium sulfate, filtered and evaporated. The residue was dissolved acetone/water (25 mL/5 mL) and silver nitrate (2.38 g, 14.0 mmol) added.

The reaction mixture was stirred at room temperature for 24 hours. The suspension was filtered through a pad of celite and the filtrate diluted with ethyl acetate. The solution was washed with water and brine. The organic phase was dried over anhydrous magnesium sulfate, filtered and evaporated. The residue was purified by flash column chromatography (eluent—100% i-hexane to 8:1 i-hexane/ethyl acetate) to afford the title compound (0.537 g, 33%).

$^1$H NMR (400 MHz, CDCl$_3$); δ 10.46-10.45 (m, 1H), 8.46 (s, 1H), 8.35 (d, J=8.2 Hz, 1H), 8.20 (d, J=8.2 Hz, 1H), 4.00 (s, 3H).

Synthesis of ethyl 3-ethoxy-4-formylbenzoate

A solution of 4-formyl-3-hydroxybenzoic acid (1.0 g, 6.02 mmol) in DMF (20 mL) was added with potassium carbonate (2.49 g, 18.1 mmol) and ethyl iodide (2.82 g, 18.1 mmol). The reaction mixture was stirred at room temperature for 72 hours. The reaction mixture was concentrated at reduced pressure and the residue partitioned between ethyl acetate and water. The organic extract was washed with brine (×2), poured through a hydrophobic frit and the solvent evaporated at reduced pressure. The residue was purified by flash column chromatography (eluent—100% i-hexane to 4:1 i-hexane/ethyl acetate) to afford the title compound (1.41 g, 100%).

$^1$H NMR (400 MHz, CDCl$_3$); δ 10.55 (s, 1H), 7.87 (d, J=8.3 Hz, 1H), 7.66 (d, J=8.3 Hz, 2H), 4.40 (q, J=7.2 Hz, 2H), 4.23 (q, J=7.0 Hz, 2H), 1.51 (dd, J=6.9, 6.9 Hz, 3H), 1.41 (dd, J=7.1, 7.1 Hz, 3H).

Synthesis of methyl 2-fluoro-4-formyl-5-methoxybenzoate

A solution of methyl 2-fluoro-5-methoxy-4-methylbenzoate (0.576 g, 2.91 mmol) in carbon tetrachloride (20 mL) was added with N-bromosuccinimide (0.57 g, 3.2 mmol) and benzoyl peroxide (cat). The reaction mixture was heated at 70° C. for 6 hours and then allowed to cool. The suspension was filtered and the filtrate evaporated at reduced pressure. The residue was dissolved in DCM and washed with water, 1M aqueous sodium thiosulfate and the organic phase passed through a hydrophobic frit. The filtrate was concentrated at reduced pressure and the residue purified by flash column chromatography (eluent—100% i-hexane to 4:1 i-hexane/ethyl acetate) to afford methyl 4-(bromomethyl)-2-fluoro-5-methoxybenzoate (0.591 g, 2.13 mmol). This material was dissolved in acetonitrile (20 mL) and treated with pyridine N-oxide (0.203 g, 2.13 mmol) and silver (I) oxide (0.247 g, 1.07 mmol) and the mixture stirred at room temperature for 18 hours. The suspension was filtered through a pad of celite and the filter pad washed with further acetonitrile. The filtrate was evaporated and the residue dissolved in DCM. The DCM solution was washed with water and then passed through a hydrophobic frit and the solvent was evaporated. The residue purified by flash column chromatography (eluent—100% i-hexane to 4:1 i-hexane/ethyl acetate) to afford the title compound (0.230 g, 37%).

$^1$H NMR (400 MHz, CDCl$_3$); δ 10.45-10.44 (m, 1H), 7.39-7.52 (m, 2H), 3.98 (s, 3H), 3.97 (s, 3H).

Procedure B

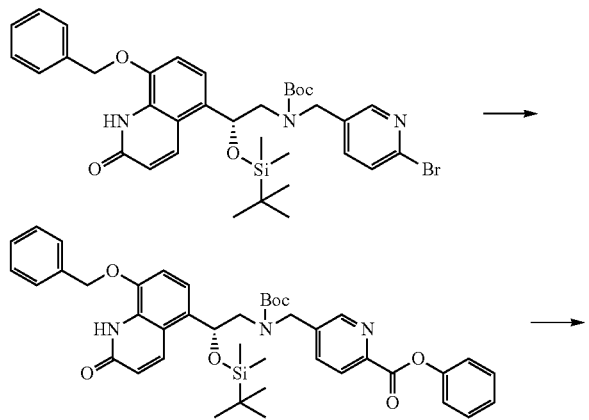

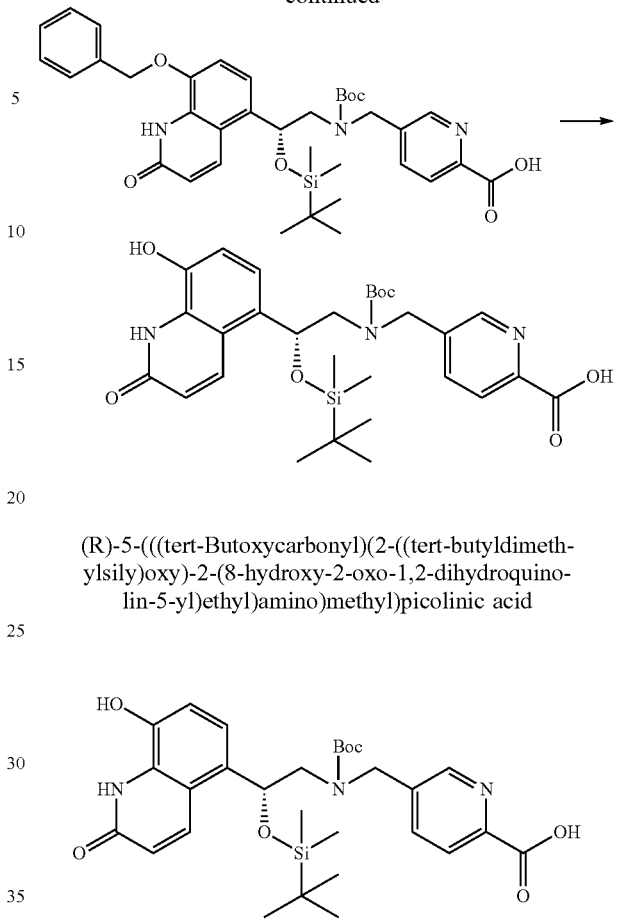

(R)-5-((((tert-Butoxycarbonyl)(2-((tert-butyldimethylsily)oxy)-2-(8-hydroxy-2-oxo-1,2-dihydroquinolin-5-yl)ethyl)amino)methyl)picolinic acid A solution of tert-butyl (R)-(2-(8-(benzyloxy)-2-oxo-1,2-dihydroquinolin-5-yl)-2-((tert-butyldimethylsilyl)oxy) ethyl)((6-bromopyridin-3-yl)methyl)carbamate (prepared as described in Procedure A using 2-bromo-5-formylpyridine in Step 2) (1.47 g, 2.12 mmol) in toluene (50 mL) was added with phenyl formate (1.03 g, 8.47 mmol), 4,5-bis(diphenylphosphino)-9,9-dimethylxanthene (0.294 g, 0.24 mmol), triethylamine (0.59 mL, 4.24 mmol) and the mixture was de-gassed for 15 minutes with nitrogen. Palladium acetate (0.057 g, 0.25 mmol) was added and the mixture was heated at 80° C. for 18 hours. Further phenyl formate (1.03 g, 8.47 mmol), 4,5-bis(diphenylphosphino)-9,9-dimethylxanthene (0.294 g, 0.24 mmol), triethylamine (0.59 mL, 4.24 mmol) and palladium acetate (0.057 g, 0.25 mmol) was added and the reaction heated at 80° C. for a further 24 hours. The reaction mixture was evaporated at reduced pressure to about ⅓ of the initial volume and then diluted with ethyl acetate. The organic phase was washed with water, brine, dried over anhydrous magnesium sulfate, filtered and the filtrate evaporated at reduced pressure. The residue was purified by flash column chromatography (eluent—100% iso-hexane to 100% ethyl acetate) to afford the major component. This material was dissolved in methanol (20 mL) and 2M aqueous sodium hydroxide added (2 mL) added. The reaction mixture was stirred at room temperature for 18 hours. The reaction mixture was concentrated and water added. The aqueous was washed with ether and then the aqueous pH adjusted to 5. The aqueous was extracted with DCM (×3), the combined DCM extracts were passed through a hydrophobic frit and evaporated at reduced pressure. The residue was dissolved in ethanol (30 mL) and 10% Pd-C(0.064 g) added followed by 1-methyl-1,4-cyclohexadiene (0.282 g, 3.00 mmol). The reaction mixture was heated to reflux and refluxed for three hours. The reaction mixture was filtered and the filtrate evaporated at reduced pressure to afford the title compound (0.314 g, 26%).

LCMS Method 1; Rt 3.37 min; ES+ 570.6

Analogously prepared were:

| Structure | LCMS (Method 1 unless stated otherwise) | Starting material |
|---|---|---|
| 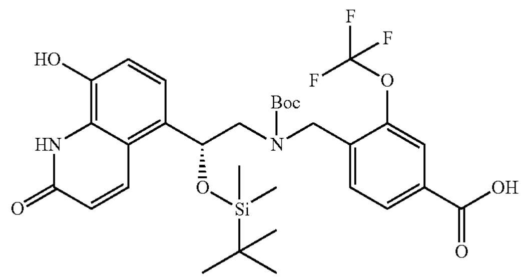 [SMILES: CC(C)(C)OC(=O)N(Cc1ccc(C(=O)O)cc1OC(F)(F)F)C[C@H](O[Si](C)(C)C(C)(C)C)c1ccc(O)c2[nH]c(=O)ccc12] | Rt 3.02 min; ES+ 635.2 method 2 | methyl 4-formyl-3-methoxybenzoate |
| 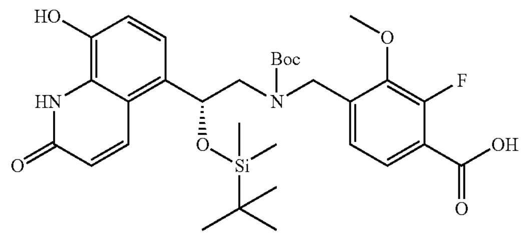 [SMILES: COc1c(CN(C[C@H](O[Si](C)(C)C(C)(C)C)c2ccc(O)c3[nH]c(=O)ccc23)C(=O)OC(C)(C)C)ccc(C(=O)O)c1F] | Rt 2.93 min; ES+ 617.4 | 4-bromo-3-fluoro-2-methoxybenzaldehyde |
| 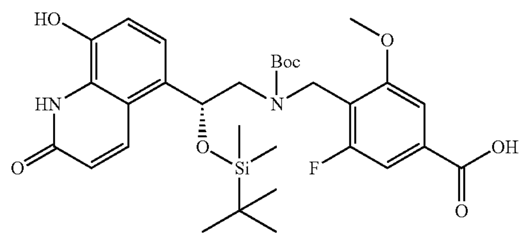 [SMILES: COc1cc(C(=O)O)cc(F)c1CN(C[C@H](O[Si](C)(C)C(C)(C)C)c1ccc(O)c2[nH]c(=O)ccc12)C(=O)OC(C)(C)C] | Rt 3.75 min; ES+ 617.4 | 4-bromo-2-fluoro-6-methoxybenzaldehyde |
| 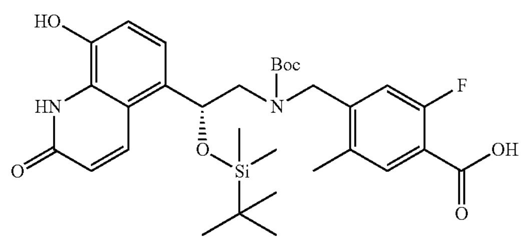 [SMILES: Cc1cc(C(=O)O)c(F)cc1CN(C[C@H](O[Si](C)(C)C(C)(C)C)c1ccc(O)c2[nH]c(=O)ccc12)C(=O)OC(C)(C)C] | Rt 3.65 min; ES+ 601.6 | 4-bromo-5-fluoro-2-methylbenzaldehyde |
| 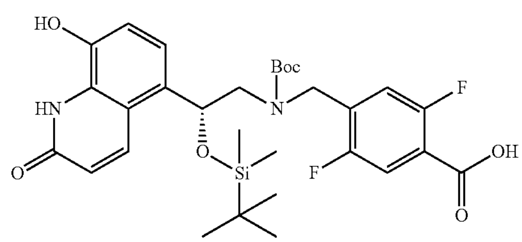 [SMILES: CC(C)(C)OC(=O)N(Cc1cc(F)c(C(=O)O)cc1F)C[C@H](O[Si](C)(C)C(C)(C)C)c1ccc(O)c2[nH]c(=O)ccc12] | Rt 3.69 min; ES+ 605.6 | 4-bromo-2,5-difluorobenzaldehyde |
| 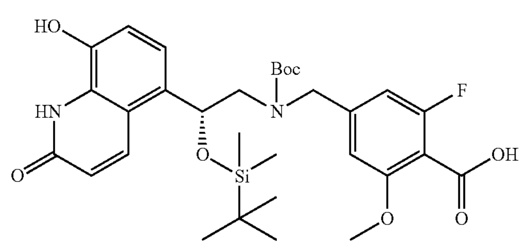 [SMILES: COc1cc(CN(C[C@H](O[Si](C)(C)C(C)(C)C)c2ccc(O)c3[nH]c(=O)ccc23)C(=O)OC(C)(C)C)cc(F)c1C(=O)O] | Rt 3.59 min; ES+ 617.6 | 4-bromo-3-fluoro-5-methoxybenzaldehyde |

| Structure | LCMS (Method 1 unless stated otherwise) | Starting material |
|---|---|---|
| 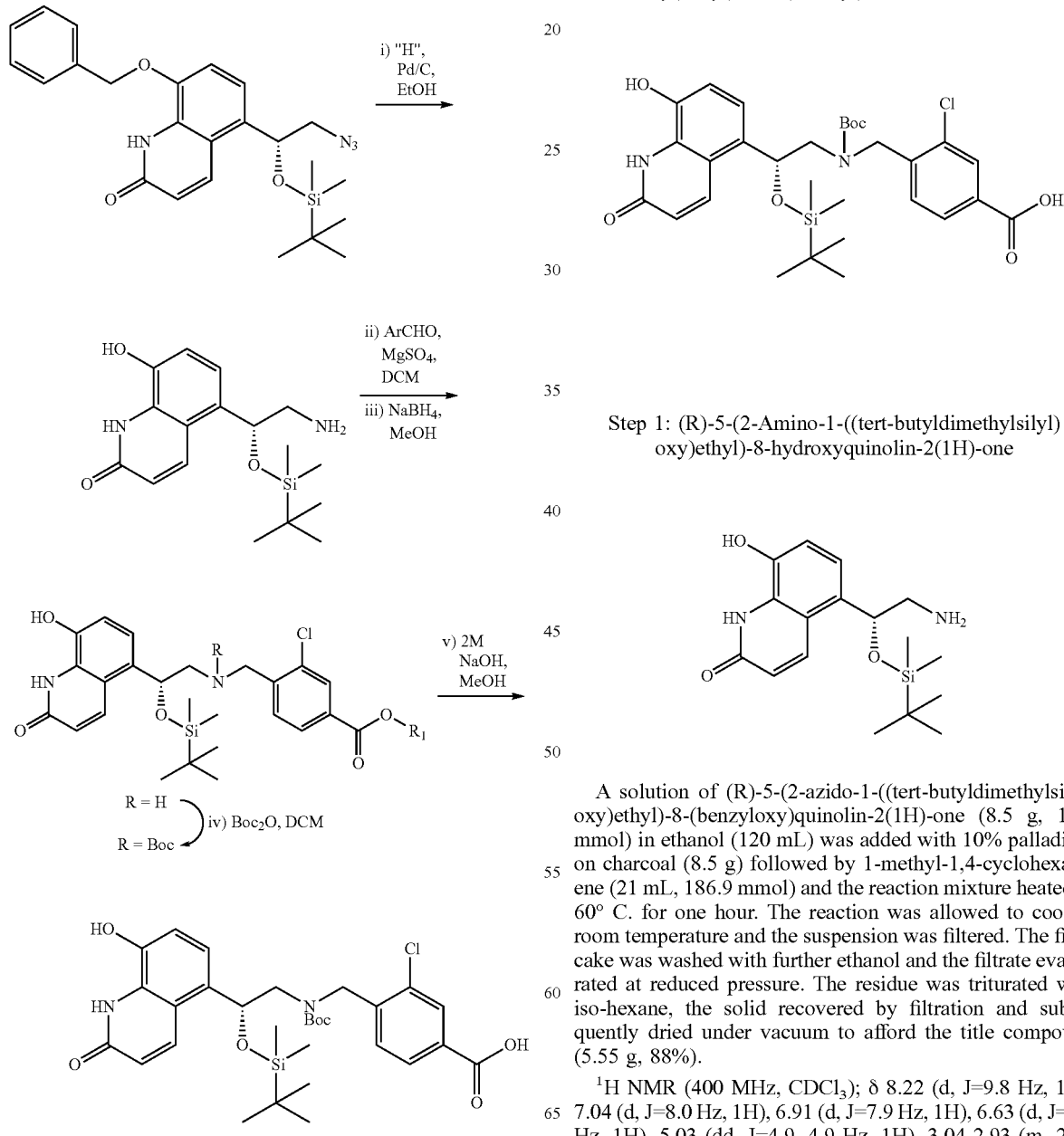 | Rt 3.58 min; ES+ 594.3 | 4-bromo-3-cyanobenzaldehyde |

Procedure C (R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-chlorobenzoic acid Step 1: (R)-5-(2-Amino-1-((tert-butyldimethylsilyl)oxy)ethyl)-8-hydroxyquinolin-2(1H)-one A solution of (R)-5-(2-azido-1-((tert-butyldimethylsilyl)oxy)ethyl)-8-(benzyloxy)quinolin-2(1H)-one (8.5 g, 18.9 mmol) in ethanol (120 mL) was added with 10% palladium on charcoal (8.5 g) followed by 1-methyl-1,4-cyclohexadiene (21 mL, 186.9 mmol) and the reaction mixture heated to 60° C. for one hour. The reaction was allowed to cool to room temperature and the suspension was filtered. The filter cake was washed with further ethanol and the filtrate evaporated at reduced pressure. The residue was triturated with iso-hexane, the solid recovered by filtration and subsequently dried under vacuum to afford the title compound (5.55 g, 88%).

$^1$H NMR (400 MHz, CDCl$_3$); δ 8.22 (d, J=9.8 Hz, 1H), 7.04 (d, J=8.0 Hz, 1H), 6.91 (d, J=7.9 Hz, 1H), 6.63 (d, J=9.3 Hz, 1H), 5.03 (dd, J=4.9, 4.9 Hz, 1H), 3.04-2.93 (m, 2H), 0.92-0.85 (m, 9H), 0.20 (s, 3H), −0.18 (s, 3H).

Step 2: (R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-chlorobenzoic acid

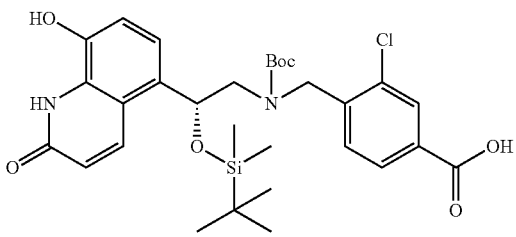

The title compound was prepared as in Procedure A using Steps 2, 3 and 4 using methyl 3-chloro-4-formyl benzoate in Step 2.

LCMS Method 1; Rt 3.76; ES+ 603.3/605.4.
Analogously prepared were:

Synthesis of phenyl 2-chloro-4-formyl-5-methoxybenzoate

A stirred solution of 4-bromo-2-methoxybenzaldehyde (1.0 g, 4.56 g) in acetonitrile (15 mL) was added with N-chlorosuccinimide (0.731 g, 5.48 mmol) and the reaction mixture was heated at 80° C. for 18 hours. The reaction mixture was diluted with ethyl acetate and washed with water and brine (×2). The organic phase was dried over anhydrous magnesium sulfate, filtered and the solvent evaporated at reduced pressure. The residue was dissolved in toluene (20 mL) and phenyl formate (2 mL, 18.3 mmol), 4,5-bis(diphenylphosphino)-9,9-dimethylxanthene (0.642 g, 1.11 mmol), triethylamine (1.27 mL, 9.13 mmol) was added and the mixture was de-gassed for 15 minutes with nitrogen. Palladium acetate (0.122 g, 0.54 mmol) was added and the mixture was heated at 80° C. for 18 hours. The reaction mixture was evaporated at reduced pressure to about ⅓ of the initial volume and then diluted with ethyl acetate. The organic phase was washed with water, brine, dried over anhydrous magnesium sulfate, filtered and the filtrate evaporated at reduced pressure. The residue was purified by flash column chromatography (eluent—100% iso-hexane to 100% ethyl acetate) to afford the title compound (0.554 g, 42%).

$^1$H NMR (400 MHz, CDCl$_3$) δ 10.47 (s, 1H), 7.93 (s, 1H), 7.58 (s, 1H), 7.46-7.31 (m, 5H), 4.02 (s, 3H).

| Structure | LCMS (Method 1 unless stated otherwise) | Starting material |
|---|---|---|
| 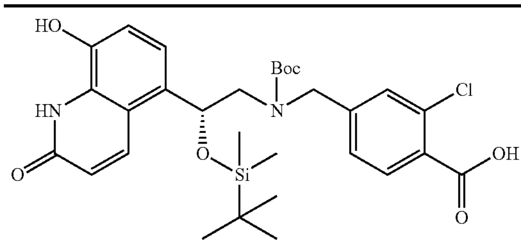 | Rt 3.70; ES+ 603.3/605.4 | methyl 2-chloro-4-formylbenzoate |
| 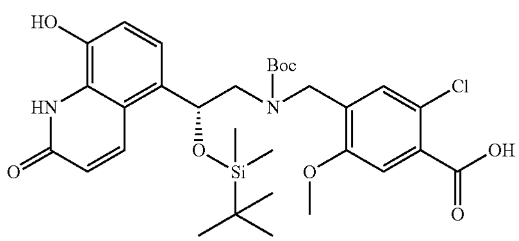 [SMILES: COc1cc(C(=O)O)c(Cl)cc1CN(C[C@H](O[Si](C)(C)C(C)(C)C)c1ccc(O)c2[nH]c(=O)ccc12)C(=O)OC(C)(C)C] | Rt 3.88; ES+ 633.5/635.6 | phenyl 2-chloro-4-formyl-5-methoxybenzoate |
| 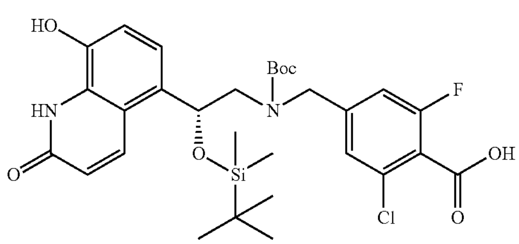 [SMILES: CC(C)(C)OC(=O)N(Cc1cc(F)c(C(=O)O)c(Cl)c1)C[C@H](O[Si](C)(C)C(C)(C)C)c1ccc(O)c2[nH]c(=O)ccc12] | Rt 3.70 min; ES+ 621.4 | 4-bromo-3-fluoro-5-chlorobenzaldehyde |

Procedure D

Preparation of (R)-4-(2-((tert-butoxycarbonyl)(2-((tert-butyldimethylsilyl)oxy)-2-(8-hydroxy-2-oxo-1,2-dihydroquinolin-5-yl)ethyl)amino)ethyl)benzoic acid

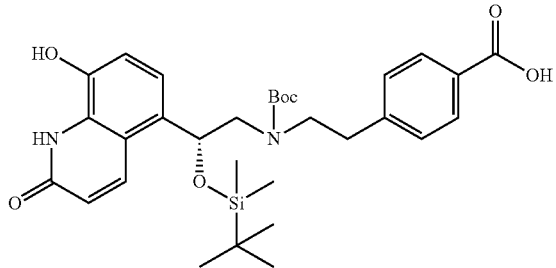 [SMILES: CC(C)(C)OC(=O)N(CCc1ccc(C(=O)O)cc1)C[C@H](O[Si](C)(C)C(C)(C)C)c1ccc(O)c2[nH]c(=O)ccc12]

Step 1: (R)-8-(Benzyloxy)-5-(1-((tert-butyldimethylsilyl)oxy)-2-((4-hydroxyphenethyl)amino)ethyl)quinolin-2(1H)-one

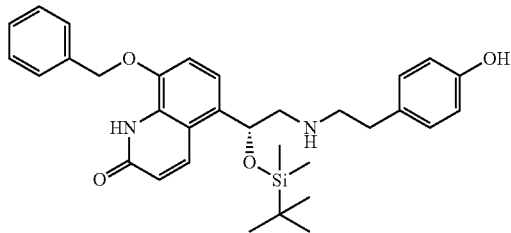 [SMILES: CC(C)(C)[Si](C)(C)O[C@@H](CNCCc1ccc(O)cc1)c1ccc(OCc2ccccc2)c2[nH]c(=O)ccc12]

A mixture of (R)-8-(benzyloxy)-5-(2-bromo-1-((tert-butyldimethylsilyl)oxy)ethyl)quinolin-2(1H)-one (1.0 g, 2.05 mmol) in NMP (2 mL) was added with tyramine (1.41 g, 10.2 mmol). The mixture was heated at 80° C. for 18 hours. The mixture was diluted with ethyl acetate and washed sequentially with 10% aqueous potassium hydrogen sulfate and brine (×2). The organic phase was dried over anhydrous magnesium sulfate and the filtrate was evaporated under reduced pressure to afford the title compound (2.58 g, 93%).

¹H NMR (400 MHz, CDCl₃); δ 9.30-9.30 (m, 1H), 8.27 (d, J=9.9 Hz, 1H), 7.46-7.38 (m, 6H), 7.08 (d, J=8.3 Hz, 1H), 6.97 (dd, J=4.8, 8.4 Hz, 3H), 6.71 (d, J=8.5 Hz, 2H), 6.65 (d, J=9.9 Hz, 1H), 5.16 (s, 2H), 5.14-5.07 (m, 1H), 2.97-2.82 (m, 3H), 2.78-2.68 (m, 3H), 1.65 (br s, 1H), 0.82 (s, 9H), 0.00 (s, 3H), −0.22 (s, 3H).

Step 2: (R)-tert-Butyl (2-(8-(benzyloxy)-2-oxo-1,2-dihydroquinolin-5-yl)-2-((tert-butyldimethylsilyl)oxy)ethyl)(4-hydroxyphenethyl)carbamate

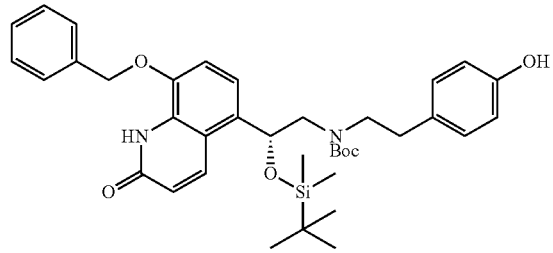 [SMILES: CC(C)(C)OC(=O)N(CCc1ccc(O)cc1)C[C@H](O[Si](C)(C)C(C)(C)C)c1ccc(OCc2ccccc2)c2[nH]c(=O)ccc12]

A stirred solution of (R)-8-(benzyloxy)-5-(1-((tert-butyldimethylsilyl)oxy)-2-((4-hydroxyphenethyl)amino)ethyl)quinolin-2(1H)-one (6.0 g, 11.02 mmol) in DCM (75 mL) was added with a solution of di-tert-butyldicarbonate (2.18 g, 16.5 mmol) in DCM (15 mL). The reaction mixture was stirred at room temperature for 2 hours. The solvent was evaporated under reduced pressure and the residue purified by flash column chromatography (eluent—100% iso-hexane to 3:2 iso-hexane/ethyl acetate) to afford the title compound (6.30 g, 89%).

¹H NMR (400 MHz, DMSO-d₆, 100° C.); δ 9.94-9.92 (m, 1H), 8.74 (s, 1H), 8.29 (d, J=9.9 Hz, 1H), 7.56 (d, J=7.2 Hz, 2H), 7.44-7.35 (m, 3H), 7.24 (d, J=8.3 Hz, 1H), 7.14 (d, J=8.4 Hz, 1H), 6.92 (d, J=8.4 Hz, 2H), 6.70-6.67 (m, 2H), 6.56 (d, J=9.9 Hz, 1H), 5.31 (s, 3H), 3.37-3.23 (m, 4H), 2.66-2.55 (m, 2H), 1.39 (s, 9H), 0.86 (s, 9H), 0.04 (s, 3H), −0.13 (s, 3H).

Step 3: (R)-4-(2-((2-(8-(Benzyloxy)-2-oxo-1,2-dihydroquinolin-5-yl)-2-((tert-butyldimethylsilyl)oxy)ethyl)(tert-butoxycarbonyl)amino)ethyl)phenyl trifluoromethanesulfonate

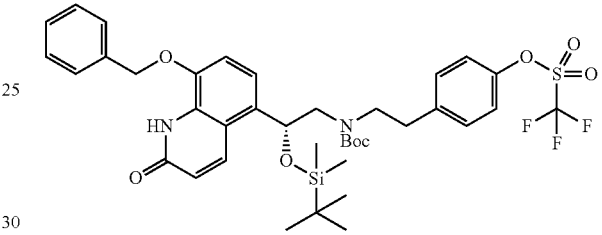

A cooled solution of (R)-tert-butyl (2-(8-(benzyloxy)-2-oxo-1,2-dihydroquinolin-5-yl)-2-((tert-butyldimethylsilyl)oxy)ethyl)(4-hydroxyphenethyl)carbamate (6.3 g, 9.78 mmol) in DCM (100 mL) at 0° C. was added with triethylamine (2.72 mL, 19.56 mmol) followed by 2-[N,N-bis(trifluoromethanesulfonyl)amino]-5-chloropyridine (4.21 g, 10.76 mmol) and the mixture was stirred at 0° C. for 2 hours. The coolant was removed and 2M aqueous sodium hydroxide (25 mL) was added to the reaction mixture, and the mixture was stirred for 15 minutes. The organic phase was separated, dried over anhydrous magnesium sulfate, filtered and the filtrate evaporated under reduced pressure to afford the title compound (7.3 g, 96%).

¹H NMR (400 MHz, DMSO-d₆, 100° C.); δ 8.74 (s, 1H), 8.29 (d, J=9.9 Hz, 1H), 7.56 (d, J=7.2 Hz, 2H), 7.44-7.35 (m, 3H), 7.24 (d, J=8.3 Hz, 1H), 7.14 (d, J=8.4 Hz, 1H), 6.92 (d, J=8.4 Hz, 2H), 6.70-6.67 (m, 2H), 6.56 (d, J=9.9 Hz, 1H), 5.31 (s, 3H), 2.96 (s, 4H), 2.66-2.55 (m, 2H), 1.39 (s, 9H), 0.86 (s, 9H), 0.04 (s, 3H), −0.13 (s, 3H).

Step 4: (R)-Phenyl 4-(2-((2-(8-(benzyloxy)-2-oxo-1,2-dihydroquinolin-5-yl)-2-((tert-butyldimethylsilyl)oxy)ethyl)(tert-butoxycarbonyl)amino)ethyl)benzoate

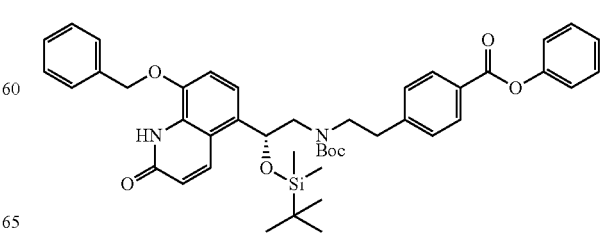

A solution of (R)-4-(2-((2-(8-(benzyloxy)-2-oxo-1,2-dihydroquinolin-5-yl)-2-((tert-butyldimethylsilyl)oxy)ethyl)(tert-butoxycarbonyl)amino)ethyl)phenyl trifluoromethanesulfonate (7.29 g, 9.4 mmol) in toluene (75 mL) was added with phenyl formate (4 mL, 37.57 mmol), 4,5-bis(diphenylphosphino)-9,9-dimethylxanthene (1.3 g, 2.25 mmol), triethylamine (2.61 mL, 18.81 mmol) and the mixture was de-gassed for 15 minutes with nitrogen. Palladium acetate (0.242 g, 1.12 mmol) was added and the mixture was heated at 80° C. for 6 hours. The reaction mixture was evaporated under reduced pressure to about ⅓ of the initial volume and then diluted with ethyl acetate. The organic phase was washed with water, brine, dried over anhydrous magnesium sulfate, filtered and the filtrate evaporated under reduced pressure. The residue was purified by flash column chromatography (eluent—100% iso-hexane to 100% ethyl acetate) to afford the title compound (4.5 g, 64%).

$^1$H NMR (400 MHz, DMSO-$d_6$, 100° C.); δ 9.98-9.96 (m, 1H), 8.29 (d, J=9.9 Hz, 1H), 8.05 (d, J=8.3 Hz, 2H), 7.56 (d, J=7.2 Hz, 2H), 7.51-7.46 (m, 2H), 7.43-7.27 (m, 8H), 7.24 (s, 1H), 7.17 (d, J=8.3 Hz, 1H), 6.57 (d, J=9.9 Hz, 1H), 5.35 (d, J=1.9 Hz, 1H), 5.32 (s, 2H), 3.49-3.34 (m, 4H), 2.90-2.80 (m, 2H), 1.39 (s, 9H), 0.87 (s, 9H), 0.06 (s, 3H), −0.12 (s, 3H).

Step 5: (R)-4-(2-((2-(8-(Benzyloxy)-2-oxo-1,2-dihydroquinolin-5-yl)-2-((tert-butyldimethylsilyl)oxy)ethyl)(tert-butoxycarbonyl)amino)ethyl)benzoic acid

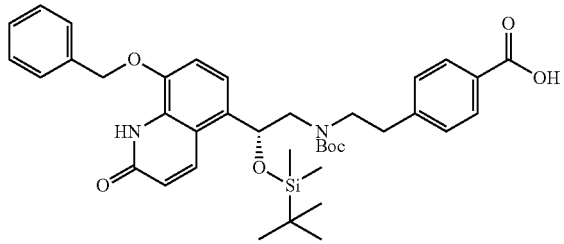 [SMILES: CC(C)(C)OC(=O)N(CCc1ccc(C(=O)O)cc1)C[C@H](O[Si](C)(C)C(C)(C)C)c1ccc(OCc2ccccc2)c2[nH]c(=O)ccc12]

A solution of (R)-phenyl 4-(2-((2-(8-(benzyloxy)-2-oxo-1,2-dihydroquinolin-5-yl)-2-((tert-butyldimethylsilyl)oxy)ethyl)(tert-butoxycarbonyl)amino)ethyl)benzoate (4.5 g, 6.0 mmol) in THF (30 mL) was added with 2M aqueous sodium hydroxide (30 mL) and the mixture was stirred at room temperature for 16 hours. The solvent was evaporated under reduced pressure to half the initial volume and then diluted with water (25 mL). The resulting mixture was acidified to pH 3 using 2M aqueous hydrochloric acid and then extracted with ethyl acetate (×3). The combined organic phases were washed sequentially with water, brine (25 ml), dried over anhydrous magnesium sulfate, filtered and the filtrate evaporated under reduced pressure to afford the title compound (4 g, 100%). Material used directly in the next step.

Step 6: (R)-4-(2-((tert-Butoxycarbonyl)(2-((tert-butyldimethylsilyl)oxy)-2-(8-hydroxy-2-oxo-1,2-dihydroquinolin-5-yl)ethyl)amino)ethyl)benzoic acid

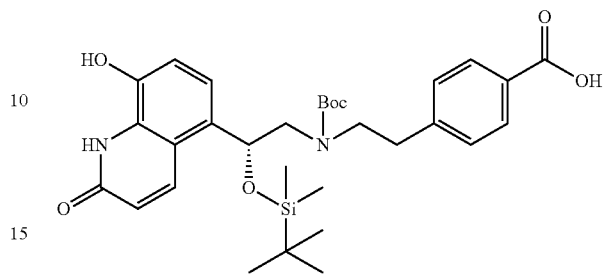

A solution of (R)-4-(2-((2-(8-(benzyloxy)-2-oxo-1,2-dihydroquinolin-5-yl)-2-((tert-butyldimethylsilyl)oxy)ethyl)(tert-butoxycarbonyl)amino)ethyl)benzoic acid (4 g, 5.95 mmol) in ethanol (100 mL) was added with 10% Pd—C(2 g) and 1-methyl-1,4-cyclohexadiene (3.29 ml, 29.76 mmol) and the mixture was heated at 80° C. for 3.5 hours. The reaction mixture was filtered through celite and the celite washed with further ethanol. The filtrate was evaporated under reduced pressure to afford the title compound (3.5 g, 100%).

LCMS Method 1; Rt 3.65 ES$^+$583.6

Procedure D1

Analogously prepared was 2-((tert-butoxycarbonyl)((R)-2-((tert-butyldimethylsilyl)oxy)-2-(8-hydroxy-2-oxo-1,2-dihydroquinolin-5-yl)ethyl)amino)-2,3-dihydro-1H-indene-5-carboxylic acid starting with 5-bromo-2,3-dihydro-1H-inden-2-amine (in place of tyramine) and omitting Step 3.

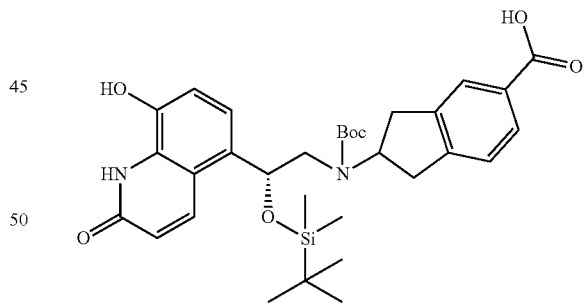

The key intermediate (phenyl 2-(((R)-2-(8-(benzyloxy)-2-oxo-1,2-dihydroquinolin-5-yl)-2-((tert-butyldimethylsilyl)oxy)ethyl)(tert-butoxycarbonyl)-amino)-2,3-dihydro-1H-indene-5-carboxylate) was separated into the individual stereoisomers by SFC (YMC Cellulose-SC column, eluent 40/60 IPA (0.1% DEA)/carbon dioxide; flow rate 100.0 mL/min, 120 bar pressure, 40° C., GLS 60PSI, system 4500 PSI). Individual isomers observed at retention time of 5.11 minutes and 6.43 minutes.

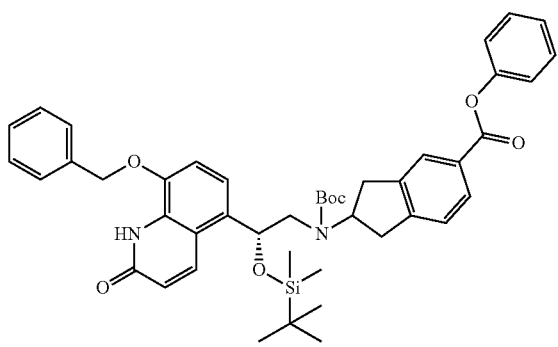 [SMILES: CC(C)(C)OC(=O)N(C[C@H](O[Si](C)(C)C(C)(C)C)c1ccc(OCc2ccccc2)c2[nH]c(=O)ccc12)C1Cc2ccc(C(=O)Oc3ccccc3)cc2C1]

LCMS Method 1; Rt 4.59; ES⁺ 761.5 enantiomer 1
LCMS Method 1; Rt 4.58; ES⁺ 761.5 enantiomer 2

Procedure E

Preparation of Chiral Intermediate

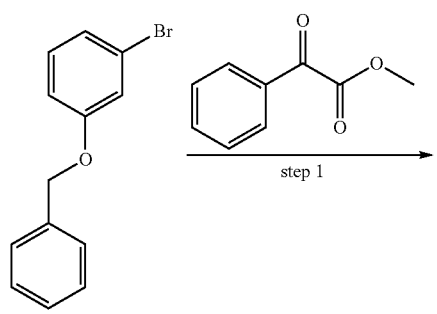

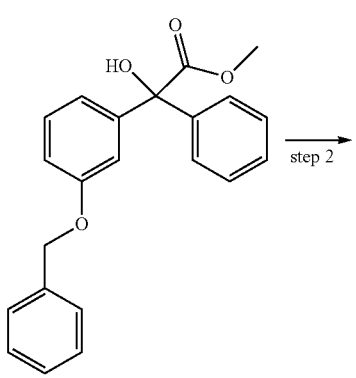

Step 1: Methyl 2-(3-(benzyloxy)phenyl)-2-hydroxy-2-phenylacetate

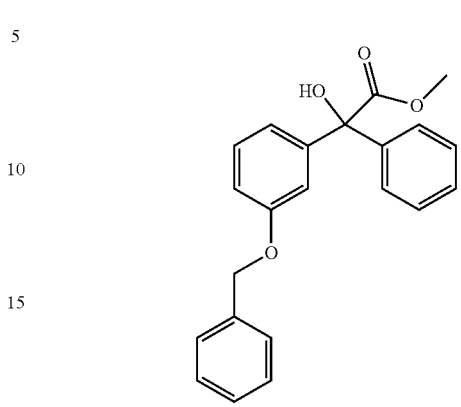

Magnesium turnings (40.9 g, 1.71 mol) were placed in the three necked round bottom flask under argon. Anhydrous THF (1800 mL) and crystals of iodine (6.18 g, 0.024 mol) were added then 1-(benzyloxy)-3-bromobenzene (384.69 g, 1.46 mol) was added in portions. The internal temperature rose to 60° C. and the reaction foamed. The reaction was stirred for 2.5 hours at reflux. In another flask, a solution of methyl benzylformate (200.00 g, 1.22 mol) in anhydrous THF (2000 mL) was cooled to −70° C. under argon and to this the Grignard reagent was added dropwise over 3 hours. The reaction was allowed to slowly warm to room temperature and stirred at this temperature for 18 hours. The reaction was quenched with ammonium chloride solution. Layers were separated and the aqueous layer was extracted with ethyl acetate. The combined organic fractions were washed with brine and dried over anhydrous magnesium sulfate. The filtrate was evaporated at reduced pressure to afford an oil. The resultant oil was evaporated with hexane twice to afford a solid (473.15 g).

The solid was refluxed with 4730 ml hexane (10 ml/g) for 5 min, then allowed to cool to room temperature and stirred for 1 hour, then filtered and washed with hexane to obtain 386.34 g (HPLC: 83.85%). The product was crystallized in 3930 ml iPrOH (13 ml/g). The mixture was milky at reflux, was filtered (solid: 5.85 g, HPLC: 95.95%) and the filtrate was allowed to crystallized for 18 hours. The resulting precipitate was stirred for 1.5 hour at 10° C., then filtered and washed with hexane to afford the title product (180.54 g, 42%).

$^1$H NMR (400 MHz, DMSO-d$_6$); δ 7.44-7.22 (m, 11H), 6.98-6.93 (m, 2H), 6.92-6.88 (m, 1H), 6.68 (s, 1H, OH), 5.05 (s, 2H), 3.70 (s, 3H).

Step 2: Methyl 2-hydroxy-2-(3-hydroxyphenyl)-2-phenylacetate

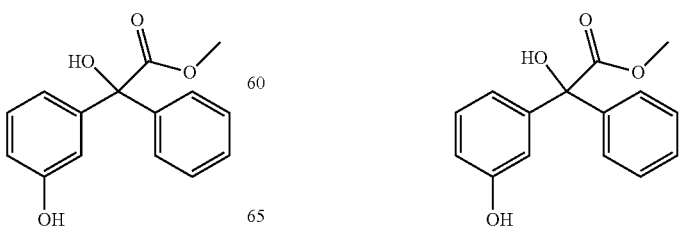

180.00 g of methyl 2-(3-(benzyloxy)phenyl)-2-hydroxy-2-phenylacetate (0.52 mol) was divided into 6 parts: 30.00 g each. 30.00 g of methyl 2-(3-(benzyloxy)phenyl)-2-hydroxy-2-phenylacetate was dissolved in MeOH (1380 mL) and degassed. The Pd/C catalyst (wet, 20% wt) was added and the reaction mixture was stirred under a hydrogen atmosphere (via balloon) for 2.5 hours. The reaction mixture was filtered through a Celite pad and washed with MeOH. The filtrate was concentrated and the residue was adsorbed on silica (22 g, 1 g SiO2/1 g crude) and purified via dry flash chromatography (820 g SiO2, 5 g SiO2/1 g ther. yield, AcOEt/hex=1/1). The resulting oil residue was evaporated with hexane/toluene and product obtained as a solid (157.82 g, 96%).

$^1$H NMR (400 MHz, DMSO-$d_6$); δ 9.36 (s, 1H, OH), 7.35-7.29 (m, 4H), 7.31-7.24 (m, 1H), 7.11 (t, J=7.8 Hz, 1H), 6.78-6.70 (m, 2H), 6.67 (ddd, J=7.9, 2.2, 1.0 Hz, 1H), 6.56 (s, 1H, OH), 3.70 (s, 3H).

The individual enantiomers were separated by preparative chromatography.
Column: CHIRALPAK®AD-H 5 µm-250×50 mm
Mobile phase: Carbon Dioxide/Methanol 90/10
Flow rate: 300 g/min
Detection: UV 280 nm
Temperature: 25° C.
Pressure: 130 bars
Procedure F

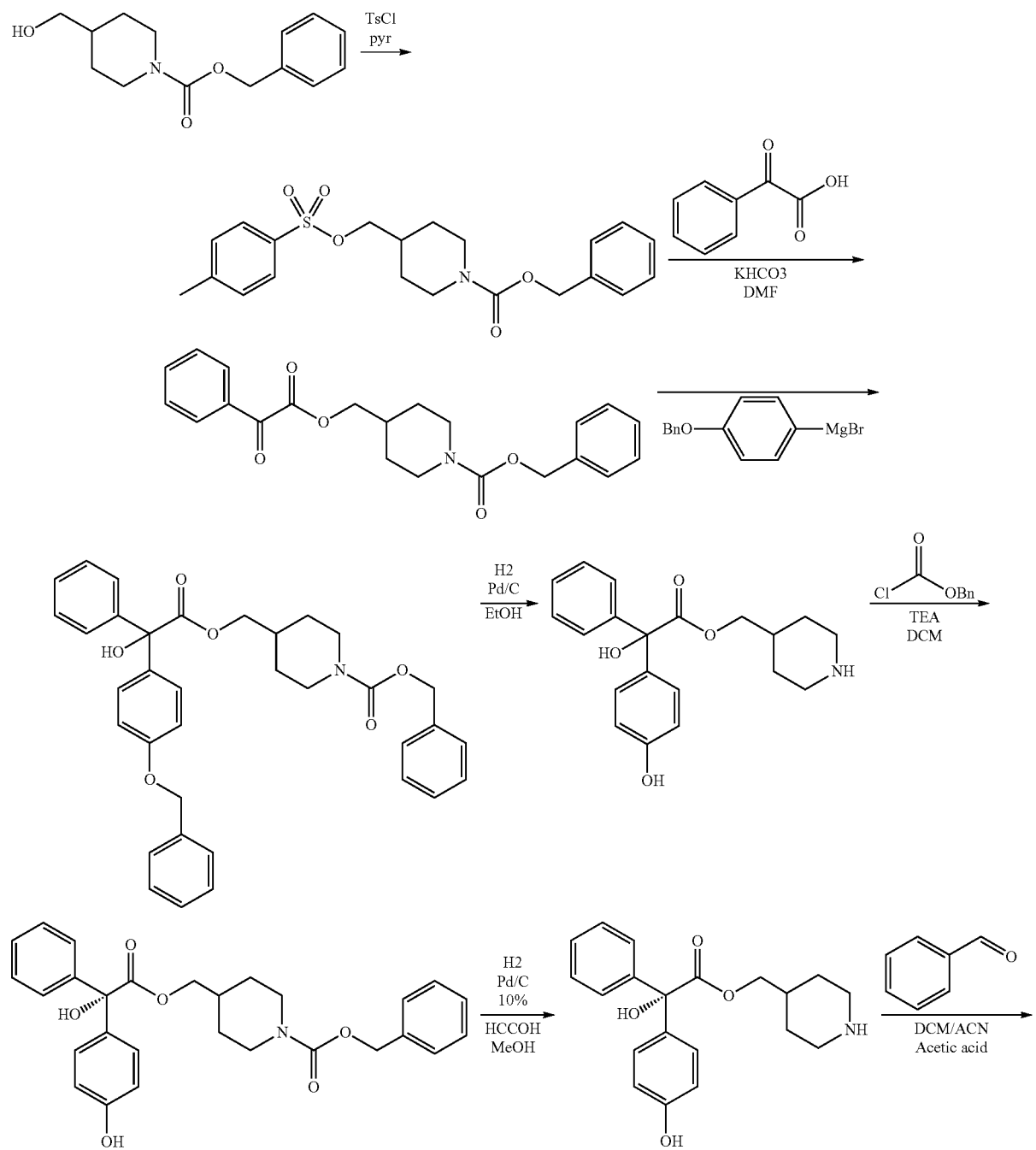

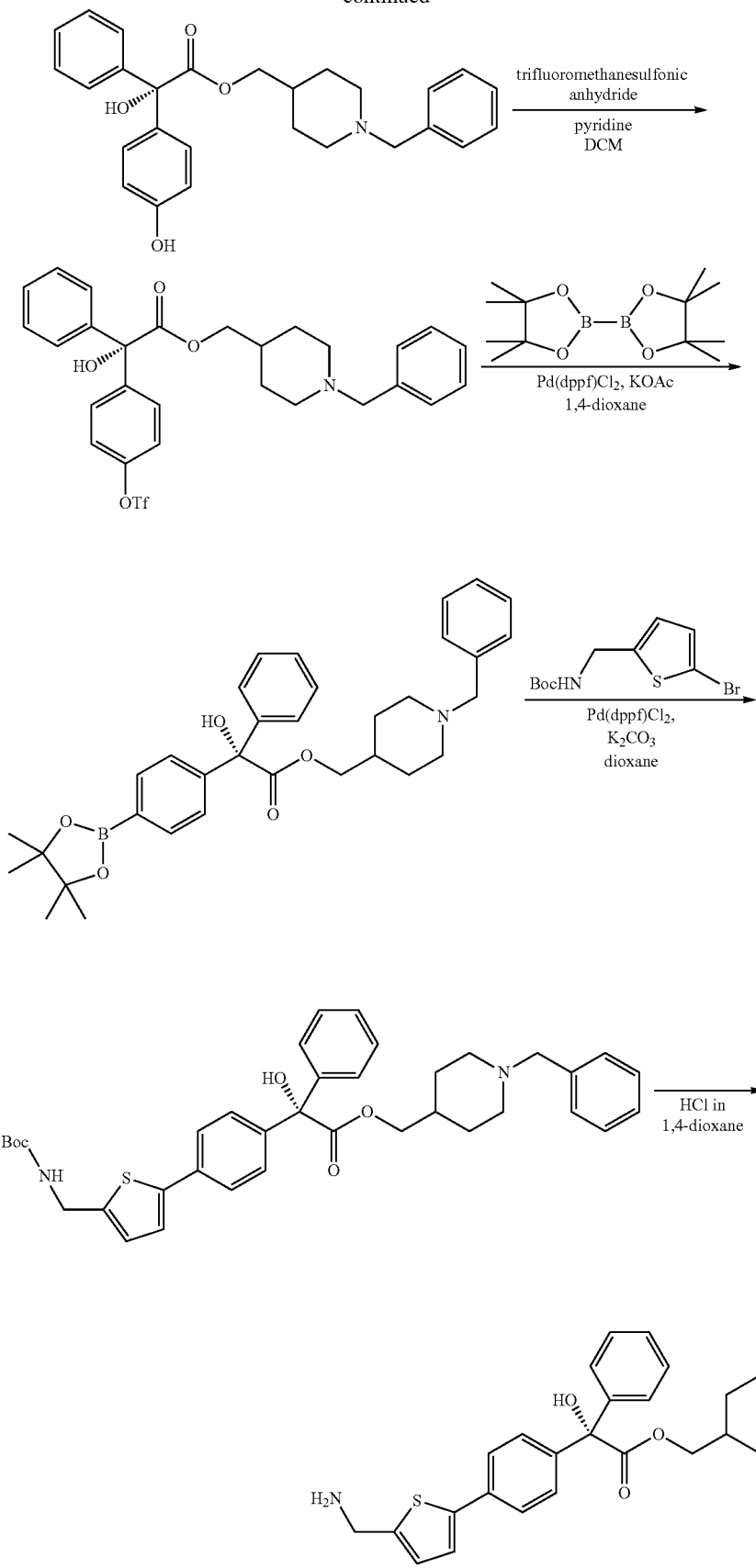

Preparation of (1-benzylpiperidin-4-yl)methyl (S)-2-(4-(5-(aminomethyl)thiophen-2-yl)phenyl)-2-hydroxy-2-phenylacetate dihydrochloride

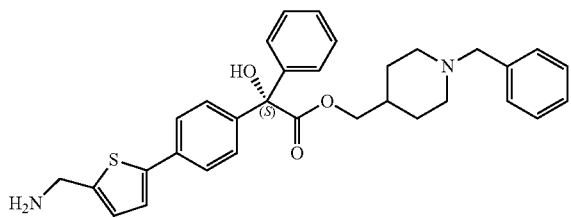

Step 1: Benzyl 4-((tosyloxy)methyl)piperidine-1-carboxylate

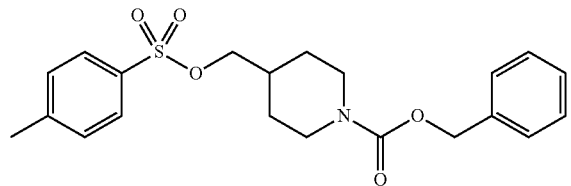 [SMILES: Cc1ccc(S(=O)(=O)OCC2CCN(C(=O)OCc3ccccc3)CC2)cc1]

A stirred solution of benzyl 4-(hydroxymethyl)piperidine-1-carboxylate (49.86 g, 200 mmol) in anhydrous pyridine (200 mL) at 0° C. under nitrogen was added with portionwise p-toluenesulfonyl chloride (41.94 g, 220 mmol). The reaction was stirred at 0° C. for 100 minutes before warming to room temperature. After 18 hours the reaction mixture was re-cooled to 0° C. and aqueous saturated aqueous sodium hydrogen carbonate was cautiously added. The resultant suspension was stirred at room temperature for 4 hours. The suspension was filtered and the filter cake washed with water. The solid was dried under vacuum in the presence of P$_2$O$_5$ to afford the title compound (76.47 g, 95%). $^1$H NMR (400 MHz, CDCl$_3$); δ 7.77 (d, J=8.3 Hz, 2H), 7.37-7.29 (m, 7H), 5.10 (s, 2H), 4.17 (m, 2H), 3.85 (d, J=6.5 Hz, 2H), 2.74-2.73 (m, 2H), 2.45 (s, 3H), 1.92-1.80 (m, 1H), 1.67 (d, J=13.1 Hz, 2H), 1.18-1.06 (m, 2H).

Step 2: Benzyl 4-((2-oxo-2-phenylacetoxy)methyl)piperidine-1-carboxylate

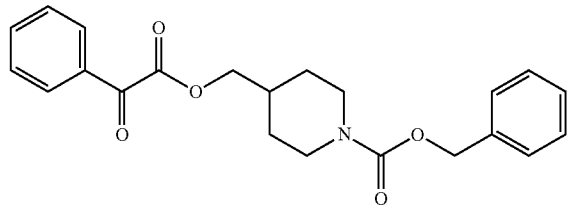 [SMILES: O=C(OCC1CCN(C(=O)OCc2ccccc2)CC1)C(=O)c1ccccc1]

A solution of phenylglyoxylic acid (8.64 g, 56.3 mmol) in DMF (100 mL) was added with potassium hydrogen carbonate (11.52 g, 112.6 mmol) and stirred at room temperature for 10 minutes. Benzyl 4-((tosyloxy)methyl)piperidine-1-carboxylate (25.5 g, 62.0 mmol) was added and the reaction mixture heated at 60° C. for 18 hours. The reaction mixture was cooled and diluted with ethyl acetate. The mixture was washed with saturated aqueous sodium hydrogen carbonate and brine. The organic phase was dried over anhydrous magnesium sulfate, filtered and the filtrate evaporated under reduced pressure. The residue was purified by flash column chromatography (eluent—100% iso-hexane to 1:4 ethyl acetate/iso-hexane) to afford the title compound (13.2 g, 61%).
$^1$H NMR (400 MHz, CDCl$_3$); δ 8.01-7.98 (m, 2H), 7.68 (dd, J=7.5, 7.5 Hz, 1H), 7.53 (dd, J=7.8, 7.8 Hz, 2H), 7.36 (d, J=3.8 Hz, 5H), 5.13 (s, 2H), 4.25 (d, J=6.6 Hz, 4H), 2.80-2.80 (m, 2H), 2.05-1.94 (m, 1H), 1.79 (dd, J=2.0, 10.9 Hz, 2H), 1.32-1.16 (m, 2H).

Step 3: Benzyl 4-((2-(4-(benzyloxy)phenyl)-2-hydroxy-2-phenylacetoxy)methyl)piperidine-1-carboxylate

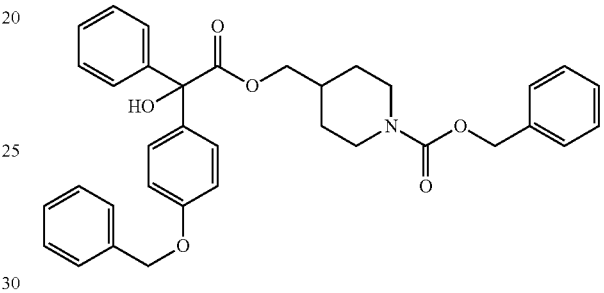

A stirred solution of benzyl 4-((2-oxo-2-phenylacetoxy) methyl)piperidine-1-carboxylate 10.59 g, 27.8 mmol) in THF (120 mL) cooled to −78° C. was added with a solution of (4-(benzyloxy)phenyl)magnesium bromide (0.8 M in THF, 38 mL, 30.6 mmol). The reaction mixture was slowly allowed to warm to 10° C. over 18 hours. The reaction mixture was stirred at room temperature for 2 hours. The reaction mixture was diluted with ethyl acetate and washed with aqueous 1M hydrochloric acid and brine. The organic phase was dried over anhydrous magnesium sulfate, filtered and the filtrate evaporated under reduced pressure. The residue was purified by flash column chromatography (eluent—100% iso-hexane to 1:4 ethyl acetate/iso-hexane) to afford the title compound
(8.67 g, 55%).
$^1$H NMR (400 MHz, CDCl$_3$); δ 7.42-7.42 (m, 17H), 6.94-6.91 (m, 2H), 5.09 (d, J=18.7 Hz, 4H), 4.15-4.07 (m, 5H), 2.68-2.65 (m, 2H), 1.82-1.73 (m, 1H), 1.53-1.44 (m, 2H), 1.10-1.06 (m, 2H).

Step 4: Piperidin-4-ylmethyl 2-hydroxy-2-(4-hydroxyphenyl)-2-phenylacetate

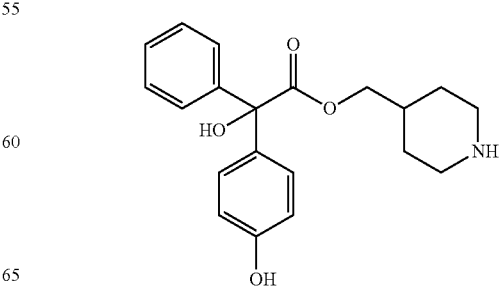

The title compound was prepared as described in Procedure A Step 5.

$^1$H NMR (400 MHz, CDCl$_3$); δ 7.43 (dd, J=1.6, 8.0 Hz, 2H), 7.35-7.30 (m, 3H), 7.20 (d, J=8.6 Hz, 2H), 6.67 (d, J=8.8 Hz, 2H), 4.15 (dd, J=6.4, 10.7 Hz, 1H), 4.00 (dd, J=6.1, 10.9 Hz, 1H), 3.57-3.56 (m, 3H), 3.05 (d, J=12.4 Hz, 2H), 2.58-2.48 (m, 2H), 1.79-1.69 (m, 1H), 1.54-1.46 (m, 2H), 1.27-1.05 (m, 2H).

Step 5: Benzyl 4-((2-hydroxy-2-(4-hydroxyphenyl)-2-phenylacetoxy)methyl)piperidine-1-carboxylate

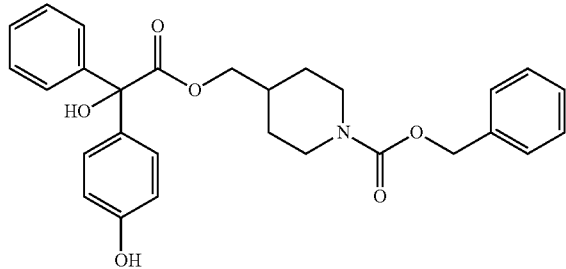 [SMILES: O=C(OCc1ccccc1)N1CCC(COC(=O)C(O)(c2ccccc2)c2ccc(O)cc2)CC1]

A cooled (0° C.) solution of piperidin-4-ylmethyl 2-hydroxy-2-(4-hydroxyphenyl)-2-phenylacetate (12.8 g, 37.5 mmol) and triethylamine (21 mL, 150 mmol) in DCM (375 mL) was added with dropwise benzyl chloroformate (10.7 mL, 75 mmol). The reaction mixture was allowed to warm slowly to room temperature over 18 hours. The reaction mixture was washed with saturated aqueous sodium hydrogen carbonate and the organic phase was dried over anhydrous magnesium sulfate, filtered and the filtrate evaporated under reduced pressure. The residue was dissolved in DCM (190 mL) and N-methylpiperazine (42.1 mL, 379 mmol) and the reaction mixture stirred at room temperature for 18 hours. The reaction mixture was washed with saturated aqueous sodium hydrogen carbonate and the organic phase was dried over anhydrous magnesium sulfate, filtered and the filtrate evaporated under reduced pressure. The residue was purified by flash column chromatography (eluent—100% DCM to 20:1 DCM/methanol). This reaction was performed twice on the same scale to afford the title compound (28.2 g, 79%).

$^1$H NMR (400 MHz, CDCl$_3$); δ 7.39-7.31 (m, 9H), 7.26 (s, 3H), 7.24 (s, 1H), 6.76 (d, J=8.8 Hz, 2H), 5.30-5.26 (m, 1H), 5.12 (s, 1H), 4.16-4.07 (m, 5H), 2.67-2.66 (m, 2H), 1.80-1.71 (m, 1H), 1.50-1.44 (m, 2H), 1.11-0.99 (m, 2H).

The material was separated into the individual enantiomers using SFC (LUX Cellulose-4 column, eluent 40/60 methanol/carbon dioxide; flow rate 100.0 mL/min, 120 bar pressure, 40° C., GLS 40PSI, system 4200 PSI). Individual isomers observed at retention time of 2.3 minutes and 3.4 minutes.

Step 6: Piperidin-4-ylmethyl (S)-2-hydroxy-2-(4-hydroxyphenyl)-2-phenylacetate×HCOOH

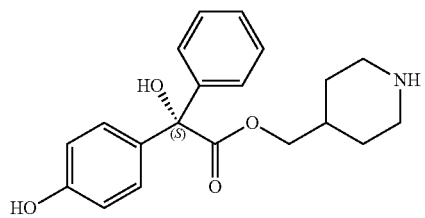

Benzyl (S)-4-((2-hydroxy-2-(4-hydroxyphenyl)-2-phenylacetoxy)methyl)piperidine-1-carboxylate (3 g, 6.31 mmol) was dissolved in methanol (20 ml). Formic acid (0.476 ml, 12.62 mmol) and Pd—C 10% wet (0.631 mmol) were added and the mixture was hydrogenated for 2 h at room temperature under balloon pressure of H$_2$. The solid was filtered off and the filtered was concentrated under reduced pressure to afford the title compound (2.15 g, 100%) as a transparent oil.

UPLC-MS Method 3; Rt 0.37 min, ES+ 342.02

Step 7: 1-benzylpiperidin-4-yl)methyl (S)-2-hydroxy-2-(4-hydroxyphenyl)-2-phenylacetate

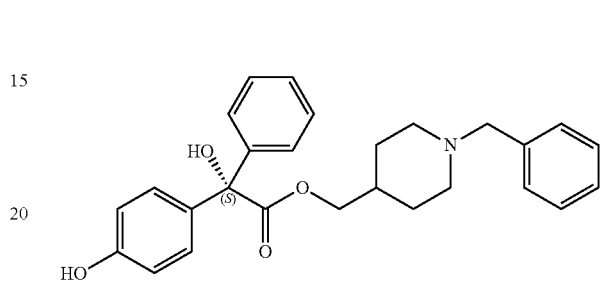

A stirred solution of piperidin-4-ylmethyl (S)-2-hydroxy-2-(4-hydroxyphenyl)-2-phenylacetate (2.15 g, 8.20 mmol) in acetonitrile (20 ml) and DCM (20 ml) benzaldehyde (1.125 ml, 11.07 mmol) acetic acid (0.633 ml, 11.07 mmol) and sodium triacetoxyborohydride (2.39 g, 10.79 mmol) were added and the mixture was stirred overnight at room temperature. Reaction mixture was partitioned between ethyl acetate/sat NaHCO$_3$, washed twice with brine. The organic layer was dried over Na$_2$SO$_4$ and dried under reduced pressure to afford the title compound (4 g, 9.27 mmol, 113%). UPLC-MS Method 3; Rt 0.56 min, ES+ 431.85

Step 8: (1-benzylpiperidin-4-yl)methyl (S)-2-hydroxy-2-phenyl-2-(4-(((trifluoromethyl)sulfonyl)oxy)phenyl)acetate

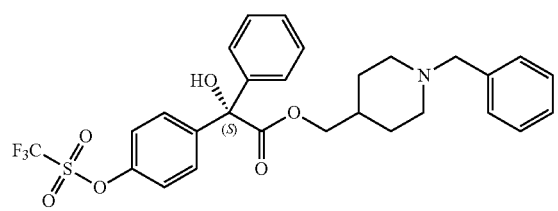

A stirred solution of (1-benzylpiperidin-4-yl)methyl (S)-2-hydroxy-2-(4-hydroxyphenyl)-2-phenylacetate (3 g, 6.95 mmol), pyridine (2 ml, 24.83 mmol) was added with and the solution was cooled to 0° C. in an ice bath. A solution of trifluoromethanesulfonic anhydride (0.351 ml, 2.086 mmol) in DCM dry (5 ml) was added dropwise and the mixture was slowly warmed up to room temperature and then kept stirring for 30 min. Aliquots of pyridine (1 ml, 0.5 ml) and trifluoromethanesulfonic anhydride (0.351 ml, 0.1 ml) in DCM (5 ml×2) were added. After 30 min stirring the mixture was diluted with DCM and washed with 1M HCl, dried over Na$_2$SO$_4$ and concentrated under reduced pressure to give the crude (2.88 g) as an orange solid. An aliquot (2.38 g) was purified by flash chromatography (eluent—0 to 10% MEOH in DCM) to obtain the title compound (2.1 g, 53.6%) as an orange oil.

UPLC-MS Method 3; Rt 0.84 min, ES+ 563.81

Step 9: (1-benzylpiperidin-4-yl)methyl (S)-2-hydroxy-2-phenyl-2-(4-(4,4,5,5-tetramethyl-1,3,2-dioxaborolan-2-yl)phenyl)acetate

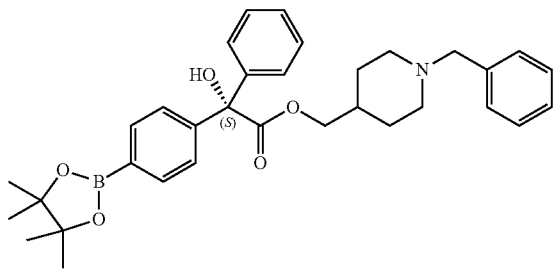

(1-benzylpiperidin-4-yl)methyl (S)-2-hydroxy-2-phenyl-2-(4-(((trifluoromethyl)sulfonyl)oxy)-phenyl) acetate (2.1 g, 3.73 mmol), 4,4,4',4',5,5,5',5'-octamethyl-2,2'-bi(1,3,2-dioxaborolane) (1.892 g, 7.45 mmol) and potassium acetate (1.097 g, 11.18 mmol) were mixed in dioxane dry (9 ml). The mixture was degassed bubbling nitrogen for 5 min before adding [1,1'-Bis(diphenylphosphino)-ferrocene]dichloropalladium(II) (0.273 g, 0.373 mmol). The mixture was degassed again for 5 min and stirred overnight at 85° C. After being cooled to room temperature the mixture was diluted with ethyl acetate and washed by water The organic layer was dried over Na₂SO4, filtered and concentrated under reduced pressure to afford the title compound (3 g, 5.54 mmol, 149%) as a dark red oil.

UPLC-MS Method 3; Rt 0.85 min, ES+ 541.93

Step 10: (1-benzylpiperidin-4-yl)methyl (S)-2-(4-(5-(((tert-butoxycarbonyl)amino)methyl)thiophen-2-yl)phenyl)-2-hydroxy-2-phenylacetate

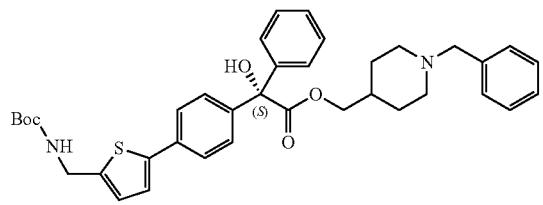

(1-Benzylpiperidin-4-yl)methyl (S)-2-hydroxy-2-phenyl-2-(4-(4,4,5,5-tetramethyl-1,3,2-dioxaborolan-2-yl)phenyl) acetate (300 mg, 0.554 mmol), tert-butyl ((5-bromothiophen-2-yl)methyl)carbamate (178 mg, 0.609 mmol) and potassium carbonate 2N aqueous solution (0.831 ml) were mixed in 1,4-dioxane (2 ml). The solution was degassed with N₂ for 3 min before adding ([1,1'-Bis(diphenylphosphino)ferrocene]dichloropalladium(II) (40.5 mg, 0.055 mmol). The mixture was degassed again for 5 min and then heated at 70° C. for 3 hours. The cooled-down mixture was treated with water and ethyl acetate (5 ml), the organic layer was dried over Na₂SO₄ then concentrated under reduced pressure. The crude was purified by flash chromatography (eluent—0 to 100% ethyl acetate in heptane) to obtain the title compound (75 mg, 47%) as a transparent oil.

UPLC-MS Method 3; Rt 0.87 min, ES+ 627.01

Step 11: (1-benzylpiperidin-4-yl)methyl (S)-2-(4-(5-(aminomethyl)thiophen-2-yl)phenyl)-2-hydroxy-2-phenylacetate

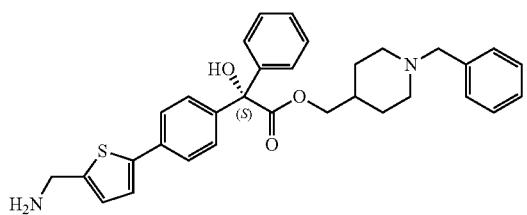

(1-Benzylpiperidin-4-yl)methyl (S)-2-(4-(5-(((tert-butoxycarbonyl)amino)-methyl)thiophen-2-yl)phenyl)-2-hydroxy-2-phenylacetate (52 mg, 0.083 mmol) was dissolved in 1,4-dioxane\HCl 4 N (0.8 ml), then the mixture was stirred for 3 h. Diethyl ether (5 ml) was added and the precipitate that had formed was filtered off and washed with ethyl ether to give the titled compound as a white solid hydrochloric salt (59 mg, 96%).

UPLC-MS Method 3; Rt 0.43 min, ES+ 527.68

Analogously prepared were also:

| Structure (×2 HCl) | LCMS (Method 3) | Commercially available starting material |
|---|---|---|
|  | Rt 0.69 min, ES+ 528 |  |

-continued
| Structure (×2 HCl) | LCMS (Method 3) | Commercially available starting material |
|---|---|---|
| | Rt 0.43 min, ES+ 527.68 | |
| | Rt 0.40 min, ES+ 527.75 | |
Procedure G
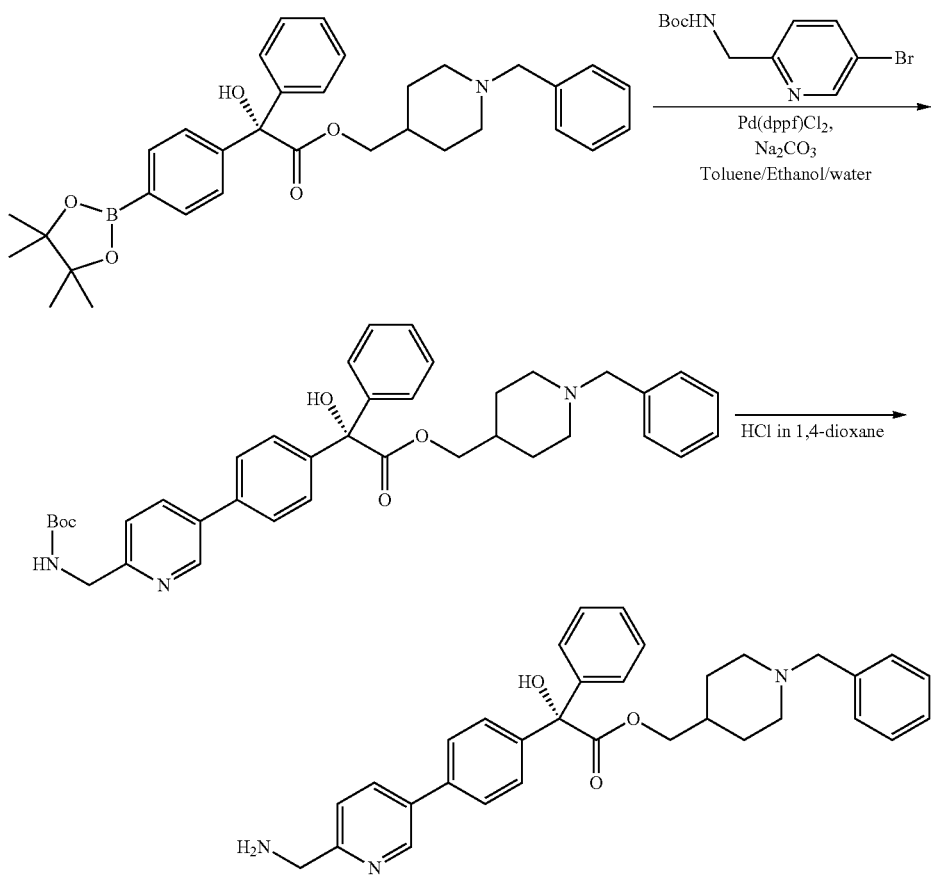

Preparation of (1-benzylpiperidin-4-yl)methyl (S)-2-(4-(6-(aminomethyl)pyridin-3-yl)phenyl)-2-hydroxy-2-phenylacetate dihydrochloride

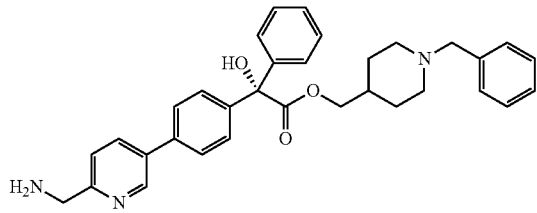 [SMILES: NCc1ccc(-c2ccc([C@](O)(C(=O)OCC3CCN(Cc4ccccc4)CC3)c3ccccc3)cc2)cn1]

Step 1: (1-benzylpiperidin-4-yl)methyl (S)-2-(4-(6-(((tert-butoxycarbonyl)amino)methyl)pyridin-3-yl)phenyl)-2-hydroxy-2-phenylacetate

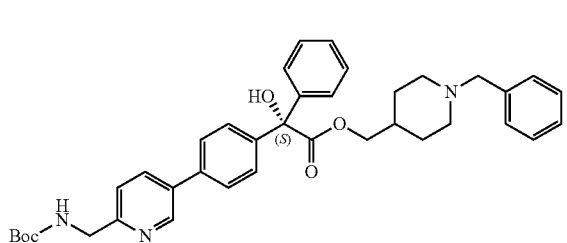

(1-Benzylpiperidin-4-yl)methyl (S)-2-hydroxy-2-phenyl-2-(4-(4,4,5,5-tetramethyl-1,3,2-dioxaborolan-2-yl)phenyl)acetate (300 mg, 0.554 mmol), prepared as described in Procedure A Step 1-3, tert-butyl ((5-bromopyridin-2-yl)methyl)carbamate (106 mg, 0.369 mmol) and $Na_2CO_3$ (157 mg, 1.477 mmol) were mixed in toluene/ethanol/water (4.9 ml, 4:2:1). The mixture was degassed bubbling nitrogen inside the solution for 5 min before adding Tetrakis(triphenylphosphine)palladium(0) $(Pd(PPh_3)_4)$(42.7 mg, 0.037 mmol). The reaction mixture was irradiated by microwaves at 100° C. for 15 min×3 times. The mixture was diluted with Ethyl acetate and washed by water and brine. The organic layer was dried over $Na_2SO_4$ filtered and concentrated under reduced pressure to get a crude (1 g). The crude was dissolved in DMF (1 ml) and purified by reverse phase column chromatography (C18 cartridge, gradient elution from 100:0 to 0:100 A/B, A: water/MeCN 95:5+0.1% HCOOH, B: MeCN/water 95:5+0.1% HCOOH) to afford the title compound (122 mg, 53.1% yield) as a red oil.

UPLC-MS Method 3; Rt 0.75 min, ES+ 621.81

Step 2: (1-benzylpiperidin-4-yl)methyl (S)-2-(4-(6-(aminomethyl)pyridin-3-yl)phenyl)-2-hydroxy-2-phenylacetate dihydrochloride

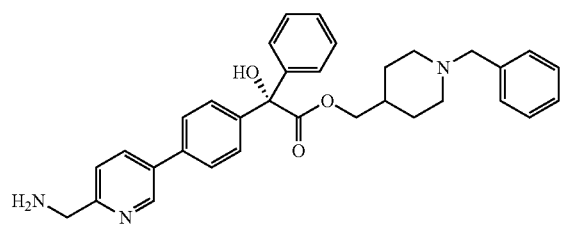 [SMILES: NCc1ccc(-c2ccc([C@](O)(C(=O)OCC3CCN(Cc4ccccc4)CC3)c3ccccc3)cc2)cn1]

The title compound was prepared as in Procedure F using Step 11.

UPLC-MS Method 3; Rt 0.49 min, ES+ 858.20

Procedure H

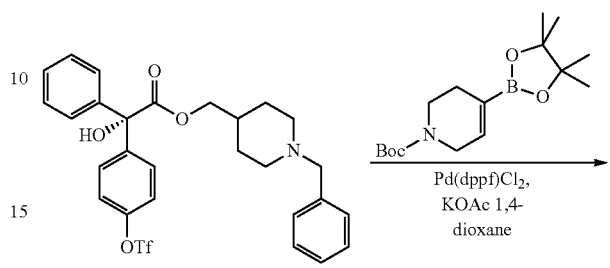

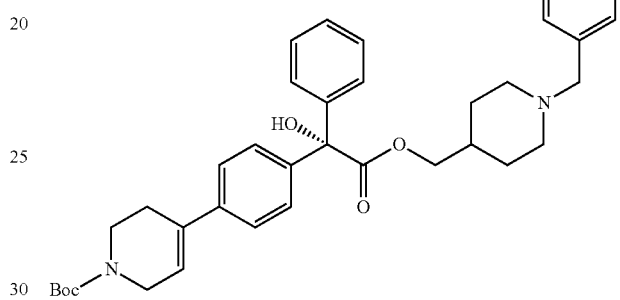

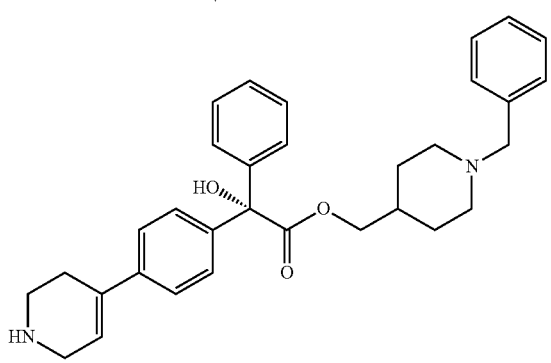

Preparation of (1-benzylpiperidin-4-yl)methyl (S)-2-hydroxy-2-phenyl-2-(4-(1,2,3,6-tetrahydropyridin-4-yl)phenyl)acetate

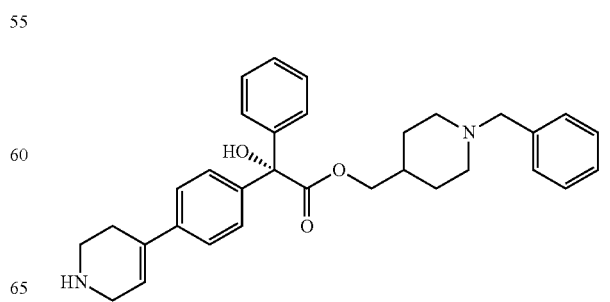

Step 1: Tert-butyl (S)-4-(4-(2-((1-benzylpiperidin-4-yl)methoxy)-1-hydroxy-2-oxo-1-phenylethyl)phenyl)-3,6-dihydropyridine-1(2H)-carboxylate

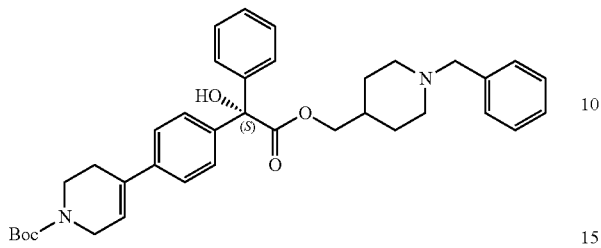

Tert-butyl 4-(4,4,5,5-tetramethyl-1,3,2-dioxaborolan-2-yl)-5,6-dihydropyridine-1(2H)-carboxylate (91 mg, 0.293 mmol), prepared as described in Procedure A Step 1-2, and $K_2CO_3$ 2 M (0.399 ml, 0.798 mmol) were added to (1-benzylpiperidin-4-yl)methyl 2-hydroxy-2-phenyl-2-(4-(((trifluoromethyl)sulfonyl)oxy)phenyl)acetate (150 mg, 0.266 mmol) in 1,4-dioxane (2 ml, 0.266 mmol). The solution was degassed with N2 for 10 min. PdCl$_2$(dppf) (19.47 mg, 0.027 mmol) was added and the mixture was stirred under N$_2$ at 80° C. After ½ hour boronate (20 mg) and catalyst (6 mg) were added.

After a further 1 hour the mixture was diluted ethyl acetate (30 ml) and washed with brine (10 ml), the organic layer was dried over Na$_2$SO$_4$, filtered and concentrated under reduced pressure to obtain a dark oil. The residue was purified by flash column chromatography (eluent—0 to 100% ethyl acetate in heptane) to obtain the title compound (101 mg, 64%) as a dark oil.

UPLC-MS Method 1; Rt 1.10 min, ES+ 1076.84

Step 2: (1-benzylpiperidin-4-yl)methyl (S)-2-hydroxy-2-phenyl-2-(4-(1,2,3,6-tetrahydropyridin-4-yl)phenyl)acetate dihydrochloride

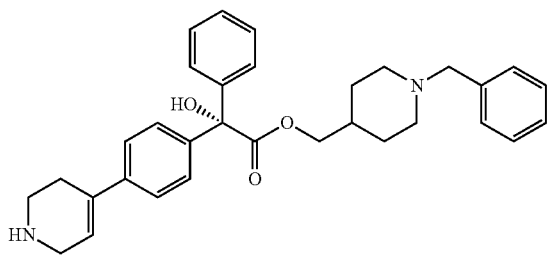 [SMILES: O=C(OCC1CCN(Cc2ccccc2)CC1)[C@](O)(c1ccccc1)c1ccc(C2=CCNCC2)cc1]

The title compound was prepared as in Procedure F using Step 11.

UPLC-MS Method 3; Rt 0.38 min, ES+ 497.32

Analogously prepared was also:

| Starting (×2 HCl) | LCMS (Method 3) | Starting material |
|---|---|---|
| (structure shown) | Rt 0.38 min, ES+ 497.32 | (structure shown) |

Scheme 1

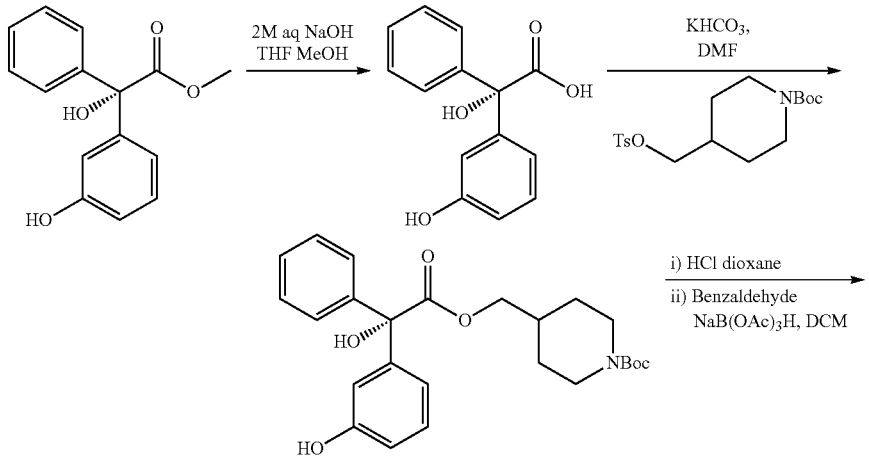

-continued
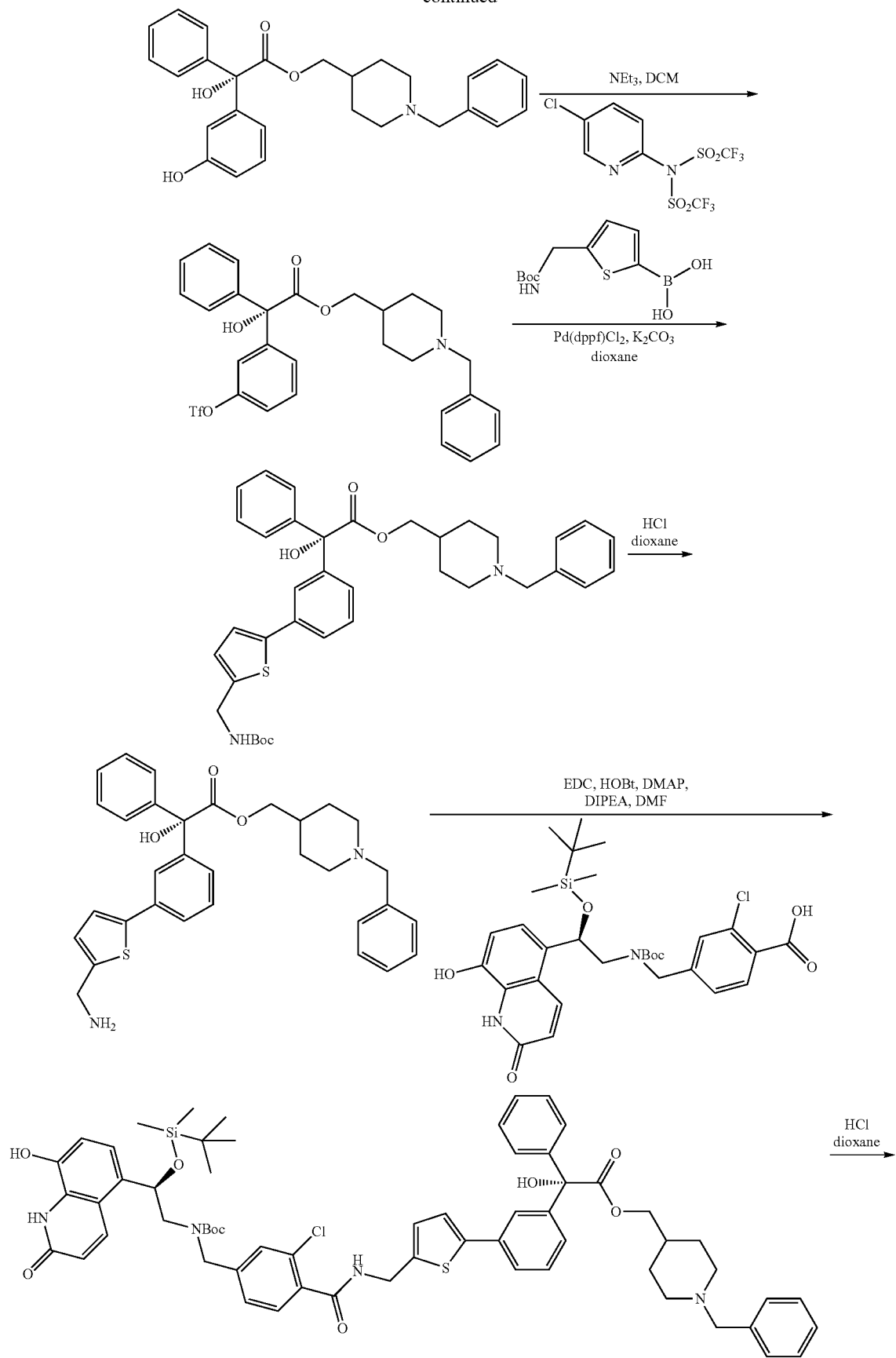

-continued

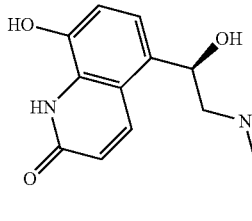

Example 1

(1-Benzylpiperidin-4-yl)methyl (S)-2-(3-(5-((2-chloro-4-((((R)-2-hydroxy-2-(8-hydroxy-2-oxo-1,2-dihydroquinolin-5-yl)ethyl)amino)methyl)benzamido-)methyl)thiophen-2-yl)phenyl)-2-hydroxy-2-phenylacetate (Compound 1)

Step 1: (S)-2-Hydroxy-2-(3-hydroxyphenyl)-2-phenylacetic acid

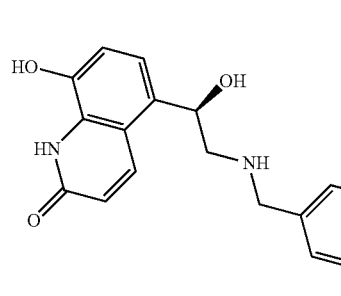

A stirred solution of methyl (S)-2-hydroxy-2-(3-hydroxyphenyl)-2-phenylacetate (2.58 g, 10.0 mmol) in THF (25 mL) and methanol (25 mL) was added with a solution of aqueous sodium hydroxide (2M, 25 mL). The reaction mixture was stirred at 30° C. for 2 hours and the solvent evaporated at reduced pressure. The residue was diluted with ethyl acetate and the mixture cooled to 0° C. The reaction mixture was cautiously acidified with aqueous hydrochloric acid (2M) to a pH of 2. The mixture was separated and the organic phase was extracted with further ethyl acetate (×2). The combined organic extracts were washed with brine, dried (magnesium sulfate), filtered and evaporated under reduced pressure. The residue was azeotroped sequentially with toluene and acetonitrile to afford the title compound (2.34 g, 97%).

$^1$H NMR (400 MHz, DMSO-d$_6$): δ 13.14 (s, 1H), 9.32 (s, 1H), 7.40-7.37 (m, 2H), 7.34-7.26 (m, 3H), 7.12 (dd, J=8.0, 8.0 Hz, 1H), 6.83-6.80 (m, 2H), 6.68-6.65 (m, 1H), 6.23 (m, 1H).

Step 2: (S)-tert-Butyl 4-((2-hydroxy-2-(3-hydroxyphenyl)-2-phenylacetoxy)methyl)-piperidine-1-carboxylate

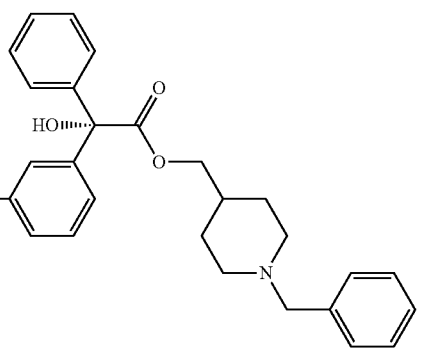

A stirred solution of (S)-2-hydroxy-2-(3-hydroxyphenyl)-2-phenylacetic acid (10.69 g, 43.77 mmol) in DMF (30 mL) was added with potassium hydrogen carbonate (8.76 g, 87.5 mmol) and the mixture stirred at room temperature for 10 minutes. A solution of tert-butyl 4-(tosyloxymethyl)piperidine-1-carboxylate (16.17 g, 43.77 mmol) in DMF (55 mL) was added and the reaction mixture heated at 60° C. for 27 hours. Diluted with ethyl acetate and washed with aqueous sodium hydrogen carbonate (×2), brine and dried over anhydrous magnesium sulfate. The filtrate was evaporated under reduced pressure and the residue purified by flash column chromatography (eluent—100% iso-hexane to 2:3 iso-hexane/ethyl acetate) to afford the title compound (13.42 g, 69%).

$^1$H NMR (400 MHz, DMSO-d$_6$); δ 9.35 (s, 1H), 7.33 (d, J=4.4 Hz, 4H), 7.31-7.26 (m, 1H), 7.12 (dd, J=7.8, 7.8 Hz, 1H), 6.77-6.73 (m, 2H), 6.69-6.66 (m, 1H), 6.50 (s, 1H), 4.07-3.99 (m, 2H), 3.87 (d, J=11.4 Hz, 2H), 2.68-2.63 (m, 2H), 1.76-1.67 (m, 1H), 1.48 (d, J=12.0 Hz, 2H), 1.38 (s, 9H), 1.10-0.83 (m, 2H).

Step 3: (S)-Piperidin-4-ylmethyl 2-hydroxy-2-(3-hydroxyphenyl)-2-phenylacetate hydrochloride

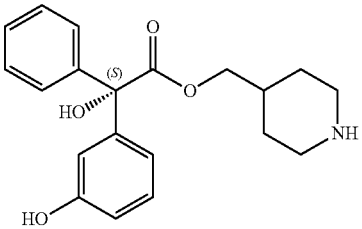

A solution of (S)-tert-butyl 4-((2-hydroxy-2-(3-hydroxyphenyl)-2-phenylacetoxy)methyl)piperidine-1-carboxylate (7.07 g, 16.01 mmol) in 1,4-dioxane (20 mL) was added with a solution of HCl in dioxane (4M, 80 mL) and the reaction mixture was stirred at room temperature for 90 minutes. The solvent was evaporated under reduced pressure to afford the title compound (5.9 g, 97%).

$^1$H NMR (400 MHz, DMSO-d$_6$); δ 9.38 (s, 1H), 8.69-8.68 (m, 1H), 8.39 (s, 1H), 7.34 (d, J=4.0 Hz, 4H), 7.32-7.27 (m, 1H), 7.13 (dd, J=7.8, 7.8 Hz, 1H), 6.78-6.74 (m, 2H), 6.70-6.67 (m, 1H), 6.52 (s, 1H), 4.02 (d, J=6.5 Hz, 2H), 3.21 (d, J=12.4 Hz, 2H), 2.86-2.77 (m, 2H), 1.92-1.84 (m, 1H), 1.68 (d, J=13.9 Hz, 2H), 1.35-1.25 (m, 2H).

Step 4: (S)-(1-Benzylpiperidin-4-yl)methyl 2-hydroxy-2-(3-hydroxyphenyl)-2-phenylacetate

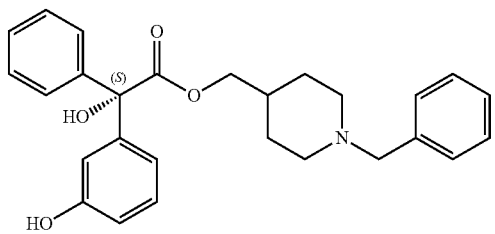

A stirred suspension of (S)-piperidin-4-ylmethyl 2-hydroxy-2-(3-hydroxyphenyl)-2-phenylacetate hydrochloride (5.9 g, 15.61 mmol) in DCM (160 mL) was added with benzaldehyde (2.38 mL, 23.4 mmol) and stirred at 30° C. for 1 hour. Sodium triacetoxyborohydride (6.62 g, 31.2 mmol) was added and the reaction mixture stirred at 30° C. for 2 hours. Further sodium triacetoxyborohydride (1.65 g, 7.8 mmol) was added and the mixture stirred at 30° C. for 18 hours. The reaction mixture was quenched with saturated aqueous sodium hydrogen carbonate and the organic phase removed. The aqueous phase was extracted with further DCM. The combined organic phases were washed with brine, dried over anhydrous magnesium sulfate, filtered and the filtrate evaporated under reduced pressure. The residue was purified by flash column chromatography (eluent—100% DCM to 9:1 DCM/methanol) to afford the title compound (13.42 g, 69%).

$^1$H NMR (400 MHz, DMSO-d$_6$); δ 9.33 (s, 1H), 7.34-7.25 (m, 9H), 7.11 (dd, J=7.8, 7.8 Hz, 1H), 6.76-6.73 (m, 2H), 6.68-6.65 (m, 1H), 6.48 (s, 1H), 5.77 (s, 1H), 3.99 (d, J=6.3 Hz, 2H), 3.40 (s, 2H), 2.72 (d, J=11.4 Hz, 2H), 1.86-1.79 (m, 2H), 1.54-1.43 (m, 3H), 1.12 (q, J=11.8 Hz, 2H).

Step 5: (1-Benzylpiperidin-4-yl)methyl (S)-2-hydroxy-2-phenyl-2-(3-(((trifluoromethyl)sulfonyl)oxy)phenyl)acetate

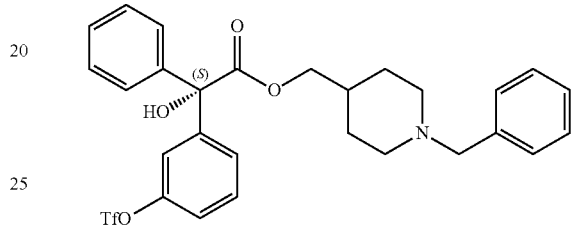

A stirred solution of (S)-(1-benzylpiperidin-4-yl)methyl 2-hydroxy-2-(3-hydroxyphenyl)-2-phenylacetate (1.00 g, 2.32 mmol) and triethylamine (0.42 mL, 3.02 mmol) in anhydrous DCM (4 mL) was added with N-(5-chloro-2-pyridyl)bis(trifluoromethanesulfonimide) (1.09 g, 2.79 mmol). The reaction mixture was stirred at room temperature for 18 hours. The reaction mixture was quenched with saturated aqueous sodium hydrogen carbonate and the mixture extracted with DCM (×2). The combined DCM extracts were passed through a hydrophobic frit and solvent evaporated at reduced pressure. The residue was dissolved in acetonitrile and applied to an SCX-2 cartridge. The cartridge was washed with further acetonitrile (3 column volumes) and then with a 10% triethylamine/acetonitrile solution (4 column volumes). The combined 10% triethylamine/acetonitrile extracts were evaporated at reduced pressure to afford the title compound (1.17 g, 89%).

$^1$H NMR (400 MHz, CDCl$_3$); δ 7.53-7.51 (m, 1H), 7.44-7.39 (m, 2H), 7.37-7.27 (m, 9H), 7.25-7.21 (m, 2H), 4.32 (s, 1H), 4.12 (d, J=6.6 Hz, 2H), 3.45 (s, 2H), 2.81 (d, J=11.4 Hz, 2H), 1.92-1.84 (m, 2H), 1.67-1.59 (m, 1H), 1.51-1.43 (m, 2H), 1.27-1.15 (m, 2H).

Step 6: (1-Benzylpiperidin-4-yl)methyl (S)-2-(3-(5-(((tert-butoxycarbonyl)amino)methyl)thiophen-2-yl)phenyl)-2-hydroxy-2-phenylacetate

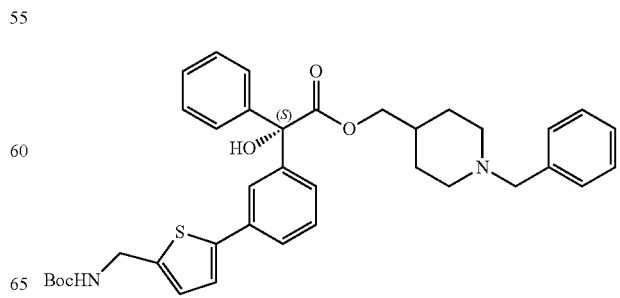

A stirred solution of (1-benzylpiperidin-4-yl)methyl (S)-2-hydroxy-2-phenyl-2-(3-(((trifluoromethyl)sulfonyl)oxy)phenyl)acetate (0.529 g, 0.94 mmol) in anhydrous 1,4-dioxane (7 mL) was added with (5-(((tert-butoxycarbonyl)amino)methyl)thiophen-2-yl)boronic acid (0.265 g, 1.03 mmol) and a solution of aqueous potassium carbonate (1.8 M, 1.57 mL, 2.82 mmol). This mixture was thoroughly degassed with nitrogen and Pd(dppf)Cl₂ (0.077 g, 0.09 mmol) added. The mixture was degassed again and then heated at 80° C. for 3 hours. The reaction mixture was diluted with ethyl acetate and washed with brine. The organic phase was dried over anhydrous magnesium sulfate, filtered and the filtrate evaporated at reduced pressure. The residue was purified by flash column chromatography (eluent—100% DCM to 9:1 DCM/methanol) to afford the title compound (0.38 g, 63%).

¹H NMR (400 MHz, DMSO-d₆); δ 7.63-7.51 (m, 3H), 7.43-7.32 (m, 9H), 7.31-7.26 (m, 4H), 6.94 (d, J=3.5 Hz, 1H), 6.78 (s, 1H), 4.30 (d, J=5.8 Hz, 2H), 4.07 (d, J=6.1 Hz, 2H), 3.44 (s, 2H), 2.75 (d, J=10.6 Hz, 2H), 1.87 (dd, J=11.1, 11.1 Hz, 2H), 1.63-1.51 (m, 3H), 1.45 (s, 9H), 1.22-1.12 (m, 2H).

Step 7: (1-Benzylpiperidin-4-yl)methyl (S)-2-(3-(5-(aminomethyl)thiophen-2-yl)phenyl)-2-hydroxy-2-phenylacetate dihydrochloride

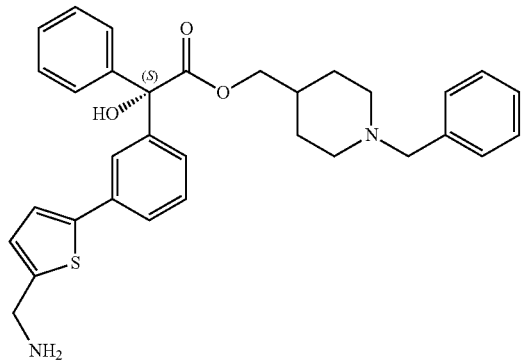

A stirred solution of (1-benzylpiperidin-4-yl)methyl (S)-2-(3-(5-(((tert-butoxycarbonyl)amino)methyl)thiophen-2-yl)phenyl)-2-hydroxy-2-phenylacetate (0.383 g, 0.61 mmol) in anhydrous 1,4-dioxane (1.4 mL) was added with a solution of HCl in dioxane (4M, 3 mL) and the mixture stirred at room temperature for 1 hour. The solvent was evaporated at reduced pressure to afford the title compound (quantitative yield).

LCMS Method 1; Rt 2.47 min; ES⁺ 583.6

Step 8: (1-Benzylpiperidin-4-yl)methyl (S)-2-(3-(5-((4-(((tert-butoxycarbonyl)((R)-2-((tert-butyldimethylsilyl)oxy)-2-(8-hydroxy-2-oxo-1,2-dihydroquinolin-5-yl)ethyl)amino)methyl)-2-chlorobenzamido)methyl)thiophen-2-yl)phenyl)-2-hydroxy-2-phenylacetate

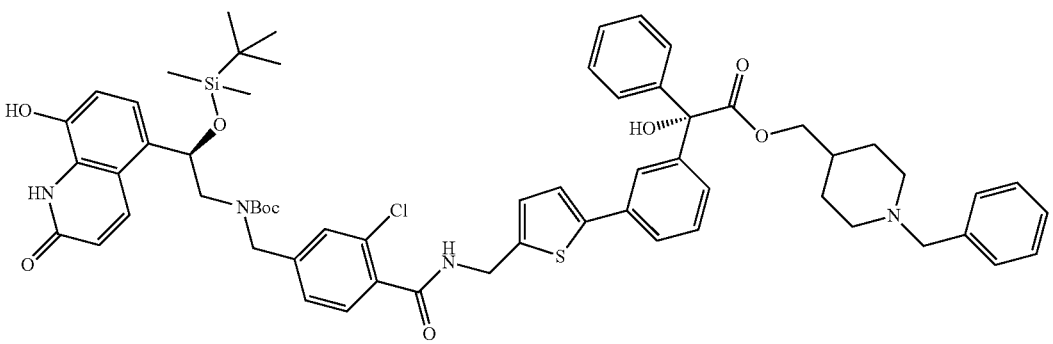 [SMILES: CC(C)(C)OC(=O)N(Cc1ccc(C(=O)NCc2ccc(-c3cccc([C@](O)(C(=O)OCC4CCN(Cc5ccccc5)CC4)c4ccccc4)c3)s2)c(Cl)c1)C[C@H](O[Si](C)(C)C(C)(C)C)c1ccc(O)c2[nH]c(=O)ccc12]

DMF (4 mL) was added to (R)-4-(((tert-butoxycarbonyl)(2-((tert-butyldimethylsilyl)oxy)-2-(8-hydroxy-2-oxo-1,2-dihydroquinolin-5-yl)ethyl)amino)methyl)-2-chlorobenzoic acid (0.154 g, 0.25 mmol), EDCI (0.049 g, 0.24 mmol), HOBT (0.034 g, 0.26 mmol) and 4-DMAP (0.031 g, 0.26 mmol). The reaction mixture was stirred at room temperature for 5 minutes and then a solution of (1-benzylpiperidin-4-yl)methyl (S)-2-(3-(5-(aminomethyl)thiophen-2-yl)phenyl)-2-hydroxy-2-phenylacetate dihydrochloride (0.122 g, 0.20 mmol) in DMF (1 mL) was added followed by DIPEA (0.142 mL, 0.82 mmol). The reaction mixture was stirred at room temperature for 18 hours. The reaction mixture was diluted with ethyl acetate and washed with saturated sodium hydrogen carbonate and brine. The organic phase was dried over anhydrous magnesium sulfate, filtered and the filtrate evaporated at reduced pressure. The residue was purified by reverse phase column chromatography to afford the title compound (0.18 g, 62%).

LCMS Method 1; Rt 3.33 min; ES⁺ 1112

Step 9: (1-Benzylpiperidin-4-yl)methyl (S)-2-(3-(5-((2-chloro-4-((((R)-2-hydroxy-2-(8-hydroxy-2-oxo-1,2-dihydroquinolin-5-yl)ethyl)amino)methyl)benzamido)-methyl)thiophen-2-yl)phenyl)-2-hydroxy-2-phenylacetate (Compound 1)

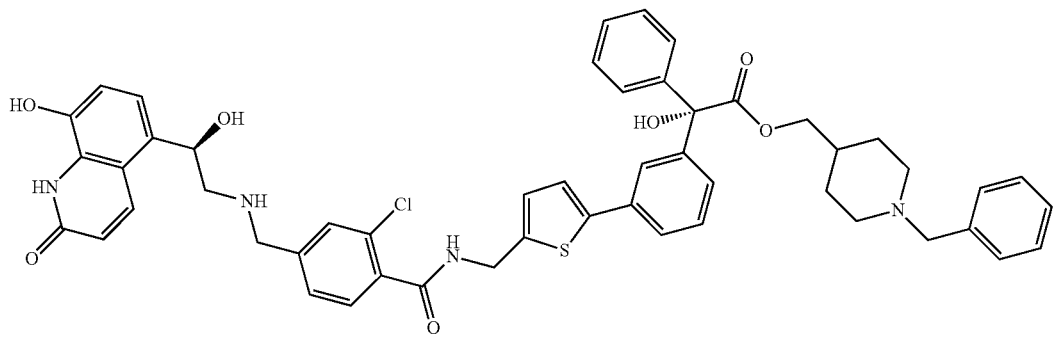 [SMILES: O=C(NCc1ccc(-c2cccc([C@](O)(C(=O)OCC3CCN(Cc4ccccc4)CC3)c3ccccc3)c2)s1)c1ccc(CNC[C@H](O)c2ccc(O)c3[nH]c(=O)ccc23)cc1Cl]

A stirred solution of (1-benzylpiperidin-4-yl)methyl (S)-2-(3-(5-((4-(((tert-butoxycarbonyl)((R)-2-((tert-butyldimethylsilyl)oxy)-2-(8-hydroxy-2-oxo-1,2-dihydroquinolin-5-yl)ethyl)amino)methyl)-2-chlorobenzamido)methyl)thiophen-2-yl)phenyl)-2-hydroxy-2-phenylacetate (0.18 g, 0.14 mmol) in 1,4-dioxane (1 mL) was added with a solution of HCl in dioxane (1 mL). The reaction mixture was stirred at room temperature for 1 hour. The solvent was evaporated at reduced pressure. The residue was purified by reverse phase column chromatography to afford the title compound.

The following compounds were prepared as described in Example 1 with the appropriate acid used in Step 8.

| Compound number | Appropriate acid |
|---|---|
| 1A | 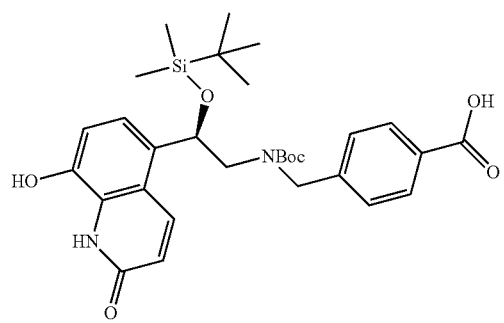 [SMILES: CC(C)(C)OC(=O)N(Cc1ccc(C(=O)O)cc1)C[C@H](O[Si](C)(C)C(C)(C)C)c1ccc(O)c2[nH]c(=O)ccc12] |
| 1B | 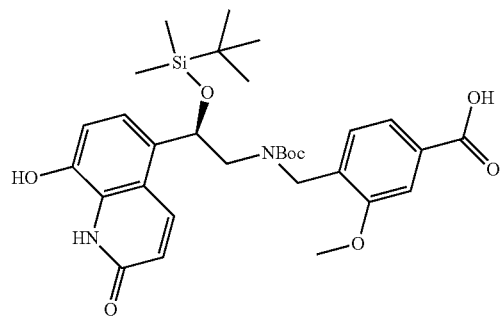 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |

1C 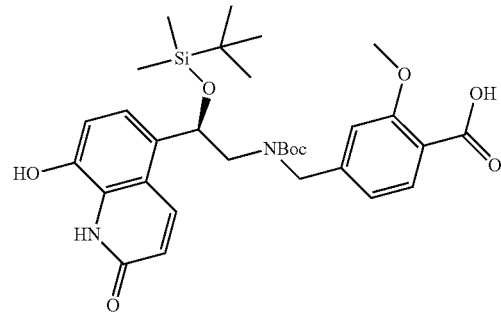 [SMILES: COc1cc(CN(C[C@H](O[Si](C)(C)C(C)(C)C)c2ccc(O)c3[nH]c(=O)ccc23)C(=O)OC(C)(C)C)ccc1C(=O)O]
1D 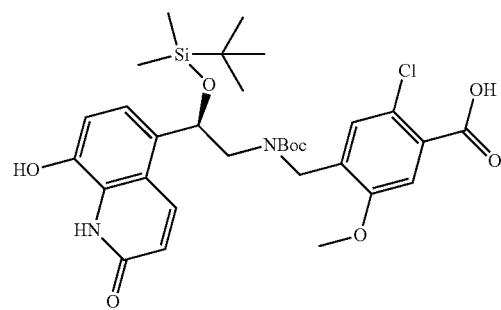 [SMILES: COc1cc(C(=O)O)c(Cl)cc1CN(C[C@H](O[Si](C)(C)C(C)(C)C)c1ccc(O)c2[nH]c(=O)ccc12)C(=O)OC(C)(C)C]
1E 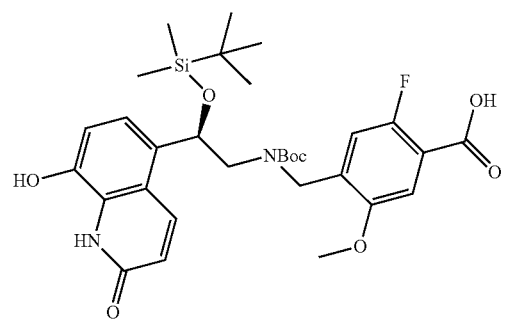 [SMILES: COc1cc(C(=O)O)c(F)cc1CN(C[C@H](O[Si](C)(C)C(C)(C)C)c1ccc(O)c2[nH]c(=O)ccc12)C(=O)OC(C)(C)C]
1F 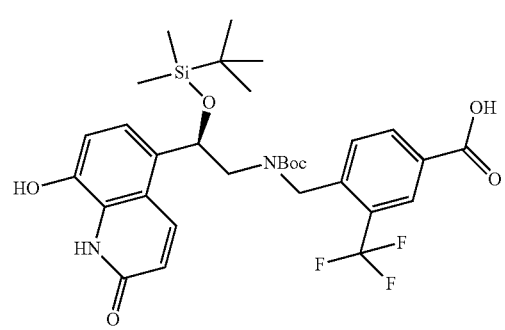 [SMILES: CC(C)(C)OC(=O)N(Cc1ccc(C(=O)O)cc1C(F)(F)F)C[C@H](O[Si](C)(C)C(C)(C)C)c1ccc(O)c2[nH]c(=O)ccc12]
1G 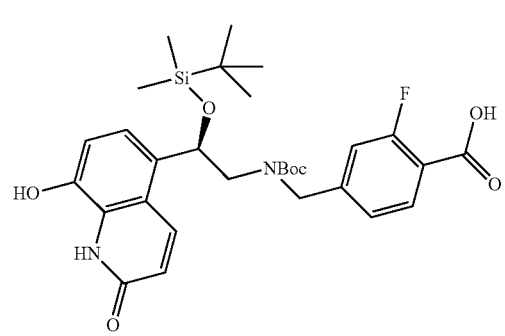 [SMILES: CC(C)(C)OC(=O)N(Cc1ccc(C(=O)O)c(F)c1)C[C@H](O[Si](C)(C)C(C)(C)C)c1ccc(O)c2[nH]c(=O)ccc12]

-continued
1H
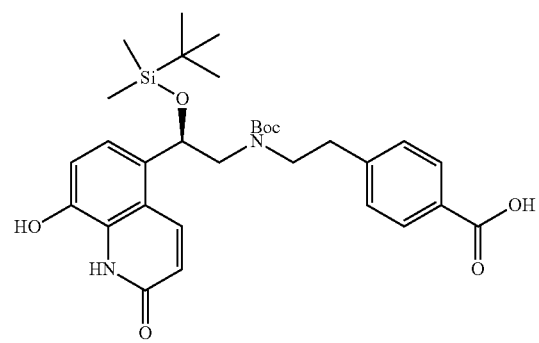 [SMILES: CC(C)(C)OC(=O)N(CCc1ccc(C(=O)O)cc1)C[C@H](O[Si](C)(C)C(C)(C)C)c1ccc(O)c2[nH]c(=O)ccc12]
1I
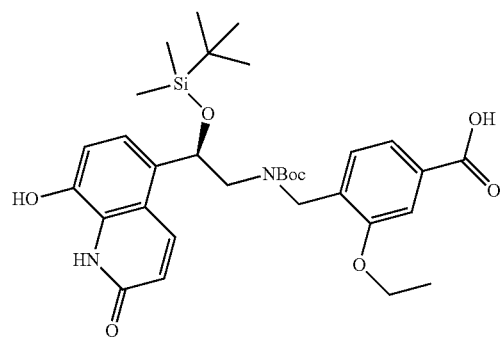 [SMILES: CCOc1cc(C(=O)O)ccc1CN(C[C@H](O[Si](C)(C)C(C)(C)C)c1ccc(O)c2[nH]c(=O)ccc12)C(=O)OC(C)(C)C]
1J
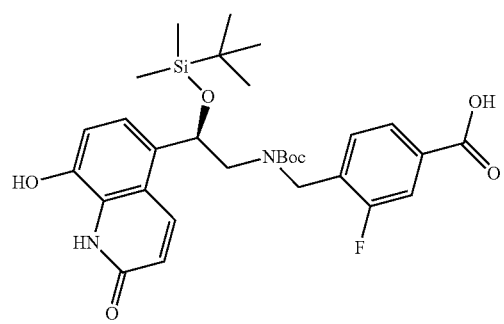 [SMILES: CC(C)(C)OC(=O)N(Cc1ccc(C(=O)O)cc1F)C[C@H](O[Si](C)(C)C(C)(C)C)c1ccc(O)c2[nH]c(=O)ccc12]
1K
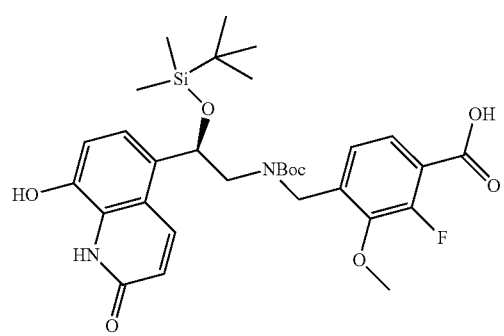 [SMILES: COc1c(CN(C[C@H](O[Si](C)(C)C(C)(C)C)c2ccc(O)c3[nH]c(=O)ccc23)C(=O)OC(C)(C)C)ccc(C(=O)O)c1F]

1L 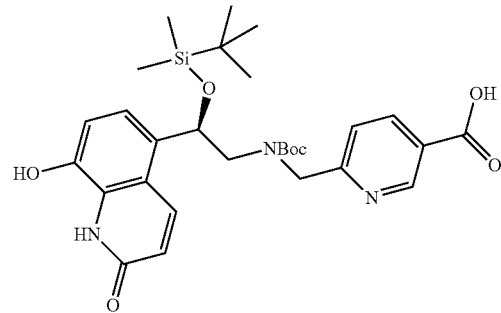 [SMILES: CC(C)(C)OC(=O)N(Cc1ccc(C(=O)O)cn1)C[C@H](O[Si](C)(C)C(C)(C)C)c1ccc(O)c2[nH]c(=O)ccc12]
1M 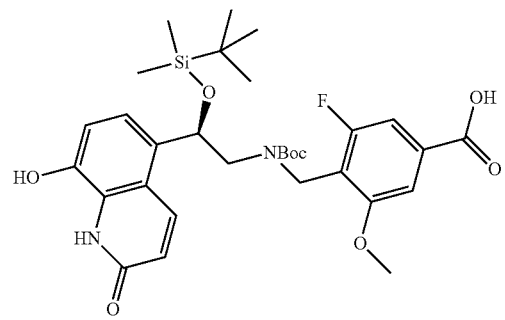 [SMILES: COc1cc(C(=O)O)cc(F)c1CN(C[C@H](O[Si](C)(C)C(C)(C)C)c1ccc(O)c2[nH]c(=O)ccc12)C(=O)OC(C)(C)C]
1N 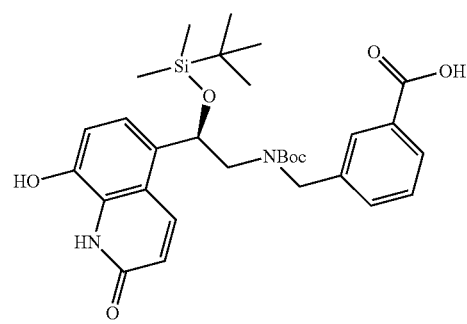 [SMILES: CC(C)(C)OC(=O)N(Cc1cccc(C(=O)O)c1)C[C@H](O[Si](C)(C)C(C)(C)C)c1ccc(O)c2[nH]c(=O)ccc12]
1O 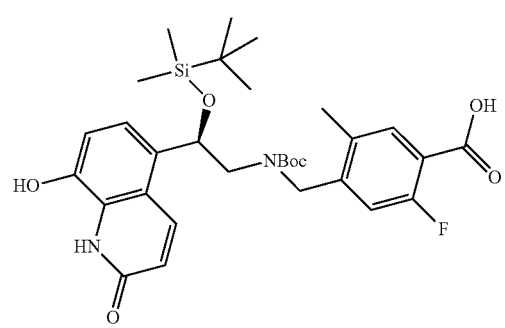 [SMILES: Cc1cc(C(=O)O)c(F)cc1CN(C[C@H](O[Si](C)(C)C(C)(C)C)c1ccc(O)c2[nH]c(=O)ccc12)C(=O)OC(C)(C)C]
1P 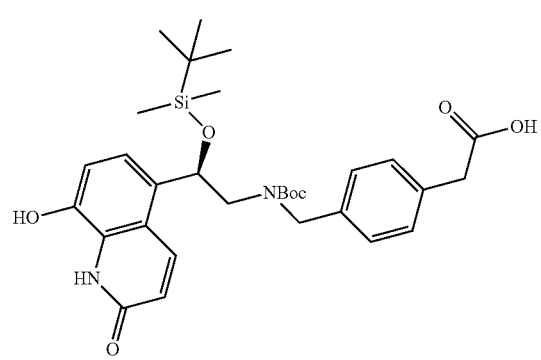 [SMILES: CC(C)(C)OC(=O)N(Cc1ccc(CC(=O)O)cc1)C[C@H](O[Si](C)(C)C(C)(C)C)c1ccc(O)c2[nH]c(=O)ccc12]

1Q 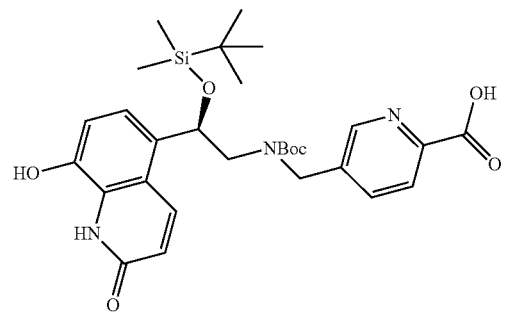 [SMILES: CC(C)(C)OC(=O)N(Cc1ccc(C(=O)O)nc1)C[C@H](O[Si](C)(C)C(C)(C)C)c1ccc(O)c2[nH]c(=O)ccc12]
1R 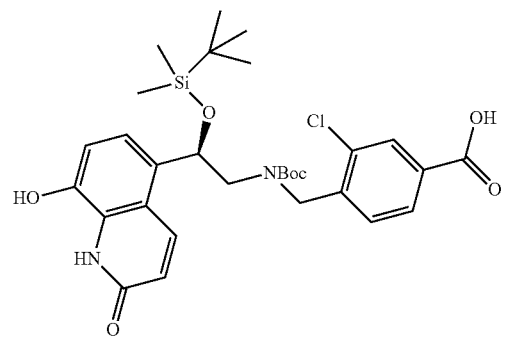 [SMILES: CC(C)(C)OC(=O)N(Cc1ccc(C(=O)O)cc1Cl)C[C@H](O[Si](C)(C)C(C)(C)C)c1ccc(O)c2[nH]c(=O)ccc12]
1S 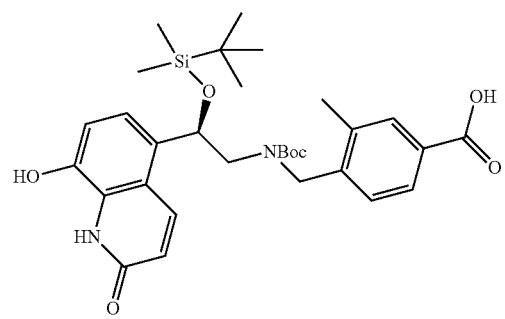 [SMILES: Cc1cc(C(=O)O)ccc1CN(C[C@H](O[Si](C)(C)C(C)(C)C)c1ccc(O)c2[nH]c(=O)ccc12)C(=O)OC(C)(C)C]
1T 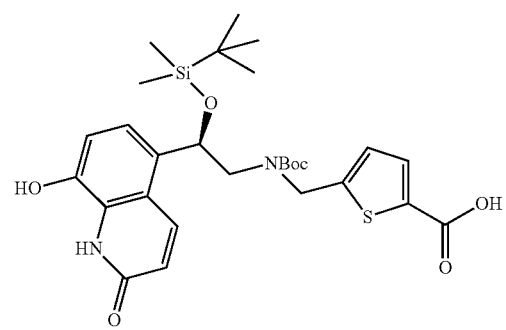 [SMILES: CC(C)(C)OC(=O)N(Cc1ccc(C(=O)O)s1)C[C@H](O[Si](C)(C)C(C)(C)C)c1ccc(O)c2[nH]c(=O)ccc12]
1U 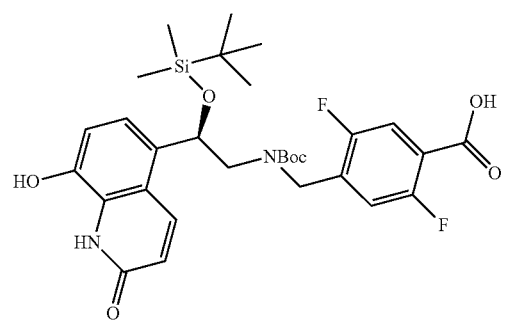 [SMILES: CC(C)(C)OC(=O)N(Cc1cc(F)c(C(=O)O)cc1F)C[C@H](O[Si](C)(C)C(C)(C)C)c1ccc(O)c2[nH]c(=O)ccc12]

| | |
|---|---|
| 1V | 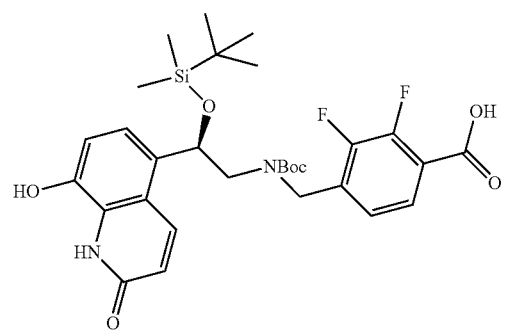 [SMILES: CC(C)(C)OC(=O)N(Cc1ccc(C(=O)O)c(F)c1F)C[C@H](O[Si](C)(C)C(C)(C)C)c1ccc(O)c2[nH]c(=O)ccc12] |
| 1W | 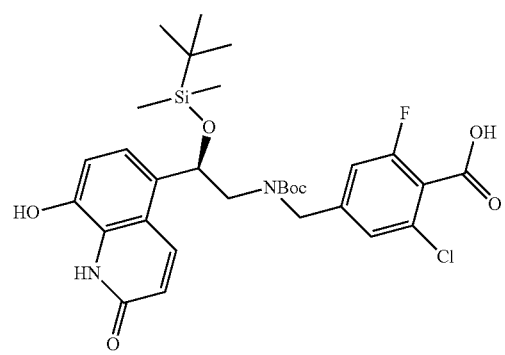 [SMILES: CC(C)(C)OC(=O)N(Cc1cc(F)c(C(=O)O)c(Cl)c1)C[C@H](O[Si](C)(C)C(C)(C)C)c1ccc(O)c2[nH]c(=O)ccc12] |
| 1X | 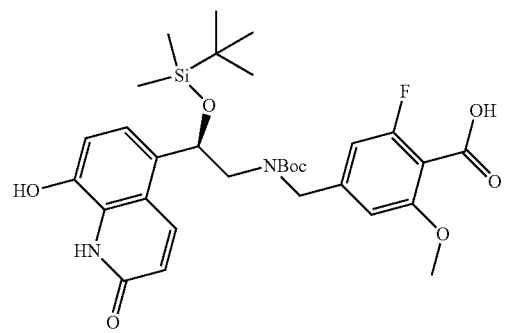 [SMILES: COc1cc(CN(C[C@H](O[Si](C)(C)C(C)(C)C)c2ccc(O)c3[nH]c(=O)ccc23)C(=O)OC(C)(C)C)cc(F)c1C(=O)O] |
| Compound number | Structure |
|---|---|
| 1A | 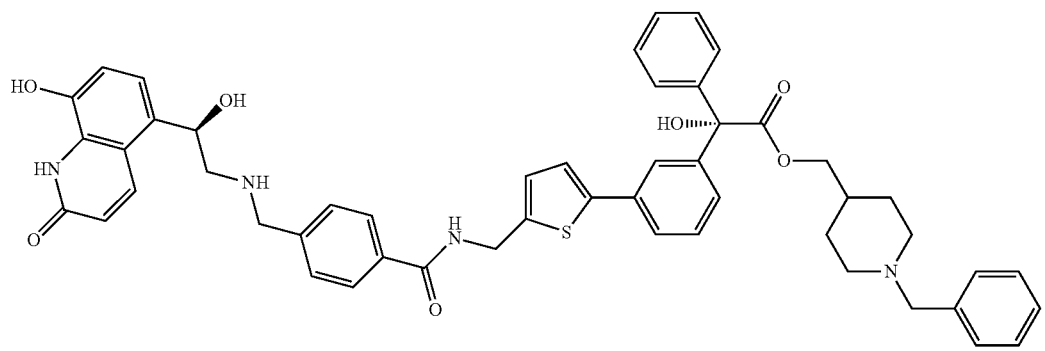 [SMILES: O=C(NCc1ccc(-c2cccc([C@](O)(C(=O)OCC3CCN(Cc4ccccc4)CC3)c3ccccc3)c2)s1)c1ccc(CNC[C@H](O)c2ccc(O)c3[nH]c(=O)ccc23)cc1] |

-continued
1B
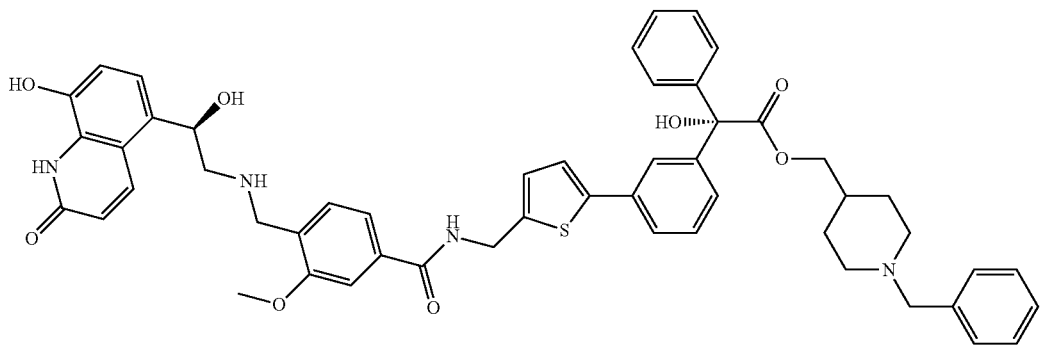 [SMILES: COc1cc(C(=O)NCc2ccc(-c3cccc([C@](O)(C(=O)OCC4CCN(Cc5ccccc5)CC4)c4ccccc4)c3)s2)ccc1CNC[C@H](O)c1ccc(O)c2[nH]c(=O)ccc12]
1C
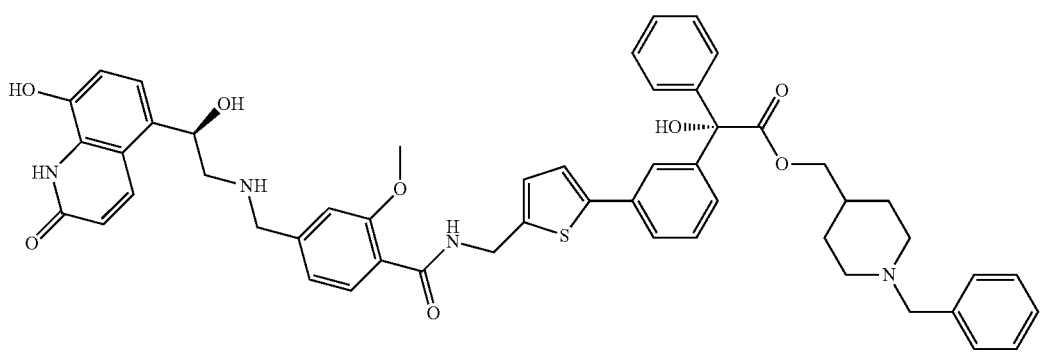 [SMILES: COc1cc(CNC[C@H](O)c2ccc(O)c3[nH]c(=O)ccc23)ccc1C(=O)NCc1ccc(-c2cccc([C@](O)(C(=O)OCC3CCN(Cc4ccccc4)CC3)c3ccccc3)c2)s1]
1D
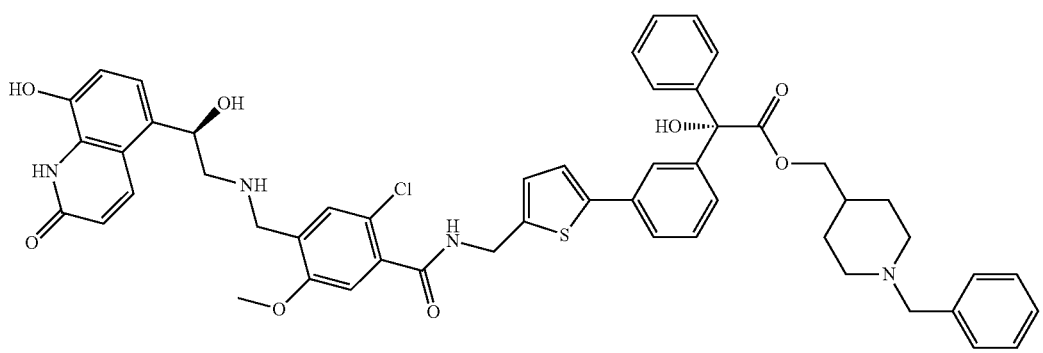 [SMILES: COc1cc(C(=O)NCc2ccc(-c3cccc([C@](O)(C(=O)OCC4CCN(Cc5ccccc5)CC4)c4ccccc4)c3)s2)c(Cl)cc1CNC[C@H](O)c1ccc(O)c2[nH]c(=O)ccc12]
1E
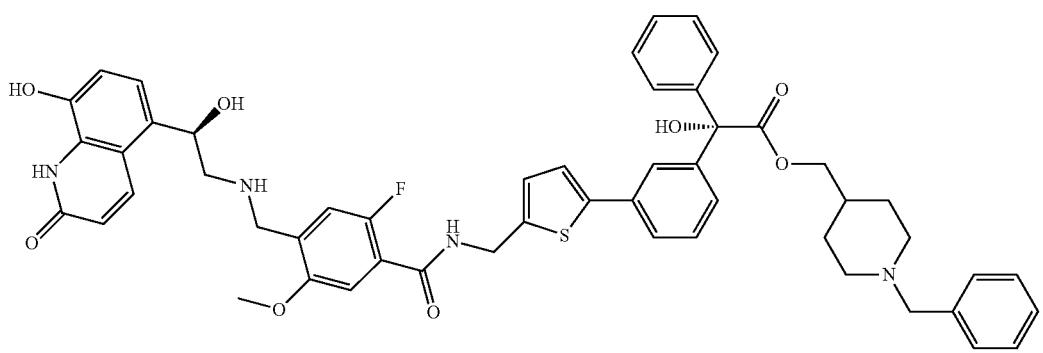 [SMILES: COc1cc(C(=O)NCc2ccc(-c3cccc([C@](O)(C(=O)OCC4CCN(Cc5ccccc5)CC4)c4ccccc4)c3)s2)c(F)cc1CNC[C@H](O)c1ccc(O)c2[nH]c(=O)ccc12]

1F
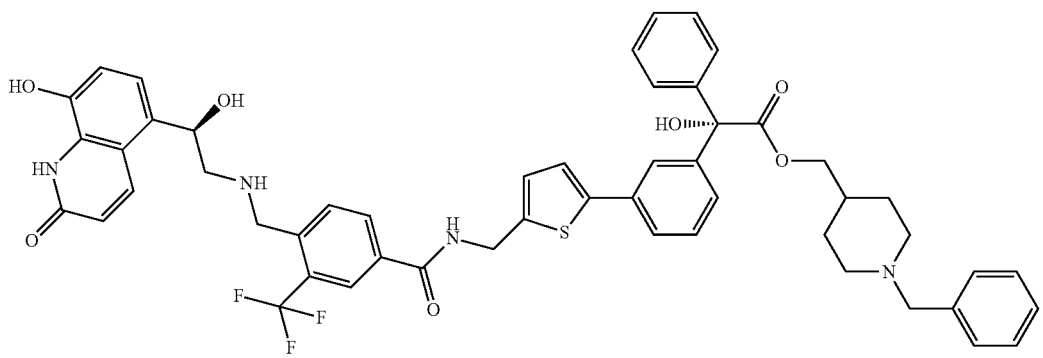 [SMILES: O=C(NCc1ccc(-c2cccc([C@](O)(C(=O)OCC3CCN(Cc4ccccc4)CC3)c3ccccc3)c2)s1)c1ccc(CNC[C@H](O)c2ccc(O)c3[nH]c(=O)ccc23)c(C(F)(F)F)c1]
1G
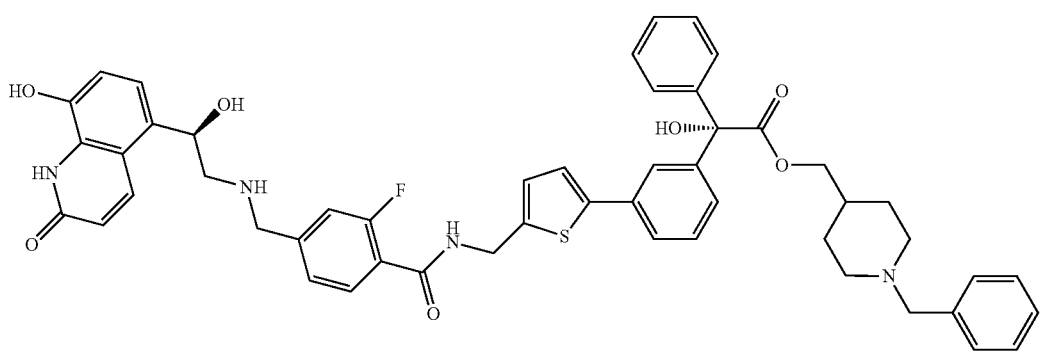
1H
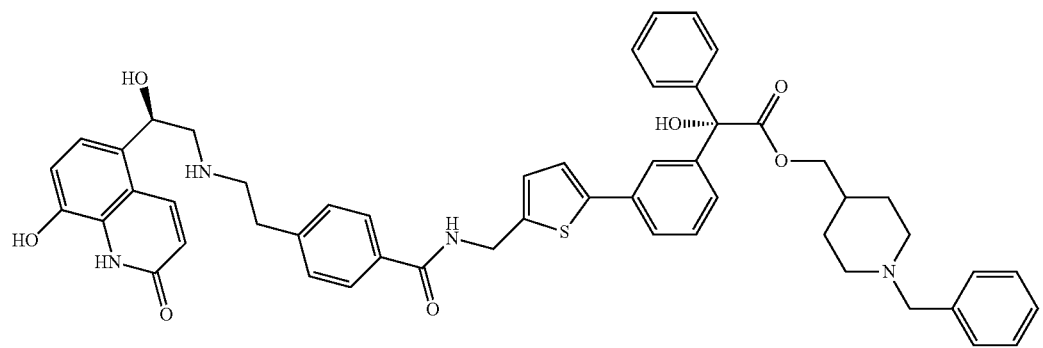 [SMILES: O=C(NCc1ccc(-c2cccc([C@](O)(C(=O)OCC3CCN(Cc4ccccc4)CC3)c3ccccc3)c2)s1)c1ccc(CCNC[C@H](O)c2ccc(O)c3[nH]c(=O)ccc23)cc1]
1I
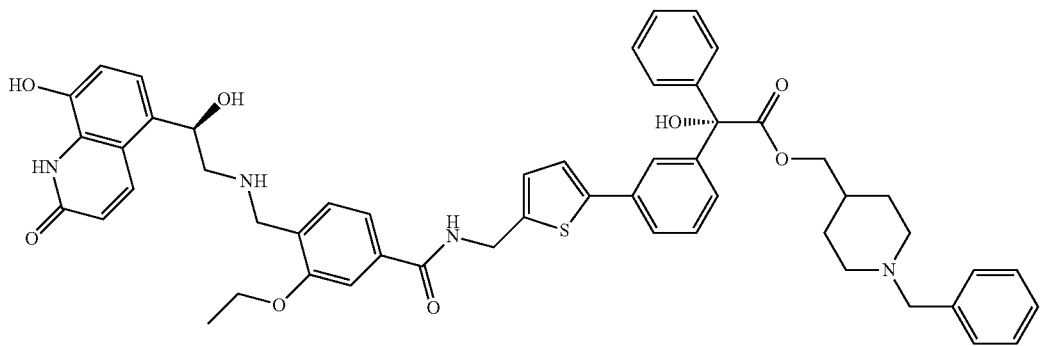 [SMILES: CCOc1cc(C(=O)NCc2ccc(-c3cccc([C@](O)(C(=O)OCC4CCN(Cc5ccccc5)CC4)c4ccccc4)c3)s2)ccc1CNC[C@H](O)c1ccc(O)c2[nH]c(=O)ccc12]

1J
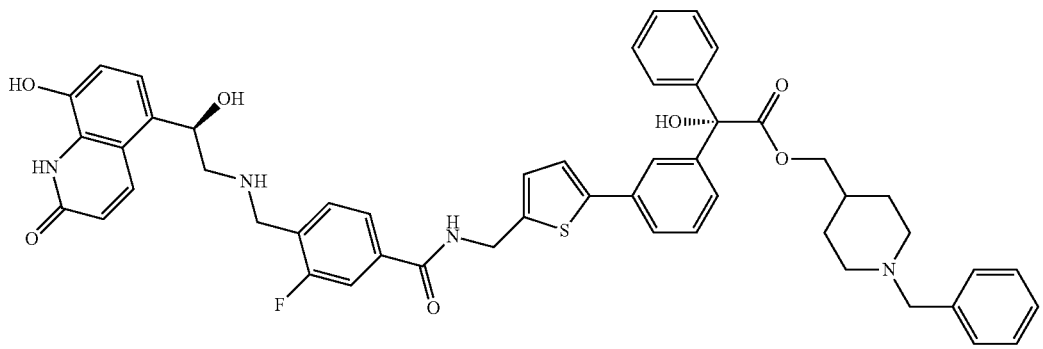 [SMILES: O=C(NCc1ccc(-c2cccc([C@](O)(C(=O)OCC3CCN(Cc4ccccc4)CC3)c3ccccc3)c2)s1)c1ccc(CNC[C@H](O)c2ccc(O)c3[nH]c(=O)ccc23)c(F)c1]
1K
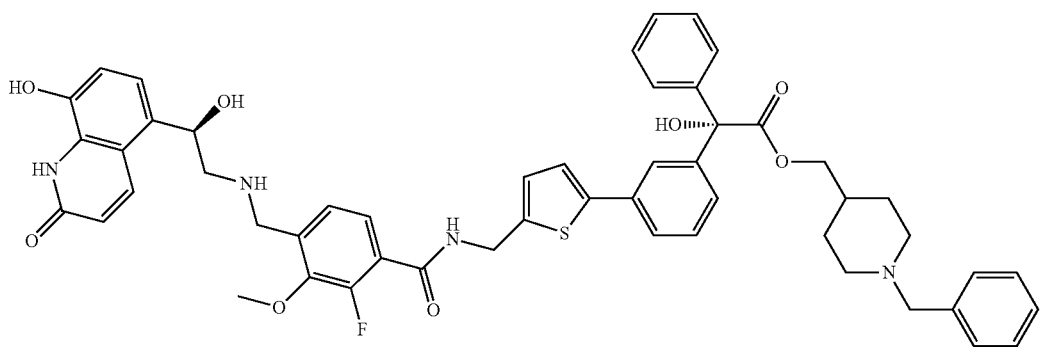 [SMILES: COc1c(CNC[C@H](O)c2ccc(O)c3[nH]c(=O)ccc23)ccc(C(=O)NCc2ccc(-c3cccc([C@](O)(C(=O)OCC4CCN(Cc5ccccc5)CC4)c4ccccc4)c3)s2)c1F]
1L
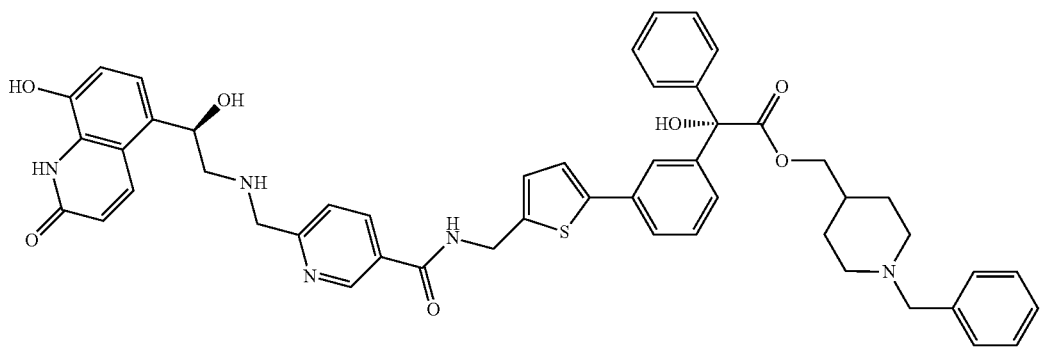
1M
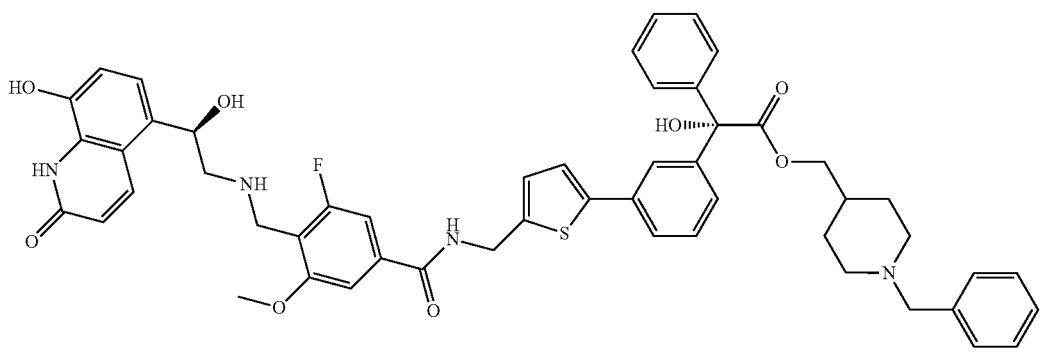 [SMILES: COc1cc(C(=O)NCc2ccc(-c3cccc([C@](O)(C(=O)OCC4CCN(Cc5ccccc5)CC4)c4ccccc4)c3)s2)cc(F)c1CNC[C@H](O)c1ccc(O)c2[nH]c(=O)ccc12]

1N 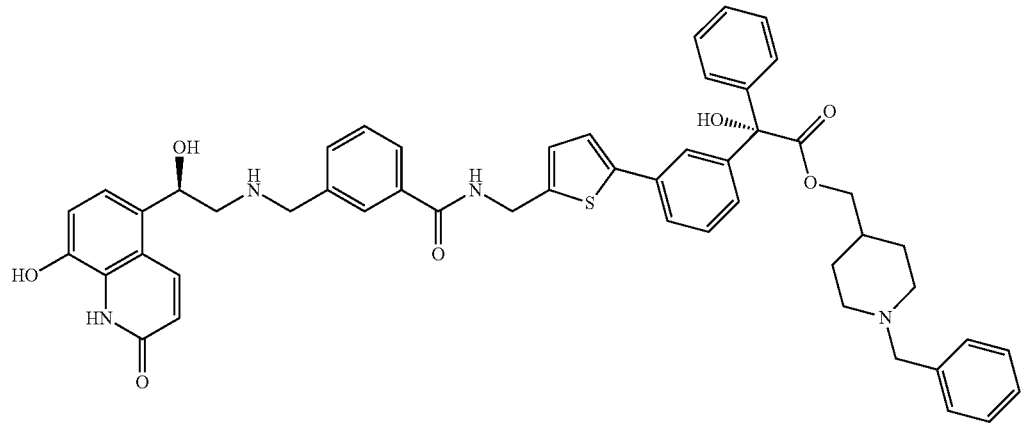 [SMILES: O=C(NCc1ccc(-c2cccc([C@](O)(C(=O)OCC3CCN(Cc4ccccc4)CC3)c3ccccc3)c2)s1)c1cccc(CNC[C@H](O)c2ccc(O)c3[nH]c(=O)ccc23)c1]
1O 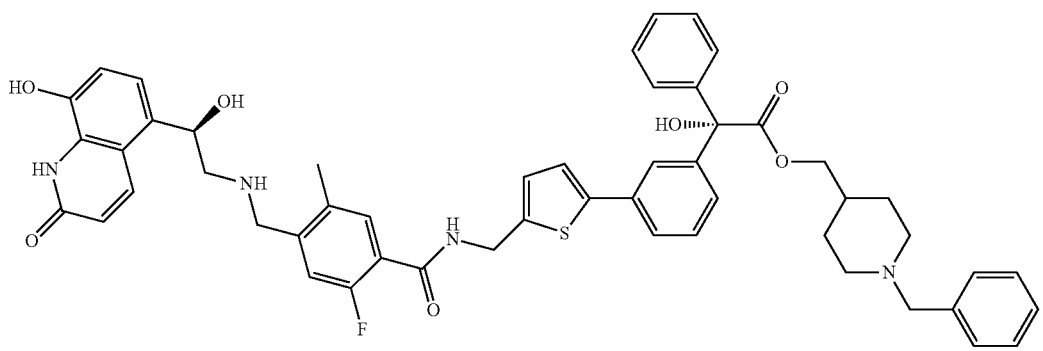 [SMILES: Cc1cc(C(=O)NCc2ccc(-c3cccc([C@](O)(C(=O)OCC4CCN(Cc5ccccc5)CC4)c4ccccc4)c3)s2)c(F)cc1CNC[C@H](O)c1ccc(O)c2[nH]c(=O)ccc12]
1P 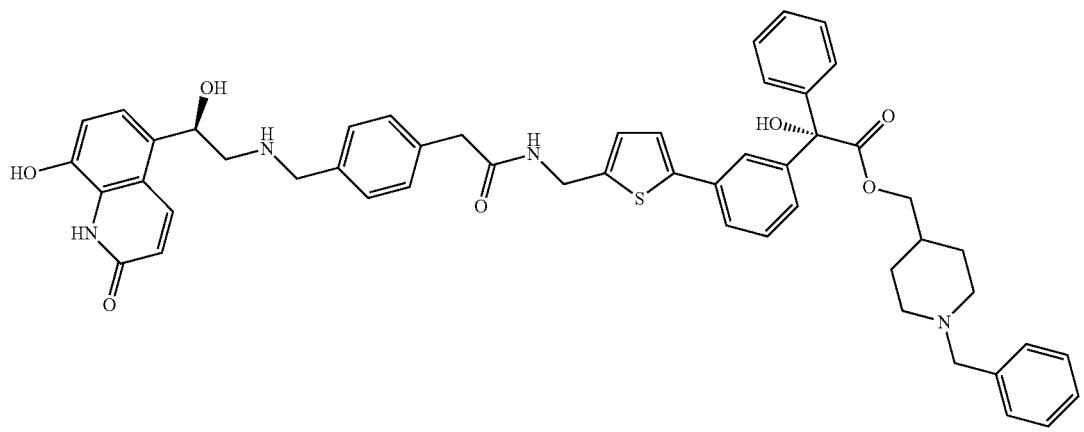 [SMILES: O=C(Cc1ccc(CNC[C@H](O)c2ccc(O)c3[nH]c(=O)ccc23)cc1)NCc1ccc(-c2cccc([C@](O)(C(=O)OCC3CCN(Cc4ccccc4)CC3)c3ccccc3)c2)s1]
1Q 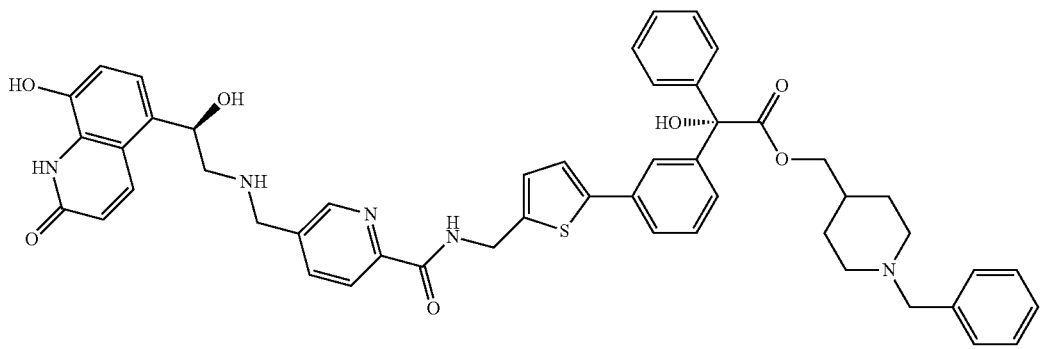 [SMILES: O=C(NCc1ccc(-c2cccc([C@](O)(C(=O)OCC3CCN(Cc4ccccc4)CC3)c3ccccc3)c2)s1)c1ccc(CNC[C@H](O)c2ccc(O)c3[nH]c(=O)ccc23)cn1]

1R
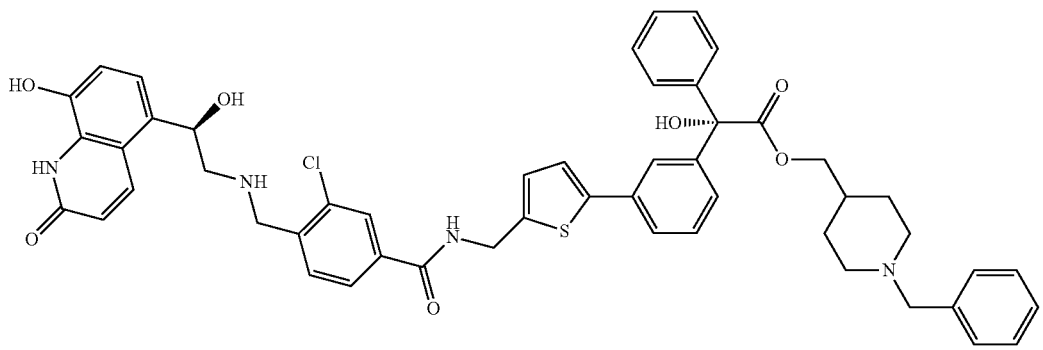 [SMILES: O=C(NCc1ccc(-c2cccc([C@](O)(C(=O)OCC3CCN(Cc4ccccc4)CC3)c3ccccc3)c2)s1)c1ccc(CNC[C@H](O)c2ccc(O)c3[nH]c(=O)ccc23)c(Cl)c1]
1S
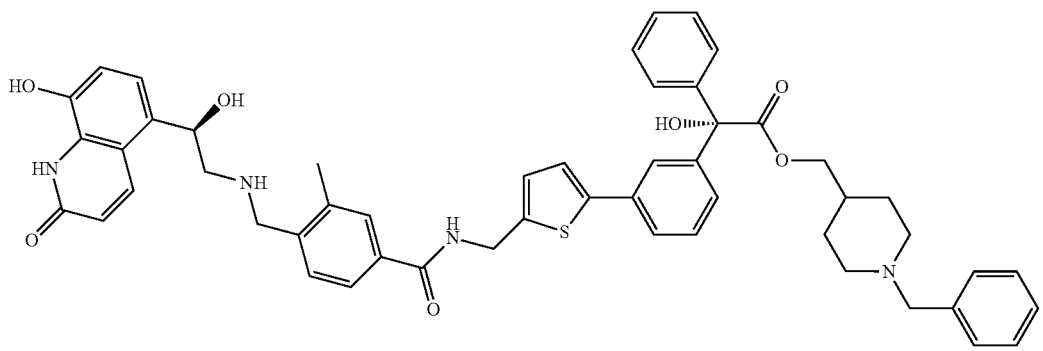 [SMILES: Cc1cc(C(=O)NCc2ccc(-c3cccc([C@](O)(C(=O)OCC4CCN(Cc5ccccc5)CC4)c4ccccc4)c3)s2)ccc1CNC[C@H](O)c1ccc(O)c2[nH]c(=O)ccc12]
1T
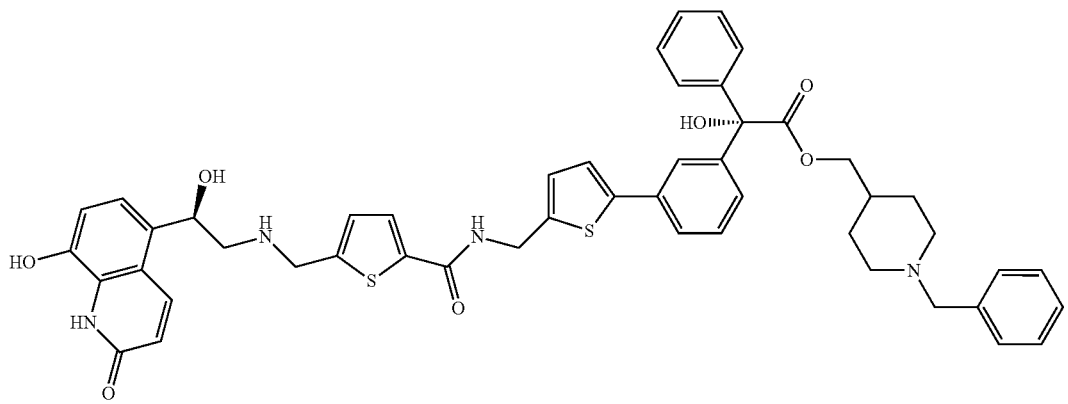 [SMILES: O=C(NCc1ccc(-c2cccc([C@](O)(C(=O)OCC3CCN(Cc4ccccc4)CC3)c3ccccc3)c2)s1)c1ccc(CNC[C@H](O)c2ccc(O)c3[nH]c(=O)ccc23)s1]
1U
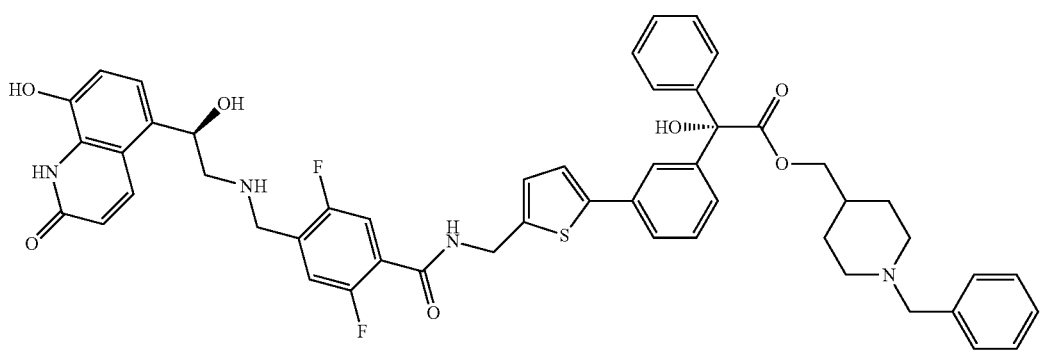 [SMILES: O=C(NCc1ccc(-c2cccc([C@](O)(C(=O)OCC3CCN(Cc4ccccc4)CC3)c3ccccc3)c2)s1)c1cc(F)c(CNC[C@H](O)c2ccc(O)c3[nH]c(=O)ccc23)cc1F]

-continued
1V
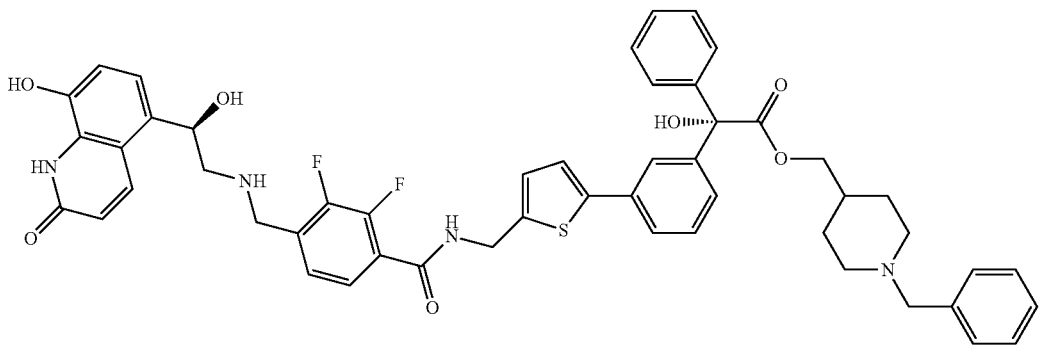 [SMILES: O=C(NCc1ccc(-c2cccc([C@](O)(C(=O)OCC3CCN(Cc4ccccc4)CC3)c3ccccc3)c2)s1)c1ccc(CNC[C@H](O)c2ccc(O)c3[nH]c(=O)ccc23)c(F)c1F]
1W
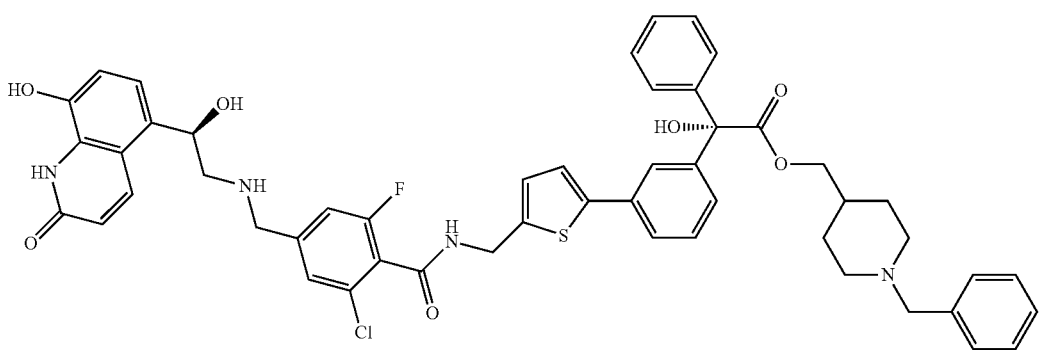 [SMILES: O=C(NCc1ccc(-c2cccc([C@](O)(C(=O)OCC3CCN(Cc4ccccc4)CC3)c3ccccc3)c2)s1)c1c(F)cc(CNC[C@H](O)c2ccc(O)c3[nH]c(=O)ccc23)cc1Cl]
1X
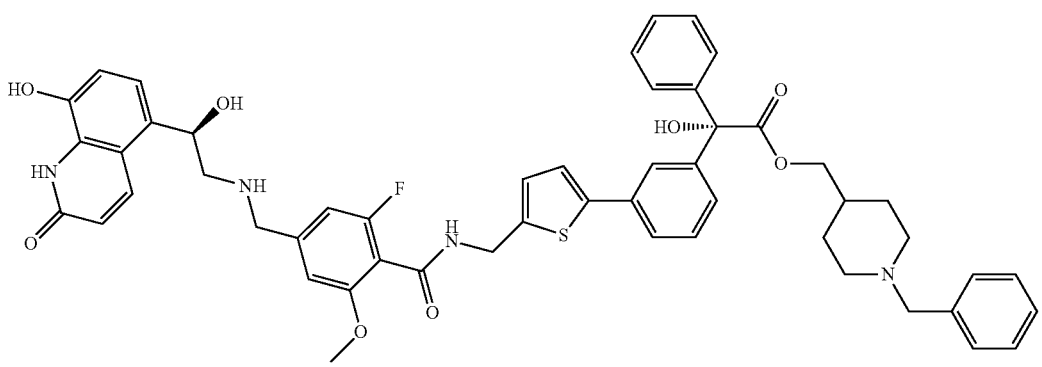 [SMILES: COc1cc(CNC[C@H](O)c2ccc(O)c3[nH]c(=O)ccc23)cc(F)c1C(=O)NCc1ccc(-c2cccc([C@](O)(C(=O)OCC3CCN(Cc4ccccc4)CC3)c3ccccc3)c2)s1]
Scheme 2
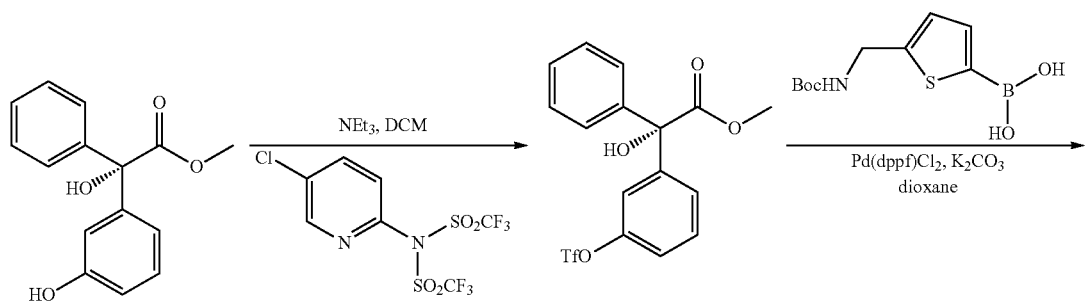

111 112
-continued
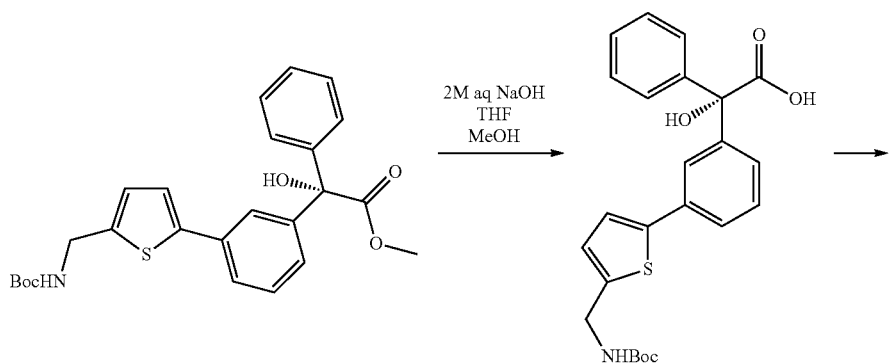
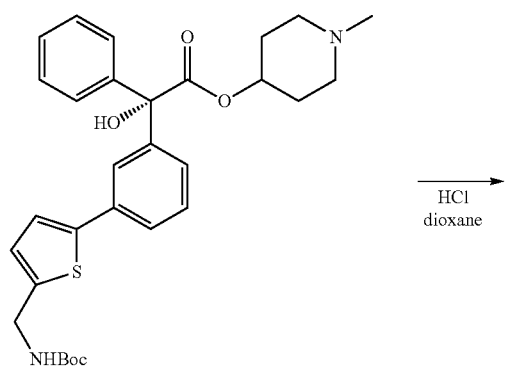
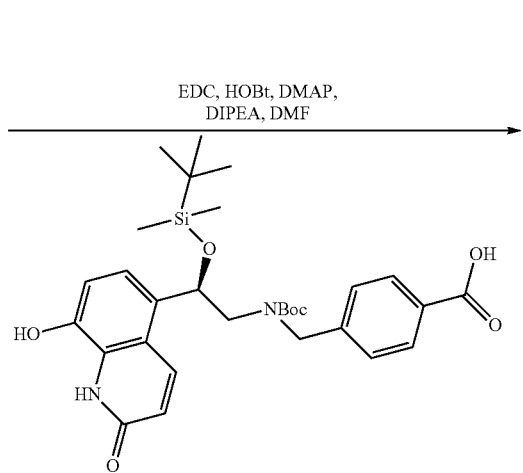
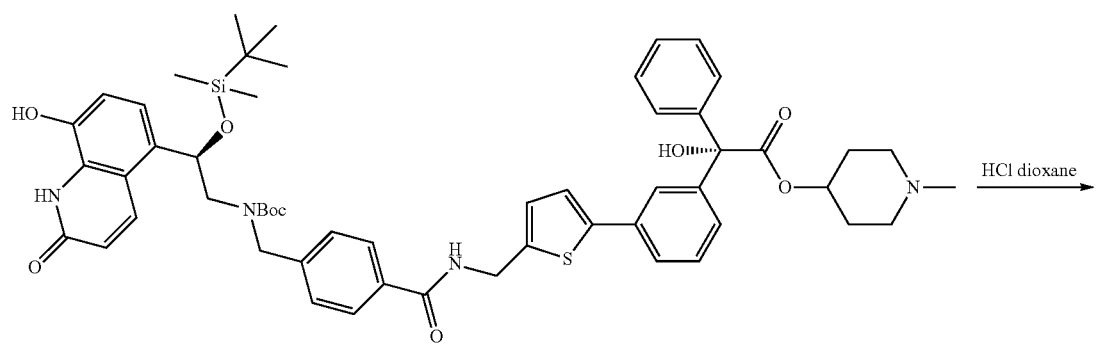

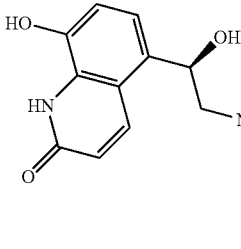

Example 2
1-Methylpiperidin-4-yl (S)-2-hydroxy-2-(3-(5-((4-((((R)-2-hydroxy-2-(8-hydroxy-2-oxo-1,2-dihydroquinolin-5-yl)ethyl)amido)methyl)-thiophen-2-yl)phenyl)-2-phenylacetate (Compound 2)

Step 1: Methyl (S)-2-hydroxy-2-phenyl-2-(3-(((trifluoromethyl)sulfonyl)oxy)-phenyl)acetate

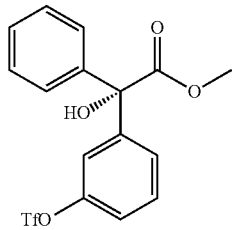 [SMILES: COC(=O)[C@](O)(c1ccccc1)c1cccc(OS(=O)(=O)C(F)(F)F)c1]

A stirred solution of (S)-2-hydroxy-2-(3-hydroxyphenyl)-2-phenylacetic acid (2.5 g, 9.68 mmol) in DCM (50 mL) was added with 2-[N,N-bis(trifluoromethanesulfonyl)-amino]-5-chloropyridine (4.55 g, 11.6 mmol) and triethylamine (2.69 mL 19.4 mmol) and the reaction mixture stirred at room temperature for 18 hours. The reaction mixture was washed with saturated aqueous sodium hydrogen carbonate (×2) and brine (×2). The organic phase was dried over anhydrous magnesium sulfate, filtered and the filtrate evaporated at reduced pressure. The residue was purified by flash column chromatography (eluent—100% iso-hexane to 2:1 iso-hexane/ethyl acetate) to afford the title compound (3.7 g, 98%).
LCMS Method 1; Rt 3.59 min; ES+ 389.

Step 2: Methyl (S)-2-(3-(5-(((tert-butoxycarbonyl)amino)methyl)thiophen-2-yl)phenyl)-2-hydroxy-2-phenylacetate

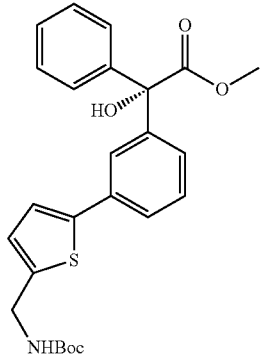 [SMILES: COC(=O)[C@](O)(c1ccccc1)c1cccc(-c2ccc(CNC(=O)OC(C)(C)C)s2)c1]

The title compound was prepared as described in Example 1 Step 6
LCMS Method 1; Rt 3.64 min; ES+M+Na 476.

Step 3: (S)-2-(3-(5-(((tert-Butoxycarbonyl)amino)methyl)thiophen-2-yl)phenyl)-2-hydroxy-2-phenylacetic acid

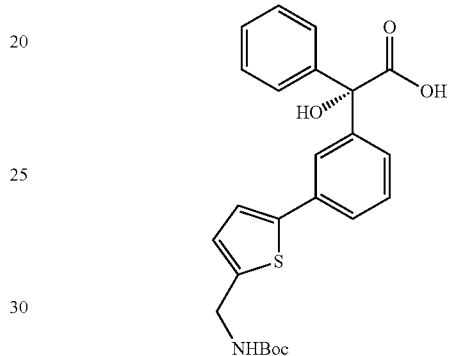

A solution of methyl (S)-2-(3-(5-(((tert-butoxycarbonyl)amino)methyl)thiophen-2-yl)phenyl)-2-hydroxy-2-phenylacetate (3.8 g, 8.38 mmol) in THF/methanol (20 mL/20 mL) was added with a solution of aqueous 2M sodium hydroxide (25 mL) and the reaction mixture was stirred at room temperature for 2 hours. The reaction mixture was concentrated to ⅓ volume and the pH adjusted to 3 with 2M aqueous hydrochloric acid. The aqueous phase was extracted with ethyl acetate (×3). The combined organic phases were washed with brine, dried over anhydrous magnesium sulfate, filtered and the filtrate evaporated at reduced pressure to afford the title compound (3.2 g, 87%).
LCMS Method 1; Rt 3.44 min; ES– 438.

Step 4: 1-Methylpiperidin-4-yl (S)-2-(3-(5-(((tert-butoxycarbonyl)amino)-methyl)thiophen-2-yl)phenyl)-2-hydroxy-2-phenylacetate

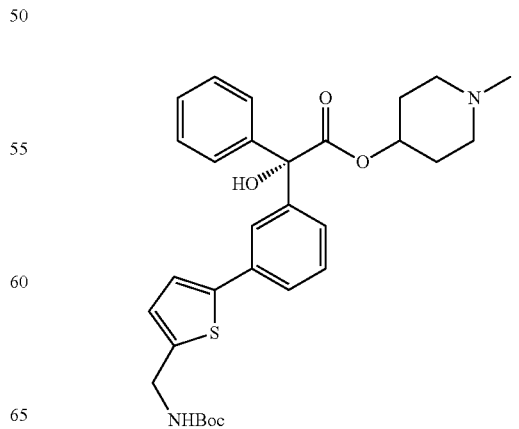

A solution of (S)-2-(3-(5-(((tert-butoxycarbonyl)amino)methyl)thiophen-2-yl)phenyl)-2-hydroxy-2-phenylacetic acid (0.20 g, 0.46 mmol) in DMF (3 mL) was added with 1,1'-carbonyldiimidazole (0.221 g, 1.36 mmol) and the mixture stirred at room temperature for 15 minutes. 1-Methyl-4-piperidinol (0.209 g, 1.82 mmol) was added and the mixture stirred at 60° C. for 18 hours. The reaction mixture was diluted with ethyl acetate and washed with saturated aqueous sodium carbonate (×2) and brine (×2). The organic phase was dried over anhydrous magnesium sulfate, filtered and the filtrate evaporated at reduced pressure to afford the title compound (0.29 g, 0.100%).

LCMS Method 1; Rt 2.86 min; ES+ 537.

Step 5: 1-Methylpiperidin-4-yl (S)-2-(3-(5-((4-(((tert-butoxycarbonyl)((R)-2-((tert-butyldimethylsilyl)oxy)-2-(8-hydroxy-2-oxo-1,2-dihydroquinolin-5-yl)ethyl)amino)methyl)benzamido)methyl)thiophen-2-yl)phenyl)-2-hydroxy-2-phenylacetate

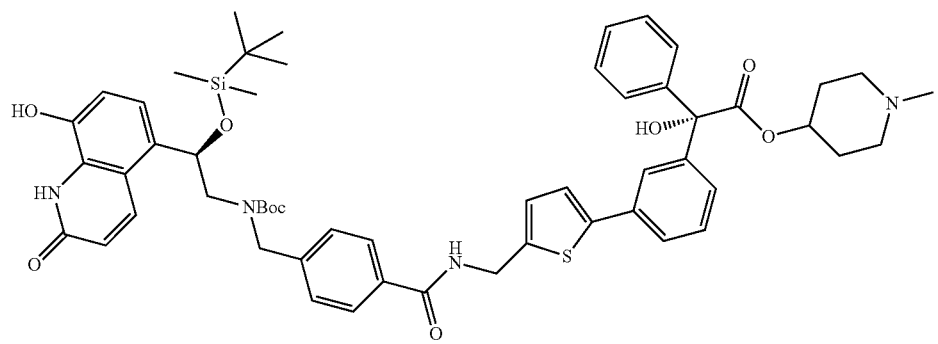 [SMILES: CN1CCC(OC(=O)[C@](O)(c2ccccc2)c2cccc(-c3ccc(CNC(=O)c4ccc(CN(C[C@H](O[Si](C)(C)C(C)(C)C)c5ccc(O)c6[nH]c(=O)ccc56)C(=O)OC(C)(C)C)cc4)s3)c2)CC1]

The title compound was prepared as described in Example 1 Step 7 and Step 8.

LCMS Method 1; Rt 3.21 min; ES+ 987.

Step 6: 1-Methylpiperidin-4-yl (S)-2-hydroxy-2-(3-(5-((4-((((R)-2-hydroxy-2-(8-hydroxy-2-oxo-1,2-dihydroquinolin-5-yl)ethyl)amino)methyl)benzamido)-methyl)thiophen-2-yl)phenyl)-2-phenylacetate (Compound 2)

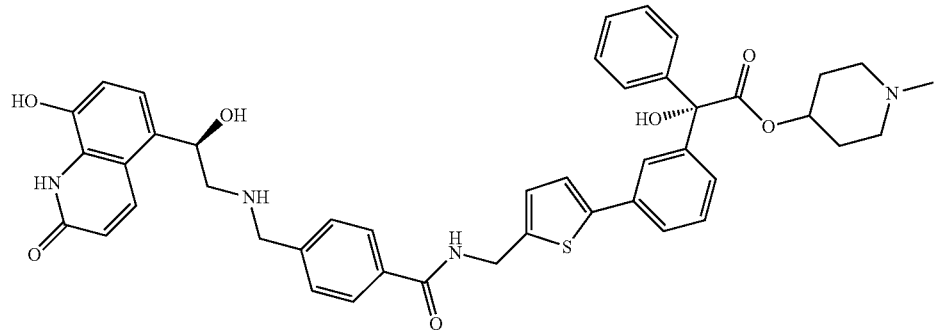 [SMILES: CN1CCC(OC(=O)[C@](O)(c2ccccc2)c2cccc(-c3ccc(CNC(=O)c4ccc(CNC[C@H](O)c5ccc(O)c6[nH]c(=O)ccc56)cc4)s3)c2)CC1]

The title compound was prepared as described in Example 1 Step 9.

The following compounds were prepared as described in Example 2 with the appropriate alcohol used in Step 4.

| Compound No. | Appropriate alcohol |
| --- | --- |
| 2A | HO—⟨piperidine-N-CH2-C6H4-OMe⟩ |
| 2B | HO—⟨N-methylpiperidine⟩ |

-continued
| | |
|---|---|
| 2C | 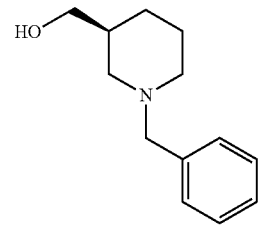 [SMILES: OC[C@H]1CCCN(Cc2ccccc2)C1] |
| 2D | 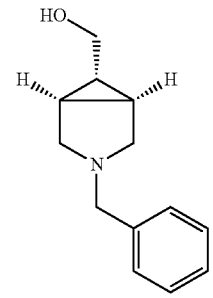 [SMILES: OC[C@@H]1[C@H]2CN(Cc3ccccc3)C[C@@H]12] |
| 2E | 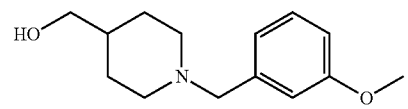 [SMILES: COc1cccc(CN2CCC(CO)CC2)c1] |
| 2F | 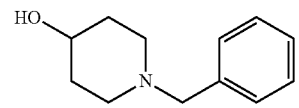 [SMILES: OC1CCN(Cc2ccccc2)CC1] |
| 2G | 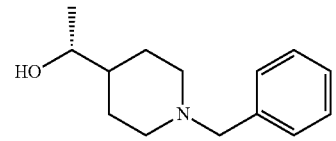 [SMILES: C[C@@H](O)C1CCN(Cc2ccccc2)CC1] |
| 2H | 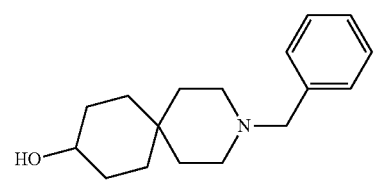 [SMILES: OC1CCC2(CC1)CCN(Cc1ccccc1)CC2] |
| Compound No. | Structure |
|---|---|
| 2A | 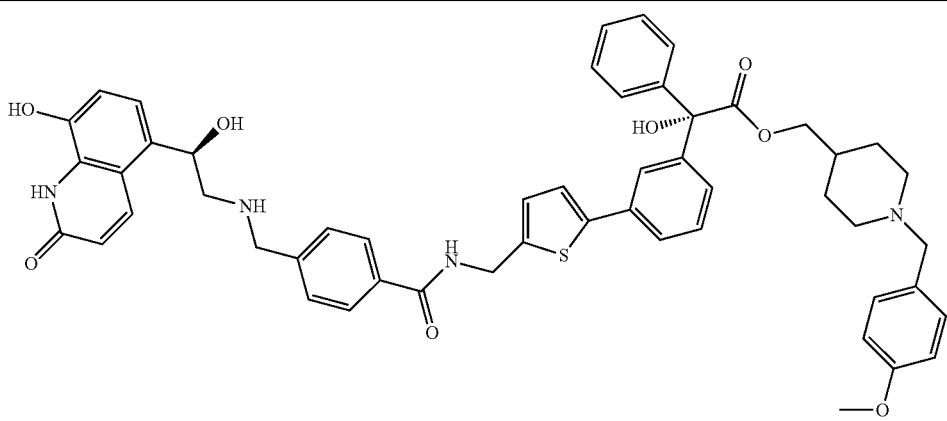 |

-continued
2B
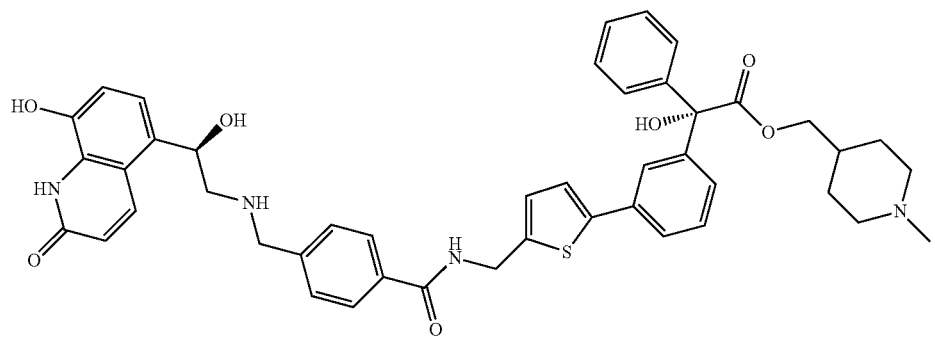 [SMILES: CN1CCC(COC(=O)[C@](O)(c2ccccc2)c2cccc(-c3ccc(CNC(=O)c4ccc(CNC[C@H](O)c5ccc(O)c6[nH]c(=O)ccc56)cc4)s3)c2)CC1]
2C
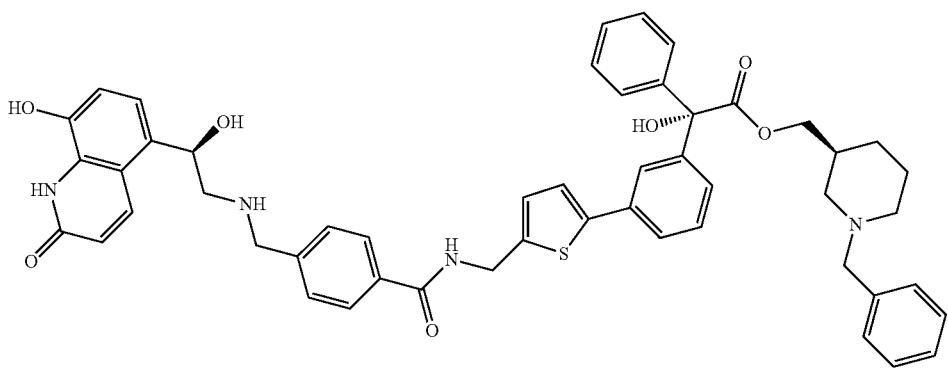 [SMILES: O=C(NCc1ccc(-c2cccc([C@](O)(C(=O)OC[C@H]3CCCN(Cc4ccccc4)C3)c3ccccc3)c2)s1)c1ccc(CNC[C@H](O)c2ccc(O)c3[nH]c(=O)ccc23)cc1]
2D
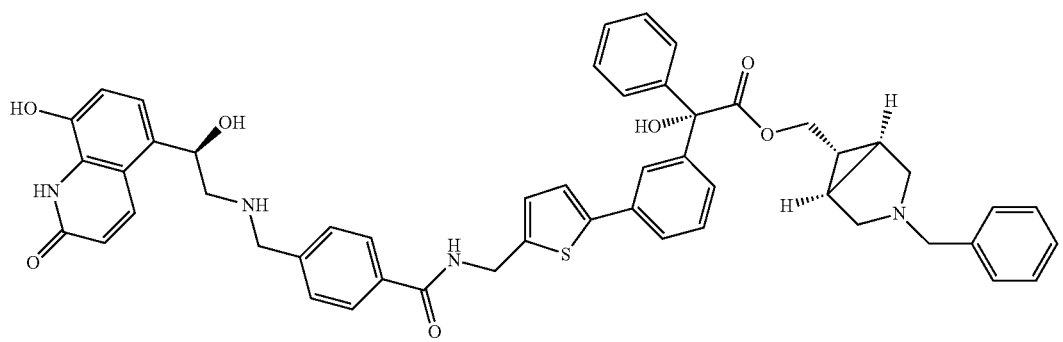 [SMILES: O=C(NCc1ccc(-c2cccc([C@](O)(C(=O)OC[C@@H]3[C@H]4CN(Cc5ccccc5)C[C@@H]34)c3ccccc3)c2)s1)c1ccc(CNC[C@H](O)c2ccc(O)c3[nH]c(=O)ccc23)cc1]
2E
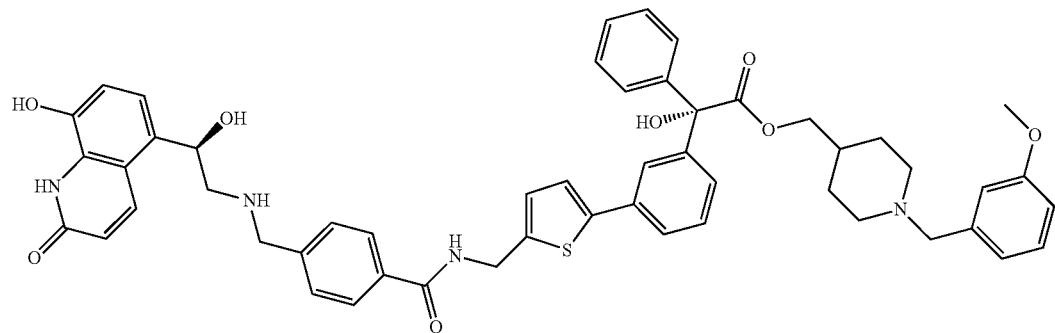 [SMILES: COc1cccc(CN2CCC(COC(=O)[C@](O)(c3ccccc3)c3cccc(-c4ccc(CNC(=O)c5ccc(CNC[C@H](O)c6ccc(O)c7[nH]c(=O)ccc67)cc5)s4)c3)CC2)c1]

2F
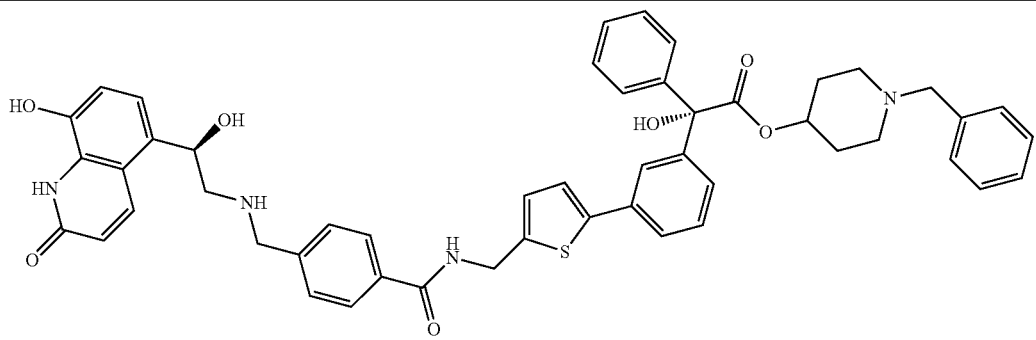
2G
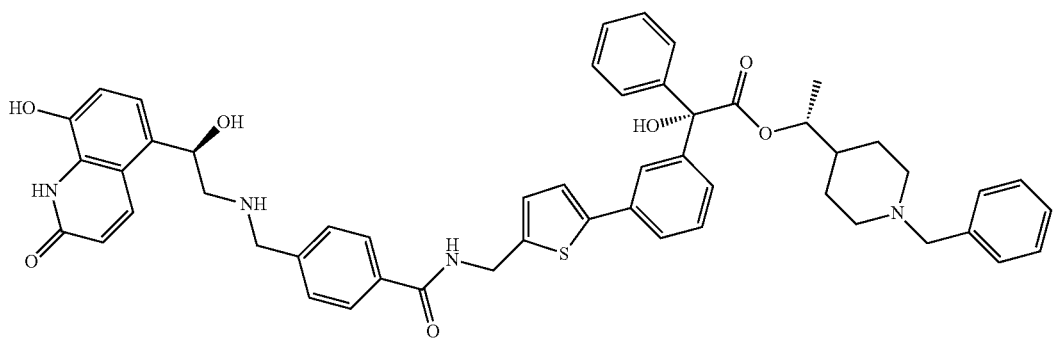
2H
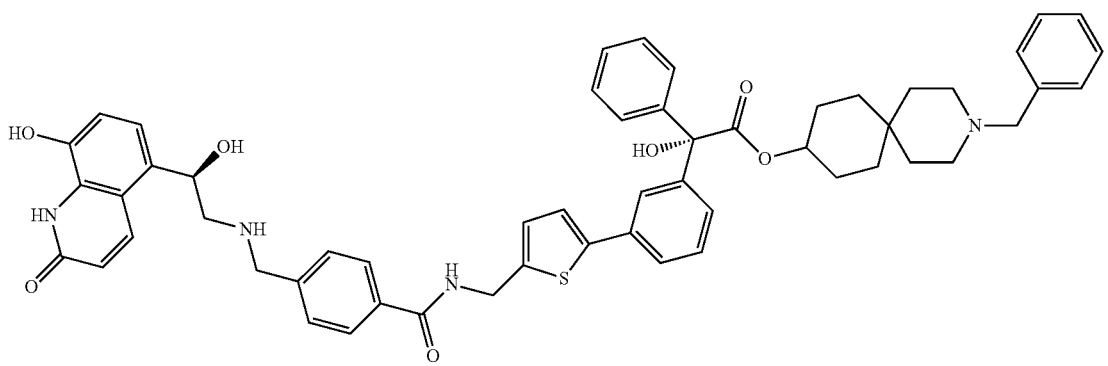 [SMILES: O=C(NCc1ccc(-c2cccc([C@](O)(C(=O)OC3CCC4(CC3)CCN(Cc3ccccc3)CC4)c3ccccc3)c2)s1)c1ccc(CNC[C@H](O)c2ccc(O)c3[nH]c(=O)ccc23)cc1]
Example 3
(1-Benzylpiperidin-4-yl)methyl (S)-2-hydroxy-2-(3-(1-(4-(2-(((R)-2-hydroxy-2-(8-hydroxy-2-oxo-1,2-dihydroquinolin-5-yl)ethyl)amino)ethyl)benzoyl)-1,2,3,6-tetrahydropyridin-4-yl)phenyl)-2-phenylacetate (Compound no. 3)
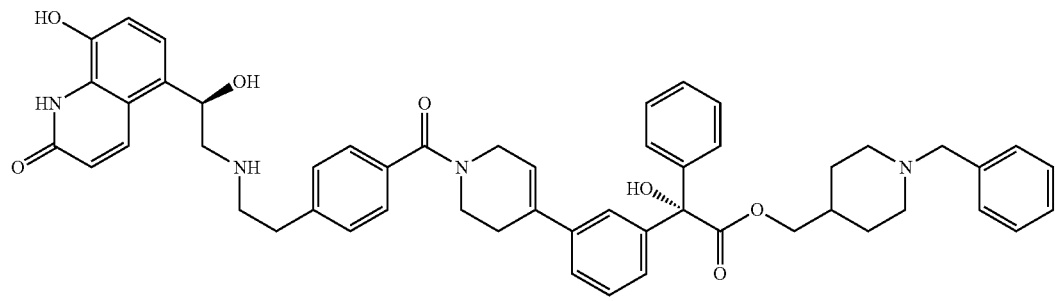 [SMILES: O=C(c1ccc(CCNC[C@H](O)c2ccc(O)c3[nH]c(=O)ccc23)cc1)N1CC=C(c2cccc([C@](O)(C(=O)OCC3CCN(Cc4ccccc4)CC3)c3ccccc3)c2)CC1]

The title compounds was prepared according to Example 1 with tert-butyl 4-(4,4,5,5-tetramethyl-1,3,2-dioxaborolan-2-yl)-3,6-dihydropyridine-1(2H)-carboxylate used in Step 6 and (R)-4-(2-((tert-butoxycarbonyl)(2-((tert-butyldimethylsilyl)oxy)-2-(8-hydroxy-2-oxo-1,2-dihydroquinolin-5-yl)ethyl)amino)ethyl)benzoic acid used in Step 8.

The following compounds were prepared as described in Example 3 with the appropriate boronate species and acid in the relevant steps.

| Compound No. | Appropriate boronate | Acid |
|---|---|---|
| 3A | | |
| 3B | | |
| 3C | | |
| 3D | | |

-continued
| | | |
|---|---|---|
| 3E | 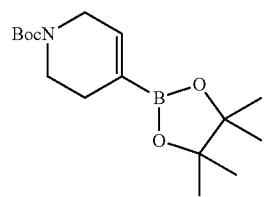 [SMILES: CC(C)(C)OC(=O)N1CC=C(B2OC(C)(C)C(C)(C)O2)CC1] | 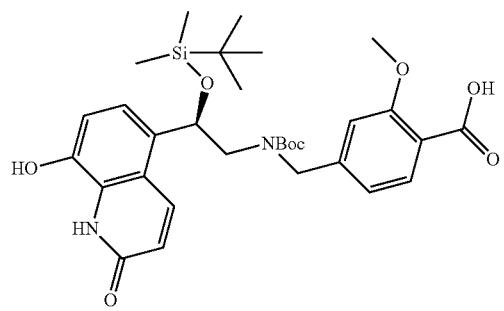 [SMILES: COc1cc(CN(C[C@H](O[Si](C)(C)C(C)(C)C)c2ccc(O)c3[nH]c(=O)ccc23)C(=O)OC(C)(C)C)ccc1C(=O)O] |
| 3F | 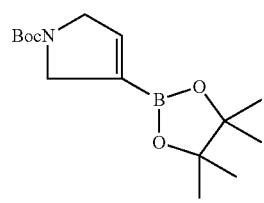 [SMILES: CC(C)(C)OC(=O)N1CC=C(B2OC(C)(C)C(C)(C)O2)C1] | 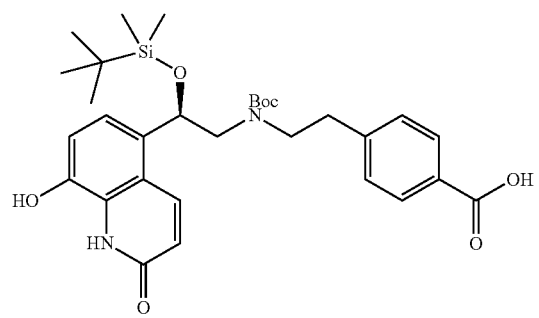 [SMILES: CC(C)(C)OC(=O)N(CCc1ccc(C(=O)O)cc1)C[C@H](O[Si](C)(C)C(C)(C)C)c1ccc(O)c2[nH]c(=O)ccc12] |
| 3G | 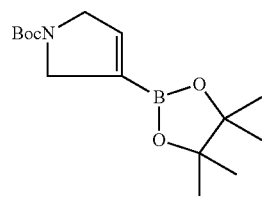 [SMILES: CC(C)(C)OC(=O)N1CC=C(B2OC(C)(C)C(C)(C)O2)C1] | 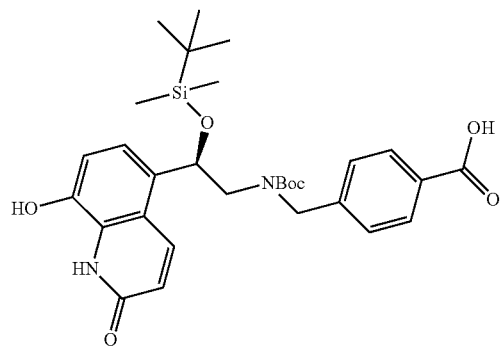 [SMILES: CC(C)(C)OC(=O)N(Cc1ccc(C(=O)O)cc1)C[C@H](O[Si](C)(C)C(C)(C)C)c1ccc(O)c2[nH]c(=O)ccc12] |
| 3H | 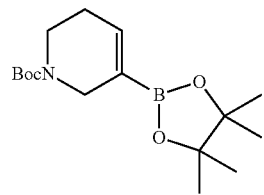 [SMILES: CC(C)(C)OC(=O)N1CCC=C(B2OC(C)(C)C(C)(C)O2)C1] | 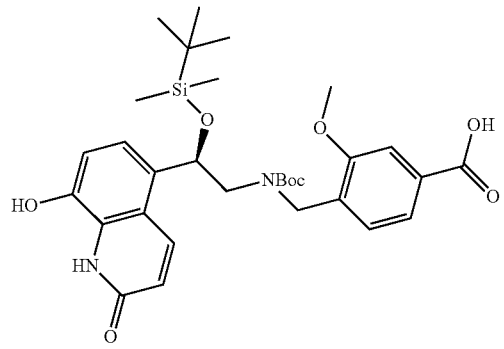 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |

-continued
| 3I | 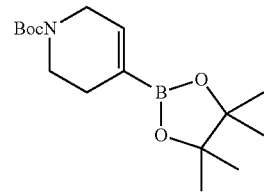 [SMILES: CC(C)(C)OC(=O)N1CC=C(B2OC(C)(C)C(C)(C)O2)CC1] | 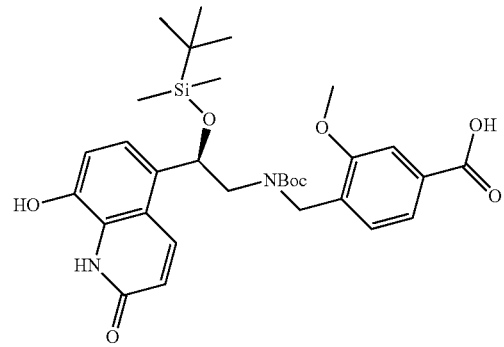 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |
|---|---|---|
| 3J | 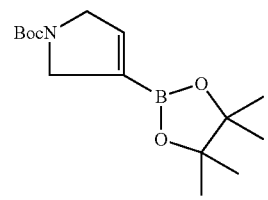 [SMILES: CC(C)(C)OC(=O)N1CC=C(B2OC(C)(C)C(C)(C)O2)C1] | 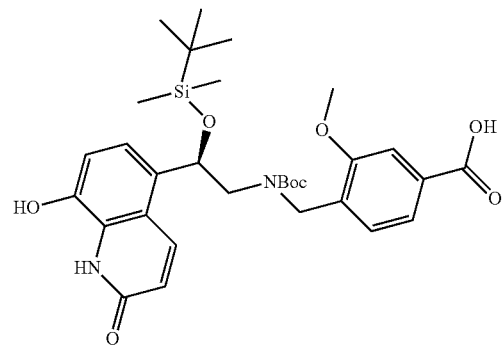 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |
| Compound No. | Structure |
|---|---|
| 3A | 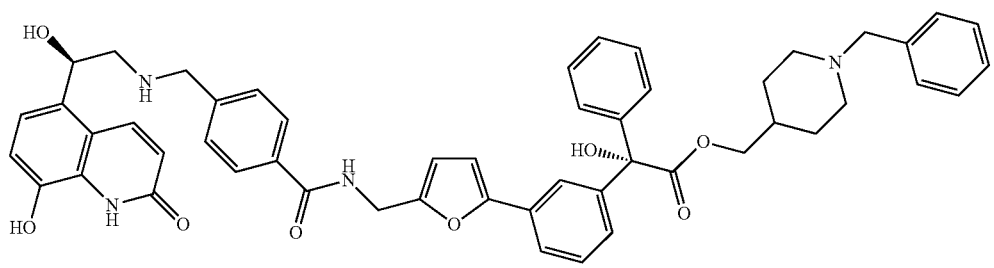 [SMILES: O=C(NCc1ccc(-c2cccc([C@](O)(C(=O)OCC3CCN(Cc4ccccc4)CC3)c3ccccc3)c2)o1)c1ccc(CNC[C@H](O)c2ccc(O)c3[nH]c(=O)ccc23)cc1] |
| 3B | 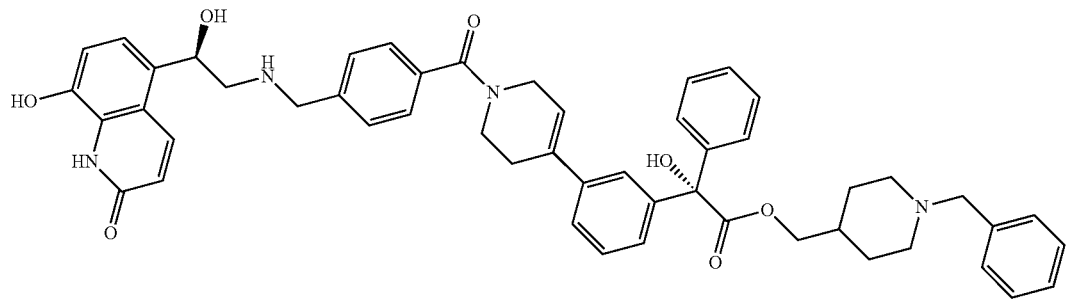 [SMILES: O=C(c1ccc(CNC[C@H](O)c2ccc(O)c3[nH]c(=O)ccc23)cc1)N1CC=C(c2cccc([C@](O)(C(=O)OCC3CCN(Cc4ccccc4)CC3)c3ccccc3)c2)CC1] |
| 3C | 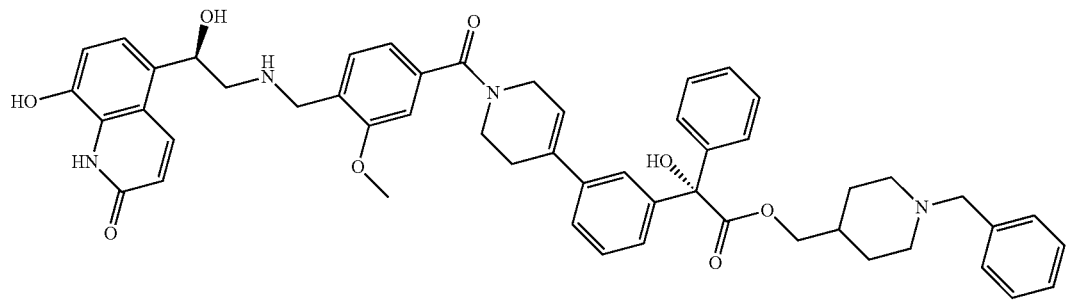 [SMILES: COc1cc(C(=O)N2CC=C(c3cccc([C@](O)(C(=O)OCC4CCN(Cc5ccccc5)CC4)c4ccccc4)c3)CC2)ccc1CNC[C@H](O)c1ccc(O)c2[nH]c(=O)ccc12] |

3D 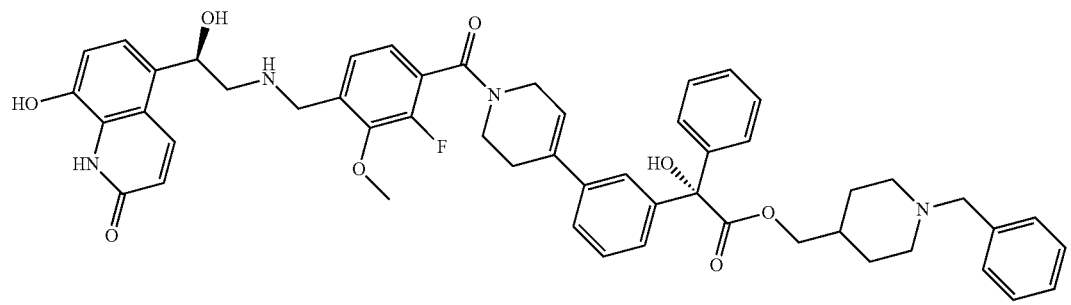 [SMILES: COc1c(CNC[C@H](O)c2ccc(O)c3[nH]c(=O)ccc23)ccc(C(=O)N2CC=C(c3cccc([C@](O)(C(=O)OCC4CCN(Cc5ccccc5)CC4)c4ccccc4)c3)CC2)c1F]
3E 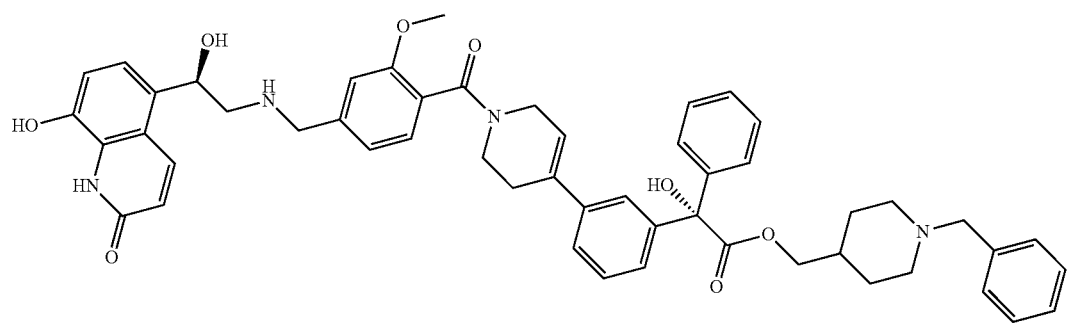 [SMILES: COc1cc(CNC[C@H](O)c2ccc(O)c3[nH]c(=O)ccc23)ccc1C(=O)N1CC=C(c2cccc([C@](O)(C(=O)OCC3CCN(Cc4ccccc4)CC3)c3ccccc3)c2)CC1]
3F 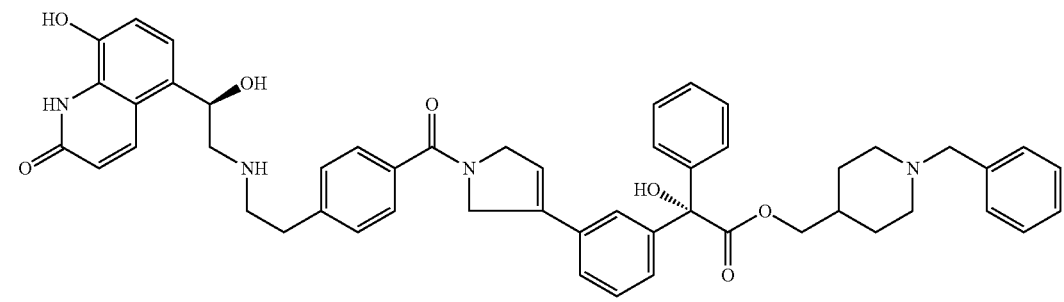 [SMILES: O=C(c1ccc(CCNC[C@H](O)c2ccc(O)c3[nH]c(=O)ccc23)cc1)N1CC=C(c2cccc([C@](O)(C(=O)OCC3CCN(Cc4ccccc4)CC3)c3ccccc3)c2)C1]
3G 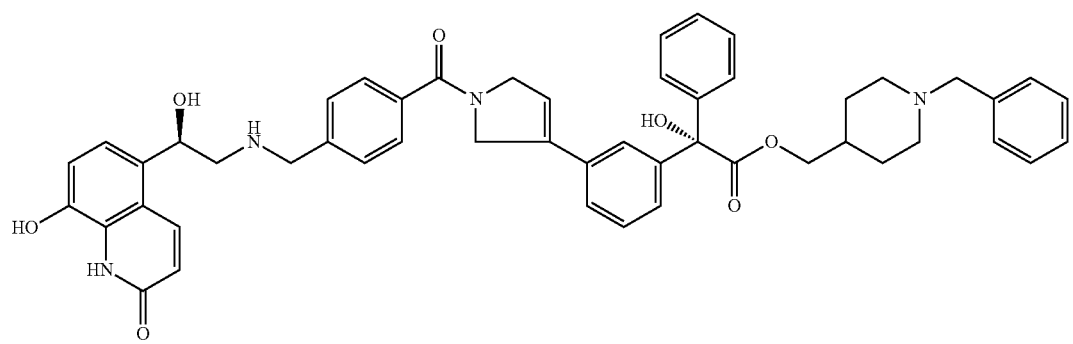 [SMILES: O=C(c1ccc(CNC[C@H](O)c2ccc(O)c3[nH]c(=O)ccc23)cc1)N1CC=C(c2cccc([C@](O)(C(=O)OCC3CCN(Cc4ccccc4)CC3)c3ccccc3)c2)C1]
3H 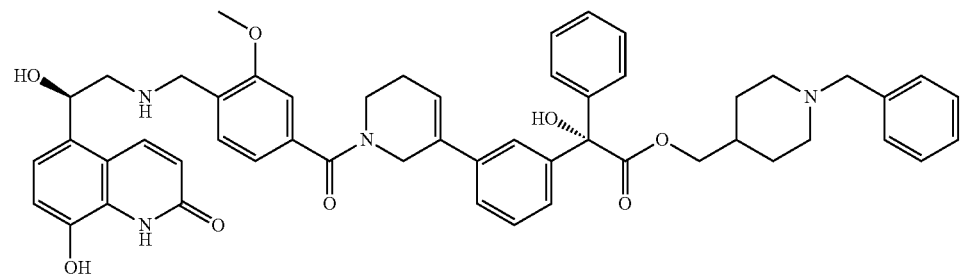 [SMILES: COc1cc(C(=O)N2CCC=C(c3cccc([C@](O)(C(=O)OCC4CCN(Cc5ccccc5)CC4)c4ccccc4)c3)C2)ccc1CNC[C@H](O)c1ccc(O)c2[nH]c(=O)ccc12]

3I

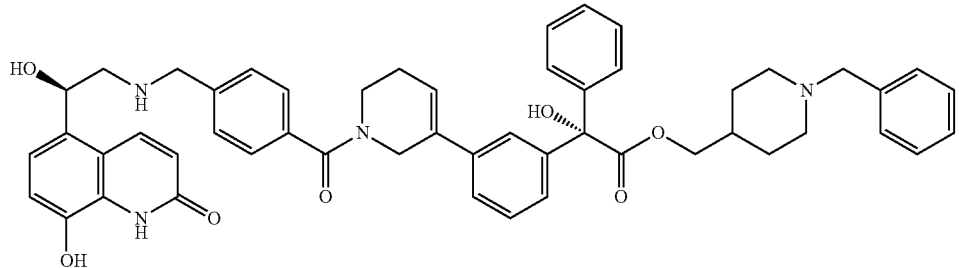 [SMILES: O=C(c1ccc(CNC[C@H](O)c2ccc(O)c3[nH]c(=O)ccc23)cc1)N1CCC=C(c2cccc([C@](O)(C(=O)OCC3CCN(Cc4ccccc4)CC3)c3ccccc3)c2)C1]

3J

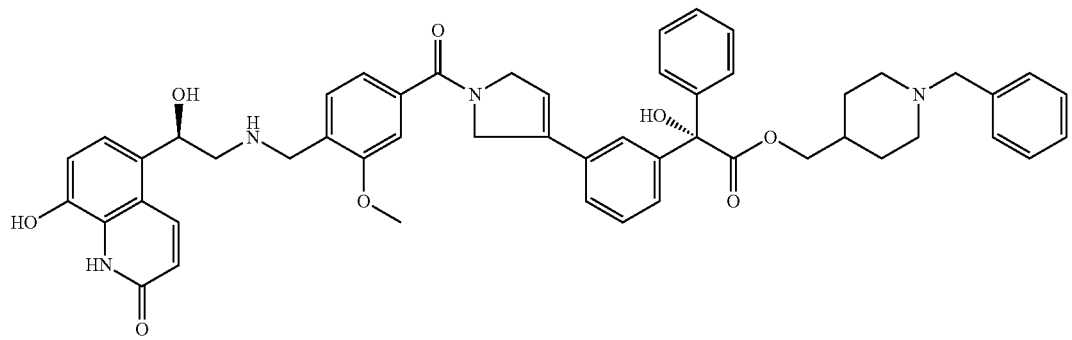 [SMILES: COc1cc(C(=O)N2CC=C(c3cccc([C@](O)(C(=O)OCC4CCN(Cc5ccccc5)CC4)c4ccccc4)c3)C2)ccc1CNC[C@H](O)c1ccc(O)c2[nH]c(=O)ccc12]

Example 4

(1-Benzylpiperidin-4-yl)methyl (S)-2-hydroxy-2-(3-(2-((4-((((R)-2-hydroxy-2-(8-hydroxy-2-oxo-1,2-dihydroquinolin-5-yl)ethyl)amino)methyl)benzamido)-methyl)pyrimidin-5-yl)phenyl)-2-phenylacetate (Compound 4)

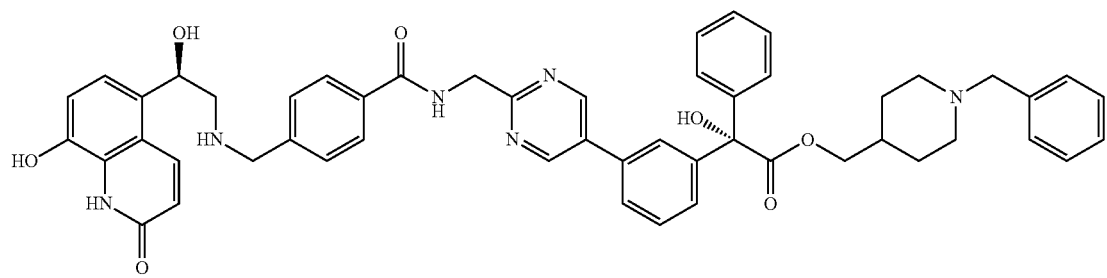 [SMILES: O=C(NCc1ncc(-c2cccc([C@](O)(C(=O)OCC3CCN(Cc4ccccc4)CC3)c3ccccc3)c2)cn1)c1ccc(CNC[C@H](O)c2ccc(O)c3[nH]c(=O)ccc23)cc1]

Step 1: (1-Benzylpiperidin-4-yl)methyl (S)-2-(3-(2-(((tert-butoxycarbonyl)amino)-methyl)pyrimidin-5-yl)phenyl)-2-hydroxy-2-phenylacetate

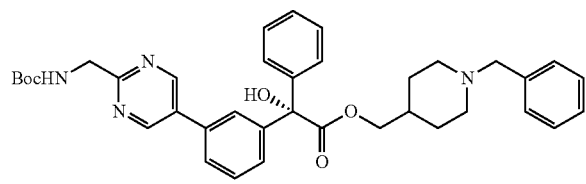 [SMILES: CC(C)(C)OC(=O)NCc1ncc(-c2cccc([C@](O)(C(=O)OCC3CCN(Cc4ccccc4)CC3)c3ccccc3)c2)cn1]

A solution of (1-benzylpiperidin-4-yl)methyl (S)-2-hydroxy-2-phenyl-2-(3-(((trifluoromethyl)sulfonyl)oxy)phenyl)acetate (0.3 g, 0.53 mmol) in 1,4-dioxane (5 mL) was added with potassium carbonate (0.16 g, 1.59 mmol and bis(pinacolato)diboron (0.15 g, 0.58 mmol). The mixture was thoroughly de-gassed and then treated with Pd(dppf)Cl$_2$ (0.043 g. 0.053 mmol). The resultant mixture was heated at 80° C. for 1 hour. An additional portion of Pd(dppf)Cl$_2$ (0.043 g. 0.053 mmol) was added and heating continued for a further 1 hour. The reaction mixture was cooled to room temperature. A solution of tert-butyl ((5-chloropyrimidin-2-yl)methyl)carbamate (0.25 g, 0.87 mmol) in 1,4-dioxane (2 mL) was added followed by an aqueous solution of potassium carbonate (1.8M, 0.8 mL, 1.4 mmol). The reaction mixture was thoroughly de-gassed and then treated with Pd(dppf)Cl$_2$ (0.043 g. 0.053 mmol). The resultant mixture was heated at 80° C. for 1 hour. An additional portion of Pd(dppf)Cl$_2$ (0.043 g. 0.053 mmol) was added and heating continued for a further 1 hour. The mixture was diluted with ethyl acetate and washed with brine. The organic phase was dried over anhydrous magnesium sulfate, filtered and the filtrate evaporated at reduced pressure. The residue was purified by flash column chromatography (eluent—100% DCM to 9:1 DCM/methanol) to afford the title compound (0.17 g, 52%).

$^1$H NMR (400 MHz, CDCl$_3$); δ 8.84 (s, 2H), 7.63 (s, 1H), 7.53-7.24 (m, 14H), 5.6 (s, 1H), 4.64-4.62 (m, 2H), 4.14 (s, 2H), 3.46 (s, 2H), 2.84-2.77 (m, 2H), 1.92-1.88 (m, 2H), 1.66-1.52 (m, 14H).

Step 2: 1-Benzylpiperidin-4-yl)methyl (S)-2-hydroxy-2-(3-(2-((4-((((R)-2-hydroxy-2-(8-hydroxy-2-oxo-1,2-dihydroquinolin-5-yl)ethyl)amino)methyl)benzamido)-methyl)pyrimidin-5-yl)phenyl)-2-phenylacetate (Compound 4)

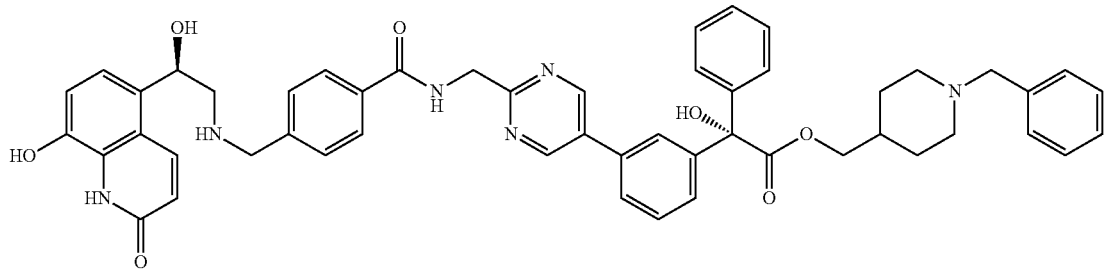 [SMILES: O=C(NCc1ncc(-c2cccc([C@](O)(C(=O)OCC3CCN(Cc4ccccc4)CC3)c3ccccc3)c2)cn1)c1ccc(CNC[C@H](O)c2ccc(O)c3[nH]c(=O)ccc23)cc1]

The title compounds was prepared according to Example 1 with (1-benzylpiperidin-4-yl)methyl (S)-2-(3-(2-(((tert-butoxycarbonyl)amino)methyl)pyrimidin-5-yl)phenyl)-2-hydroxy-2-phenylacetate used in Step 7 and (R)-4-(2-((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid used in Step 8

The following compounds were prepared as described in Example 4 with the appropriate chloride in Step 1 and acid in Step 2.

| Compound No. | Appropriate chloride | Acid |
| --- | --- | --- |
| 4A | ![BocHN-CH2-pyrimidine-Cl] | ![acid structure 4A] |
| 4B | ![BocHN-CH2-pyrazine-Cl] | ![acid structure 4B] |

-continued
| | | |
|---|---|---|
| 4C | 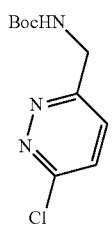 | 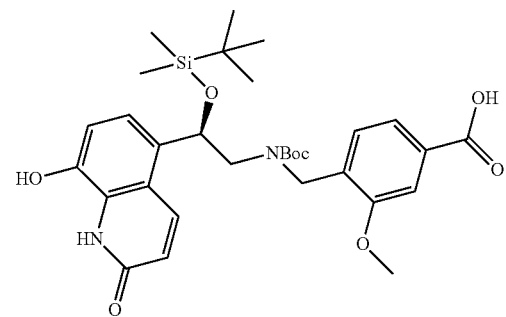 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |
| 4D | 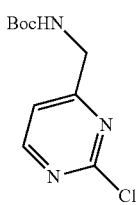 | 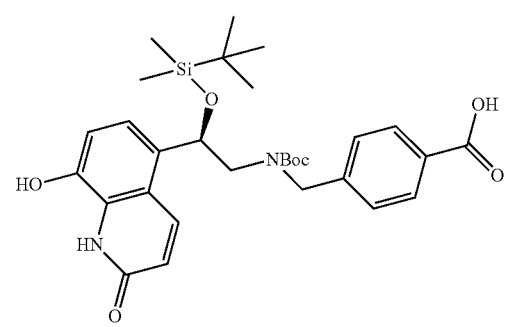 [SMILES: CC(C)(C)OC(=O)N(Cc1ccc(C(=O)O)cc1)C[C@H](O[Si](C)(C)C(C)(C)C)c1ccc(O)c2[nH]c(=O)ccc12] |
| 4E | 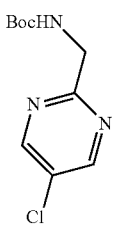 [SMILES: CC(C)(C)OC(=O)NCc1ncc(Cl)cn1] | 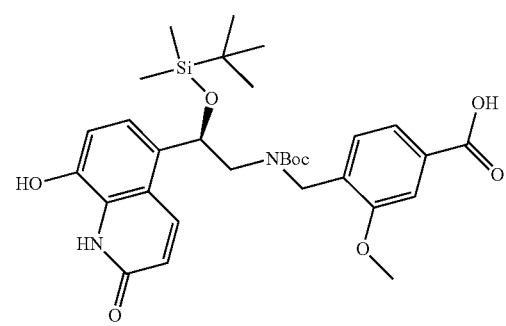 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |
| 4F | 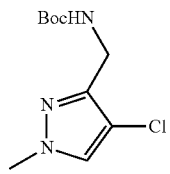 [SMILES: Cn1cc(Cl)c(CNC(=O)OC(C)(C)C)n1] | 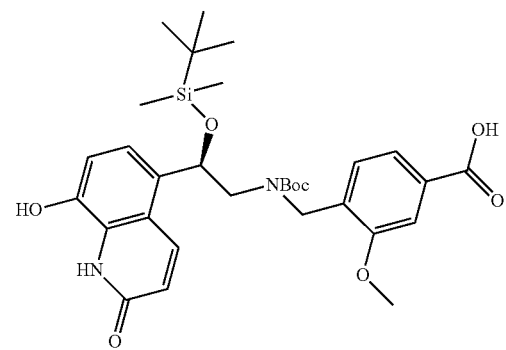 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |

| | | |
|---|---|---|
| 4G | 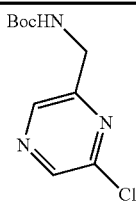 | 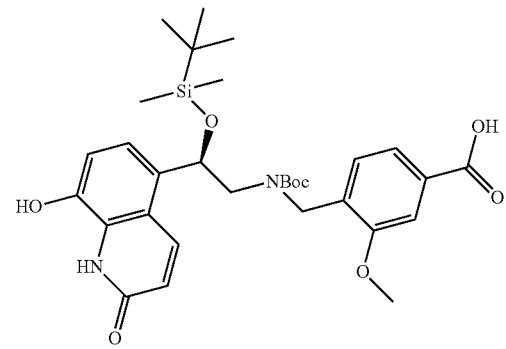 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |
| 4H | 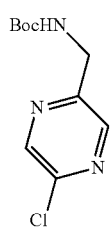 | 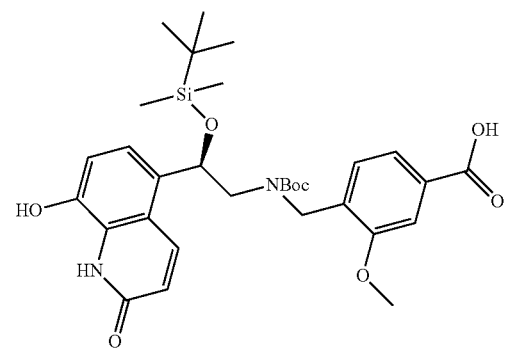 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |
| Compound No. | Structure |
|---|---|
| 4A | 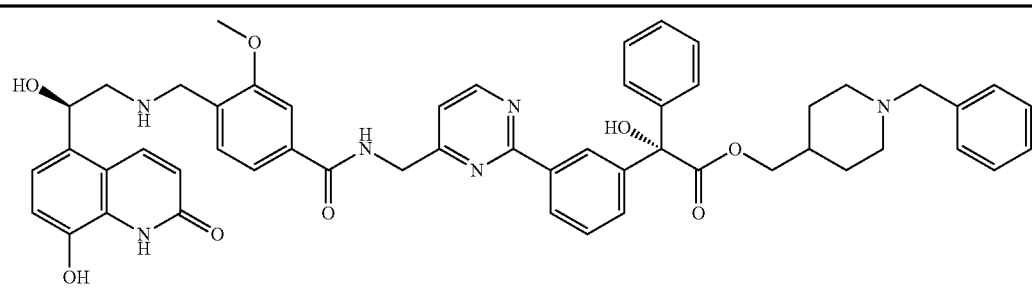 |
| 4B | 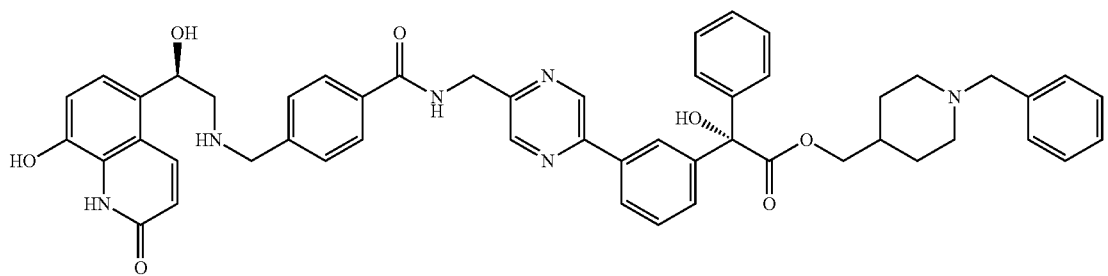 [SMILES: O=C(NCc1cnc(-c2cccc([C@](O)(C(=O)OCC3CCN(Cc4ccccc4)CC3)c3ccccc3)c2)cn1)c1ccc(CNC[C@H](O)c2ccc(O)c3[nH]c(=O)ccc23)cc1] |
| 4C | 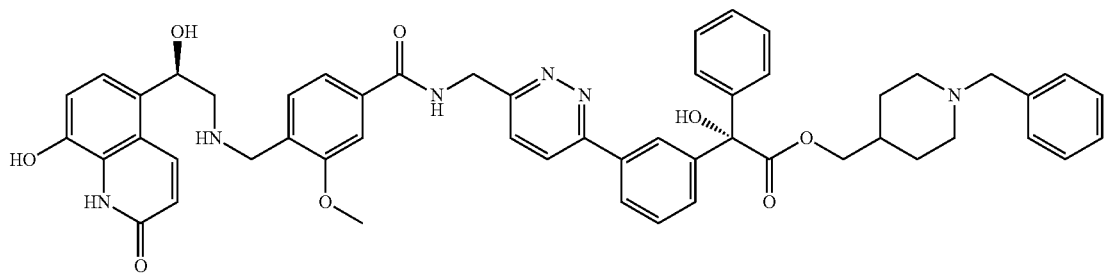 [SMILES: COc1cc(C(=O)NCc2ccc(-c3cccc([C@](O)(C(=O)OCC4CCN(Cc5ccccc5)CC4)c4ccccc4)c3)nn2)ccc1CNC[C@H](O)c1ccc(O)c2[nH]c(=O)ccc12] |

4D
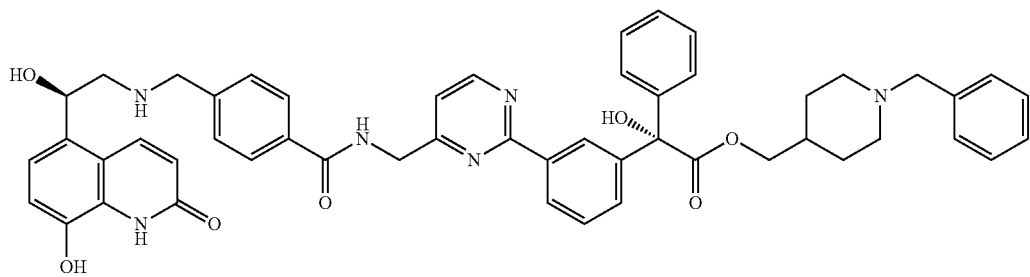 [SMILES: O=C(NCc1ccnc(-c2cccc([C@](O)(C(=O)OCC3CCN(Cc4ccccc4)CC3)c3ccccc3)c2)n1)c1ccc(CNC[C@H](O)c2ccc(O)c3[nH]c(=O)ccc23)cc1]
4E
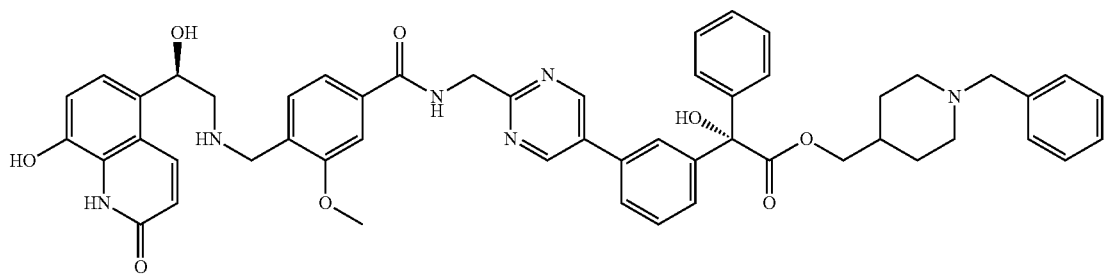 [SMILES: COc1cc(C(=O)NCc2ncc(-c3cccc([C@](O)(C(=O)OCC4CCN(Cc5ccccc5)CC4)c4ccccc4)c3)cn2)ccc1CNC[C@H](O)c1ccc(O)c2[nH]c(=O)ccc12]
4F
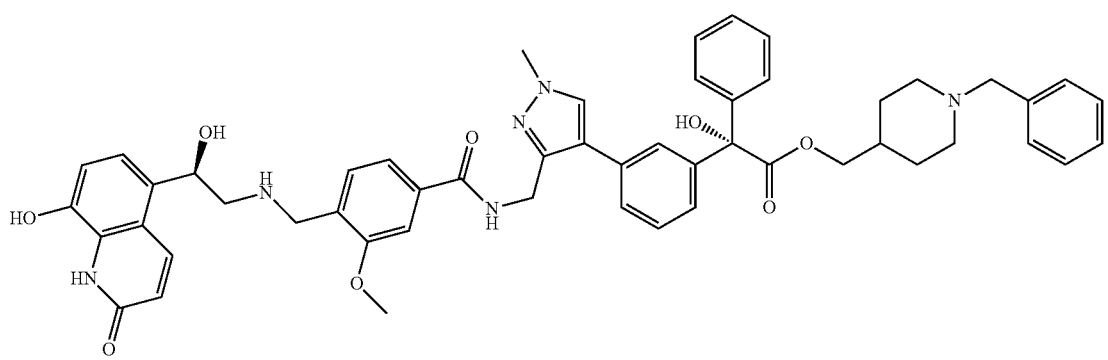 [SMILES: COc1cc(C(=O)NCc2nn(C)cc2-c2cccc([C@](O)(C(=O)OCC3CCN(Cc4ccccc4)CC3)c3ccccc3)c2)ccc1CNC[C@H](O)c1ccc(O)c2[nH]c(=O)ccc12]
4G
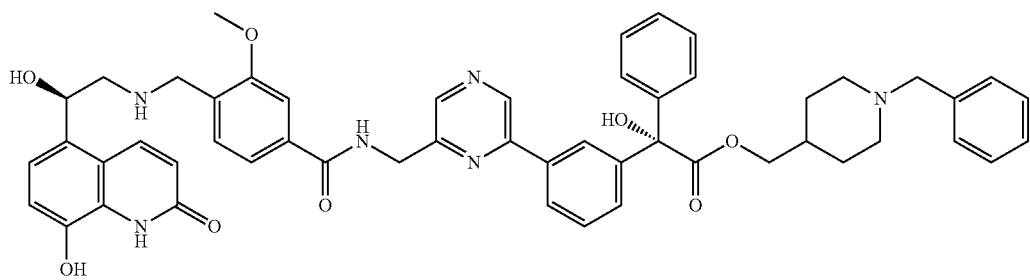 [SMILES: COc1cc(C(=O)NCc2cncc(-c3cccc([C@](O)(C(=O)OCC4CCN(Cc5ccccc5)CC4)c4ccccc4)c3)n2)ccc1CNC[C@H](O)c1ccc(O)c2[nH]c(=O)ccc12]
4H
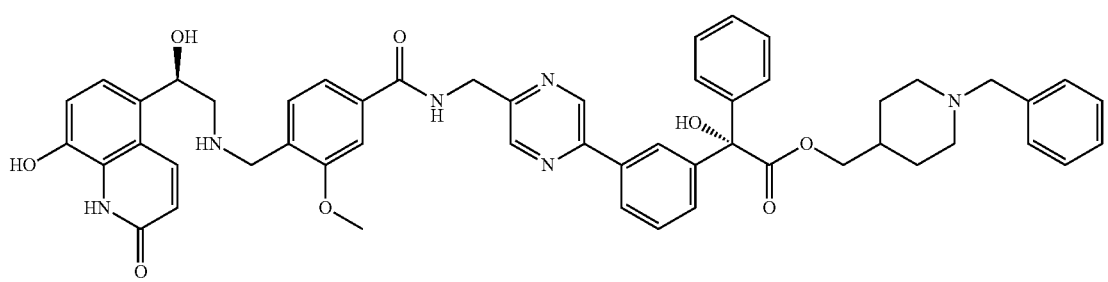 [SMILES: COc1cc(C(=O)NCc2cnc(-c3cccc([C@](O)(C(=O)OCC4CCN(Cc5ccccc5)CC4)c4ccccc4)c3)cn2)ccc1CNC[C@H](O)c1ccc(O)c2[nH]c(=O)ccc12]

Example 5

(1-Benzylpiperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)-thiophen-3-yl)phenyl)-2-phenylacetate (Compound 5)

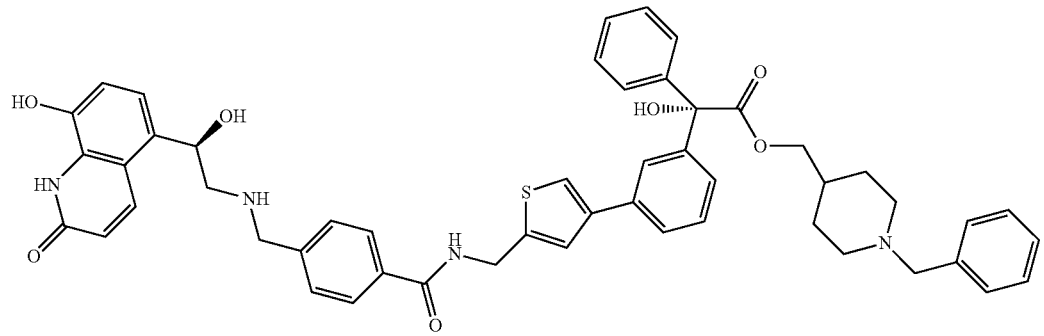 [SMILES: O=C(NCc1cc(-c2cccc([C@](O)(C(=O)OCC3CCN(Cc4ccccc4)CC3)c3ccccc3)c2)cs1)c1ccc(CNC[C@H](O)c2ccc(O)c3[nH]c(=O)ccc23)cc1]

Step 1: (1-Benzylpiperidin-4-yl)methyl (S)-2-(3-(5-(((tert-butoxycarbonyl)amino)methyl)thiophen-3-yl)phenyl)-2-hydroxy-2-phenylacetate

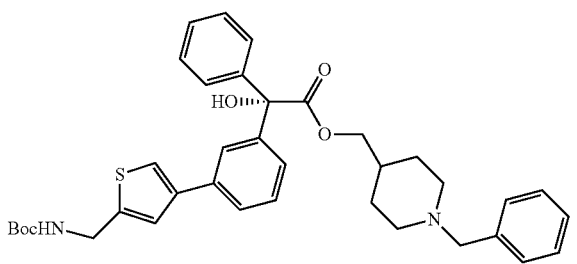 [SMILES: CC(C)(C)OC(=O)NCc1cc(-c2cccc([C@](O)(C(=O)OCC3CCN(Cc4ccccc4)CC3)c3ccccc3)c2)cs1]

A solution of (1-benzylpiperidin-4-yl)methyl (S)-2-hydroxy-2-phenyl-2-(3-(((trifluoromethyl)sulfonyl)oxy)phenyl)acetate (0.25 g, 0.45 mmol) in ethanol (8 mL) was added with tert-butyl ((4-bromothiophen-2-yl)methyl)carbamate (0.143 g, 0.50 mmol), X-Phos-Pd-G2 (0.035 g, 0.05 mmol), X-Phos (0.043 g, 0.088 mmol), potassium acetate (0.13 g, 1.33 mmol) and hypodiboric acid (0.12 g, 1.33 mmol). The reaction was thoroughly de-gassed and then heated at 80° C. for 1.5 hour. An aqueous solution of potassium carbonate (1.8 M, 0.29 mL) was added the reaction thoroughly de-gassed and then heated at 80° C. for 1 hour. The reaction mixture was diluted with ethyl acetate and washed with brine. The organic phase was dried over anhydrous magnesium sulphate, filtered and the filtrate evaporated at reduced pressure. The residue was purified by flash column chromatography (eluent—0% iso-hexane to 100% ethyl acetate) to afford the title compound (0.13 g, 46%).

$^1$H NMR (400 MHz, DMSO-$d_6$); δ 7.63-7.51 (m, 3H), 7.43-7.24 (m, 12H), 6.72 (s, 1H), 4.30 (d, J=5.8 Hz, 2H), 4.07 (d, J=6.1 Hz, 2H), 3.44 (s, 2H), 2.75 (d, J=10.6 Hz, 2H), 1.87 (dd, J=11.1, 11.1 Hz, 2H), 1.63-1.51 (m, 3H), 1.45 (s, 9H), 1.22-1.12 (m, 2H).

Step 2: (1-Benzylpiperidin-4-yl)methyl (S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)-thiophen-3-yl)phenyl)-2-phenylacetate (Compound 5)

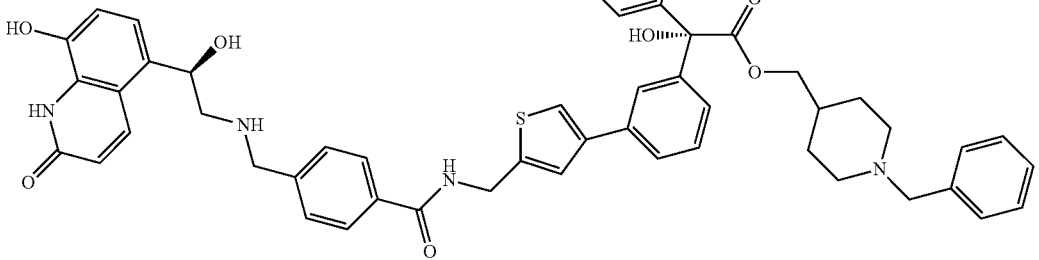

The title compounds was prepared according to Example 1 with (1-Benzylpiperidin-4-yl)methyl (S)-2-(3-(5-(((tert-butoxycarbonyl)amino)methyl)thiophen-3-yl)phenyl)-2-hydroxy-2-phenylacetate used in Step 7 and (R)-4-(2-((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid used in Step 8.

The following compounds were prepared as described in Example 5 with the appropriate halide in Step 1 and acid in Step 2.

| Compound No. | Appropriate bromide | Acid |
| --- | --- | --- |
| 5A | | |
| 5B | | |
| 5C | | |
| 5D | | |

| | |
|---|---|
| 5E | 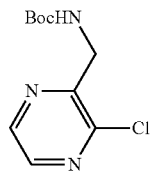 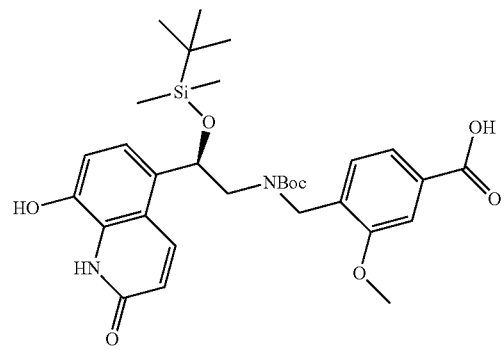 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |
| Compound No. | Structure |
|---|---|
| 5A | 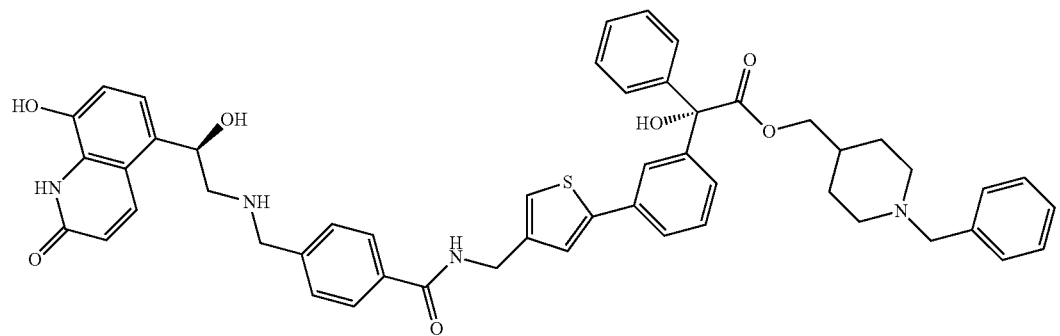 [SMILES: O=C(NCc1csc(-c2cccc([C@](O)(C(=O)OCC3CCN(Cc4ccccc4)CC3)c3ccccc3)c2)c1)c1ccc(CNC[C@H](O)c2ccc(O)c3[nH]c(=O)ccc23)cc1] |
| 5B | 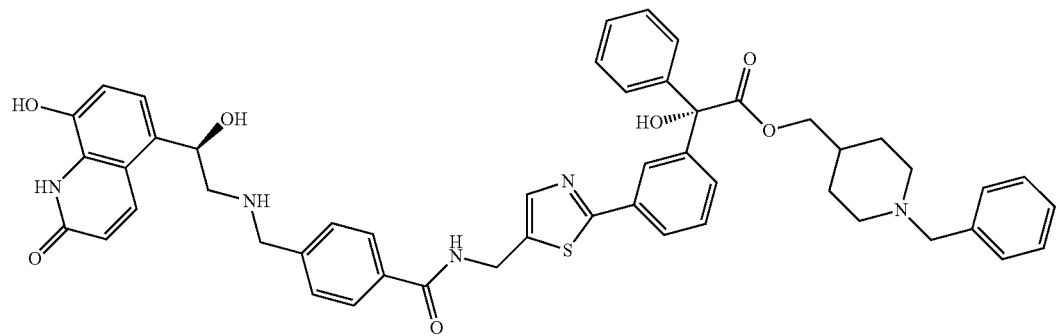 [SMILES: O=C(NCc1cnc(-c2cccc([C@](O)(C(=O)OCC3CCN(Cc4ccccc4)CC3)c3ccccc3)c2)s1)c1ccc(CNC[C@H](O)c2ccc(O)c3[nH]c(=O)ccc23)cc1] |
| 5C | 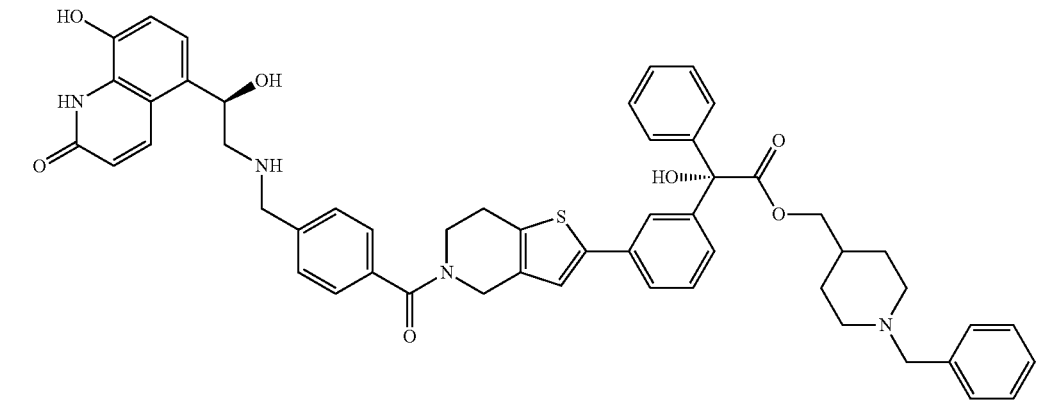 [SMILES: O=C(c1ccc(CNC[C@H](O)c2ccc(O)c3[nH]c(=O)ccc23)cc1)N1CCc2sc(-c3cccc([C@](O)(C(=O)OCC4CCN(Cc5ccccc5)CC4)c4ccccc4)c3)cc2C1] |

5D
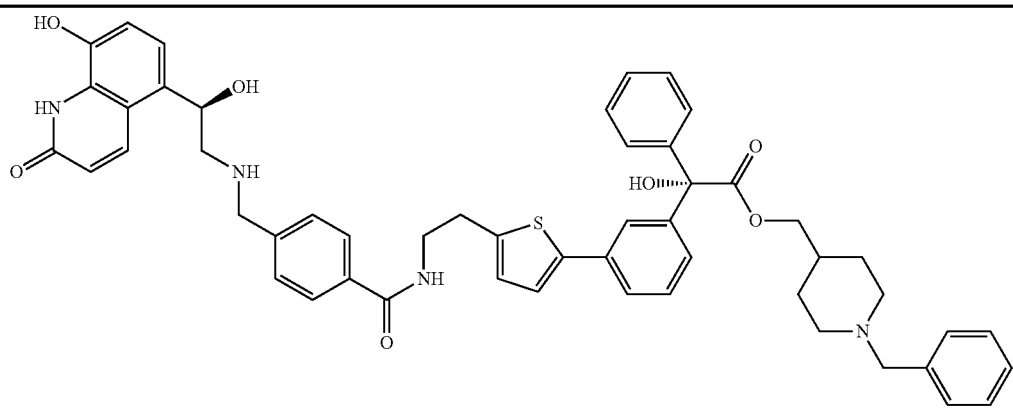
5E
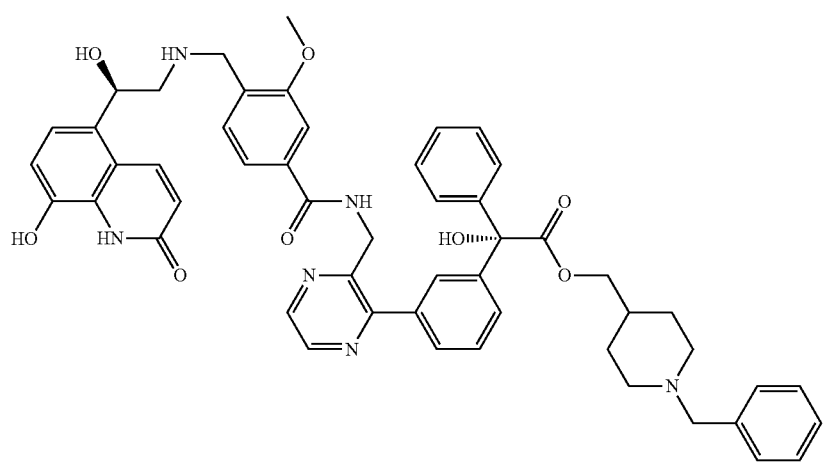 [SMILES: COc1cc(C(=O)NCc2nccnc2-c2cccc([C@](O)(C(=O)OCC3CCN(Cc4ccccc4)CC3)c3ccccc3)c2)ccc1CNC[C@H](O)c1ccc(O)c2[nH]c(=O)ccc12]
Example 6
(1-Benzylpiperidin-4-yl)methyl (S)-2-hydroxy-2-(3-(4-(4-((((R)-2-hydroxy-2-(8-hydroxy-2-oxo-1,2-dihydroquinolin-5-yl)ethyl)amino)methyl)piperidine-1-carbonyl)pyridin-2-yl)phenyl)-2-phenylacetate (Compound 6)
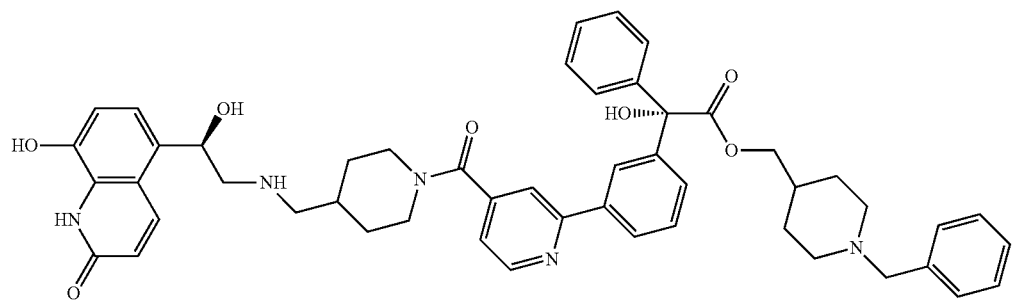 [SMILES: O=C(c1ccnc(-c2cccc([C@](O)(C(=O)OCC3CCN(Cc4ccccc4)CC3)c3ccccc3)c2)c1)N1CCC(CNC[C@H](O)c2ccc(O)c3[nH]c(=O)ccc23)CC1]

Step 1: (R)-8-(Benzyloxy)-5-(2-(((1-benzylpiperidin-4-yl)methyl)amino)-1-((tert-butyldimethylsilyl)oxy)ethyl)quinolin-2(1H)-one

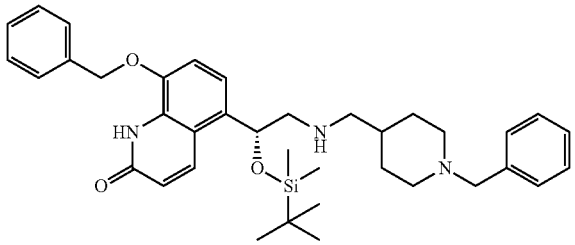 [SMILES: CC(C)(C)[Si](C)(C)O[C@@H](CNCC1CCN(Cc2ccccc2)CC1)c1ccc(OCc2ccccc2)c2[nH]c(=O)ccc12]

A mixture of (R)-8-(benzyloxy)-5-(2-bromo-1-((tert-butyldimethylsilyl)oxy)ethyl)quinolin-2(1H)-one (2.39 g, 4.90 mmol) in NMP (4 mL) was added with (1-benzylpiperidin-4-yl)methanamine (5 g, 24.5 mmol). The mixture was heated at 80° C. for 18 hours. The mixture was diluted with ethyl acetate and washed sequentially with water (×2) and brine (×2). The organic phase was dried over anhydrous magnesium sulfate and the filtrate was evaporated. The residue was purified by flash column chromatography (eluent—100% DCM to 40:1 DCM/7M $NH_3$/MeOH) to afford the title compound (2.65 g, 88%).

$^1$H NMR (400 MHz, $CDCl_3$); δ 9.19-9.15 (m, 1H), 8.30-8.28 (s, 1H), 7.43-7.41 (m, 5H), 7.31 (d, J=4.4 Hz, 5H), 7.12 (d, J=8.3 Hz, 1H), 7.00 (d, J=8.3 Hz, 1H), 6.66 (d, J=9.9 Hz, 1H); 5.16 (s, 2H), 5.15-5.10 (m, 1H), 3.49 (s, 2H), 2.95-2.84 (m, 3H), 2.71 (dd, J=4.0, 12.2 Hz, 1H), 2.56-2.43 (m, 2H), 1.94 (dd, J=11.7, 11.7 Hz, 2H), 1.51-1.39 (m, 2H), 1.30-1.22 (m, 3H), 0.87 (s, 9H), 0.06 (s, 3H), −0.19 (s, 3H).

Step 2: (R)-tert-Butyl (2-(8-(benzyloxy)-2-oxo-1,2-dihydroquinolin-5-yl)-2-((tert-butyldimethylsilyl)oxy)ethyl)((1-benzylpiperidin-4-yl)methyl)carbamate

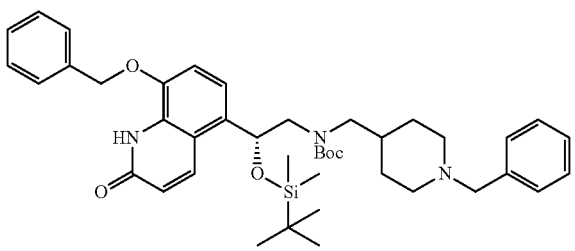 [SMILES: CC(C)(C)OC(=O)N(CC1CCN(Cc2ccccc2)CC1)C[C@H](O[Si](C)(C)C(C)(C)C)c1ccc(OCc2ccccc2)c2[nH]c(=O)ccc12]

A stirred solution of (R)-8-(benzyloxy)-5-(2-(((1-benzylpiperidin-4-yl)methyl)amino)-1-((tert-butyldimethylsilyl)oxy)ethyl)quinolin-2(1H)-one (2.65 g, 4.33 mmol) in DCM (25 mL) was added with a solution of di-tert-butyl-dicarbonate (1.13 g, 5.18 mmol) in DCM (5 mL). The reaction mixture was stirred at room temperature for 16 hours. The solvent was evaporated under reduced pressure and the residue purified by flash column chromatography (eluent—100% DCM to 30:1 DCM/7M $NH_3$/MeOH) to afford the title compound (2.83 g, 92%).

$^1$H NMR (400 MHz, DMSO-$d_6$, 100° C.); δ 9.96 (s, 1H), 8.30 (d, J=9.9 Hz, 1H), 7.55 (d, J=7.3 Hz, 2H), 7.42-7.21 (m, 9H), 7.14 (d, J=8.3 Hz, 1H), 6.55 (d, J=9.9 Hz, 1H), 5.40-5.33 (m, 1H), 5.30 (s, 2H), 3.44 (s, 2H), 3.38 (d, J=6.1 Hz, 2H), 3.12-2.97 (m, 2H), 2.95 (s, 2H), 2.78-2.73 (m, 2H), 2.00-1.88 (m, 2H), 1.40 (s, 10H), 1.22-1.09 (m, 2H), 0.87 (s, 9H), 0.06 (s, 3H), −0.13 (s, 3H).

Step 3: (R)-tert-Butyl (2-((tert-butyldimethylsilyl)oxy)-2-(8-hydroxy-2-oxo-1,2-dihydroquinolin-5-yl)ethyl)(piperidin-4-ylmethyl)carbamate

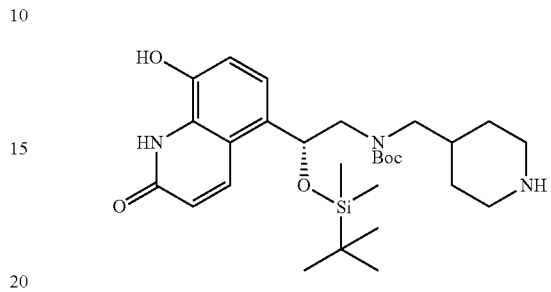

A stirred solution of (R)-tert-butyl (2-(8-(benzyloxy)-2-oxo-1,2-dihydroquinolin-5-yl)-2-((tert-butyldimethylsilyl)oxy)ethyl)((1-benzylpiperidin-4-yl)methyl)carbamate (2.80 g, 4.33 mmol) in ethanol (30 mL) was added with 10% Pd/C (2.8 g) and 1-methyl-1,4-cyclohexadiene (4.86 mL, 43.3 mmol). The reaction mixture was heated to reflux [Care—vigorous evolution of gas] and heated under reflux for 1 hour. The suspension was filtered and the filtrate evaporated under reduced pressure to afford the title compound (2.26 g, 98%).

$^1$H NMR (400 MHz, DMSO-$d_6$, 100° C.); δ 8.26 (d, J=9.9 Hz, 1H), 7.05 (d, J=8.2 Hz, 1H), 7.01 (d, J=8.0 Hz, 1H), 6.53-6.49 (m, 1H), 5.37-5.35 (m, 1H), 3.22 (d, J=12.8 Hz, 2H), 3.08 (ddd, J=7.0, 14.3, 17.8 Hz, 2H), 2.83-2.72 (m, 2H), 1.84-1.76 (m, 1H), 1.71-1.61 (m, 2H), 1.43-1.41 (m, 14H), 0.87-0.85 (m, 9H), 0.02 (s, 3H), −0.14 (d, J=2.1 Hz, 3H).

Step 4: tert-Butyl (S)-6-(3-(2-((1-benzylpiperidin-4-yl)methoxy)-1-hydroxy-2-oxo-1-phenylethyl)phenyl)pyrazine-2-carboxylate

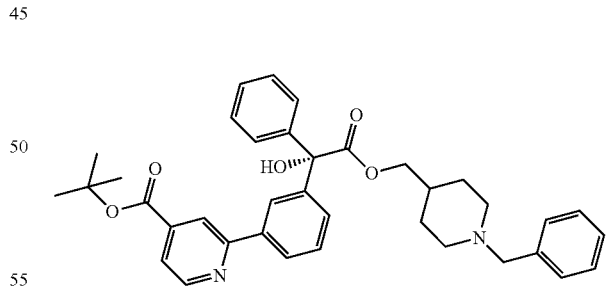

The title compound was prepared as described in Example 5 Step 1 with tert-butyl 2-chloropyridine-4-carboxylate replacing tert-butyl ((4-bromothiophen-2-yl)methyl)carbamate.

$^1$H NMR (400 MHz, $CDCl_3$); δ 8.74 (d, J=5.0 Hz, 1H), 8.30 (d, J=2.4 Hz, 1H), 8.17 (d, J=4.0 Hz, 2H), 8.00-7.98 (m, 1H), 7.70 (dd, J=1.3, 5.0 Hz, 1H), 7.52-7.40 (m, 4H), 7.35-7.30 (m, 7H), 4.23-4.07 (m, 2H), 3.76 (s, 2H), 3.08 (d, J=11.0 Hz, 2H), 2.18 (d, J=11.5 Hz, 2H), 1.78-1.71 (m, 1H), 1.61 (s, 9H), 1.59-1.46 (m, 4H).

Step 5: (S)-2-(3-(2-((1-Benzylpiperidin-4-yl)methoxy)-1-hydroxy-2-oxo-1-phenylethyl)phenyl) isonicotinic acid

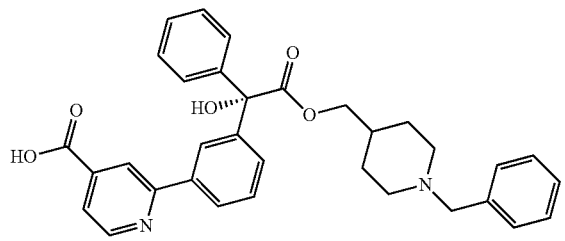 [SMILES: O=C(O)c1ccnc(-c2cccc([C@](O)(C(=O)OCC3CCN(Cc4ccccc4)CC3)c3ccccc3)c2)c1]

tert-Butyl (S)-6-(3-(2-((1-benzylpiperidin-4-yl)methoxy)-1-hydroxy-2-oxo-1-phenylethyl)phenyl)pyrazine-2-carboxylate (0.08 g, 0.13 mmol) was added with a solution of HCl in dioxane (4M, 10 mL) and stirred at room temperature for 18 hours. The solvent was evaporated at reduced pressure to afford the title compound which was used in the next step without characterization.

Step 6: (1-Benzylpiperidin-4-yl)methyl (S)-2-hydroxy-2-(3-(4-(4-((((R)-2-hydroxy-2-(8-hydroxy-2-oxo-1,2-dihydroquinolin-5-yl)ethyl)amino)methyl)piperidine-1-carbonyl)pyridin-2-yl)phenyl)-2-phenylacetate (Compound 6)

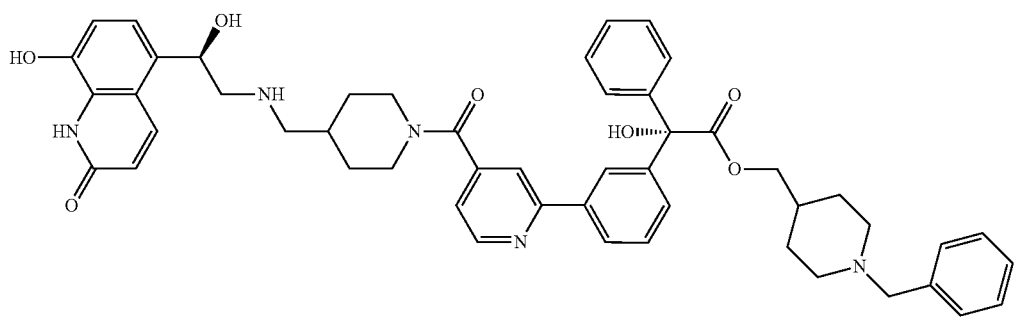 [SMILES: O=C(c1ccnc(-c2cccc([C@](O)(C(=O)OCC3CCN(Cc4ccccc4)CC3)c3ccccc3)c2)c1)N1CCC(CNC[C@H](O)c2ccc(O)c3[nH]c(=O)ccc23)CC1]

The title compound was prepared as in Example 1 Step 8 and Step 9.

The following compounds were prepared as described in Example 6 with the appropriate halide in Step 1.

| Compound No. | Appropriate bromide |
|---|---|
| 6A | ![structure] tert-butyl 6-chloropyrazine-2-carboxylate |
| 6B | ![structure] tert-butyl 4-chloropicolinate |
| 6C | ![structure] tert-butyl 5-chloropicolinate |
| 6D | ![structure] tert-butyl 6-chloronicotinate |

-continued
| | |
|---|---|
| 6E | 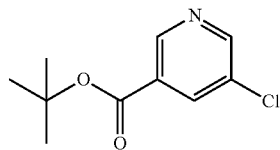 |
| 6F | 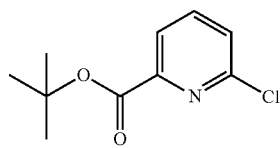 |
| Compound No. | Structure |
|---|---|
| 6A | 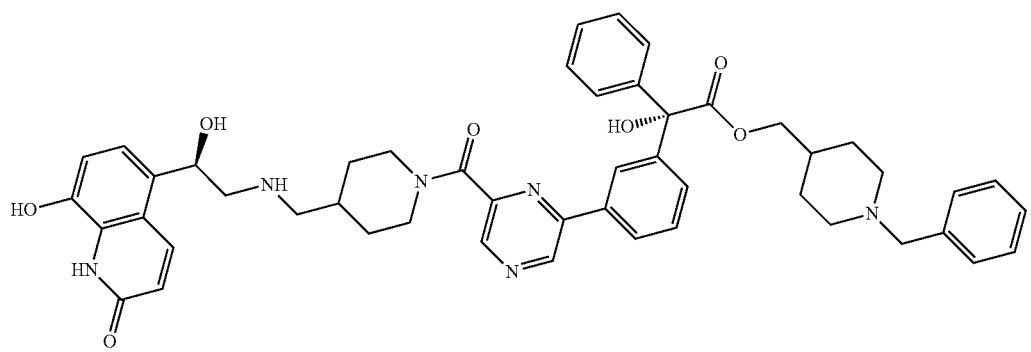 [SMILES: O=C(c1cncc(-c2cccc([C@](O)(C(=O)OCC3CCN(Cc4ccccc4)CC3)c3ccccc3)c2)n1)N1CCC(CNC[C@H](O)c2ccc(O)c3[nH]c(=O)ccc23)CC1] |
| 6B | 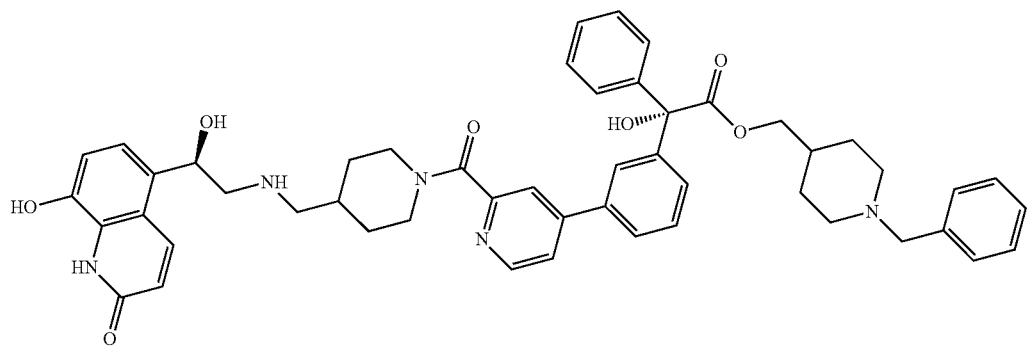 [SMILES: O=C(c1cc(-c2cccc([C@](O)(C(=O)OCC3CCN(Cc4ccccc4)CC3)c3ccccc3)c2)ccn1)N1CCC(CNC[C@H](O)c2ccc(O)c3[nH]c(=O)ccc23)CC1] |
| 6C | 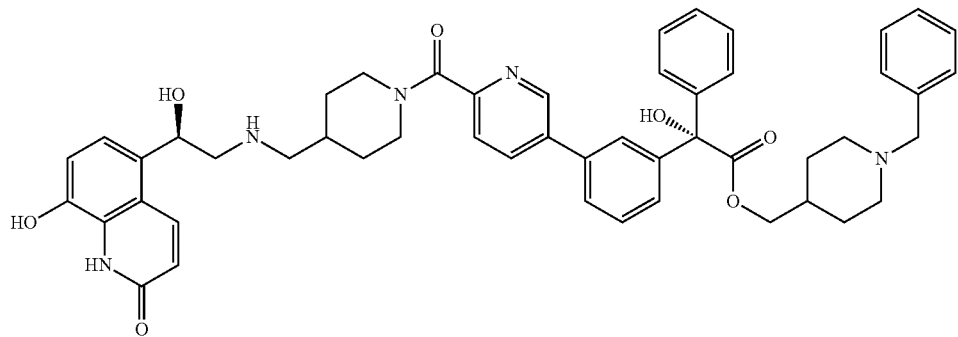 [SMILES: O=C(c1ccc(-c2cccc([C@](O)(C(=O)OCC3CCN(Cc4ccccc4)CC3)c3ccccc3)c2)cn1)N1CCC(CNC[C@H](O)c2ccc(O)c3[nH]c(=O)ccc23)CC1] |

6D
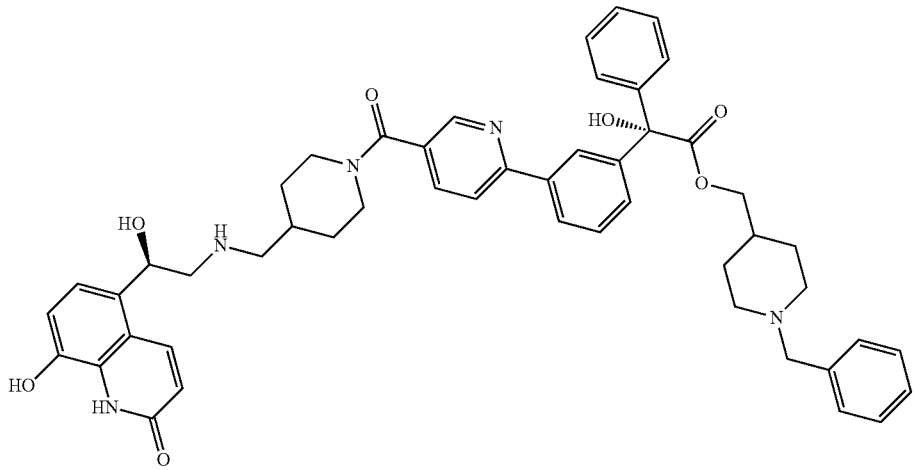 [SMILES: O=C(c1ccc(-c2cccc([C@](O)(C(=O)OCC3CCN(Cc4ccccc4)CC3)c3ccccc3)c2)nc1)N1CCC(CNC[C@H](O)c2ccc(O)c3[nH]c(=O)ccc23)CC1]
6E
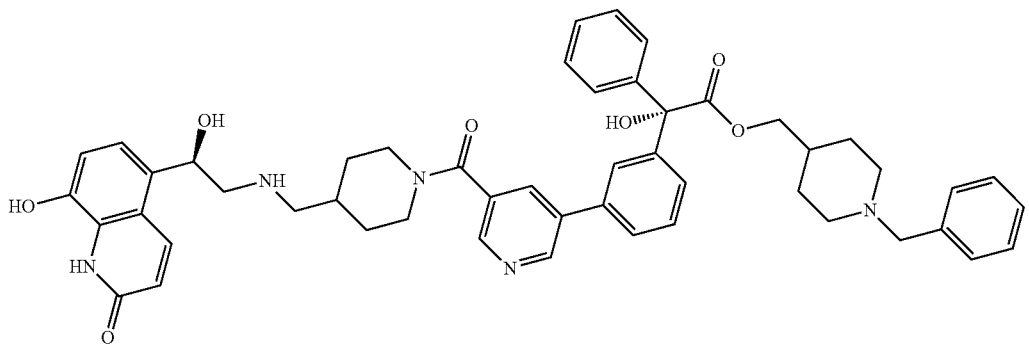 [SMILES: O=C(c1cncc(-c2cccc([C@](O)(C(=O)OCC3CCN(Cc4ccccc4)CC3)c3ccccc3)c2)c1)N1CCC(CNC[C@H](O)c2ccc(O)c3[nH]c(=O)ccc23)CC1]
6F
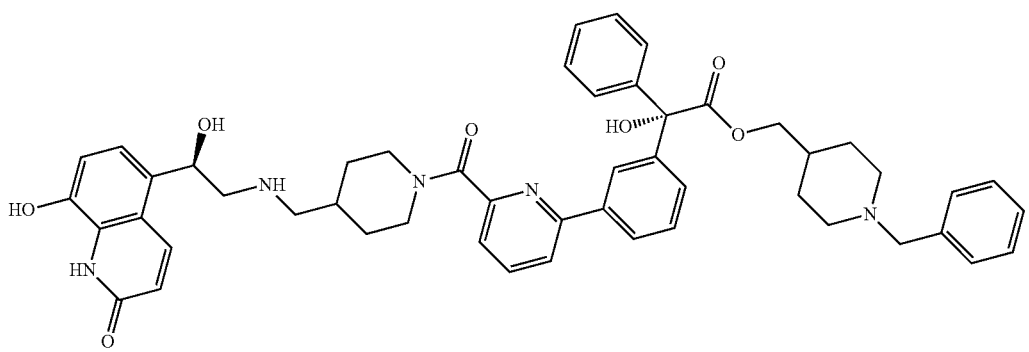 [SMILES: O=C(c1cccc(-c2cccc([C@](O)(C(=O)OCC3CCN(Cc4ccccc4)CC3)c3ccccc3)c2)n1)N1CCC(CNC[C@H](O)c2ccc(O)c3[nH]c(=O)ccc23)CC1]

Example 7

(1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)benzoyl)piperidin-4-yl)phenyl)-2-phenylacetate (Compound 7)

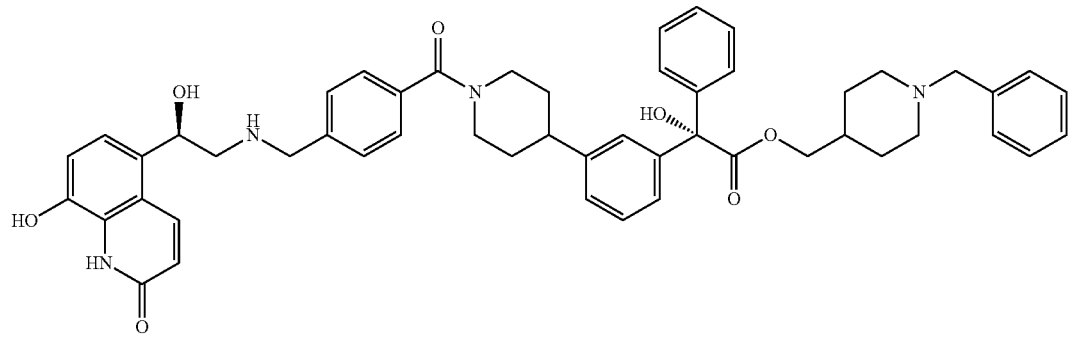 [SMILES: O=C(c1ccc(CNC[C@H](O)c2ccc(O)c3[nH]c(=O)ccc23)cc1)N1CCC(c2cccc([C@](O)(C(=O)OCC3CCN(Cc4ccccc4)CC3)c3ccccc3)c2)CC1]

Step 1: tert-Butyl (S)-4-(3-(1-hydroxy-2-methoxy-2-oxo-1-phenylethyl)phenyl)-3,6-dihydropyridine-1(2H)-carboxylate

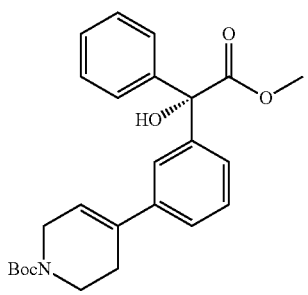 [SMILES: COC(=O)[C@](O)(c1ccccc1)c1cccc(C2=CCN(C(=O)OC(C)(C)C)CC2)c1]

The title compound was prepared as described in Example 2 Step 1 and 2.

$^1$H NMR (400 MHz, CDCl$_3$); δ 7.44-7.28 (m, 10H), 5.99 (brs, 1H), 4.05 (s, 2H), 3.87 (s, 3H), 3.62-3.57 (m, 2H), 2.48 (br s, 2H), 1.48 (s, 9H).

Step 2: tert-butyl (S)-4-(3-(1-hydroxy-2-methoxy-2-oxo-1-phenylethyl)phenyl)piperidine-1-carboxylate

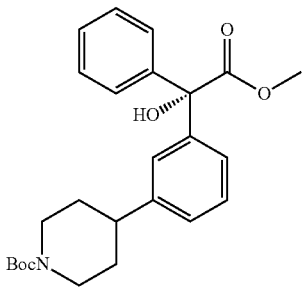 [SMILES: COC(=O)[C@](O)(c1ccccc1)c1cccc(C2CCN(C(=O)OC(C)(C)C)CC2)c1]

A solution of tert-butyl (S)-4-(3-(1-hydroxy-2-methoxy-2-oxo-1-phenylethyl)phenyl)-3,6-dihydropyridine-1(2H)-carboxylate (4.9 g, 11.58 mmol) in ethanol (100 mL) was added with palladium on carbon (2.5 g) and 1-methyl-1,4-cyclohexadiene (6.50 mL, 57.9 mmol). The reaction mixture heated to reflux and heated at this temperature for two hours. The suspension was filtered and the filtrate evaporated at reduced pressure to afford the title compound (3.2 g, 65%).

$^1$H NMR (400 MHz, CDCl$_3$); δ 7.43-7.39 (m, 2H), 7.36-7.27 (m, 6H), 7.24-7.22 (m, 1H), 7.16 (d, J=7.3 Hz, 1H), 4.17 (s, 2H), 3.86 (s, 3H), 3.72 (dd, J=6.1, 6.1 Hz, 1H), 2.77 (dd, J=12.0, 12.0 Hz, 2H), 2.67-2.58 (m, 1H), 2.44 (dd, J=6.1, 6.1 Hz, 1H), 1.79 (d, J=12.9 Hz, 2H), 1.48 (s, 9H).

Step 3: (1-Benzylpiperidin-4-yl)methyl (S)-2-hydroxy-2-(3-(1-(4-((((R)-2-hydroxy-2-(8-hydroxy-2-oxo-1,2-dihydroquinolin-5-yl)ethyl)amino)methyl)benzoyl)piperidin-4-yl)phenyl)-2-phenylacetate (Compound 7)

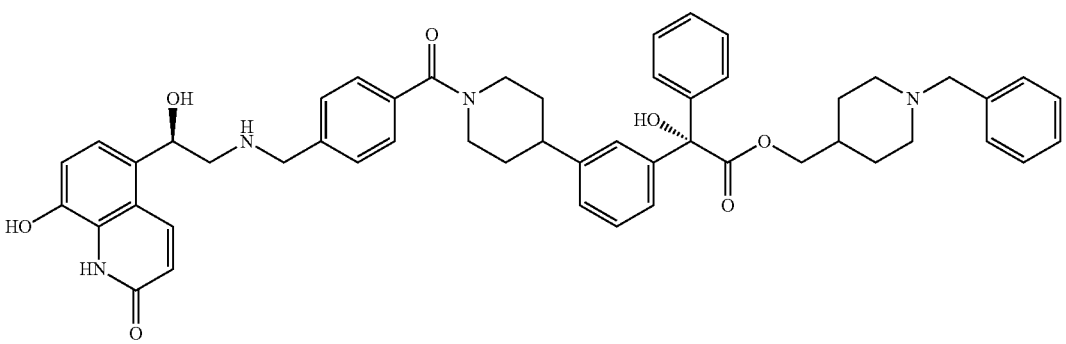 [SMILES: O=C(c1ccc(CNC[C@H](O)c2ccc(O)c3[nH]c(=O)ccc23)cc1)N1CCC(c2cccc([C@](O)(C(=O)OCC3CCN(Cc4ccccc4)CC3)c3ccccc3)c2)CC1]

The title compound was prepared as described in Example 2 Step 3, 4, 5 and Step 6.

The following compounds were prepared as described in Example 7.

| Compound No. | Structure |
|---|---|
| 7A | 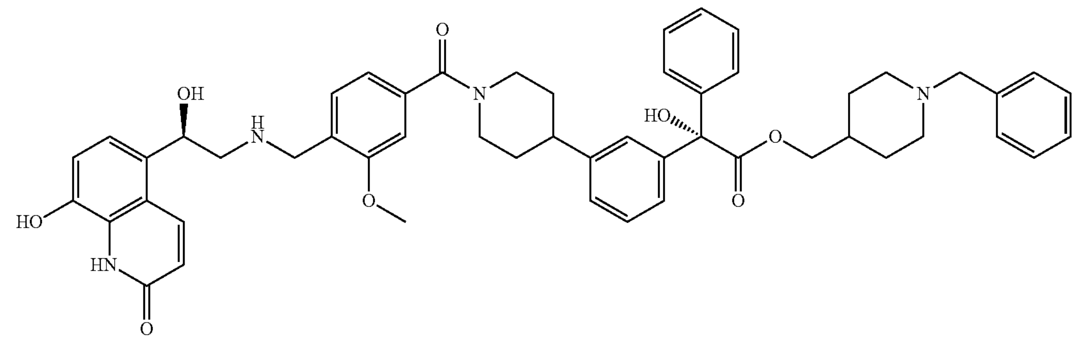 [SMILES: COc1cc(C(=O)N2CCC(c3cccc([C@](O)(C(=O)OCC4CCN(Cc5ccccc5)CC4)c4ccccc4)c3)CC2)ccc1CNC[C@H](O)c1ccc(O)c2[nH]c(=O)ccc12] |
| 7B | 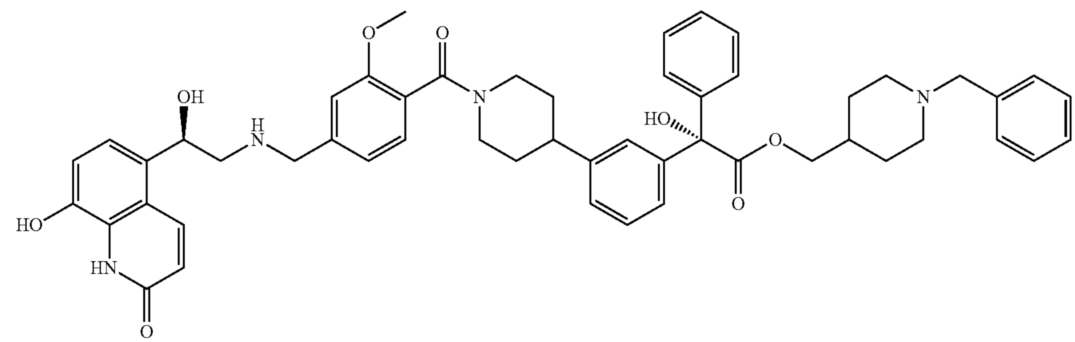 [SMILES: COc1cc(CNC[C@H](O)c2ccc(O)c3[nH]c(=O)ccc23)ccc1C(=O)N1CCC(c2cccc([C@](O)(C(=O)OCC3CCN(Cc4ccccc4)CC3)c3ccccc3)c2)CC1] |
| 7C | 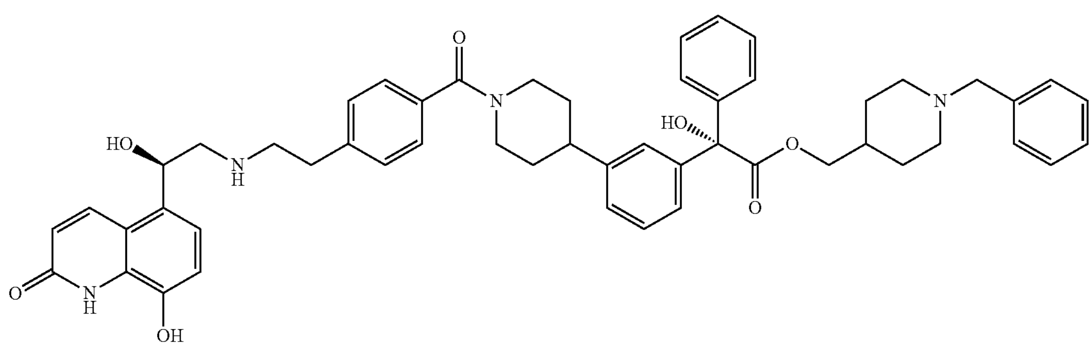 [SMILES: O=C(c1ccc(CCNC[C@H](O)c2ccc(O)c3[nH]c(=O)ccc23)cc1)N1CCC(c2cccc([C@](O)(C(=O)OCC3CCN(Cc4ccccc4)CC3)c3ccccc3)c2)CC1] |
| 7D | 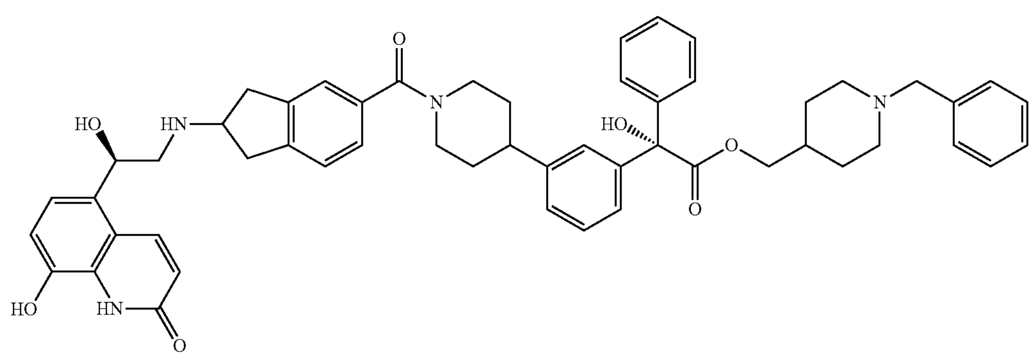 [SMILES: O=C(c1ccc2c(c1)CC(NC[C@H](O)c1ccc(O)c3[nH]c(=O)ccc13)C2)N1CCC(c2cccc([C@](O)(C(=O)OCC3CCN(Cc4ccccc4)CC3)c3ccccc3)c2)CC1] |

Example 8

(1-Benzylpiperidin-4-yl)methyl (S)-2-hydroxy-2-(3-(1-((4-(2-(((R)-2-hydroxy-2-(8-hydroxy-2-oxo-1,2-dihydroquinolin-5-yl)ethyl)amino)ethyl)benzoyl)-glycyl)-1,2,3,6-tetrahydropyridin-4-yl)phenyl)-2-phenylacetate (Compound 8)

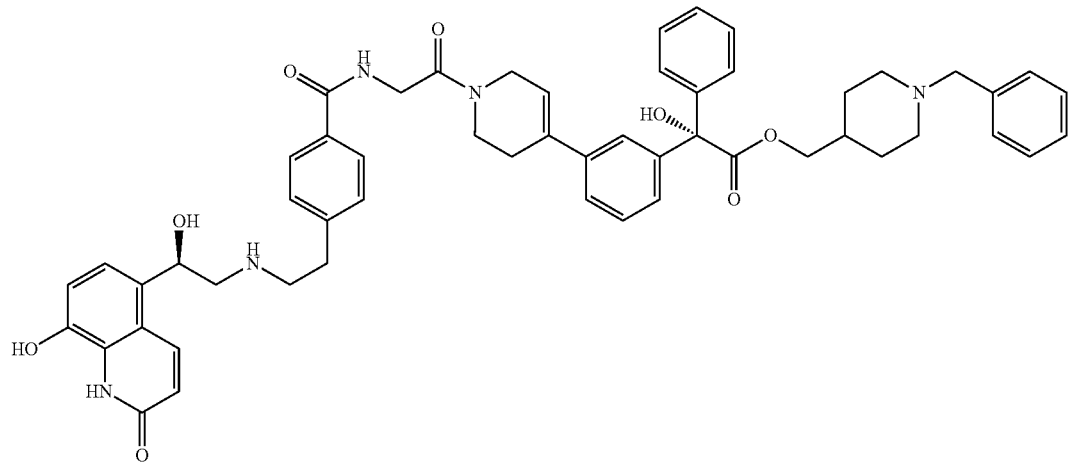 [SMILES: O=C(NCC(=O)N1CC=C(c2cccc([C@](O)(C(=O)OCC3CCN(Cc4ccccc4)CC3)c3ccccc3)c2)CC1)c1ccc(CCNC[C@H](O)c2ccc(O)c3[nH]c(=O)ccc23)cc1]

Step 1: (1-Benzylpiperidin-4-yl)methyl (S)-2-(3-(1-((tert-butoxycarbonyl)glycyl)-1,2,3,6-tetrahydropyridin-4-yl)phenyl)-2-hydroxy-2-phenylacetate

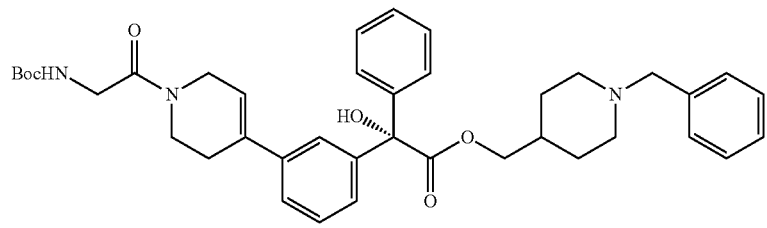 [SMILES: CC(C)(C)OC(=O)NCC(=O)N1CC=C(c2cccc([C@](O)(C(=O)OCC3CCN(Cc4ccccc4)CC3)c3ccccc3)c2)CC1]

The title compounds was prepared according to Example 1 with tert-butyl 4-(4,4,5,5-tetramethyl-1,3,2-dioxaborolan-2-yl)-3,6-dihydropyridine-1(2H)-carboxylate used in Step 6 and Boc-glycine used in Step 8.

$^1$H NMR (400 MHz, CDCl$_3$); δ 7.45 (d, J=5.5 Hz, 1H), 7.42-7.38 (m, 2H), 7.34-7.27 (m, 11H), 7.25-7.22 (m, 1H), 6.02 and 5.94 (s, 1H, combined), 5.55 (s, 1H), 4.26-4.20 (m, 2H), 4.15-4.09 (m, 3H), 4.03-3.96 (m, 3H), 3.80 (dd, J=5.8, 5.8 Hz, 1H), 3.55 (dd, J=5.6, 5.6 Hz, 1H), 3.45 (s, 2H), 2.80 (d, J=11.7 Hz, 2H), 2.50-2.50 (m, 2H), 1.91-1.83 (m, 2H), 1.46 (s, 9H), 1.28-0.83 (m, 3H).

Step 2: (1-Benzylpiperidin-4-yl)methyl (S)-2-hydroxy-2-(3-(1-((4-(2-(((R)-2-hydroxy-2-(8-hydroxy-2-oxo-1,2-dihydroquinolin-5-yl)ethyl)amino)ethyl)benzoyl)glycyl)-1,2,3,6-tetrahydropyridin-4-yl)phenyl)-2-phenylacetate (Compound 8)

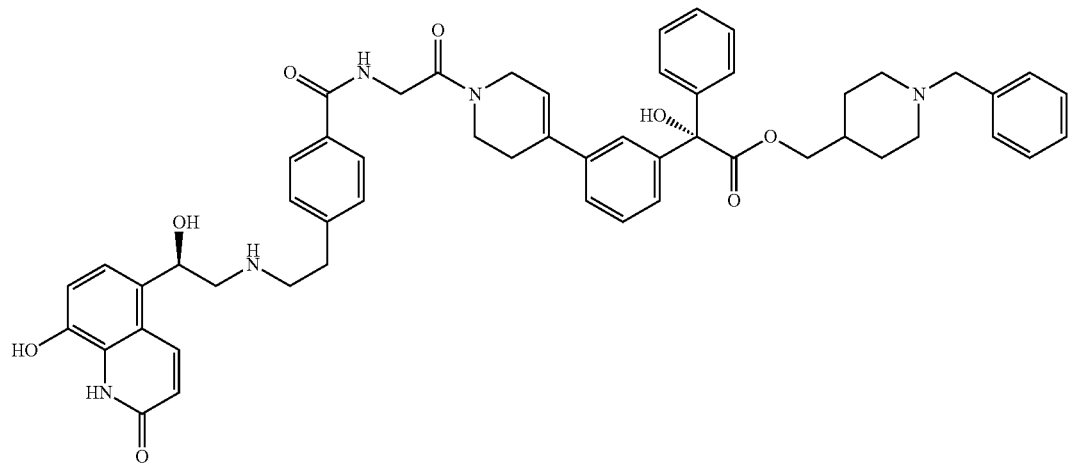 [SMILES: O=C(NCC(=O)N1CC=C(c2cccc([C@](O)(C(=O)OCC3CCN(Cc4ccccc4)CC3)c3ccccc3)c2)CC1)c1ccc(CCNC[C@H](O)c2ccc(O)c3[nH]c(=O)ccc23)cc1]

The title compound was prepared as described in Example 1 with (1-benzylpiperidin-4-yl)methyl (S)-2-(3-(1-((tert-butoxycarbonyl)glycyl)-1,2,3,6-tetrahydropyridin-4-yl)phenyl)-2-hydroxy-2-phenylacetate used in Step 7 and the subsequent product used in Step 8 (coupling with (R)-4-(2-((tert-butoxycarbonyl)(2-((tert-butyldimethylsilyl)oxy)-2-(8-hydroxy-2-oxo-1,2-dihydroquinolin-5-yl)ethyl)amino)ethyl)benzoic acid) and Step 9.

The following compounds were prepared as described in Example 8.

| Compound No. | Structure |
|---|---|
| 8A | 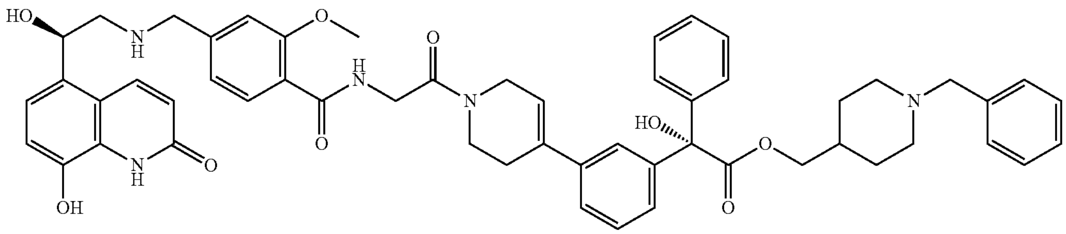 [SMILES: COc1cc(CNC[C@H](O)c2ccc(O)c3[nH]c(=O)ccc23)ccc1C(=O)NCC(=O)N1CC=C(c2cccc([C@](O)(C(=O)OCC3CCN(Cc4ccccc4)CC3)c3ccccc3)c2)CC1] |
| 8B | 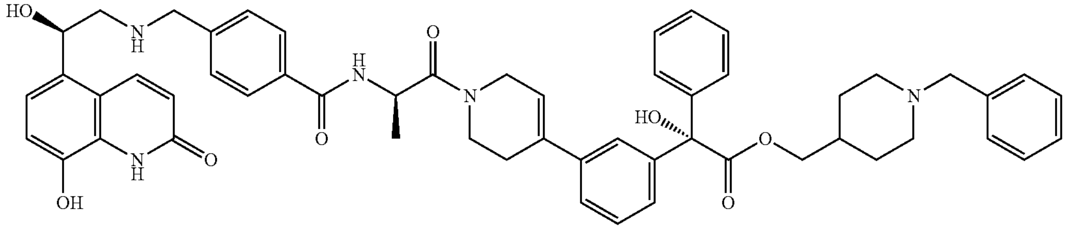 [SMILES: C[C@@H](NC(=O)c1ccc(CNC[C@H](O)c2ccc(O)c3[nH]c(=O)ccc23)cc1)C(=O)N1CC=C(c2cccc([C@](O)(C(=O)OCC3CCN(Cc4ccccc4)CC3)c3ccccc3)c2)CC1] |

| Compound No. | Structure |
|---|---|
| 8C | 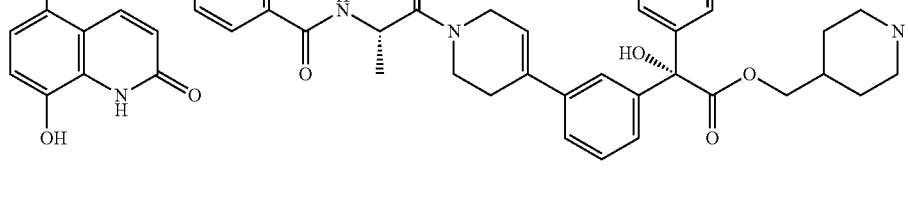 |
| 8D | 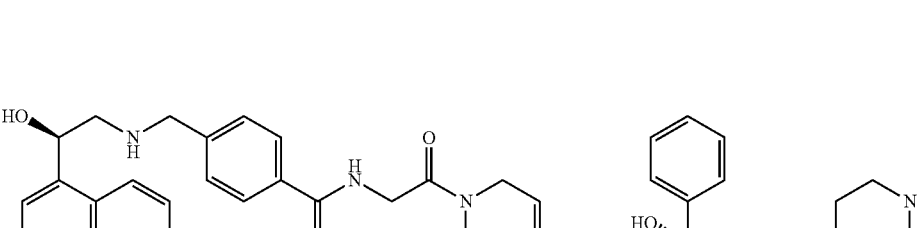 |
| 8E | 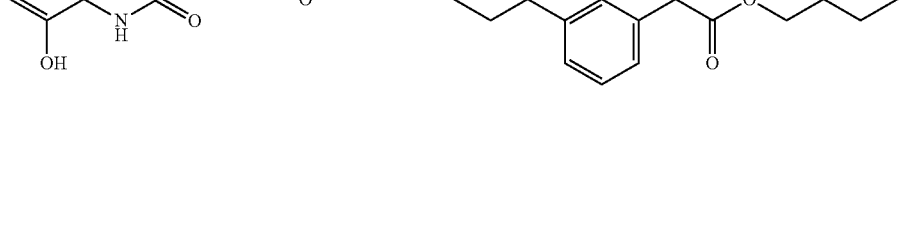 |
| 8F | 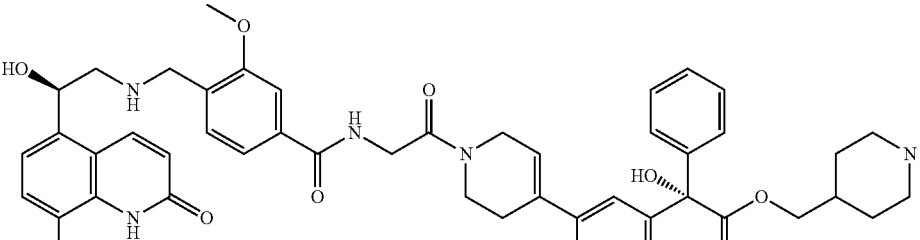 |

Example 9

(1-Benzylpiperidin-4-yl)methyl (S)-2-hydroxy-2-(3-(6-((((1R,3S)-3-(4-((((R)-2-hydroxy-2-(8-hydroxy-2-oxo-1,2-dihydroquinolin-5-yl)ethyl)amino)methyl)-benzamido)cyclobutyl)carbamoyl)pyrazin-2-yl)phenyl)-2-phenylacetate (Compound 9)

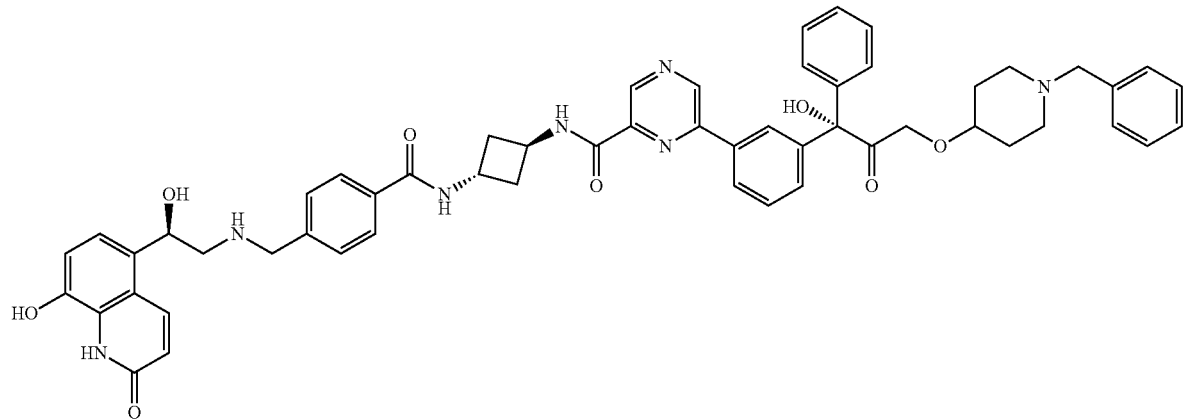 [SMILES: O=C(N[C@H]1C[C@H](NC(=O)c2cncc(-c3cccc([C@](O)(C(=O)COC4CCN(Cc5ccccc5)CC4)c4ccccc4)c3)n2)C1)c1ccc(CNC[C@H](O)c2ccc(O)c3[nH]c(=O)ccc23)cc1]

Step 1: tert-Butyl ((trans)-3-(6-chloropyrazine-2-carboxamido)cyclobutyl)carbamate

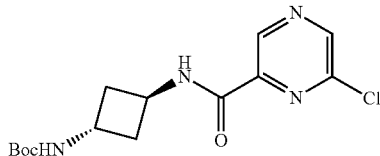 [SMILES: CC(C)(C)OC(=O)N[C@H]1C[C@H](NC(=O)c2cncc(Cl)n2)C1]

A stirred solution of 6-chloropyrazine-2-carboxylic acid (0.25 g, 1.58 mmol) in DMF (3 mL) was added with DIPEA (0.42 mL, 2.37 mmol) and HATU (0.72 g, 1.9 mmol). The reaction mixture was stirred at room temperature for 20 minutes. A solution of tert-butyl (trans-3-aminocyclobutyl)carbamate (0.32 g, 1.74 mmol) in DMF (3 mL) was added and the reaction mixture was stirred at room temperature for 18 hours. The reaction mixture was diluted with ethyl acetate and was washed sequentially with saturated aqueous sodium hydrogen carbonate (×2) and brine. The organic phase was dried over anhydrous magnesium sulfate, filtered and the filtrate evaporated at reduced pressure to afford the title compound (0.530 g, 93%).

$^1$H NMR (400 MHz, DMSO-d$_6$); δ 9.18 (d, J=7.5 Hz, 1H), 9.11 (s, 1H), 9.01 (s, 1H), 7.30 (d, J=7.0 Hz, 1H), 4.54-4.49 (m, 1H), 4.08-4.01 (m, 1H), 2.70 (s, 1H), 2.48-2.39 (m, 2H), 2.27-2.19 (m, 2H), 1.40 (s, 9H).

Step 2: tert-Butyl (trans-3-(6-(4,4,5,5-tetramethyl-1,3,2-dioxaborolan-2-yl)pyrazine-2-carboxamido)cyclobutyl)carbamate

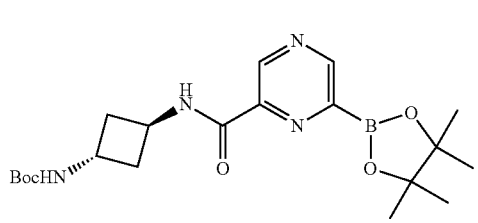 [SMILES: CC(C)(C)OC(=O)N[C@H]1C[C@H](NC(=O)c2cncc(B3OC(C)(C)C(C)(C)O3)n2)C1]

A solution of tert-butyl ((trans)-3-(6-chloropyrazine-2-carboxamido)cyclobutyl)carbamate (0.196 g, 0.66 mmol), bis-pinacolatodiboronate ester (0.168 g, 0.66 mmol) and potassium carbonate (0.177 g, 1.8 mmol) in 1,4-dioxane (5 mL) was degassed with nitrogen for 5 minutes. Pd(dppf)Cl$_2$ DCM adduct (0.049 g, 0.06 mmol) was added and the reaction degassed for a further 5 minutes. The reaction mixture was heated at 80° C. for 3 hours. The reaction mixture was diluted with ethyl acetate and was washed sequentially with saturated aqueous sodium hydrogen carbonate (×2) and brine. The organic phase was dried over anhydrous magnesium sulfate, filtered and the filtrate evaporated at reduced pressure to afford the title compound which was used directly in the next step.

Step 3: (1-Benzylpiperidin-4-yl)methyl (S)-2-hydroxy-2-(3-(6-((((1R,3S)-3-(4-(((((R)-2-hydroxy-2-(8-hydroxy-2-oxo-1,2-dihydroquinolin-5-yl)ethyl)amino)methyl)benzamido)cyclobutyl)carbamoyl)pyrazin-2-yl)phenyl)-2-phenylacetate (Compound 9)

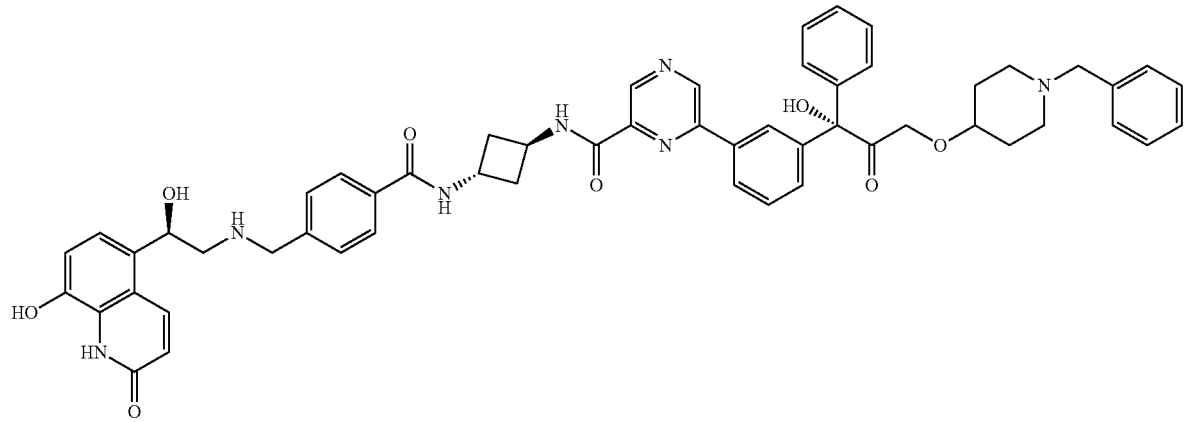 [SMILES: O=C(N[C@H]1C[C@H](NC(=O)c2cncc(-c3cccc([C@](O)(C(=O)COC4CCN(Cc5ccccc5)CC4)c4ccccc4)c3)n2)C1)c1ccc(CNC[C@H](O)c2ccc(O)c3[nH]c(=O)ccc23)cc1]

The title compound was prepared as described in Example 1 with tert-butyl (trans-3-(6-(4,4,5,5-tetramethyl-1,3,2-dioxaborolan-2-yl)pyrazine-2-carboxamido)cyclobutyl)carbamate used in place of (5-(((tert-butoxycarbonyl)amino)methyl)thiophen-2-yl)boronic acid in Step 6 and the product from this step used in the subsequent steps in Example 1.

Example 10

(1-Benzylpiperidin-4-yl)methyl (S)-2-hydroxy-2-(3-(6-((3-(((R)-2-hydroxy-2-(8-hydroxy-2-oxo-1,2-dihydroquinolin-5-yl)ethyl)amino)propyl)carbamoyl)pyrazin-2-yl)phenyl)-2-phenylacetate (Compound 10)

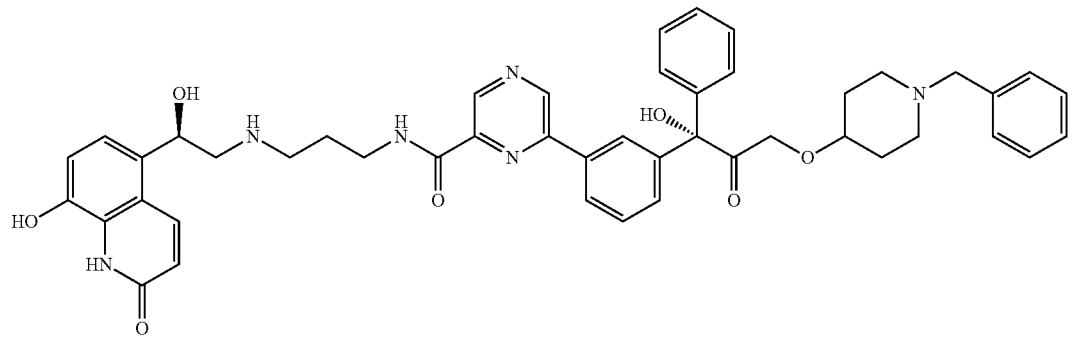 [SMILES: O=C(NCCCNC[C@H](O)c1ccc(O)c2[nH]c(=O)ccc12)c1cncc(-c2cccc([C@](O)(C(=O)COC3CCN(Cc4ccccc4)CC3)c3ccccc3)c2)n1]

Step 1: 6-Chloro-N-(3,3-diethoxypropyl)pyrazine-2-carboxamide

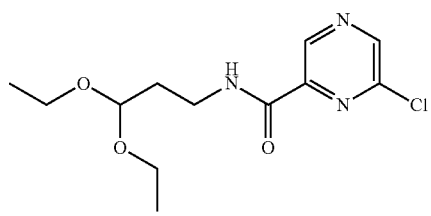 [SMILES: CCOC(CCNC(=O)c1cncc(Cl)n1)OCC]

The title compound was prepared as described in Example 9 Step 1.

¹H NMR (400 MHz, CDCl₃); δ 9.30-9.28 (m, 1H), 8.75-8.72 (m, 1H), 8.37-8.28 (m, 1H), 4.66 (dd, J=4.9, 4.9 Hz, 1H), 3.78-3.69 (m, 2H), 3.65-3.50 (m, 4H), 1.99-1.93 (m, 2H), 1.29 (dd, J=7.1, 7.1 Hz, 6H).

Step 2: N-(3,3-Diethoxypropyl)-6-(4,4,5,5-tetramethyl-1,3,2-dioxaborolan-2-yl)pyrazine-2-carboxamide

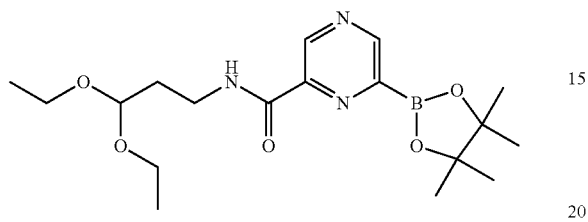

The title compound was prepared as described in Example 9 Step 2 and used immediately with no purification.

Step 3: (1-Benzylpiperidin-4-yl)methyl (S)-2-(3-(6-((3,3-diethoxypropyl)carbamoyl)-pyrazin-2-yl)phenyl)-2-hydroxy-2-phenylacetate

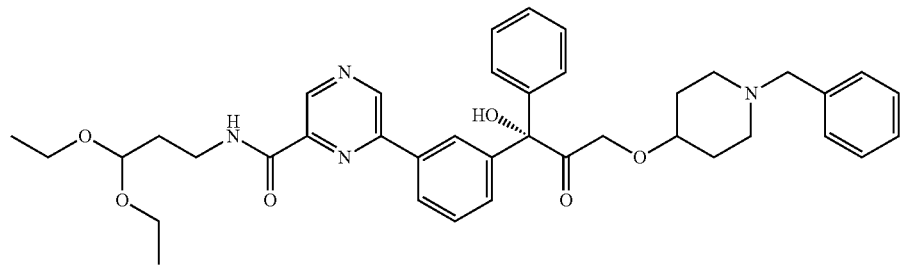 [SMILES: CCOC(CCNC(=O)c1cncc(-c2cccc([C@](O)(C(=O)COC3CCN(Cc4ccccc4)CC3)c3ccccc3)c2)n1)OCC]

The title compound was prepared as described in Example 1 Step 6 with N-(3,3-diethoxypropyl)-6-(4,4,5,5-tetramethyl-1,3,2-dioxaborolan-2-yl)pyrazine-2-carboxamide used in place of added (5-(((tert-butoxycarbonyl)amino)methyl)thiophen-2-yl)boronic acid. The product was used in the next step with no purification.

Step 4: (R)-5-(2-Amino-1-hydroxyethyl)-8-hydroxyquinolin-2(1H)-one hydrochloride

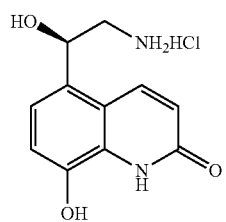

A solution of (R)-5-(2-azido-1-((tert-butyldimethylsilyl)oxy)ethyl)-8-(benzyloxy)quinolin-2(1H)-one (4.50 g, 10.0 mmol) in ethanol (50 mL) was added with 10% palladium on charcoal (4.50 g) followed by 1-methyl-1,4-cyclohexadiene (11.0 mL, 97.9 mmol). The reaction was warmed to 60° C. and then stirred at 60° C. for 2 hours. The reaction mixture was allowed to cool and filtered through a pad of celite. The filtercake was washed with further ethanol and the filtrate was evaporated under reduced pressure. The residue was evaporated from iso-propanol (×2) and dissolved in iso-propanol (30 mL). HCl in dioxane (4M, 50 mL, 200 mmol) was added and the reaction mixture stirred at room temperature for 18 hours. The resulting suspension was filtered, the filtercake washed with di ethyl ether and the solid dried under vacuum in the presence of P₂O₅ to afford the title compound (1.65 g, 62%).

¹H NMR (400 MHz, MeOD): δ 7.71 (d, J=9.8 Hz, 1H), 6.57 (d, J=8.2 Hz, 1H), 6.31 (d, J=8.2 Hz, 1H), 6.02 (dd, J=9.8, 6.5 Hz, 1H), 4.58 (dd, J=9.6, 3.5 Hz, 1H), 2.47-2.31 (m, 2H).

Step 5: (1-Benzylpiperidin-4-yl)methyl (S)-2-hydroxy-2-(3-(6-((3-(((R)-2-hydroxy-2-(8-hydroxy-2-oxo-1,2-dihydroquinolin-5-yl)ethyl)amino)propyl)carbamoyl)pyrazin-2-yl)phenyl)-2-phenylacetate (Compound 10)

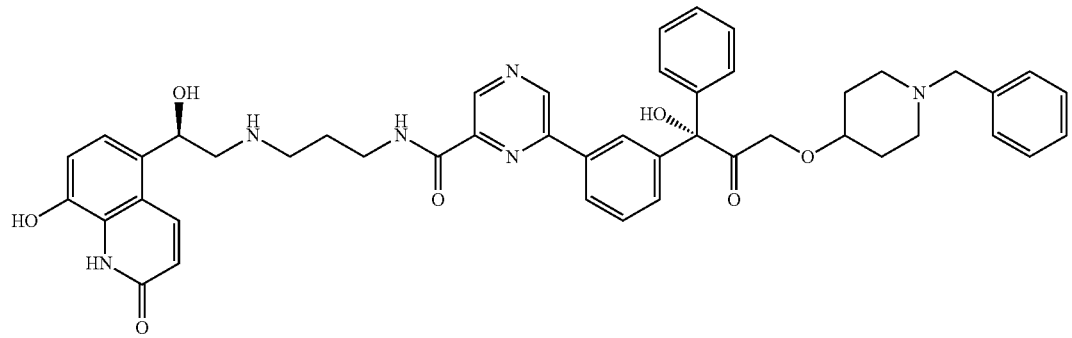 [SMILES: O=C(NCCCNC[C@H](O)c1ccc(O)c2[nH]c(=O)ccc12)c1cncc(-c2cccc([C@](O)(C(=O)COC3CCN(Cc4ccccc4)CC3)c3ccccc3)c2)n1]

A stirred solution of (1-benzylpiperidin-4-yl)methyl (S)-2-(3-(6-((3,3-diethoxypropyl)carbamoyl)pyrazin-2-yl)phenyl)-2-hydroxy-2-phenylacetate (0.66 g, 0.90 mmol) in THF (5 mL) was added with 10% aqueous hydrochloric acid (5 mL). The resulting mixture was stirred at room temperature for 2 hours. The mixture was added with 10% aqueous potassium carbonate and then extracted with ethyl acetate (×2). The combined organic phases were dried and the filtrate was evaporated under reduced pressure. The residue was dissolved in methanol (3 mL) and added to a pre-stirred (10 minutes) mixture of (R)-5-(2-amino-1-hydroxyethyl)-8-hydroxyquinolin-2(1H)-one hydrochloride (0.30 g, 1.18 mmol, 80% purity) and triethylamine (0.20 g, 2 mmol) in methanol (3 mL). This mixture was stirred at room temperature for 1 hour and then sodium triacetoxyborohydride (0.63 g, 3.0 mmol) followed by acetic acid (0.15 mL, 4.0 mmol) were added. The reaction mixture was stirred for a further 1 hour. The reaction mixture was diluted with iso-butanol and washed with water. The aqueous phase was extracted with further iso-butanol. The combined iso-butanol extracts were evaporated under reduced pressure. The residue was purified by reverse phase preparative HPLC to afford the title compound.

Example 11

(1-Benzyl-4-methylpiperidin-4-yl)methyl (S)-2-(3-(5-((2-chloro-4-((((R)-2-hydroxy-2-(8-hydroxy-2-oxo-1,2-dihydroquinolin-5-yl)ethyl)amino)methyl)-5-methoxybenzamido)methyl)thiophen-2-yl)phenyl)-2-hydroxy-2-phenylacetate (Compound 11)

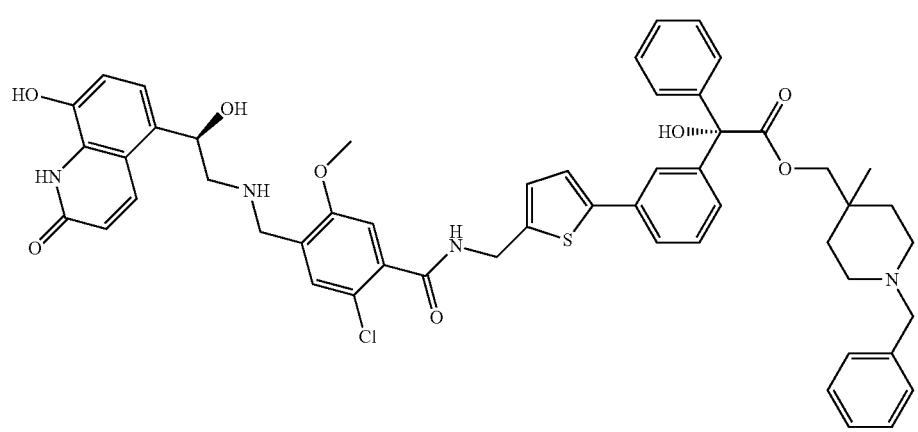 [SMILES: COc1cc(C(=O)NCc2ccc(-c3cccc([C@](O)(C(=O)OCC4(C)CCN(Cc5ccccc5)CC4)c4ccccc4)c3)s2)c(Cl)cc1CNC[C@H](O)c1ccc(O)c2[nH]c(=O)ccc12]

The title compound was prepared as described in Example 2 with the requisite alcohol in Step 4 and the requisite acid in Step 5.

| Requisite acid | Requisite alcohol |
|---|---|
| 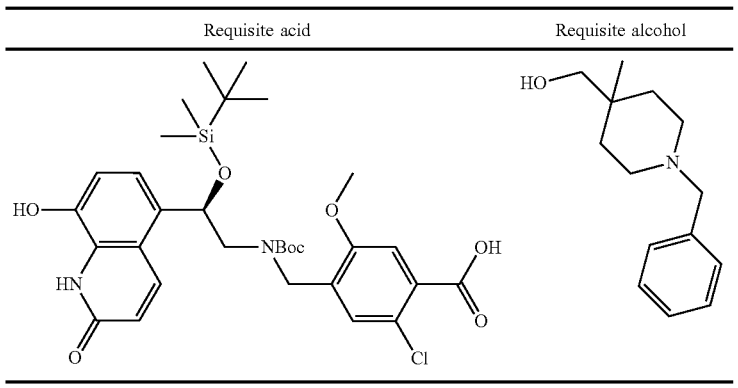 | |

Example 12

(1-Benzylpiperidin-4-yl)methyl (S)-2-hydroxy-2-(3-(5-((5-((((R)-2-hydroxy-2-(8-hydroxy-2-oxo-1,2-dihydroquinolin-5-yl)ethyl)amino)methyl)-1,3-dioxoisoindolin-2-yl)methyl)thiophen-2-yl)phenyl)-2-phenylacetate (Compound 12)

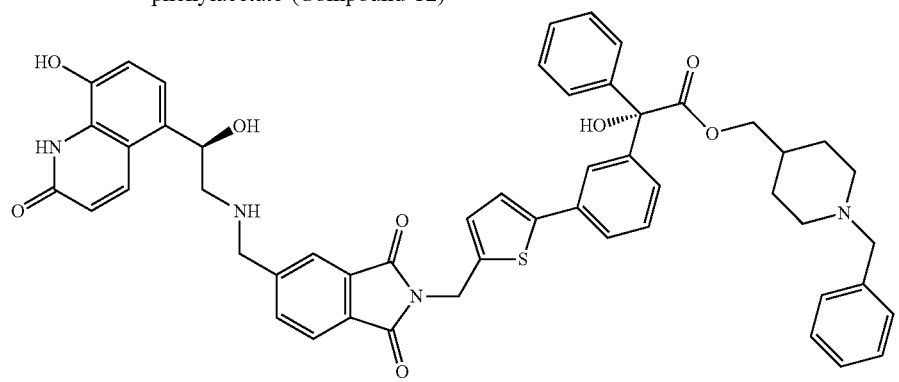

The title compound was prepared as described in Example 1 with the requisite acid used in Step 8. The compound was formed by an acid promoted cyclisation of the amide onto the nitrile in the final de-protection step.

| Requisite acid |
|---|
| 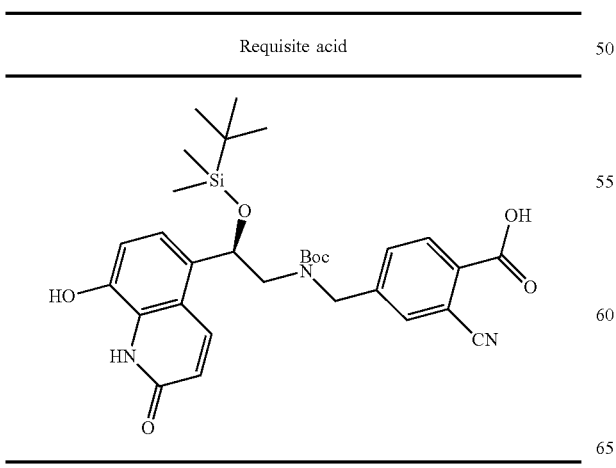 |

Example 13

(1-Benzylpiperidin-4-yl)methyl (S)-2-hydroxy-2-(3-(1-((4-(2-(((R)-2-hydroxy-2-(8-hydroxy-2-oxo-1,2-dihydroquinolin-5-yl)ethyl)amino)ethyl)benzoyl)-glycyl)piperidin-4-yl)phenyl)-2-phenylacetate (Compound 13)

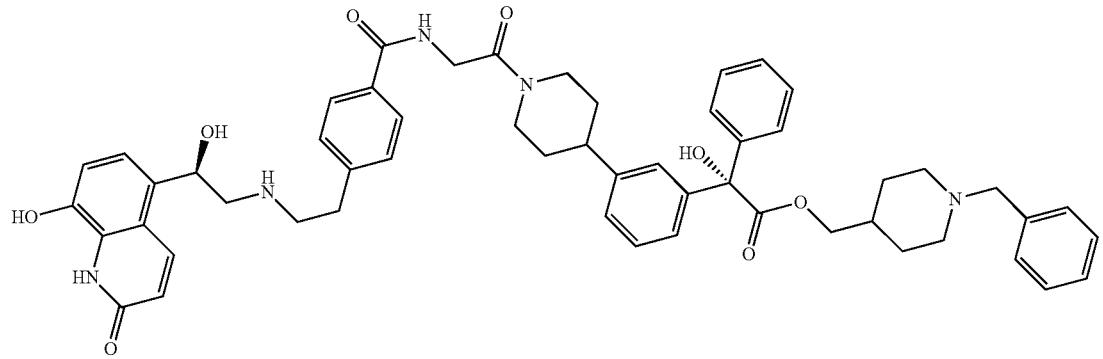 [SMILES: O=C(NCC(=O)N1CCC(c2cccc([C@](O)(C(=O)OCC3CCN(Cc4ccccc4)CC3)c3ccccc3)c2)CC1)c1ccc(CCNC[C@H](O)c2ccc(O)c3[nH]c(=O)ccc23)cc1]

The title compound was prepared as described in Example 7 and Example 8.

Example 14

(1-Benzylpiperidin-4-yl)methyl (S)-2-hydroxy-2-(3-(3-((4-((((R)-2-hydroxy-2-(8-hydroxy-2-oxo-1,2-dihydroquinolin-5-yl)ethyl)amino)methyl)-benzyl)carbamoyl)-1-methyl-1H-pyrazol-5-yl)phenyl)-2-phenylacetate (Compound 14)

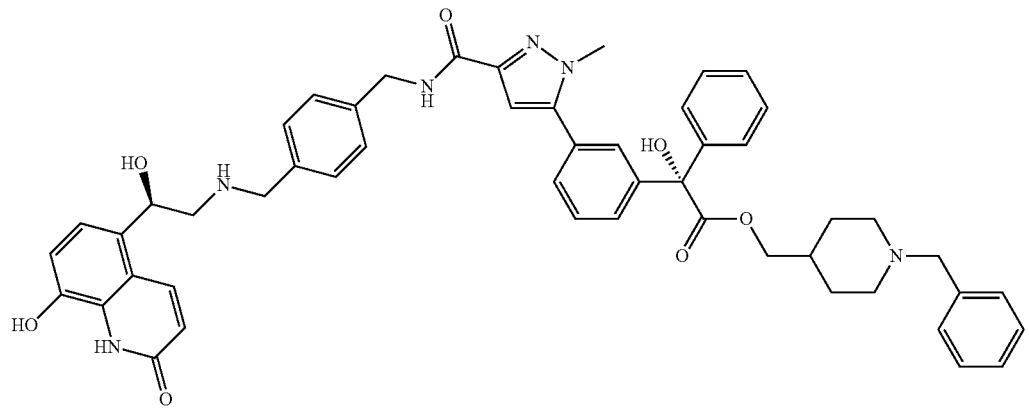 [SMILES: Cn1nc(C(=O)NCc2ccc(CNC[C@H](O)c3ccc(O)c4[nH]c(=O)ccc34)cc2)cc1-c1cccc([C@](O)(C(=O)OCC2CCN(Cc3ccccc3)CC2)c2ccccc2)c1]

Step 1: N-(4-(1,3-Dioxolan-2-yl)benzyl)-5-bromo-1-methyl-1H-pyrazole-3-carboxamide

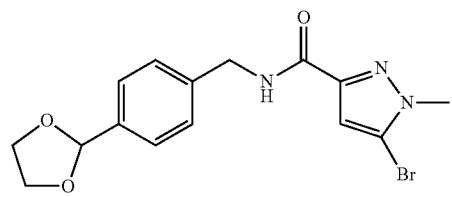 [SMILES: Cn1nc(C(=O)NCc2ccc(C3OCCO3)cc2)cc1Br]

The title compound was prepared as described in Example 9 Step 1.

¹H NMR (400 MHz, CDCl₃); δ 7.46 (d, J=8.0 Hz, 2H), 7.37-7.33 (m, 2H), 7.05 (s, 1H), 6.84 (s, 1H), 5.81 (s, 1H), 4.60 (d, J=6.0 Hz, 2H), 4.14-4.01 (m, 4H), 3.86 (s, 3H).

Step 2: N-(4-(1,3-Dioxolan-2-yl)benzyl)-1-methyl-5-(4,4,5,5-tetramethyl-1,3,2-dioxaborolan-2-yl)-1H-pyrazole-3-carboxamide

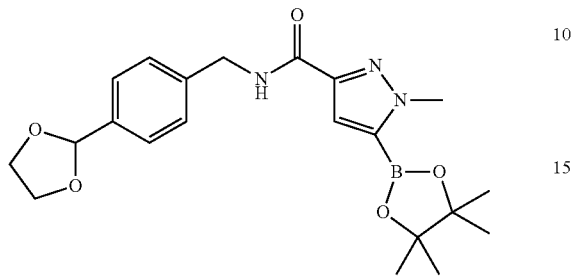

The title compound was prepared as described in Example 9 Step 2. The material used directly in the next step.

Step 3: (1-Benzylpiperidin-4-yl)methyl (S)-2-(3-(3-((4-(1,3-dioxolan-2-yl)benzyl)carbamoyl)-1-methyl-1H-pyrazol-5-yl)phenyl)-2-hydroxy-2-phenylacetate

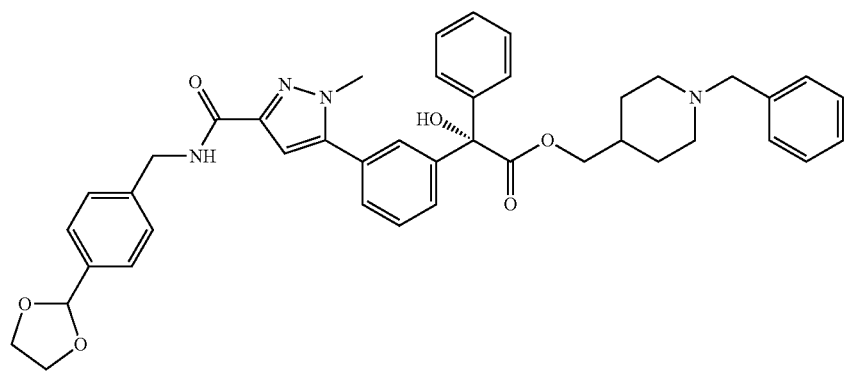 [SMILES: Cn1nc(C(=O)NCc2ccc(C3OCCO3)cc2)cc1-c1cccc([C@](O)(C(=O)OCC2CCN(Cc3ccccc3)CC2)c2ccccc2)c1]

The title compound was prepared as described in Example 1 Step 6 with N-(4-(1,3-dioxolan-2-yl)benzyl)-1-methyl-5-(4,4,5,5-tetramethyl-1,3,2-dioxaborolan-2-yl)-1H-pyrazole-3-carboxamide used in place of added (5-(((tert-butoxycarbonyl)amino)methyl)thiophen-2-yl)boronic acid.

LCMS Method 1; Rt 2.86 min; ES+ 701.3.

Step 4: (1-Benzylpiperidin-4-yl)methyl (S)-2-hydroxy-2-(3-(3-((4-((((R)-2-hydroxy-2-(8-hydroxy-2-oxo-1,2-dihydroquinolin-5-yl)ethyl)amino)methyl)benzyl)carbamoyl)-1-methyl-1H-pyrazol-5-yl)phenyl)-2-phenylacetate (Compound 14)

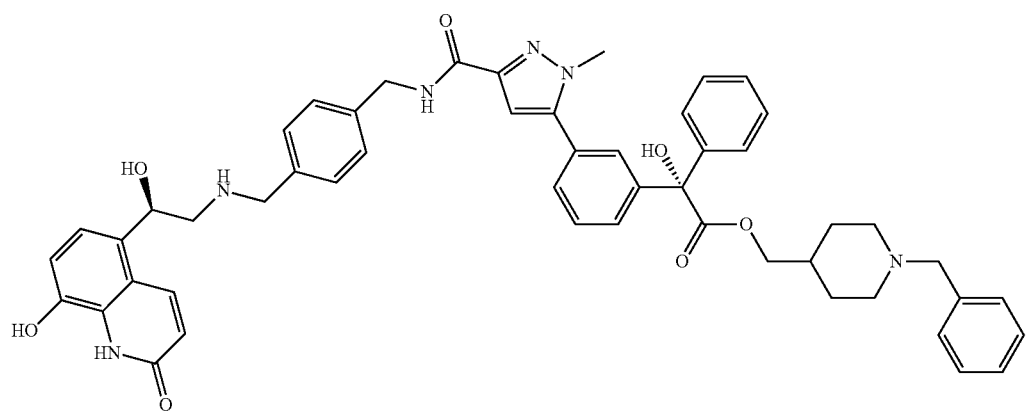 [SMILES: Cn1nc(C(=O)NCc2ccc(CNC[C@H](O)c3ccc(O)c4[nH]c(=O)ccc34)cc2)cc1-c1cccc([C@](O)(C(=O)OCC2CCN(Cc3ccccc3)CC2)c2ccccc2)c1]

The title compound was prepared as described in Example 10 Step 5.
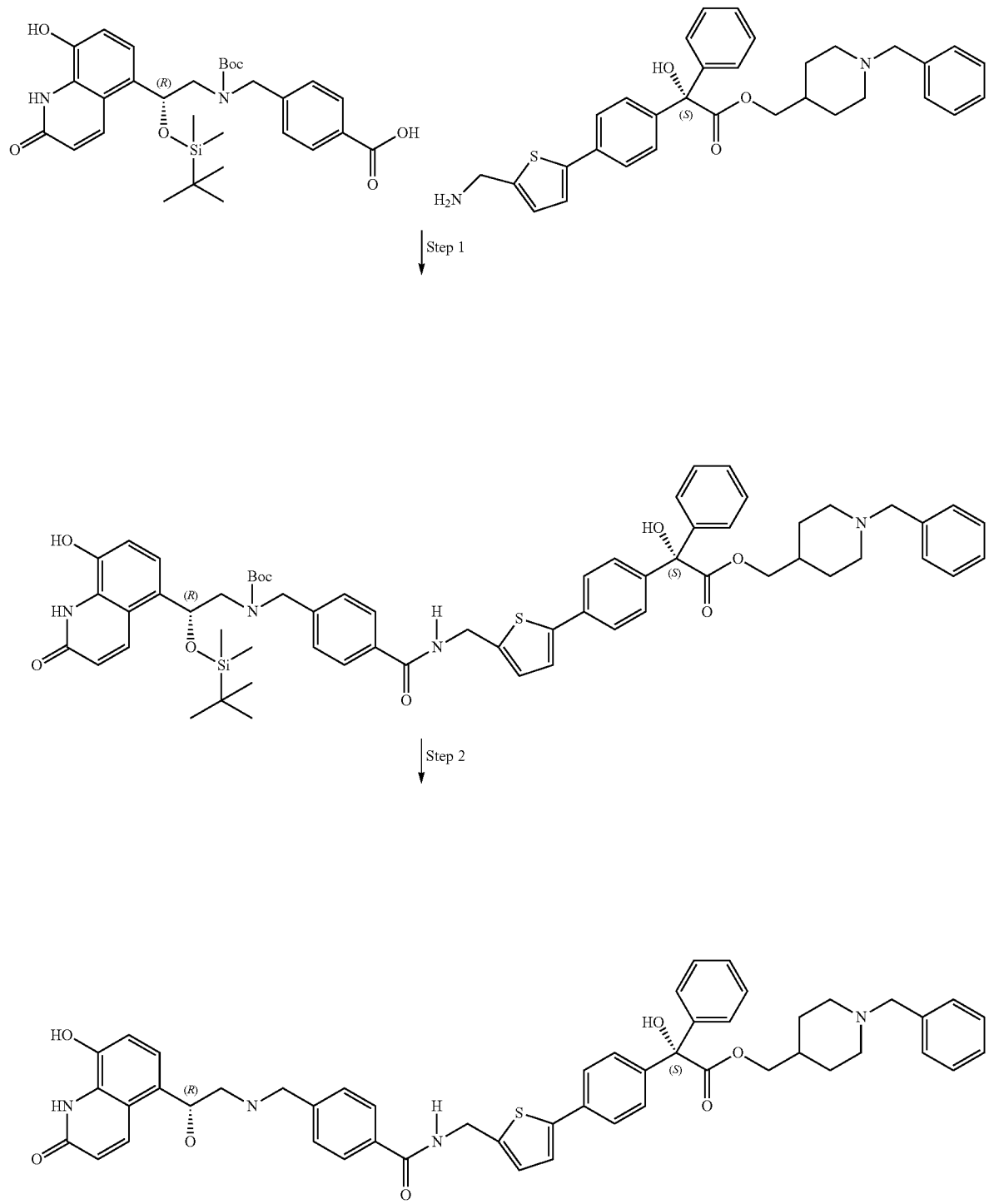
Scheme 3

Example 15

(1-benzylpiperidin-4-yl)methyl (S)-2-hydroxy-2-(4-(5-((4-((((R)-2-hydroxy-2-(8-hydroxy-2-oxo-1,2-dihydroquinolin-5-yl)ethyl)amino)methyl)benzamido)methyl)-thiophen-2-yl)phenyl)-2-phenylacetate×2 HCOOH (Compound 15)

Step 1: (1-benzylpiperidin-4-yl)methyl (S)-2-(4-(5-((4-((((tert-butoxycarbonyl)((R)-2-((tert-butyldimethylsilyl)oxy)-2-(8-hydroxy-2-oxo-1,2-dihydroquinolin-5-yl)ethyl)amino)methyl)benzamido)methyl)thiophen-2-yl)phenyl)-2-hydroxy-2-phenylacetate

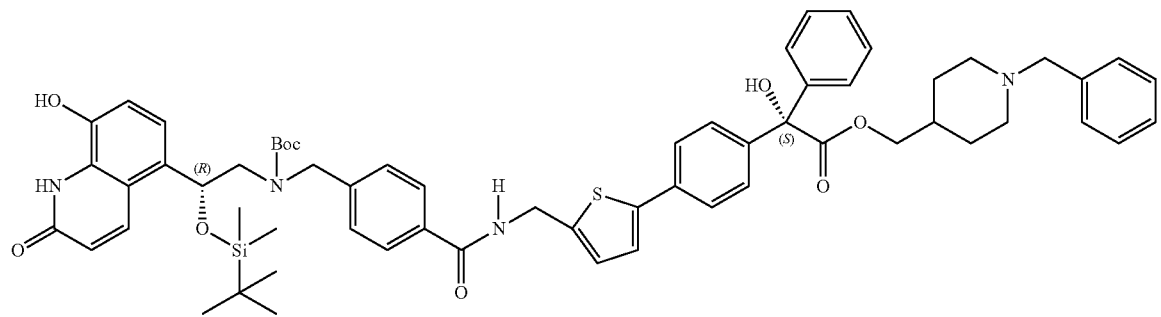

(1-Benzylpiperidin-4-yl)methyl (S)-2-(4-(5-(aminomethyl)thiophen-2-yl)phenyl)-2-hydroxy-2-phenylacetate×2 HCl (42 mg, 0.080 mmol)—prepared as described in Procedure F steps 6-11- and (R)-4-(((tert-butoxycarbonyl)(2-((tert-butyldimethylsilyl)-oxy)-2-(8-hydroxy-2-oxo-1,2-dihydroquinolin-5-yl)ethyl)amino)methyl)benzoic acid —prepared as described in Procedure A steps 1-5—(45.4 mg, 0.80 mmol), DIEA (0.042 ml, 0.24 mmol), TBTU (28.2 mg, 0.88 mmol) were dissolved in DMF (1.5 ml) and stirred overnight at rt. Reaction mixture was partitioned between ethyl acetate and saturated $NaHCO_3$ aq, washed twice with saturated $NaCl_{aq}$, organic layer anhydrified with $Na_2SO_4$ and evaporated to dryness to give an oil that was purified on reverse phase to give the title compound (39 mg, 45%) as a white solid.

UPLC-MS Method 3; Rt 1.10 min, ES+ 1076.84

Step 2: (1-benzylpiperidin-4-yl)methyl (S)-2-hydroxy-2-(4-(5-((4-(((((R)-2-hydroxy-2-(8-hydroxy-2-oxo-1,2-dihydroquinolin-5-yl)ethyl)amino)methyl) benzamido)methyl)-thiophen-2-yl)phenyl)-2-phenylacetate×2 HCOOH (1-Benzylpiperidin-4-yl)methyl (S)-2-(4-(5-((4-(((tert-butoxycarbonyl)((R)-2-((tert-butyldimethylsilyl)oxy)-2-(8-hydroxy-2-oxo-1,2-dihydroquinolin-5-yl)ethyl)amino) methyl)benzamido)methyl)thiophen-2-yl)phenyl)-2-hydroxy-2-phenylacetate (39 mg, 0.036 mmol) was dissolved in MeCN (0.7 ml) and HClaq 6 M (1.2 ml) was added. The mixture was stirred for 1 h at room temperature and then submitted to reversed phase flash chromatography (100:0 to 0:100 A/B, A: water/MeCN 95:5+0.1% HCOOH, B: MeCN/water 95:5+0.1% HCOOH) to afford the title compound (19.4 mg, 62%).

$^1$H NMR (400 MHz, DMSO-d6) δ ppm 10.28 (br. s., 1H), 9.12 (s, 1H), 8.05-8.25 (m, 3H), 7.84 (d, J=8.2 Hz, 2H), 7.56 (d, J=8.6 Hz, 2H), 7.44 (d, J=8.2 Hz, 2H), 7.14-7.38 (m, 14H), 7.06 (d, J=8.2 Hz, 1H), 7.01 (d, J=3.5 Hz, 1H), 6.91 (d, J=8.2 Hz, 1H), 6.63 (br. s., 1H), 6.48 (d, J=9.7 Hz, 1H), 5.11 (dd, J=7.7, 4.4 Hz, 1H), 4.62 (d, J=5.7 Hz, 2H), 4.00 (d, J=6.2 Hz, 2H), 3.87 (s, 2H), 3.40 (s, 2H), 2.62-2.82 (m, 4H), 1.69-1.93 (m, 2H), 1.46 (d, J=13.5 Hz, 3H), 1.12 (dd, J=12.0, 3.0 Hz, 2H)

UPLC-MS Method 4; Rt 4.69 min, ES+ 863.1

Compounds also prepared in the same fashion using the appropriate acid and base are reported in the following table:

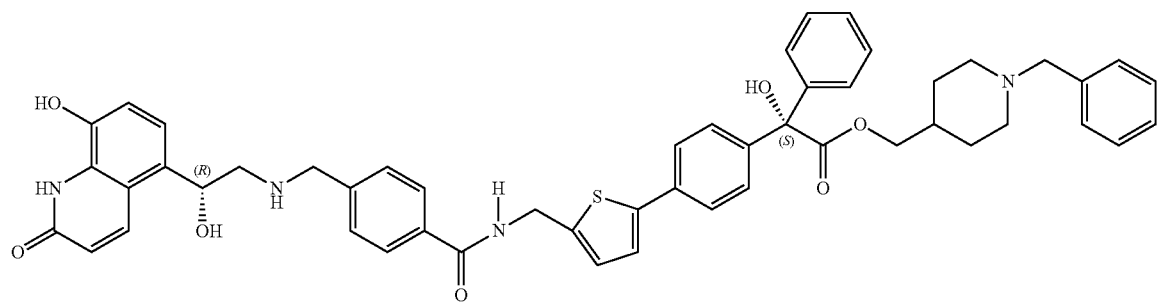

| Cpd. No. | Appropriate acid | Appropriate amine |
|---|---|---|
| 15A | (R)-5-(1-hydroxy-2-((4-carboxy-2-methoxybenzyl)amino)ethyl)-8-hydroxyquinolin-2(1H)-one | (R)-1-benzylpiperidin-4-yl)methyl 2-(5-(aminomethyl)thiophen-2-yl)phenyl)-2-hydroxy-2-phenylacetate |
| 15B | (R)-5-(1-hydroxy-2-((4-carboxybenzyl)amino)ethyl)-8-hydroxyquinolin-2(1H)-one | (S)-1-benzylpiperidin-4-yl)methyl 2-(4-(5-(aminomethyl)thiophen-3-yl)phenyl)-2-hydroxy-2-phenylacetate |
| 15C | (R)-5-(1-hydroxy-2-((4-carboxybenzyl)amino)ethyl)-8-hydroxyquinolin-2(1H)-one | (S)-1-benzylpiperidin-4-yl)methyl 2-(4-(5-(aminomethyl)thiazol-2-yl)phenyl)-2-hydroxy-2-phenylacetate |
| 15D | (R)-5-(1-hydroxy-2-((4-carboxybenzyl)amino)ethyl)-8-hydroxyquinolin-2(1H)-one | (S)-1-benzylpiperidin-4-yl)methyl 2-(4-(6-(aminomethyl)pyridin-3-yl)phenyl)-2-hydroxy-2-phenylacetate |
| 15E | (R)-5-(1-hydroxy-2-((4-carboxybenzyl)amino)ethyl)-8-hydroxyquinolin-2(1H)-one | (S)-1-benzylpiperidin-4-yl)methyl 2-hydroxy-2-phenyl-2-(4-(1,2,3,6-tetrahydropyridin-4-yl)phenyl)acetate |
| 15F | (R)-5-(1-hydroxy-2-((4-carboxy-2-methoxybenzyl)amino)ethyl)-8-hydroxyquinolin-2(1H)-one | (S)-1-benzylpiperidin-4-yl)methyl 2-(4-(5-(aminomethyl)thiophen-3-yl)phenyl)-2-hydroxy-2-phenylacetate |

| Cpd. No. | Final compound |
|---|---|
| 15A | 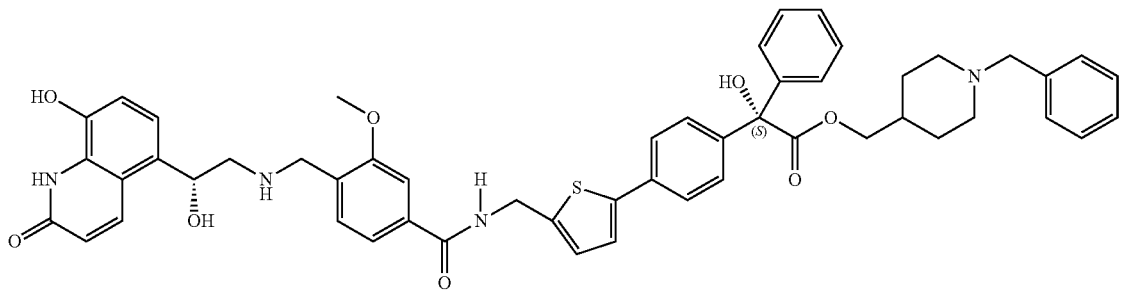 |
| 15B | 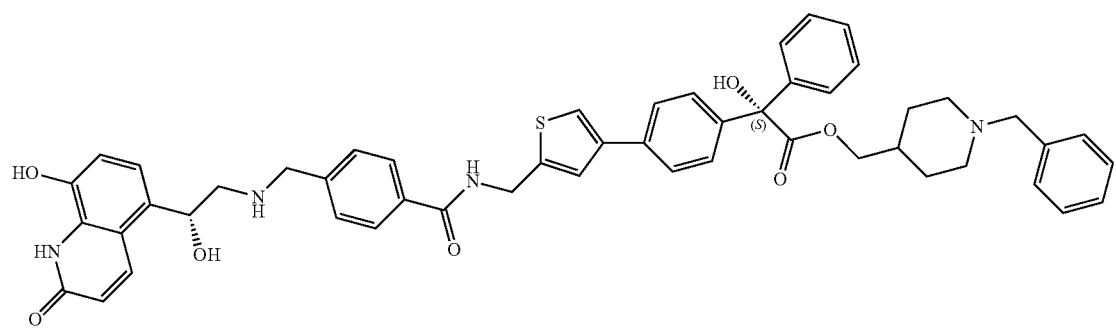 |
| 15C | 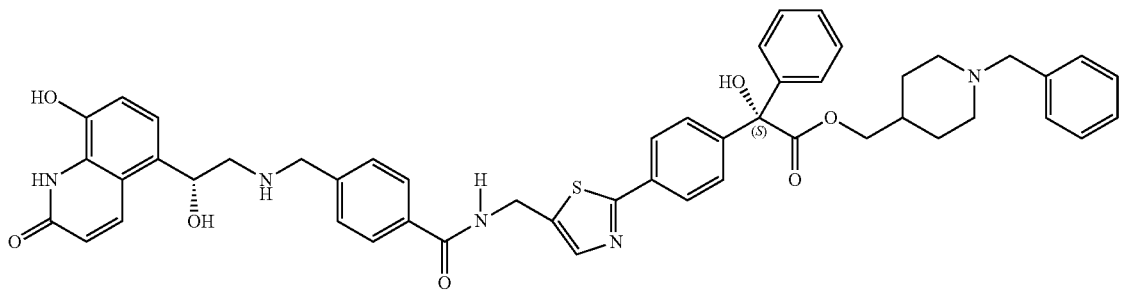 |
| 15D | 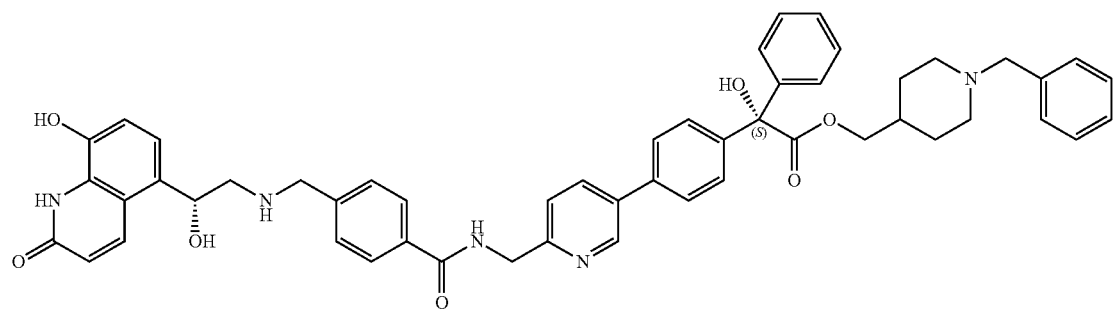 |
| 15E | 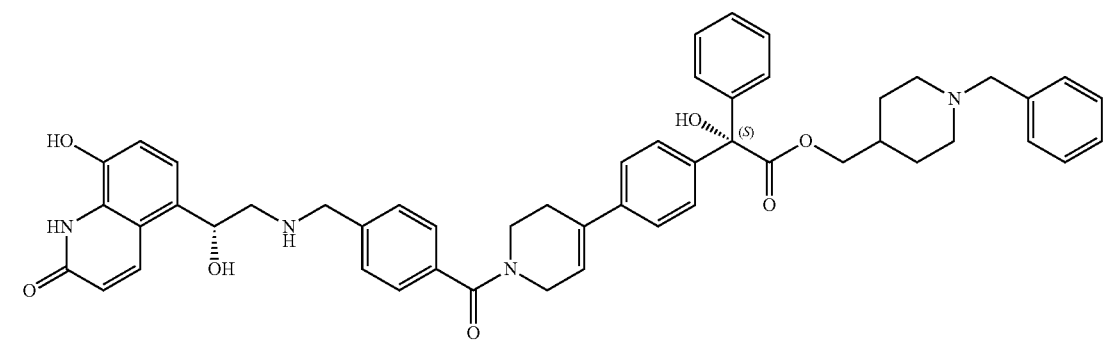 |

15F
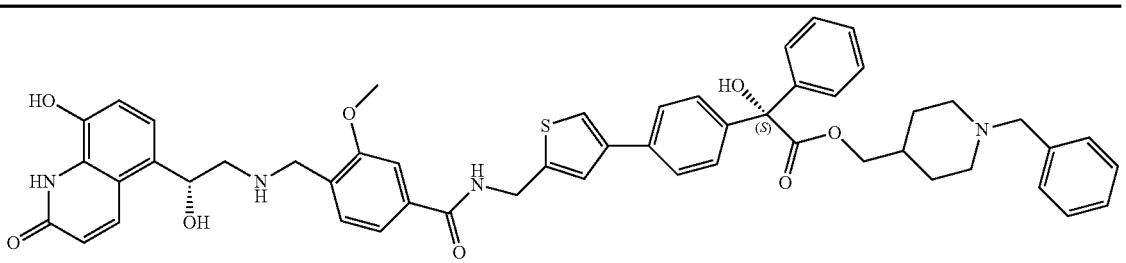

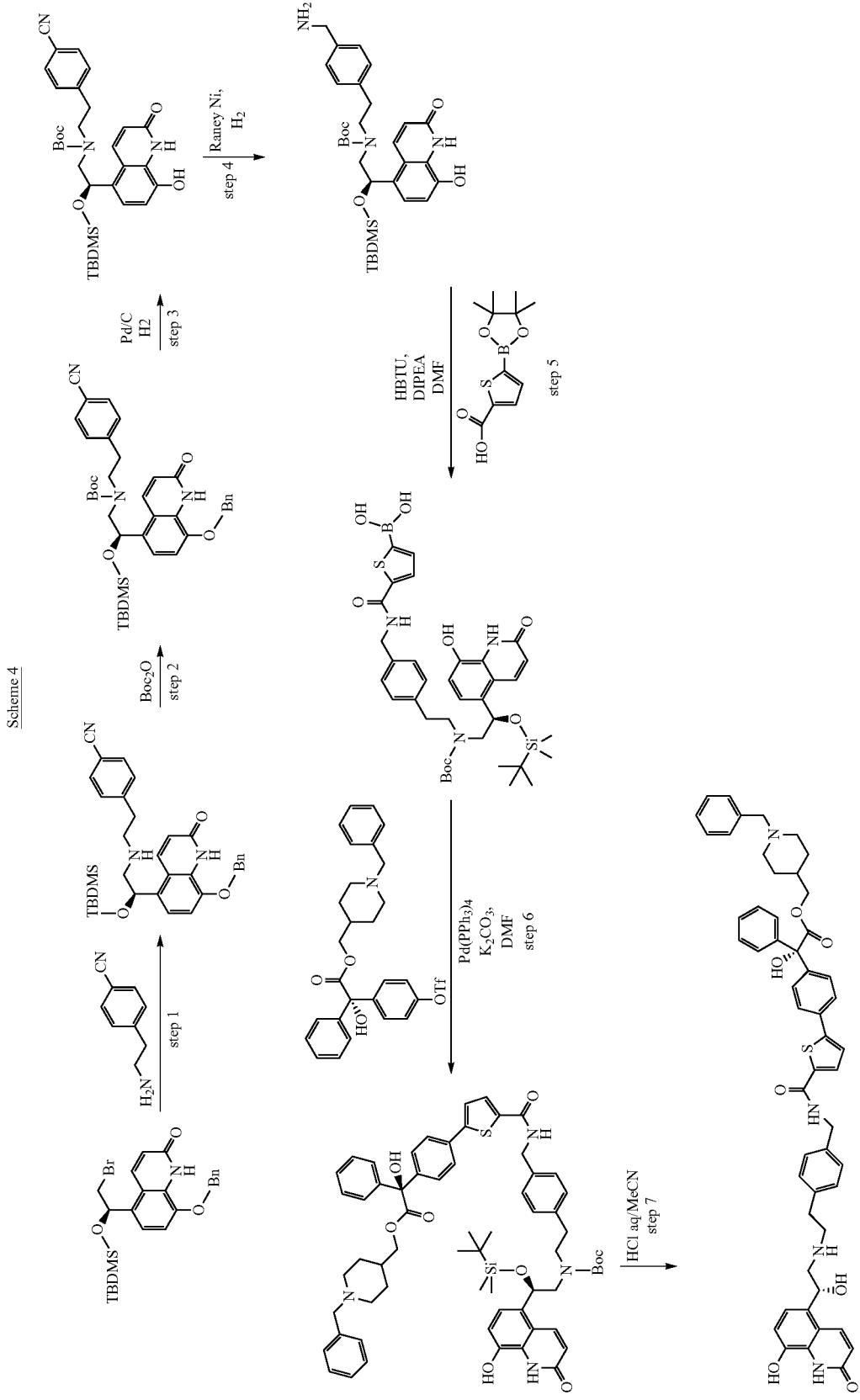

Example 16

(1-benzylpiperidin-4-yl)methyl (S)-2-hydroxy-2-(4-(5-((4-(2-(((R)-2-hydroxy-2-(8-hydroxy-2-oxo-1,2-dihydroquinolin-5-yl)ethyl)amino)ethyl)benzyl)-carbamoyl)thiophen-2-yl)phenyl)-2-phenylacetate×2 HCOOH (Compound 16)

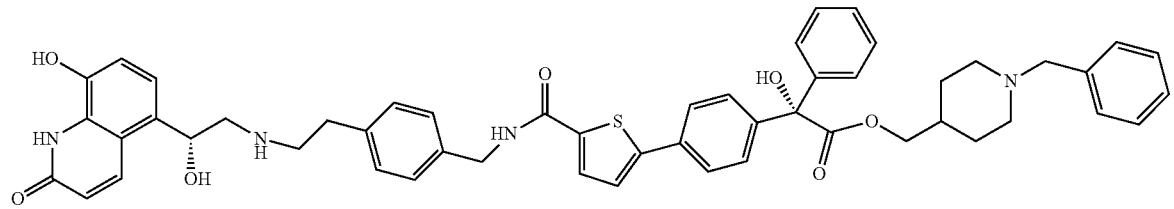 [SMILES: O=C(NCc1ccc(CCNC[C@H](O)c2ccc(O)c3[nH]c(=O)ccc23)cc1)c1ccc(-c2ccc([C@](O)(C(=O)OCC3CCN(Cc4ccccc4)CC3)c3ccccc3)cc2)s1]

Step 1: (R)-4-(2-((2-(8-(benzyloxy)-2-oxo-1,2-dihydroquinolin-5-yl)-2-((tert-butyldimethylsilyl)oxy)ethyl)amino)ethyl)benzonitrile Step 2: tert-butyl (R)-(2-(8-(benzyloxy)-2-oxo-1,2-dihydroquinolin-5-yl)-2-((tert-butyldimethylsilyl)oxy)ethyl)(4-cyanophenethyl)carbamate

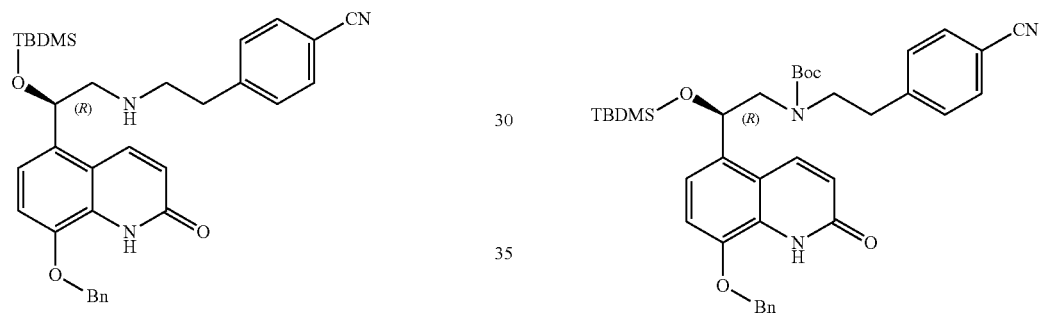

4-(2-aminoethyl)benzonitrile (7.30 g, 50.0 mmol, 1.6 eq) and DIPEA (6 ml, 30.7 mmol, 2.5 eq) were mixed in NMP (60.0 ml, 10 vol.) and stirred for 60 min at room temperature under Ar. (R)-8-(benzyloxy)-5-(2-bromo-1-((tert-butyldimethylsilyl)-oxy)ethyl)quinolin-2(1H)-one (15.54 g, 31.8 mmol, 1.0 eq) was added and the reaction was heated to 80° C. and stirred for 2 days under Ar. After cooling to room temperature reaction was quenched with water (150 ml). Mixture was extracted with AcOEt (3×100 ml). Combined organic layers were washed with brine (100 ml), dried over $MgSO_4$, filtrated and evaporated to give crude product, which was purified via flash chromatography ($SiO_2$, 0%-100% AcOEt in hexane, 5%-12% MeOH in AcOEt) to give the title compound (16.19 g, 92%).

$^1$H NMR (400 MHz, DMSO-$d_6$) δ 10.59 (s, 1H), 8.25 (d, 1H), 7.72 (d, 2H), 7.58 (d, 2H), 7.47-7.28 (m, 5H), 7.18 (d, 1H), 7.08 (d, 1H), 6.54 (d, 1H), 5.28 (s, 2H), 5.10 (dd, 1H), 2.83-2.72 (m, 4H), 2.64 (dd, 2H), 0.77 (s, 9H), −0.02 (s, 3H), −0.22 (s, 3H).

(R)-4-(2-((2-(8-(benzyloxy)-2-oxo-1,2-dihydroquinolin-5-yl)-2-((tert-butyldimethylsilyl)oxy)ethyl)amino)ethyl)benzonitrile (16.19 g, 29.2 mmol, 1.0 eq) was dissolved in DCM (46 ml, 6 vol.) and $NaHCO_3$ (4.91 g, 58.5 mmol, 2.0 eq) was added. A solution of $Boc_2O$ (7.02 g, 32.2 mmol, 1.1 eq) in DCM (65 ml, 4 vol) was added dropwise. The mixture was stirred at room temperature overnight. TLC showed full conversion. Water (160 ml) was added and the product was extracted with DCM (2×150 ml). Organic layers were combined, washed with brine (300 ml), dried over $MgSO_4$ and evaporated to give crude product, which was purified via flash chromatography ($SiO_2$, 10-50% AcOEt in hexane) to afford the title compound (17.93 g, 94%).

$^1$H NMR (400 MHz, DMSO-$d_6$) δ 10.66 (d, 1H), 8.28 (s, 1H), 7.73 (t, 2H), 7.58 (t, 2H), 7.42-7.30 (m, 5H), 7.28-7.06 (m, 2H), 6.58 (dd, 9.9 Hz, 1H), 5.53-5.32 (m, 1H), 5.29 (s, 2H), 2.79 (t, 2H), 1.65-1.31 (m, 2H), 1.31-1.22 (m, 9H), 0.85-075 (m, 11H), −0.01 (s, 3H), −0.19 (s, 3H).

Step 3: tert-butyl (R)-(2-((tert-butyldimethylsilyl)oxy)-2-(8-hydroxy-2-oxo-1,2-dihydroquinolin-5-yl)ethyl)(4-cyanophenethyl)carbamate

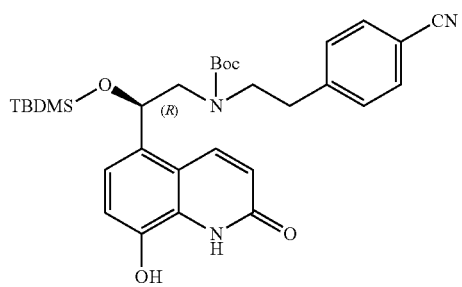

Pd/C (30% wt, 3.59 g) was added to a solution of tert-butyl (R)-(2-(8-(benzyloxy)-2-oxo-1,2-dihydroquinolin-5-yl)-2-((tert-butyldimethylsilyl)oxy)ethyl)(4-cyanophenethyl)carbamate (17.9 g, 27.0 mmol, 1.0 eq) in MeOH (269 ml, 15 vol). Mixture was degassed and filled with hydrogen. The hydrogenation was performed under $H_2$ balloon at room temperature. After 3 h TLC showed full conversion. Row material was filtered through the celite and filtrate was evaporated to give crude, which was purified via dry flash chromatography (DCM:MeOH) giving the title product (14.02 g, 96%).

$^1$H NMR (400 MHz, DMSO-$d_6$) δ 10.37 (s, 1H), 8.25 (s, 1H), 7.73 (t, 7 Hz, 2H), 7.35 (d, 2H), 7.19-7.02 (m, 1H), 6.95 (d, 1H), 6.53 (dd, 1H), 5.45-5.00 (m, 1H), 3.74-3.45 (m, 2H), 2.79 (t, 2H), 1.30 (d, 9H), 1.26-1.22 (m, 2H), 0.80 (d, 9H), −0.02 (d, 3H), −0.18 (s, 3H).

Step 4: tert-butyl (R)-(4-(aminomethyl)phenethyl)(2-((tert-butyldimethylsilyl)oxy)-2-(8-hydroxy-2-oxo-1,2-dihydroquinolin-5-yl)ethyl)carbamate

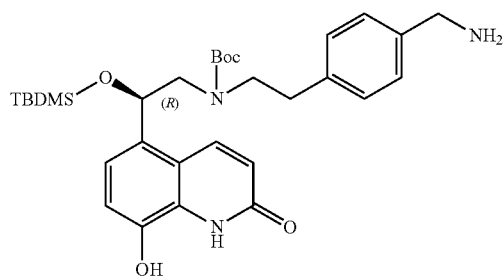

Tert-butyl (R)-(2-((tert-butyldimethylsilyl)oxy)-2-(8-hydroxy-2-oxo-1,2-dihydroquinolin-5-yl)ethyl)(4-cyanophenethyl)carbamate (13.92 g, 25 mmol, 1.0 eq) was dissolved in THF (278 ml, 20 vol.). 25% aqueous $NH_3$ solution (139 ml, 10 vol.) and Raney Ni (4.18 g, 30 wt %) were added. Row material was degassed, refilled with hydrogen and stirred overnight. UPLC showed full conversion. Row material was filtered over Celite and filtrate was evaporated to give crude (36 g). Crude was purified via reverse phase column chromatography (15 g of gel/1 g crude; ACN:$NH_{3\ aq}$ 5% to 25%) to afford the title compound (5.89 g, 43%).

UPLC-MS Method 3; Rt 0.85 min, ES+ 568.52

$^1$H NMR (400 MHz, DMSO-d6) δ ppm 8.01-8.39 (m, 1H), 6.76-7.27 (m, 6H), 6.38-6.59 (m, 2H), 4.89-5.55 (m, 1H), 3.47-3.71 (s, 2H), 2.50-2.80 (m, 4 JH), 2.55-2.77 (m, 2H), 1.25 (s, 9H), 0.94 (s, 9H), −0.02 (br. s., 3H), −0.18 (br. s., 3H)

Step 5: (R)-(5-((4-(2-(((tert-butoxycarbonyl)(2-((tert-butyldimethylsilyl)oxy)-2-(8-hydroxy-2-oxo-1,2-dihydroquinolin-5-yl)ethyl)amino)ethyl)benzyl)carbamoyl)thiophen-2-yl)boronic acid

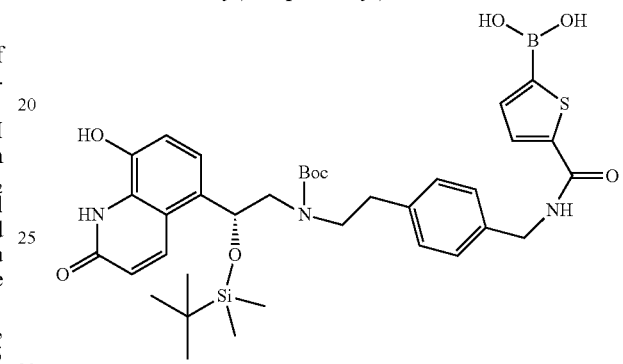

HBTU (100 mg, 0.264 mmol) was dissolved in DMF (0.8 ml) and 5-(4,4,5,5-tetramethyl-1,3,2-dioxaborolan-2-yl)thiophene-2-carboxylic acid (67.1 mg, 0.264 mmol) was added and the mixture was stirred for ½ h. The reaction was added with (R)-tert-butyl 4-(aminomethyl)phenethyl(2-((tert-butyldimethylsilyl)oxy)-2-(8-hydroxy-2-oxo-1,2-dihydroquinolin-5-yl)ethyl)carbamate (150 mg, 0.264 mmol) and DIPEA (0.138 ml, 0.793 mmol) and the mixture was stirred for 5 hr at rt. After add of water (50 ml) a solid precipitated, the solid was filtered on gooch, then dissolved in ethyl acetate, dried over $Na_2SO_4$ and the solvent was evaporated under vacuum to give a white solid of (R)-(5-((4-(2-(((tert-butoxycarbonyl)(2-((tert-butyldimethylsilyl)oxy)-2-(8-hydroxy-2-oxo-1,2-dihydroquinolin-5-yl)ethyl)amino)ethyl)benzyl)carbamoyl)thiophen-2-yl)boronic acid (166 mg, 87%).

UPLC-MS Method 3; Rt 1.27 min, ES+ 721.68

Step 6: (1-benzylpiperidin-4-yl)methyl (S)-2-(4-(5-((4-(2-((tert-butoxycarbonyl)((R)-2-((tert-butyldimethylsilyl)oxy)-2-(8-hydroxy-2-oxo-1,2-dihydroquinolin-5-yl)ethyl)amino)ethyl)benzyl)carbamoyl)thiophen-2-yl)phenyl)-2-hydroxy-2-phenylacetate

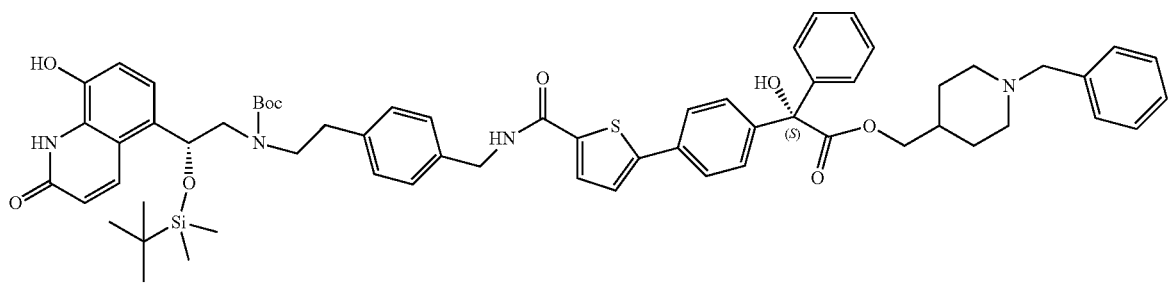

A solution of (R)-(5-((4-(2-((tert-butoxycarbonyl)(2-((tert-butyldimethylsilyl)-oxy)-2-(8-hydroxy-2-oxo-1,2-dihydroquinolin-5-yl)ethyl)amino)ethyl)-benzyl)carbamoyl)thiophen-2-yl)boronic acid (35 mg, 0.048 mmol) in DMF (2 ml) was added with (1-benzylpiperidin-4-yl)methyl 2-hydroxy-2-phenyl-2-(4-(((trifluoromethyl)sulfonyl)oxy)phenyl)acetate (24.85 mg, 0.044 mmol), prepared as described in Procedure A Steps 1-2, followed by a solution K₂CO₃ 2 M (16 ml). After stirring for 10 minutes, tetrakistriphenylphosphinepalladium (50 mg, 0.044 mmol) was added, and the resulting mixture was heated to 120° C. for 4 hours. The cooled-down mixture was treated with water and ethyl acetate (5 ml), the organic layer was dried over Na₂SO₄ then concentrated under reduced pressure. The crude was purified by flash chromatography (eluent—0 to 100% Ethyl acetate in Heptane) to obtain (1-benzylpiperidin-4-yl)methyl (S)-2-(4-(5-((4-(2-((tert-butoxycarbonyl)((R)-2-((tert-butyldimethylsilyl)oxy)-2-(8-hydroxy-2-oxo-1,2-dihydroquinolin-5-yl)ethyl)amino)ethyl)benzyl)carbamoyl)thiophen-2-yl)phenyl)-2-hydroxy-2-phenylacetate (47 mg, 19%).

UPLC-MS Method 3; Rt 1.14 min, ES+ 1090.80

Step 7: (1-benzylpiperidin-4-yl)methyl (S)-2-hydroxy-2-(4-(5-((4-(2-(((R)-2-hydroxy-2-(8-hydroxy-2-oxo-1,2-dihydroquinolin-5-yl)ethyl)amino)ethyl)benzyl)carbamoyl)-thiophen-2-yl)phenyl)-2-phenylacetate×2 HCOOH (Compound 16)

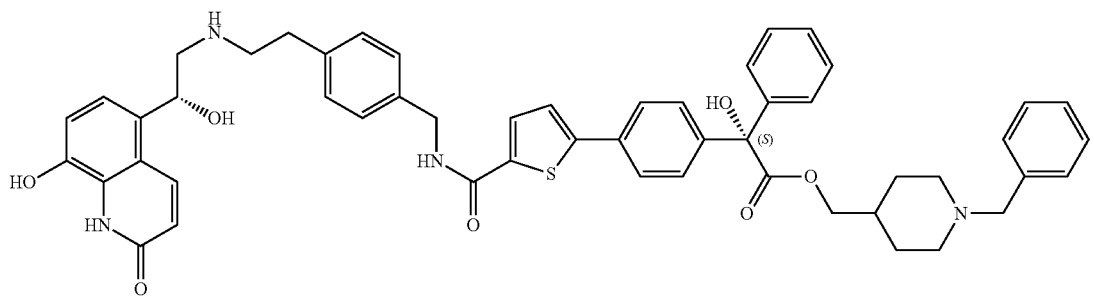

The title compound was prepared as in Example 15, following Step 2.

¹H NMR (400 MHz, DMSO-d6) δ ppm 9. 9.03 (t, J=6.0 Hz, 1H), 8.21 (m, 3H), 7.79 (d, J=4.0 Hz, 1H), 7.67 (d, J=8.4 Hz, 2H), 7.51 (d, J=3.7 Hz, 1H), 6.89-7.43 (m, 16H), 6.69 (d, J=8.4 Hz, 1H), 6.50 (d, J=9.9 Hz, 1H), 4.92-5.23 (m, 1H), 4.42 (d, J=5.5 Hz, 2 H), 4.02 (d, J=6.2 Hz, 2H), 3.30-3.60 (m, 4H), 2.66-3.00 (m, 8H), 1.79-1.98 (m, 2H), 1.37-1.65 (m, 2H), 1.03-1.31 (m, 5H)

UPLC-MS Method 4; Rt 4.94 min, ES+ 877.1

In the following, the ¹H-NMR data of the compounds of the above tables are reported.

| Cpd. No. | Rt (min) Method 1 | ¹H-NMR data (400 MHz) | Salt (2 eq unless stated) |
|---|---|---|---|
| 1 | 2.54 | (DMSO-d₆); δ 10.36 (s, 1H), 9.08 (dd, J = 5.9, 5.9 Hz, 1H), 8.23-8.20 (m, 2H), 7.64-7.59 (m, 2H), 7.49 (s, 1H), 7.43-7.39 (m, 6H), 7.39-7.26 (m, 9H), 7.12 (d, J = 8.1 Hz, 1H), 7.06 (d, J = 3.8 Hz, 1H), 6.97 (d, J = 8.3 Hz, 1H), 6.80 (s, 1H), 6.54 (d, J = 9.9 Hz, 1H), 5.13 (dd, J = 4.3, 7.8 Hz, 1H), 4.62 (d, J = 5.8 Hz, 2H), 4.08 (d, J = 6.1 Hz, 2H), 3.84 (s, 2H), 3.43 (s, 2H), 2.79-2.67 (m, 4H), 1.88 (dd, J = 11.1, 11.1 Hz, 2H), 1.62-1.48 (m, 3H), 1.23-1.11 (m, 2H). | mono-formate |
| 1A | 2.52 | (MeOD); δ 8.31 (d, J = 9.8 Hz, 1H), 7.96 (d, J = 8.3 Hz, 2H), 7.66 (d, J = 8.3 Hz, 3H), 7.59 (d, J = 7.5 Hz, 1H), 7.51-7.45 (m, 6H), 7.45-7.32 (m, 6H), 7.30 (d, J = 8.3 Hz, 1H), 7.21 (d, J = 3.6 Hz, 1H), 7.06-7.02 (m, 2H), 6.67 (d, J = 9.9 Hz, 1H), 5.45 (dd, J = 6.7, 6.7 Hz, 1H), 4.74 (s, 2H), 4.40 (s, 2H), 4.26 (s, 2H), 4.19-4.08 (m, 2H), 3.49-3.39 (m, 2H), 3.28 (d, J = 6.7 Hz, 2H), 3.04-2.89 (m, 2H), 2.04-1.91 (m, 1H), 1.81 (d, J = 13.9 Hz, 2H), 1.51-1.35 (m, 2H). | TFA |
| 1B | 2.56 | (MeOD); δ 8.27 (d, J = 9.9 Hz, 1H), 7.70-7.65 (m, 1H), 7.60-7.57 (m, 2H), 7.53 (s, 2H), 7.52-7.48 (m, 6H), 7.45-7.32 (m, 6H), 7.30 (d, J = 8.3 Hz, 1H), 7.21 (d, J = 3.6 Hz, 1H), 7.06-7.02 (m, 2H), 6.66 (d, J = 9.8 Hz, 1H), 5.45 (dd, J = 5.0, 8.3 Hz, 1H), 4.78-4.72 (m, 2H), 4.43-4.37 (m, 2H), 4.29-4.23 (m, 2H), 4.22-4.06 (m, 2H), 4.00 (s, 3H), 3.48-3.39 (m, 2H), 3.28-3.23 (m, 2H), 2.98-2.94 (m, 2H), 2.02-1.95 (m, 1H), 1.85-1.82 (m, 2H), 1.48-1.38 (m, 2H). | TFA |
| 1C | 2.52 | (MeOD); δ 8.31 (d, J = 9.8 Hz, 1H), 7.96 (d, J = 7.9 Hz, 1H), 7.69-7.65 (m, 1H), 7.61-7.58 (m, 1H), 7.51-7.45 (m, 5H), 7.45-7.40 (m, 2H), 7.39-7.33 (m, 6H), 7.30 (d, J = 8.3 Hz, 1H), 7.23-7.20 (m, 2H), 7.06-7.01 (m, 2H), 6.67 (d, J = 9.9 Hz, 1H), 5.48-5.43 (m, 1H), 4.76 (s, 2H), 4.38 (s, 2H), 4.26 (s, 2H), 4.23-4.07 (m, 2H), 4.00 (s, 3H), 3.43 (d, J = 12.3 Hz, 2H), 3.28 (d, J = 7.0 Hz, 2H), 2.99-2.88 (m, 2H), 2.03-1.93 (m, 1H), 1.87-1.83 (m, 2H), 1.48-1.36 (m, 2H). | TFA |
| 1D | 2.56 | (DMSO-d₆); δ 10.37 (br s, 1H), 9.07 (dd, J = 5.8, 5.8 Hz, 1H), 8.22-8.18 (m, 2H), 7.64-7.59 (m, 2H), 7.44-7.39 (m, 6H), 7.38-7.27 (m, 8H), 7.12 (d, J = 8.3 Hz, 1H), 7.09-7.05 (m, 2H), 6.97 (d, J = 8.1 Hz, 1H), 6.74 (br s, 1H), 6.55 (d, J = 9.9 Hz, 1H), 5.14 (dd, J = 4.4, 7.7 Hz, 1H), 4.63 (d, J = 5.8 Hz, 2H), 4.07 (d, J = 6.3 Hz, 2H), 3.85 (s, 3H), 3.80 (s, 2H), 3.44 (s, 2H), 2.80-2.73 (m, 4H), 1.88 (dd, J = 10.9, 10.9 Hz, 2H), 1.61-1.50 (m, 3H), 1.23-1.11 (m, 2H). | mono-formate |

| Cpd. No. | Rt (min) Method 1 | $^1$H-NMR data (400 MHz) | Salt (2 eq unless stated) |
|---|---|---|---|
| 1E | 2.56 | (DMSO-d$_6$); δ 10.30 (s, 1H), 8.93-8.86 (m, 1H), 8.23 (s, 1H), 8.21 (d, J = 9.9 Hz, 1H), 7.61 (d, J = 8.8 Hz, 2H), 7.39 (d, J = 4.3 Hz, 6H), 7.37-7.25 (m, 8H), 7.25-7.21 (m, 1H), 7.12 (d, J = 8.3 Hz, 1H), 7.05 (d, J = 3.8 Hz, 1H), 6.97 (d, J = 8.1 Hz, 1H), 6.78 (s, 1H), 6.54 (d, J = 9.9 Hz, 1H), 5.12 (dd, J = 4.4, 7.7 Hz, 1H), 4.65 (d, J = 5.8 Hz, 2H), 4.07 (d, J = 5.1 Hz, 2H), 3.83 (s, 3H), 3.80 (s, 2H), 3.40 (s, 2H), 2.79-2.72 (m, 4H), 1.89-1.80 (m, 2H), 1.61-1.46 (m, 3H), 1.21-1.10 (m, 2H). | mono-formate |
| 1F | 2.63 | (DMSO-d$_6$); δ 10.33-10.31 (m, 1H), 9.43 (dd, J = 5.8, 5.8 Hz, 1H), 8.23 (s, 1H), 8.21-8.17 (m, 2H), 7.92 (d, J = 8.3 Hz, 1H), 7.62-7.58 (m, 2H), 7.40-7.37 (m, 5H), 7.36-7.23 (m, 9H), 7.12 (d, J = 8.3 Hz, 1H), 7.07 (d, J = 3.5 Hz, 1H), 6.96 (d, J = 8.1 Hz, 1H), 6.78-6.77 (m, 1H), 6.53 (d, J = 9.9 Hz, 1H), 5.12 (dd, J = 4.4, 7.7 Hz, 1H), 4.68 (d, J = 5.6 Hz, 2H), 4.08-4.03 (m, 2H), 3.99 (s, 2H), 3.38 (s, 2H), 2.83-2.67 (m, 4H), 1.86-1.77 (m, 2H), 1.58-1.44 (m, 3H). | Formate |
| 1G | 2.58 | (DMSO-d$_6$); δ 10.35 (s, 1H), 8.96-8.90 (m, 1H), 8.24 (s, 1H), 8.20 (d, J = 9.9 Hz, 1H), 7.67-7.59 (m, 3H), 7.41-7.25 (m, 15H), 7.11 (d, J = 8.1 Hz, 1H), 7.04 (d, J = 3.8 Hz, 1H), 6.97 (d, J = 8.1 Hz, 1H), 6.75 (s, 1H), 6.54 (d, J = 9.9 Hz, 1H), 5.13 (dd, J = 4.3, 7.8 Hz, 1H), 4.64 (d, J = 5.8 Hz, 2H), 4.07 (d, J = 5.6 Hz, 2H), 3.86 (s, 2H), 3.41 (s, 2H), 2.80-2.68 (m, 4H), 1.85 (dd, J = 11.0, 11.0 Hz, 2H), 1.62-1.49 (m, 3H), 1.22-1.11 (m, 2H). | mono-formate |
| 1H | 2.56 | (DMSO-d$_6$); δ 8.98 (dd, J = 5.8, 5.8 Hz, 1H), 8.12 (s, 2H), 8.05 (d, J = 9.9 Hz, 1H), 7.70 (d, J = 8.3 Hz, 2H), 7.45-7.41 (m, 2H), 7.22-7.08 (m, 15H), 6.97 (d, J = 8.3 Hz, 1H), 6.87 (d, J = 3.8 Hz, 1H), 6.82 (d, J = 8.1 Hz, 1H), 6.40 (d, J = 9.9 Hz, 1H), 5.00 (dd, J = 6.2, 6.2 Hz, 1H), 4.48 (d, J = 5.8 Hz, 2H), 3.89 (d, J = 5.6 Hz, 2H), 3.23 (s, 2H), 2.86-2.75 (m, 2H), 2.70 (d, J = 6.8, 6.8 Hz, 4H), 2.59-2.52 (m, 2H), 1.67 (dd, J = 9.6, 11.4 Hz, 2H), 1.42-1.28 (m, 3H), 1.05-0.92 (m, 2H). | Formate |
| 1I | 2.56 | (DMSO-d$_6$); δ 10.34-10.34 (m, 1H), 9.12 (dd, J = 5.6, 5.6 Hz, 1H), 8.21 (s, 1H), 8.13 (d, J = 9.9 Hz, 1H), 7.56 (d, J = 8.4 Hz, 2H), 7.44 (s, 2H), 7.34 (d, J = 3.9 Hz, 6H), 7.31-7.20 (m, 8H), 7.05 (d, J = 8.3 Hz, 1H), 7.01 (d, J = 3.6 Hz, 1H), 6.92 (d, J = 8.2 Hz, 1H), 6.73 (s, 1H), 6.49 (d, J = 9.9 Hz, 1H), 5.07 (dd, J = 4.7, 7.7 Hz, 1H), 4.62 (d, J = 5.6 Hz, 2H), 4.09-4.00 (m, 4H), 3.77 (s, 2H), 3.34 (s, 2H), 2.77-2.63 (m, 4H), 1.78 (dd, J = 9.9, 11.4 Hz, 2H), 1.54-1.43 (m, 3H), 1.31 (dd, J = 7.0, 7.0 Hz, 3H), 1.16-1.05 (m, 2H). | mono-formate |
| 1J | 2.52 | (DMSO-d6); δ 10.35-10.35 (m, 1H), 9.22 (dd, J = 5.9, 5.9 Hz, 1H), 8.19 (s, 1H), 8.17-8.15 (m, 1H), 7.70 (d, J = 7.9 Hz, 1H), 7.65 (d, J = 11.3 Hz, 1H), 7.60-7.50 (m, 3H), 7.34-7.20 (m, 13H), 7.07 (d, J = 8.2 Hz, 1H), 7.01 (d, J = 3.5 Hz, 1H), 6.92 (d, J = 8.2 Hz, 1H), 6.71-6.71 (m, 1H), 6.49 (d, J = 9.9 Hz, 1H), 5.07 (dd, J = 4.3, 7.9 Hz, 1H), 4.62 (d, J = 5.6 Hz, 2H), 4.03-4.00 (m, 2H), 3.84 (s, 2H), 3.36 (s, 2H), 2.75-2.64 (m, 4H), 1.79 (dd, J = 10.7, 10.7 Hz, 2H), 1.54-1.43 (m, 3H), 1.11 (ddd, J = 8.1, 11.7, 16.0 Hz, 2H). | mono-formate |
| 1K | 2.55 | (DMSO-d6); δ 10.32-10.27 (m, 1H), 8.96 (dd, J = 5.9, 5.9 Hz, 1H), 8.18 (s, 1H), 8.15 (s, 1H), 7.59-7.55 (m, 2H), 7.35 (d, J = 4.3 Hz, 6H), 7.33-7.21 (m, 9H), 7.07 (d, J = 8.2 Hz, 1H), 7.01 (d, J = 3.6 Hz, 1H), 6.92 (d, J = 8.2 Hz, 1H), 6.74 (s, 1H), 6.50 (d, J = 9.8 Hz, 1H), 5.08 (dd, J = 4.3, 7.8 Hz, 1H), 4.60 (d, J = 5.8 Hz, 2H), 4.02 (d, J = 5.1 Hz, 2H), 3.83 (s, 3H), 3.81 (s, 2H), 3.38 (s, 2H), 2.78-2.67 (m, 4H), 1.82 (dd, J = 11.0, 11.0 Hz, 2H), 1.57-1.45 (m, 3H), 1.18-1.07 (m, 2H). | mono-formate |
| 1L | 2.54 | (DMSO-d6); δ 10.30-10.25 (m, 1H), 9.26 (dd, J = 5.8, 5.8 Hz, 1H), 8.89 (d, J = 1.5 Hz, 1H), 8.13-8.07 (m, 3H), 7.50-7.42 (m, 3H), 7.26 (d, J = 3.3 Hz, 5H), 7.24-7.18 (m, 4H), 7.16-7.12 (m, 4H), 7.00 (d, J = 8.1 Hz, 1H), 6.95 (d, J = 3.5 Hz, 1H), 6.84 (d, J = 8.1 Hz, 1H), 6.68 (s, 1H), 6.42 (d, J = 9.9 Hz, 1H), 5.03 (dd, J = 4.5, 7.8 Hz, 1H), 4.56 (d, J = 5.8 Hz, 2H), 3.96-3.90 (m, 2H), 3.84 (s, 2H), 3.25 (s, 2H), 2.71-2.55 (m, 4H), 1.69 (dd, J = 9.7, 11.7 Hz, 2H), 1.46-1.32 (m, 3H), 1.09-0.97 (m, 2H). | mono-formate |
| 1M | 2.58 | (DMSO-d6); δ 10.15-10.14 (m, 1H), 9.07 (dd, J = 5.8, 5.8 Hz, 1H), 8.00 (s, 1H), 7.92 (d, J = 9.9 Hz, 1H), 7.39-7.35 (m, 2H), 7.19-7.02 (m, 15H), 6.85-6.81 (m, 2H), 6.72 (d, J = 8.1 Hz, 1H), 6.55 (s, 1H), 6.30 (d, J = 9.9 Hz, 1H), 4.81 (dd, J = 4.8, 7.6 Hz, 1H), 4.44 (d, J = 5.8 Hz, 2H), 3.85-3.80 (m, 2H), 3.66 (s, 3H), 3.63-3.52 (m, 2H), 3.15 (s, 2H), 2.52-2.43 (m, 4H), 1.59 (dd, J = 9.9, 11.4 Hz, 2H), 1.36-1.24 (m, 3H), 0.98-0.85 (m, 2H). | mono-formate |
| 1N | 2.53 | (DMSO-d6); δ 10.30-10.24 (m, 1H), 9.10 (dd, J = 5.8, 5.8 Hz, 1H), 8.14 (s, 2H), 8.12 (d, J = 10.1 Hz, 1H), 7.84 (s, 1H), 7.70 (d, J = 7.8 Hz, 1H), 7.50-7.42 (m, 3H), 7.28-7.14 (m, 14H), 7.01 (d, J = 8.3 Hz, 1H), 6.94 (d, J = 3.8 Hz, 1H), 6.85 (d, J = 8.1 Hz, 1H), 6.67 (s, 1H), 6.41 (d, J = 9.9 Hz, 1H), 5.05 (dd, J = 4.3, 7.8 Hz, 1H), 4.55 (d, J = 5.8 Hz, 2H), 3.96-3.92 (m, 2H), 3.80 (s, 2H), 3.28 (s, 2H), 2.73-2.56 (m, 4H), 1.71 (dd, J = 9.6, 11.9 Hz, 2H), 1.47-1.36 (m, 3H), 1.09-0.97 (m, 2H). | Formate |
| 1O | 2.59 | (DMSO-d6); δ 10.26-10.22 (m, 1H), 8.79-8.73 (m, 1H), 8.13 (s, 1H), 8.12 (d, J = 10.1 Hz, 1H), 7.50-7.47 (m, 2H), 7.35 (d, J = 7.3 Hz, 1H), 7.27 (d, J = 4.0 Hz, 5H), 7.25-7.13 (m, 9H), 7.01 (d, J = 8.1 Hz, 1H), 6.92 (d, J = 3.8 Hz, 1H), 6.85 (d, J = 8.3 Hz, 1H), 6.68 (s, 1H), 6.42 (d, J = 9.3 Hz, 1H), 5.02 (dd, J = 4.5, 7.8 Hz, 1H), 4.50 (d, J = 5.8 Hz, 2H), 3.94 (d, J = 5.3 Hz, 2H), 3.65 (s, 2H), 3.27 (s, 2H), 2.73-2.56 (m, 4H), 2.14 (s, 3H), 1.75-1.67 (m, 2H), 1.48-1.33 (m, 3H), 1.10-0.98 (m, 2H). | mono-formate |
| 1P | 2.52 | (DMSO-d6); δ 10.40 (s, 1H), 8.73 (dd, J = 5.8, 5.8 Hz, 1H), 8.25 (d, J = 1.5 Hz, 1H), 8.15 (d, J = 9.9 Hz, 1H), 7.61-7.57 (m, 2H), 7.40 (d, J = 3.8 Hz, 6H), 7.38-7.31 (m, 5H), 7.28 (dd, J = 3.4, 7.5 Hz, 7H), 7.12 (d, J = 8.1 Hz, 1H), 6.99-6.95 (m, 2H), 6.54 (d, J = 9.9 Hz, 1H), 5.20-5.15 (m, 1H), 4.45 (d, J = 5.8 Hz, 2H), 4.07 (d, J = 6.1 Hz, 2H), 3.88 (s, 2H), 3.51 (s, 2H), 3.44 (s, 2H), 2.83-2.73 (m, 4H), 1.86 (dd, J = 11.2, 11.2 Hz, 2H), 1.61-1.48 (m, 3H), 1.22-1.12 (m, 2H). | mono-formate |
| 1Q | 2.52 | (DMSO-d6); δ 10.33-10.24 (m, 1H), 9.35 (dd, J = 6.3, 6.3 Hz, 1H), 8.13 (s, 1H), 8.11 (d, J = 10.2 Hz, 1H), 7.96 (d, J = 8.1 Hz, 1H), 7.87 (dd, J = 2.0, 8.1 Hz, 1H), 7.52-7.47 (m, 2H), 7.29-7.27 (m, 5H), 7.27-7.15 (m, 8H), 7.02 (d, J = 8.1 Hz, 1H), 6.94 (d, J = 3.5 Hz, 1H), 6.86 (d, J = 8.1 Hz, 1H), 6.70 (s, 1H), 6.44 (d, J = 9.9 Hz, 1H), 5.04 (dd, J = 4.3, 8.1 Hz, 1H), 4.57 (d, J = 6.3 Hz, 2H), 3.96 (ddd, J = 6.3, 10.6, 13.5 Hz, 2H), 3.82 (s, 2H), 3.28 (s, 2H), 2.68-2.58 (m, 4H), 1.72 (dd, J = 9.5, 11.7 Hz, 2H), 1.48-1.34 (m, 3H), 1.10-0.98 (m, 2H). | mono-formate |
| 1R | 2.55 | (DMSO-d6); δ 10.29-10.23 (m, 1H), 9.18 (dd, J = 5.8, 5.8 Hz, 1H), 8.10 (s, 1H), 8.09 (d, J = 8.8 Hz, 1H), 7.84 (d, J = 1.8 Hz, 1H), 7.74 (dd, J = 1.6, 8.0 Hz, 1H), 7.54-7.46 (m, 3H), 7.27-7.14 (m, 13H), 6.99 (d, J = 8.1 Hz, 1H), 6.93 (d, J = 3.8 Hz, 1H), 6.84 (d, J = 8.3 Hz, 1H), 6.68-6.66 (m, 1H), 6.41 (d, J = 9.9 Hz, 1H), 5.00 (dd, J = 4.3, 7.8 Hz, 1H), 4.53 (d, J = 5.6 Hz, 2H), 3.96-3.93 (m, 2H), 3.78 (s, 2H), 3.25 (s, 2H), 2.70-2.55 (m, 4H), 1.70 (dd, J = 9.9, 11.9 Hz, 2H), 1.46-1.32 (m, 3H), 1.08-0.95 (m, 2H). | mono-formate |

| Cpd. No. | Rt (min) Method 1 | ¹H-NMR data (400 MHz) | Salt (2 eq unless stated) |
|---|---|---|---|
| 1S | 2.55 | (DMSO-d6); δ 10.25 (s, 1H), 9.01 (dd, J = 5.9, 5.9 Hz, 1H), 8.11 (s, 1H), 8.09 (d, J = 9.9 Hz, 1H), 7.59 (d, J = 9.1 Hz, 2H), 7.50-7.45 (m, 2H), 7.27-7.12 (m, 14H), 7.01 (d, J = 8.3 Hz, 2H), 6.92 (d, J = 3.5 Hz, 1H), 6.85 (d, J = 8.1 Hz, 1H), 6.67 (s, 1H), 6.42 (d, J = 9.9 Hz, 1H), 5.03 (dd, J = 4.3, 8.1 Hz, 1H), 4.52 (d, J = 5.8 Hz, 2H), 3.94 (d, J = 5.6 Hz, 2H), 3.72 (s, 2H), 3.26 (s, 2H), 2.76-2.56 (m, 4H), 2.23 (s, 3H), 1.71 (dd, J = 9.7, 11.7 Hz, 2H), 1.47-1.32 (m, 3H), 1.09-0.96 (m, 2H). | mono-formate |
| 1T | 2.52 | (MeOD); δ 8.44 (s, 2H), 8.37 (d, J = 9.9 Hz, 1H), 7.68 (s, 1H), 7.61-7.59 (m, 2H), 7.53-7.48 (m, 6H), 7.45-7.30 (m, 8H), 7.22 (d, J = 3.5 Hz, 1H), 7.07-7.03 (m, 2H), 6.70 (d, J = 9.9 Hz, 1H), 5.48 (dd, J = 5.5, 8.2 Hz, 1H), 4.51 (d, J = 4.0 Hz, 2H), 4.28 (s, 2H), 4.15 (ddd, J = 6.7, 10.7, 21.2 Hz, 2H), 4.01 (s, 2H), 3.52-3.36 (m, 2H), 2.80-2.70 (m, 2H), 2.97 (dd, J = 12.0, 12.0 Hz, 2H), 2.02-1.96 (m, 1H), 1.85 (d, J = 13.6 Hz, 2H), 1.49-1.38 (m, 2H) | Formate |
| 1U | 2.58 | (MeOD); δ 8.45 (s, 2H), 8.35 (d, J = 10.7 Hz, 1H), 7.66 (dd, J = 1.6, 1.6 Hz, 1H), 7.61-7.57 (m, 1H), 7.49 (dd, J = 5.6, 9.6 Hz, 1H), 7.44-7.32 (m, 13H), 7.25-7.19 (m, 2H), 7.03-7.00 (m, 2H), 6.64 (d, J = 9.9 Hz, 1H), 5.29 (dd, J = 4.3, 8.6 Hz, 1H), 4.72 (s, 2H), 4.21-4.07 (m, 2H), 4.02 (d, J = 8.1 Hz, 4H), 3.29-3.20 (m, 2H), 3.02-2.90 (m, 2H), 2.74-2.64 (m, 2H), 1.94-1.85 (m, 1H), 1.74 (d, J = 13.4 Hz, 2H), 1.46-1.33 (m, 2H) | Formate |
| 1V | 2.54 | (MeOD); δ 8.37 (d, J = 9.9 Hz, 1H), 7.68 (s, 1H), 7.61-7.59 (m, 2H), 7.53-7.48 (m, 6H), 7.45-7.30 (m, 8H), 7.22 (d, J = 3.5 Hz, 1H), 7.07-7.03 (m, 2H), 6.70 (d, J = 9.9 Hz, 1H), 5.48 (dd, J = 5.5, 8.2 Hz, 1H), 4.70 (s, 2H), 4.51 (d, J = 4.0 Hz, 2H), 4.28 (s, 2H), 4.15 (ddd, J = 6.7, 10.7, 21.2 Hz, 2H), 3.52-3.36 (m, 4H), 2.97 (dd, J = 12.0, 12.0 Hz, 2H), 2.02-1.96 (m, 1H), 1.85 (d, J = 13.6 Hz, 2H), 1.49-1.38 (m, 2H) | TFA |
| 1W | 2.56 | (DMSO-d6); δ 9.32-9.31 (m, 1H), 8.17 (d, J = 9.9 Hz, 1H), 7.59-7.54 (m, 2H), 7.39-7.35 (m, 6H), 7.33-7.21 (m, 9H), 7.04-7.00 (m, 2H), 6.84 (d, J = 8.0 Hz, 1H), 6.47 (d, J = 9.8 Hz, 1H), 5.04 (dd, J = 4.3, 7.7 Hz, 1H), 4.60-4.58 (m, 2H), 4.03 (m, J = 6.3 Hz, 2H), 3.76 (s, 2H), 3.37 (m, 2H), 2.72-2.55 (m, 4H), 1.81 (dd, J = 11.4, 11.4 Hz, 2H), 1.57-1.46 (m, 3H), 1.25-1.07 (m, 2H). | None |
| 1X | 2.55 | (MeOD); δ 8.47 (s, 2H), 8.34 (d, J = 9.9 Hz, 1H), 7.67 (s, 1H), 7.64-7.61 (m, 1H), 7.44-7.36 (m, 12H), 7.28-7.21 (m, 2H), 7.05-7.01 (m, 3H), 6.91 (d, J = 9.5 Hz, 1H), 6.67 (d, J = 9.8 Hz, 1H), 5.36 (dt, J = 4.3, 4.4 Hz, 1H), 4.71 (d, J = 5.4 Hz, 2H), 4.19 (dd, J = 6.7, 11.0 Hz, 1H), 4.15-4.08 (m, 3H), 4.06 (s, 2H), 3.84 (s, 3H), 3.29-3.20 (m, 2H), 3.08-3.02 (m, 2H), 2.75-2.67 (m, 2H), 1.97-1.89 (m, 1H), 1.76 (d, J = 13.9 Hz, 2H), 1.48-1.34 (m, 2H). | Formate |

| Cpd. No. | Rt (min) method 1 | NMR data (400 MHz) | Salt (2 eq unless stated) |
|---|---|---|---|
| 2 | 2.43 | (DMSO-d6); δ 10.3 (s, 1H), 9.08 (dd, J = 5.8, 5.8 Hz, 1H), 8.16 (s, 2H), 8.08 (d, J = 9.9 Hz, 1H), 7.78 (d, J = 8.3 Hz, 2H), 7.55-7.49 (m, 2H), 7.38 (d, J = 8.3 Hz, 2H), 7.33-7.28 (m, 3H), 7.28-7.18 (m, 3H), 7.02 (d, J = 8.2 Hz, 1H), 6.96 (d, J = 3.6 Hz, 1H), 6.87 (d, J = 8.0 Hz, 1H), 6.43 (d, J = 9.9 Hz, 1H), 5.05 (dd, J = 4.5, 8.0 Hz, 1H), 4.83-4.78 (m, 1H), 4.56 (d, J = 5.5 Hz, 2H), 3.79 (s, 2H), 2.72-2.61 (m, 2H), 2.14 (dd, J = 15.4, 15.4 Hz, 4H), 1.97 (s, 3H), 1.74-1.69 (m, 2H), 1.50 (d, J = 6.8 Hz, 2H) | Formate |
| 2A | 2.54 | (DMSO-d6); δ 10.35-10.32 (m, 1H), 9.12 (dd, J = 5.8, 5.8 Hz, 1H), 8.22 (s, 1H), 8.14 (d, J = 11.0 Hz, 1H), 7.84 (d, J = 8.2 Hz, 2H), 7.56 (d, J = 8.0 Hz, 2H), 7.42 (d, J = 8.3 Hz, 2H), 7.34 (d, J = 3.9 Hz, 5H), 7.32-7.21 (m, 3H), 7.13 (d, J = 8.7 Hz, 2H), 7.07 (d, J = 8.2 Hz, 1H), 7.00 (d, J = 3.6 Hz, 1H), 6.92 (d, J = 8.2 Hz, 1H), 6.85 (d, J = 8.7 Hz, 2H), 6.60 (s, 1H), 6.48 (d, J = 9.9 Hz, 1H), 5.09 (dd, J = 4.3, 8.1 Hz, 1H), 4.61 (d, J = 5.4 Hz, 2H), 4.01 (d, J = 5.9 Hz, 2H), 3.82 (s, 2H), 3.73 (s, 3H), 3.28 (s, 2H), 2.73-2.63 (m, 4H), 1.76 (dd, J = 11.0, 11.0 Hz, 2H), 1.52-1.43 (m, 2H), 1.14-1.05 (m, 2H). | Mono-formate |
| 2B | 2.45 | (MeOD); δ 8.31 (d, J = 9.9 Hz, 1H), 7.97 (d, J = 8.4 Hz, 2H), 7.68-7.64 (m, 3H), 7.60 (d, J = 7.8 Hz, 1H), 7.45-7.28 (m, 8H), 7.22 (d, J = 3.6 Hz, 1H), 7.06-7.03 (m, 2H), 6.68 (d, J = 9.9 Hz, 1H), 5.44 (dd, J = 6.7, 6.7 Hz, 1H), 4.75 (d, J = 12.0 Hz, 2H), 4.40 (d, J = 7.2 Hz, 2H), 4.16 (dd, J = 6.1, 6.1 Hz, 2H), 3.51-3.42 (m, 2H), 3.28 (d, J = 6.5 Hz, 2H), 2.93 (dd, J = 10.9, 12.9 Hz, 2H), 2.83 (s, 3H), 1.97-1.97 (m, 1H), 1.85 (d, J = 13.9 Hz, 2H), 1.45-1.39 (m, 2H). | TFA |
| 2C | 2.55 | (MeOD); δ 8.30 (d, J = 9.9 Hz, 1H), 7.95 (d, J = 8.3 Hz, 2H), 7.69 (s, 1H), 7.65 (d, J = 8.3 Hz, 3H), 7.45-7.40 (m, 3H), 7.38 (s, 6H), 7.37-7.33 (m, 2H), 7.31-7.25 (m, 3H), 7.05 (d, J = 8.0 Hz, 2H), 6.67 (d, J = 9.9 Hz, 1H), 5.44 (dd, J = 5.6, 7.8 Hz, 1H), 4.74 (tt, J = 1.6, 4.7 Hz, 2H), 4.40 (s, 2H), 4.28 (dd, J = 4.3, 11.2 Hz, 1H), 4.18-4.00 (m, 3H), 3.42-3.37 (m, 1H), 3.30-3.24 (m, 3H), 2.69-2.61 (m, 1H), 2.45 (dd, J = 12.2, 12.2 Hz, 1H), 2.10 (ddd, J = 14.1, 14.1, 14.1 Hz, 1H), 1.89 (d, J = 14.8 Hz, 1H), 1.76-1.66 (m, 2H), 1.20-1.10 (m, 1H). | TFA |
| 2D | 2.51 | (MeOD); δ 8.31 (d, J = 9.9 Hz, 1H), 7.97 (d, J = 8.3 Hz, 2H), 7.70 (s, 1H), 7.66 (d, J = 8.4 Hz, 2H), 7.55 (s, 1H), 7.52-7.39 (m, 7H), 7.37-7.28 (m, 6H), 7.19 (d, J = 3.3 Hz, 1H), 7.06-7.02 (m, 2H), 6.67 (d, J = 9.9 Hz, 1H), 5.44 (dd, J = 6.8, 6.8 Hz, 1H), 4.74 (s, 2H), 4.40 (s, 2H), 4.30 (s, 2H), 4.21 (dd, J = 7.0, 11.7 Hz, 1H), 4.09 (dd, J = 7.2, 11.7 Hz, 1H), 3.79-3.54 (m, 1H), 3.44-3.35 (m, 3H), 3.27 (qd, J = 2.9, 13.9 Hz, 2H), 1.84 (s, 2H), 1.42 (s, 1H). | TFA |
| 2E | 2.54 | (MeOD); δ 8.30 (d, J = 9.9 Hz, 1H), 7.97 (d, J = 8.3 Hz, 2H), 7.65 (d, J = 8.4 Hz, 3H), 7.59 (d, J = 7.7 Hz, 1H), 7.45-7.28 (m, 8H), 7.21 (d, J = 3.6 Hz, 1H), 7.07-7.01 (m, 6H), 6.67 (d, J = 9.9 Hz, 1H), 5.46-5.41 (m, 1H), 4.75 (s, 2H), 4.40 (s, 2H), 4.25-4.07 (m, 4H), 3.84 (s, 3H), 3.48-3.37 (m, 2H), 3.27 (d, J = 6.3 Hz, 2H), 3.04-2.87 (m, 2H), 2.02-2.02 (m, 1H), 1.83 (d, J = 13.7 Hz, 2H), 1.45-1.43 (m, 2H). | TFA |
| 2F | 2.51 | (MeOD); δ 8.42 (s, 1H), 8.18 (d, J = 9.9 Hz, 1H), 7.75 (d, J = 8.3 Hz, 2H), 7.55 (s, 1H), 7.50 (d, J = 7.4 Hz, 1H), 7.40 (d, J = 8.3 Hz, 2H), 7.33-7.21 (m, 7H), 7.16-7.10 (m, 5H), 7.07 (dd, J = 6.8, 6.8 Hz, 2H), 6.93-6.88 (m, 2H), 6.53 (d, J = 9.8 Hz, 1H), 5.20 (dd, J = 4.0, 9.0 Hz, 1H), 4.92-4.90 (m, 1H), 4.62 (s, 2H), 3.99 (s, 2H), 3.27-3.24 (m, 2H), 2.98-2.85 (m, 2H), 2.33-2.12 (m, 4H), 1.79-1.68 (m, 2H), 1.65-1.56 (m, 2H). | mono-formate |

| Cpd. No. | Rt (min) method 1 | NMR data (400 MHz) | Salt (2 eq unless stated) |
|---|---|---|---|
| 2G | 2.55 | (MeOD); δ 8.56 (s, 1H), 8.31 (d, J = 9.9 Hz, 1H), 7.88 (d, J = 8.2 Hz, 2H), 7.70 (s, 1H), 7.62-7.59 (m, 1H), 7.51 (d, J = 8.2 Hz, 2H), 7.43-7.30 (m, 12H), 7.25-7.21 (m, 2H), 7.02-7.00 (m, 2H), 6.64 (d, J = 9.8 Hz, 1H), 5.30 (dt, J = 4.3, 4.5 Hz, 1H), 4.90-4.85 (m, 1H), 4.74 (s, 2H), 4.03 (s, 2H), 3.65-3.63 (m, 2H), 3.03-2.90 (m, 4H), 2.20-2.06 (m, 2H), 1.59-1.46 (m, 3H), 1.23-1.20 (m, 5H). | mono-formate |
| 2H | 2.60 | (MeOD); δ 8.55 (s, 1H), 8.30 (d, J = 9.9 Hz, 1H), 7.90 (d, J = 8.3 Hz, 2H), 7.67 (s, 1H), 7.61-7.53 (m, 3H), 7.44 (s, 6H), 7.40-7.35 (m, 6H), 7.25 (d, J = 8.2 Hz, 1H), 7.20 (d, J = 3.6 Hz, 1H), 7.03-7.00 (m, 2H), 6.65 (d, J = 9.8 Hz, 1H), 5.33 (dd, J = 4.0, 9.0 Hz, 1H), 5.00 (dd, J = 2.9, 2.9 Hz, 1H), 4.74 (s, 2H), 4.11 (s, 2H), 4.03 (s, 2H), 3.08-2.83 (m, 6H), 1.68-1.56 (m, 6H), 1.42-1.22 (m, 6H). | mono-formate |

| Cpd. No. | Rt (min) Method 1 | NMR data (400 MHz) | Salt (2 eq unless stated) |
|---|---|---|---|
| 3 | 2.51 | (DMSO-d6, 100° C.): δ 8.20 (d, J = 9.9 Hz, 1H), 7.50-7.46 (m, 6H), 7.44-7.29 (m, 12H), 7.17 (d, J = 8.3 Hz, 1H), 7.03 (d, J = 8.2 Hz, 1H), 6.58 (d, J = 9.9 Hz, 1H), 6.10-6.05 (m, 1H), 5.38 (dd, J = 4.7, 8.3 Hz, 1H), 4.25 (s, 2H), 4.20-4.15 (m, 2H), 4.14-4.06 (m, 2H), 3.70-3.64 (m, 2H), 3.38-3.31 (m, 5H), 3.24-3.20 (m, 2H), 3.12-3.05 (m, 3H), 3.02-2.85 (m, 2H), 1.94-1.91 (m, 1H), 1.81-1.74 (m, 2H), 1.54-1.39 (m, 2H). | TFA |
| 3A | 2.49 | (MeOD); δ 8.52 (s, 1H), 8.30 (d, J = 9.9 Hz, 1H), 7.90 (d, J = 8.4 Hz, 2H), 7.77 (s, 1H), 7.64 (d, J = 8.0 Hz, 1H), 7.56 (d, J = 8.3 Hz, 1H), 7.43-7.28 (m, 12H), 7.24 (d, J = 8.3 Hz, 1H), 7.01 (d, J = 8.2 Hz, 1H), 6.68 (d, J = 3.4 Hz, 1H), 6.64 (d, J = 9.9 Hz, 1H), 6.40 (d, J = 3.4 Hz, 1H), 5.34 (dd, J = 4.1, 9.0 Hz, 1H), 4.61 (s, 2H), 4.17 (s, 2H), 4.14-4.03 (m, 2H), 3.85 (s, 2H), 3.13-3.04 (m, 3H), 2.47-2.38 (m, 2H), 1.82-1.74 (m, 1H), 1.66-1.61 (m, 2H), 1.39-1.27 (m, 2H). | mono-formate |
| 3B | 2.48 | (DMSO-d6); δ 8.09 (d, J = 9.9 Hz, 1H), 7.60 (d, J = 8.2 Hz, 2H), 7.50-7.41 (m, 8H), 7.39-7.25 (m, 8H), 7.12 (d, J = 8.3 Hz, 1H), 6.99 (d, J = 8.2 Hz, 1H), 6.53 (d, J = 9.8 Hz, 1H), 6.05 (d, J = 3.6, 3.6 Hz, 1H), 5.37 (dd, J = 4.6, 8.2 Hz, 1H), 4.31 (d, J = 3.1 Hz, 2H), 4.21 (s, 2H), 4.15 (d, J = 2.0 Hz, 2H), 4.07 (d, J = 6.3 Hz, 2H), 3.70-3.59 (m, 2H), 3.36-3.21 (m, 2H), 3.21-3.06 (m, 2H), 2.90 (dd, J = 11.0, 11.0 Hz, 2H), 2.52-2.46 (m, 1H), 1.96-1.83 (m, 1H), 1.73 (dd, J = 3.2, 14.4 Hz, 2H), 1.56-1.36 (m, 2H). | TFA |
| 3C | 2.49 | (MeOD); δ 8.48 (s, 2H), 8.31 (d, J = 9.9 Hz, 1H), 7.55-7.48 (m, 2H), 7.45-7.28 (m, 12H), 7.19 (s, 1H), 7.12 (d, J = 7.7 Hz, 1H), 7.05 (d, J = 8.2 Hz, 1H), 6.69 (d, J = 9.8 Hz, 1H), 6.19-5.97 (m, 1H), 5.46-5.40 (m, 1H), 4.37 (s, 3H), 4.19-4.09 (m, 3H), 4.04-3.96 (m, 6H), 3.63 (s, 1H), 3.28-3.19 (m, 4H), 2.70-2.60 (m, 3H), 2.57 (s, 1H), 1.90-1.84 (m, 1H), 1.73 (d, J = 13.2 Hz, 2H), 1.48-1.35 (m, 2H). | Formate |
| 3D | 2.50 | (MeOD); δ 8.48 (s, 2H), 8.35 (d, J = 9.8 Hz, 1H), 7.53-7.49 (m, 1H), 7.45-7.27 (m, 15H), 7.14 (ddd, J = 5.9, 7.8, 11.2 Hz, 1H), 7.05 (d, J = 8.2 Hz, 1H), 6.69 (d, J = 9.8 Hz, 1H), 6.18-5.96 (m, 1H), 5.44-5.38 (m, 1H), 4.39 (d, J = 2.4 Hz, 1H), 4.28 (d, J = 5.3 Hz, 2H), 4.19-3.95 (m, 9H), 3.58 (dd, J = 5.2, 5.2 Hz, 1H), 3.25 (d, J = 12.2 Hz, 2H), 3.16 (d, J = 6.1 Hz, 2H), 2.72-2.61 (m, 3H), 2.56 (s, 1H), 1.90-1.87 (m, 1H), 1.72 (d, J = 12.4 Hz, 2H), 1.41 (ddd, J = 12.4, 12.4, 12.4 Hz, 2H). | Formate |
| 3E | 2.48 | (MeOD); δ 8.49 (s, 2H), 8.34 (d, J = 9.9 Hz, 1H), 7.52-7.48 (m, 1H), 7.45-7.25 (m, 16H), 7.21-7.15 (m, 1H), 7.05 (d, J = 8.2 Hz, 1H), 6.69 (d, J = 9.8 Hz, 1H), 6.17-5.92 (m, 1H), 5.46-5.41 (m, 1H), 4.36 (d, J = 2.3 Hz, 1H), 4.30-4.26 (m, 2H), 4.19-4.07 (m, 3H), 4.04 (s, 2H), 3.97-3.81 (m, 4H), 3.53-3.44 (m, 1H), 3.29-3.17 (m, 4H), 2.72-2.59 (m, 3H), 2.56-2.43 (m, 1H), 1.90-1.84 (m, 1H), 1.72 (d, J = 12.7 Hz, 2H), 1.41 (dd, J = 11.9, 25.0 Hz, 2H). | Formate |
| 3F | 2.51 | (MeOD); δ 8.51 (s, 2H), 8.40 (dd, J = 2.8, 9.9 Hz, 1H), 7.65-7.51 (m, 3H), 7.49-7.40 (m, 10H), 7.38-7.30 (m, 6H), 7.05 (d, J = 8.2 Hz, 1H), 6.71 (d, J = 9.8 Hz, 1H), 6.34 (s, 0.5H), 6.23 (s, 0.5H), 5.47-5.40 (m, 1H), 4.77-4.75 (m, 1H), 4.59 (d, J = 9.5 Hz, 2H), 4.42 (s, 1H), 4.13 (dd, J = 6.3, 20.0 Hz, 2H), 4.04 (s, 1H), 3.97 (s, 1H), 3.40-3.36 (m, 2H), 3.31-3.12 (m, 6H), 2.73-2.65 (m, 1H), 2.58 (dd, J = 11.8, 11.8 Hz, 2H), 1.92-1.64 (m, 3H), 1.49-1.36 (m, 2H). | Formate |
| 3G | 2.53 | (MeOD); δ 8.34 (dd, J = 9.9, 12.8 Hz, 1H), 7.77-7.66 (m, 4H), 7.59-7.48 (m, 6H), 7.43-7.29 (m, 9H), 7.08-7.04 (m, 1H), 6.72-6.67 (m, 1H), 6.31 (d, J = 37.4 Hz, 1H), 5.49-5.42 (m, 1H), 4.78 (s, 1H), 4.64-4.58 (m, 2H), 4.47-4.42 (m, 3H), 4.29 (d, J = 7.5 Hz, 2H), 4.18-4.09 (m, 2H), 3.51-3.42 (m, 2H), 3.32-3.26 (m, 2H), 3.06-2.93 (m, 2H), 2.05-1.98 (m, 1H), 1.92-1.80 (m, 2H), 1.51-1.41 (m, 2H). | TFA |
| 3H | 2.62 | (MeOD); δ 8.48 (s, 2H), 8.27 (d, J = 9.9 Hz, 1H), 7.55-7.50 (m, 1H), 7.48-7.45 (m, 1H), 7.42 (s, 6H), 7.40-7.30 (m, 6H), 7.27 (d, J = 8.1 Hz, 2H), 7.18 (s, 1H), 7.10 (d, J = 7.8 Hz, 1H), 7.04 (d, J = 8.1 Hz, 1H), 6.67 (d, J = 9.6 Hz, 1H), 6.27 (s, 1H), 5.42 (t, J = 6.7 Hz, 1H), 4.57 (s, 1H), 4.34 (s, 2H), 4.26 (s, 1H), 4.17 (d, J = 5.6 Hz, 2H), 4.06 (s, 2H), 3.97 (s, 3H), 3.90 (s, 2H), 3.59-3.51 (m, 1H), 3.29 (d, J = 13.0 Hz, 1H), 3.22 (d, J = 5.6 Hz, 2H), 2.73 (t, J = 11.6 Hz, 1H), 2.57 (t, J = 11.0 Hz, 1H), 2.46 (s, 1H), 2.40-2.37 (m, 1H), 1.91 (s, 1H), 1.76 (d, J = 13.0 Hz, 2H), 1.66 (d, J = 12.1 Hz, 1H), 1.49-1.37 (m, 2H). | Formate |
| 3I | 2.48 | (MeOD); δ 8.48 (s, 2H), 8.29 (d, J = 9.9 Hz, 1H), 7.64 (d, J = 7.6 Hz, 2H), 7.53 (d, J = 8.8 Hz, 3H), 7.42 (s, 7H), 7.35 (d, J = 8.8 Hz, 5H), 7.27 (d, J = 8.1 Hz, 2H), 7.03 (d, J = 8.3 Hz, 1H), 6.66 (d, J = 9.6 Hz, 1H), 6.24 (d, J = 21.5 Hz, 1H), 5.41 (t, J = 6.6 Hz, 1H), 4.57 (s, 1H), 4.30 (s, 2H), 4.24 (s, 1H), 4.16-3.98 (m, 4H), 3.91 (s, 1H), 3.58-3.51 (m, 3H), 3.28 (d, J = 1.3 Hz, 1H), 3.19 (d, J = 6.3 Hz, 3H), 2.77 (t, J = 11.7 Hz, 1H), 2.68-2.59 (m, 1H), 2.43-2.35 (m, 2H), 1.93 (s, 1H), 1.75 (d, J = 12.5 Hz, 2H), 1.52-1.40 (m, 2H). | Formate |
| 3J | 2.50 | (MeOD); δ 8.52 (s, 2H), 8.32 (t, J = 10.6 Hz, 1H), 7.60-7.46 (m, 3H), 7.39 (s, 7H), 7.38-7.33 (m, 3H), 7.33-7.30 (m, 2H), 7.30-7.27 (m, 2H), 7.25-7.21 (m, 1H), 7.05 (dd, J = 2.0, 8.2 Hz, 1H), 6.68 (d, J = 4.1, 9.9 Hz, 1H), 6.29 (d, J = 38.8 Hz, 1H), 5.43 (dd, J = 6.1, 11.3 Hz, 1H), 4.76 (s, 1H), 4.61 (d, J = 9.5 Hz, 2H), 4.45 (s, 1H), 4.33 (d, J = 3.5 Hz, 2H), 4.15 (d, J = 8.4 Hz, 1H), 4.10 (d, J = 6.6 Hz, 1H), 3.97 (d, J = 2.0 Hz, 4H), 3.92 (s, 1H), 3.26-3.10 (m, 4H), 2.62 (t, J = 12.2 Hz, 1H), 2.50 (t, J = 11.2 Hz, 1H), 1.91-1.79 (m, 1H), 1.73 (d, J = 15.0 Hz, 1H), 1.66 (d, J = 13.6 Hz, 1H), 1.49-1.32 (m, 2H). | Formate |

| Cpd. No. | Rt (min) method 1 | NMR data (400 MHz) | Salt (2 eq unless stated) |
|---|---|---|---|
| 4 | 2.42 | (MeOD); δ 8.98 (s, 2H), 8.28 (d, J = 9.8 Hz, 1H), 8.04 (d, J = 8.3 Hz, 2H), 7.77 (s, 1H), 7.71-7.65 (m, 3H), 7.58-7.42 (m, 9H), 7.41-7.34 (m, 3H), 7.30 (d, J = 9.1 Hz, 1H), 7.05 (d, J = 8.2 Hz, 1H), 6.69 (d, J = 9.8 Hz, 1H), 5.45 (t, J = 6.9 Hz, 1H), 4.92-4.88 (m, 2H), 4.42 (s, 2H), 4.27 (s, 2H), 4.15 (d, J = 6.5 Hz, 2H), 3.45 (d, J = 12.4 Hz, 2H), 3.28 (d, J = 6.7 Hz, 2H), 2.98-2.92 (m, 2H), 2.02-1.98 (m, 1H), 1.84 (d, J = 14.1 Hz, 2H), 1.49-1.39 (m, 2H). | TFA |
| 4A | 2.46 | (MeOD); δ 8.73 (d, J = 5.1 Hz, 1H), 8.60 (s, 1H), 8.56 (s, 1H), 8.41 (d, J = 7.7 Hz, 1H), 8.27 (d, J = 9.9 Hz, 1H), 7.58 (d, J = 8.0 Hz, 2H), 7.53 (d, J = 8.0 Hz, 1H), 7.50-7.42 (m, 4H), 7.37-7.33 (m, 9H), 7.21 (d, J = 8.2 Hz, 1H), 7.00 (d, J = 8.2 Hz, 1H), 6.62 (d, J = 9.9 Hz, 1H), 5.33 (dd, J = 4.9, 8.2 Hz, 1H), 4.75 (d, J = 2.8 Hz, 2H), 4.17 (s, 2H), 4.13-3.97 (m, 2H), 3.95 (s, 3H), 3.71 (s, 2H), 3.09-3.04 (m, 2H), 2.96 (d, J = 11.9 Hz, 2H), 2.23 (dd, J = 11.9, 11.9 Hz, 2H), 1.74-1.66 (m, 1H), 1.60 (d, J = 13.1 Hz, 2H), 1.35-1.23 (m, 2H). | mono-formate |
| 4B | 2.44 | (MeOD); δ 9.01 (s, 1H), 8.69 (s, 1H), 8.55 (s, 1H), 8.30 (d, J = 9.9 Hz, 1H), 8.21 (s, 1H), 8.03 (d, J = 7.0 Hz, 1H), 7.94 (d, J = 8.2 Hz, 2H), 7.57-7.50 (m, 4H), 7.47-7.42 (m, 2H), 7.41-7.30 (m, 8H), 7.25 (d, J = 8.3 Hz, 1H), 7.02 (d, J = 8.2 Hz, 1H), 6.65 (d, J = 9.8 Hz, 1H), 5.34 (dd, J = 4.1, 8.9 Hz, 1H), 4.78 (s, 2H), 4.16-4.11 (m, 4H), 3.76 (s, 2H), 3.07-3.01 (m, 4H), 2.35 (dd, J = 11.4, 11.4 Hz, 2H), 1.82-1.75 (m, 1H), 1.67 (d, J = 13.1 Hz, 2H), 1.40-1.28 (m, 2H). | mono-formate |
| 4C | 2.44 | (MeOD); δ 8.52 (s, 2H), 8.28-8.25 (m, 2H), 8.12 (d, J = 8.9 Hz, 1H), 8.01 (d, J = 7.7 Hz, 1H), 7.82 (d, J = 8.9 Hz, 1H), 7.63-7.54 (m, 4H), 7.51-7.43 (m, 3H), 7.40-7.35 (m, 8H), 7.26 (d, J = 8.2 Hz, 1H), 7.04 (d, J = 8.2 Hz, 1H), 6.65 (d, J = 9.8 Hz, 1H), 5.39 (dd, J = 6.7, 6.7 Hz, 1H), 4.94 (s, 2H), 4.26 (s, 2H), 4.22-4.09 (m, 2H), 3.96 (s, 3H), 3.93 (s, 2H), 3.20-3.12 (m, 4H), 2.55 (dd, J = 11.5, 11.5 Hz, 2H), 1.91-1.84 (m, 1H), 1.73 (d, J = 12.3 Hz, 2H), 1.46-1.35 (m, 2H). | Formate |
| 4D | 2.45 | (DMSO-d6); δ 8.97 (dd, J = 5.8, 5.8 Hz, 1H), 8.79 (d, J = 5.1 Hz, 1H), 8.56 (dd, J = 1.8, 1.8 Hz, 1H), 8.37-8.34 (m, 1H), 8.12 (d, J = 9.9 Hz, 1H), 8.01 (d, J = 8.4 Hz, 2H), 7.67 (d, J = 8.4 Hz, 2H), 7.55-7.51 (m, 1H), 7.49-7.42 (m, 7H), 7.38-7.30 (m, 4H), 7.14 (d, J = 8.3 Hz, 1H), 7.02 (d, J = 8.2 Hz, 1H), 6.55 (d, J = 9.9 Hz, 1H), 5.40 (dd, J = 4.7, 8.3 Hz, 1H), 4.66 (d, J = 5.8 Hz, 2H), 4.36 (s, 2H), 4.24 (s, 2H), 4.13 (d, J = 3.1 Hz, 2H), 3.33-3.25 (m, 2H), 3.19-3.15 (m, 2H), 2.92-2.92 (m, 2H), 1.93 (s, 1H), 1.80 (d, J = 13.2 Hz, 2H), 1.52-1.50 (m, 2H) | TFA |
| 4E | 2.47 | (MeOD); δ 8.99 (s, 2H), 8.21 (d, J = 9.9 Hz, 1H), 7.78 (s, 1H), 7.73-7.66 (m, 2H), 7.64-7.60 (m, 1H), 7.57-7.42 (m, 10H), 7.41-7.34 (m, 3H), 7.31 (d, J = 8.3 Hz, 1H), 7.05 (d, J = 8.2 Hz, 1H), 6.69 (d, J = 9.8 Hz, 1H), 5.44 (dd, J = 4.8, 8.3 Hz, 1H), 4.43 (s, 2H), 4.27 (s, 2H), 4.17 (s, 3H), 3.49-3.40 (m, 1H), 3.39-3.29 (m, 3H), 3.28-3.24 (m, 3H), 2.96-2.96 (m, 1H), 2.02 (s, 1H), 1.86 (d, J = 14.3 Hz, 2H), 1.55-1.36 (m, 2H).. | TFA |
| 4F | 2.46 | (MeOD); δ 8.54 (s, 1H), 8.28 (d, J = 9.9 Hz, 1H), 7.58 (s, 1H), 7.50-7.42 (m, 6H), 7.40-7.34 (m, 8H), 7.30-7.22 (m, 4H), 7.02 (d, J = 8.2 Hz, 1H), 6.64 (d, J = 9.9 Hz, 1H), 5.36 (dd, J = 5.5, 7.7 Hz, 1H), 4.70 (d, J = 3.6 Hz, 2H), 4.20 (s, 2H), 4.08-4.04 (m, 2H), 3.95 (s, 3H), 3.92 (s, 3H), 3.78 (s, 2H), 3.11-3.01 (m, 4H), 2.32 (dd, J = 11.4, 11.4 Hz, 2H), 1.78-1.70 (m, 1H), 1.60 (d, J = 12.7 Hz, 2H), 1.36-1.23 (m, 2H). | mono-formate |
| 4G | 2.47 | (MeOD); δ 8.97 (s, 1H), 8.59 (s, 1H), 8.52 (s, 2H), 8.29-8.25 (m, 2H), 8.09-8.05 (m, 1H), 7.61-7.57 (m, 2H), 7.54-7.49 (m, 3H), 7.45-7.34 (m, 10H), 7.24 (d, J = 8.3 Hz, 1H), 7.02 (d, J = 8.2 Hz, 1H), 6.63 (d, J = 9.8 Hz, 1H), 5.39 (dd, J = 6.6, 6.6 Hz, 1H), 4.81 (t, J = 29.6 Hz, 2H), 4.31 (s, 2H), 4.12-3.99 (m, 2H), 3.98 (s, 3H), 3.93 (s, 2H), 3.20-3.09 (m, 4H), 2.49 (dd, J = 12.0, 12.0 Hz, 2H), 1.83-1.75 (m, 1H), 1.65 (d, J = 13.1 Hz, 2H), 1.40-1.29 (m, 2H). | mono-formate |
| 4H | 2.45 | (DMSO-d6); δ 9.04 (d, J = 1.5 Hz, 1H), 8.96 (dd, J = 5.6, 5.6 Hz, 1H), 8.70 (s, 1H), 8.18 (s, 1H), 8.11 (d, J = 9.9 Hz, 1H), 8.03-8.00 (m, 1H), 7.64-7.50 (m, 5H), 7.49-7.44 (m, 5H), 7.43 (d, J = 1.7 Hz, 1H), 7.39-7.31 (m, 3H), 7.14 (d, J = 8.2 Hz, 1H), 7.02 (d, J = 8.2 Hz, 1H), 6.56 (d, J = 9.8 Hz, 1H), 5.39 (dd, J = 5.3, 7.6 Hz, 1H), 4.71 (d, J = 5.8 Hz, 2H), 4.33 (d, J = 6.4 Hz, 2H), 4.19 (s, 2H), 4.15-4.09 (m, 2H), 3.95 (s, 3H), 3.22 (d, J = 17.8 Hz, 2H), 3.19-3.14 (m, 2H), 2.87 (s, 2H), 1.98-1.88 (m, 1H), 1.81-1.76 (m, 2H), 1.48-1.48 (m, 2H). | TFA |

| Cpd. No. | Rt (min) Method 1 | NMR data (400 MHz) | Salt (2 eq unless stated) |
|---|---|---|---|
| 5 | 2.56 | (MeOD); δ 8.51 (s, 2H), 8.31 (d, J = 9.9 Hz, 1H), 7.92 (d, J = 8.3 Hz, 2H), 7.69 (s, 1H), 7.63-7.57 (m, 3H), 7.47-7.45 (m, 2H), 7.44-7.42 (m, 2H), 7.41-7.37 (m, 5H), 7.38-7.29 (m, 5H), 7.26 (d, J = 8.2 Hz, 1H), 7.03 (d, J = 8.2 Hz, 1H), 6.66 (d, J = 9.8 Hz, 1H), 5.38 (dd, J = 4.5, 8.7 Hz, 1H), 4.76 (s, 2H), 4.23 (s, 2H), 4.19-4.06 (m, 2H), 3.94 (s, 2H), 3.20-3.10 (m, 4H), 2.55 (t, J = 11.9 Hz, 2H), 1.89-1.79 (m, 1H), 1.68 (d, J = 12.8 Hz, 2H), 1.43-1.30 (m, 2H). | Formate |
| 5A | 2.57 | (MeOD); δ 8.56 (s, 1H), 8.31 (d, J = 9.9 Hz, 1H), 7.89 (d, J = 8.3 Hz, 2H), 7.69 (s, 1H), 7.58 (d, J = 7.5 Hz, 1H), 7.52 (d, J = 8.3 Hz, 2H), 7.45-7.41 (m, 2H), 7.40-7.35 (m, 3H), 7.35-7.30 (m, 8H), 7.24 (t, J = 4.1 Hz, 2H), 7.01 (d, J = 8.2 Hz, 1H), 6.64 (d, J = 9.8 Hz, 1H), 5.31 (dd, J = 4.0, 9.0 Hz, 1H), 4.56 (s, 2H), 4.14-4.05 (m, 4H), 3.67 (s, 2H), 3.05-2.93 (m, 4H), 2.21 (t, J = 11.5 Hz, 2H), 1.76-1.67 (m, 1H), 1.60 (d, J = 14.0 Hz, 2H), 1.35-1.23 (m, 2H). | mono-formate |
| 5B | 2.62 | (MeOD); δ 8.53 (s, 1H), 8.30 (d, J = 9.9 Hz, 1H), 8.03 (s, 1H), 7.92 (d, J = 8.1 Hz, 2H), 7.87 (d, J = 7.4 Hz, 1H), 7.74 (s, 1H), 7.59-7.52 (m, 3H), 7.47 (t, J = 7.6 Hz, 1H), 7.45-7.43 (m, 2H), 7.42-7.40 (m, 2H), 7.40-7.36 (m, 5H), 7.36-7.32 (m, 2H), 7.25 (d, J = 8.3 Hz, 1H), 7.02 (d, J = 8.2 Hz, 1H), 6.65 (d, J = 9.9 Hz, 1H), 5.36 (dd, J = 4.3, 8.7 Hz, 1H), 4.79 (s, 2H), 4.18-4.11 (m, 4H), 3.88 (s, 2H), 3.16-3.05 (m, 4H), 2.50 (t, J = 12.1 Hz, 2H), 1.88-1.80 (m, 1H), 1.69 (d, J = 13.2 Hz, 2H), 1.43-1.31 (m, 2H). | mono-formate |
| 5C | 2.60 | (DMSO-d6, 100° C.); δ 8.27 (s, 1H), 8.18 (d, J = 9.8 Hz, 1H), 7.60 (s, 1H), 7.50 (d, J = 7.4 Hz, 1H), 7.44-7.38 (m, 5H), 7.36-7.33 (m, 3H), 7.31-7.25 (m, 5H), 7.24-7.20 (m, 3H), 7.10 (d, J = 10.8 Hz, 2H), 6.96 (d, J = 7.9 Hz, 1H), 6.48 (d, J = 9.9 Hz, 1H), 5.09 (t, J = 5.9 Hz, 1H), 4.59 (s, 2H), 4.06 (d, J = 5.4 Hz, 3H), 3.86-3.75 (m, 5H), 2.90-2.78 (m, 4H), 2.72 (d, J = 10.9 Hz, 2H), 1.91 (t, J = 11.2 Hz, 2H), 1.62-1.49 (m, 3H), 1.19 (q, J = 11.6 Hz, 2H). | mono-formate |

| Cpd. No. | Rt (min) Method 1 | NMR data (400 MHz) | Salt (2 eq unless stated) |
|---|---|---|---|
| 5D | 2.54 | (MeOD); δ 8.31 (d, J = 9.8 Hz, 1H), 7.80 (d, J = 7.5 Hz, 2H), 7.64 (s, 1H), 7.55 (d, J = 7.4 Hz, 1H), 7.47-7.42 (m, 4H), 7.38-7.33 (m, 4H), 7.30-7.24 (m, 6H), 7.20-7.15 (m, 2H), 6.94 (d, J = 8.0 Hz, 1H), 6.87 (d, J = 3.4 Hz, 1H), 6.60 (d, J = 9.8 Hz, 1H), 5.23 (dd, J = 3.8, 8.5 Hz, 1H), 4.13-4.01 (m, 2H), 3.89 (s, 2H), 3.66 (t, J = 6.9 Hz, 2H), 3.44 (s, 2H), 3.15 (t, J = 6.9 Hz, 2H), 2.95-2.76 (m, 4H), 1.95-1.87 (m, 2H), 1.60 (s, 1H), 1.50 (d, J = 14.9 Hz, 2H), 1.32-1.17 (m, 2H). | None |
| 5E | 2.43 | (MeOD); δ 8.59 (d, J = 2.5 Hz, 1H), 8.56-8.53 (m, 2H), 8.25 (d, J = 9.9 Hz, 1H), 7.71 (s, 1H), 7.65 (d, J = 7.3 Hz, 1H), 7.61-7.53 (m, 6H), 7.50-7.43 (m, 8H), 7.25 (d, J = 8.3 Hz, 1H), 7.03 (d, J = 8.2 Hz, 1H), 6.65 (d, J = 9.8 Hz, 1H), 5.38 (dd, J = 6.6, 6.6 Hz, 1H), 4.74 (m, 2H), 4.26 (s, 2H), 4.16-4.06 (m, 2H), 3.95 (s, 3H), 3.87 (s, 2H), 3.15-3.08 (m, 4H), 2.46 (dd, J = 12.2, 12.2 Hz, 2H), 1.84-1.77 (m, 1H), 1.66 (d, J = 13.1 Hz, 2H), 1.41-1.30 (m, 2H). | mono-formate |

| Cpd. No. | Rt (min) Method 1 | NMR data (400 MHz) | Salt (2 eq unless stated) |
|---|---|---|---|
| 6 | 2.40 | (MeOD); δ 8.70 (d, J = 5.0 Hz, 1H), 8.53 (s, 2H), 8.41 (d, J = 9.9 Hz, 1H), 8.16 (s, 1H), 8.01-7.97 (m, 1H), 7.82 (s, 1H), 7.55-7.50 (m, 2H), 7.50-7.45 (m, 1H), 7.45-7.38 (m, 8H), 7.37-7.34 (m, 2H), 7.31 (d, J = 8.3 Hz, 1H), 7.05 (d, J = 8.3 Hz, 1H), 6.70 (d, J = 9.9 Hz, 1H), 5.44 (t, J = 6.7 Hz, 1H), 4.72 (d, J = 12.7 Hz, 1H), 4.18-4.13 (m, 2H), 3.94 (s, 2H), 3.87 (d, J = 12.8 Hz, 1H), 3.25-3.12 (m, 5H), 3.03 (d, J = 6.8 Hz, 2H), 2.97 (t, J = 12.3 Hz, 1H), 2.53 (t, J = 12.2 Hz, 2H), 2.17-2.10 (m, 1H), 2.03-1.97 (m, 1H), 1.87-1.68 (m, 4H), 1.46-1.31 (m, 4H). | Formate |
| 6A | 2.41 | (DMSO-d6, 100° C.); δ 9.16 (s, 1H), 8.74 (s, 1H), 8.23 (d, J = 9.9 Hz, 1H), 8.19-8.15 (m, 3H), 8.06-8.02 (m, 1H), 7.57-7.52 (m, 2H), 7.46-7.43 (m, 2H), 7.39-7.27 (m, 5H), 7.26-7.21 (m, 1H), 7.11 (d, J = 8.2 Hz, 1H), 6.97 (d, J = 8.2 Hz, 1H), 6.50 (d, J = 9.9 Hz, 1H), 5.07 (dd, J = 4.8, 7.7 Hz, 1H), 4.08 (ddd, J = 6.3, 10.8, 13.4 Hz, 2H), 2.99-2.95 (m, 2H), 2.90-2.67 (m, 6H), 2.59-2.56 (m, 2H), 1.93-1.85 (m, 2H), 1.78-1.71 (m, 3H), 1.62-1.53 (m, 1H), 1.49 (dd, J = 2.6, 12.9 Hz, 2H), 1.27-1.11 (m, 6H). | Formate |
| 6B | 2.39 | (MeOD); δ 8.64 (d, J = 5.3 Hz, 1H), 8.54 (s, 2H), 8.41 (d, J = 9.8 Hz, 1H), 7.87 (s, 1H), 7.81 (s, 1H), 7.79-7.74 (m, 2H), 7.57-7.54 (m, 2H), 7.45-7.42 (m, 2H), 7.42-7.41 (m, 5H), 7.39-7.34 (m, 3H), 7.31 (d, J = 8.3 Hz, 1H), 7.06 (d, J = 8.2 Hz, 1H), 6.71 (d, J = 9.8 Hz, 1H), 5.45 (t, J = 6.5 Hz, 1H), 4.75 (d, J = 13.7 Hz, 1H), 4.15 (dd, J = 3.6, 6.3 Hz, 2H), 3.91 (d, J = 12.9 Hz, 1H), 3.25 (d, J = 6.6 Hz, 2H), 3.21-3.13 (m, 3H), 3.04 (d, J = 7.0 Hz, 2H), 2.97 (t, J = 11.7 Hz, 1H), 2.50 (t, J = 12.0 Hz, 2H), 2.18-2.13 (m, 1H), 2.03-1.95 (m, 1H), 1.90-1.78 (m, 2H), 1.69 (d, J = 12.8 Hz, 2H), 1.48-1.32 (m, 4H). | formate |
| 6C | 2.43 | (MeOD); δ 8.80 (d, J = 1.9 Hz, 1H), 8.53 (s, 2H), 8.42 (d, J = 9.9 Hz, 1H), 8.16 (dd, J = 2.3, 8.0 Hz, 1H), 7.77 (s, 1H), 7.72-7.66 (m, 2H), 7.55-7.52 (m, 2H), 7.46 (dd, J = 1.4, 8.0 Hz, 2H), 7.43-7.40 (m, 5H), 7.40-7.35 (m, 3H), 7.32 (d, J = 8.2 Hz, 1H), 7.06 (d, J = 8.2 Hz, 1H), 6.71 (d, J = 9.9 Hz, 1H), 5.45 (t, J = 6.1 Hz, 1H), 4.75 (d, J = 11.0 Hz, 1H), 4.16 (d, J = 5.6 Hz, 2H), 3.90 (d, J = 14.1 Hz, 3H), 3.28-3.12 (m, 5H), 3.05 (d, J = 6.9 Hz, 2H), 2.97 (t, J = 11.9 Hz, 1H), 2.52 (t, J = 11.9 Hz, 2H), 2.18-2.12 (m, 1H), 2.04-1.97 (m, 1H), 1.91-1.78 (m, 2H), 1.71 (d, J = 13.4 Hz, 2H), 1.47-1.32 (m, 4H). | formate |
| 6D | 2.43 | (MeOD); δ 8.67 (s, 1H), 8.54 (s, 2H), 8.41 (d, J = 9.9 Hz, 1H), 8.19 (s, 1H), 8.02-8.00 (m, 1H), 7.92 (s, 2H), 7.57-7.50 (m, 2H), 7.47-7.45 (m, 2H), 7.42-7.34 (m, 8H), 7.31 (d, J = 8.7 Hz, 1H), 7.05 (d, J = 8.2 Hz, 1H), 6.71 (d, J = 9.9 Hz, 1H), 5.44 (t, J = 6.4 Hz, 2H), 4.72 (d, J = 11.6 Hz, 1H), 4.15 (t, J = 6.4 Hz, 2H), 3.89 (s, 2H), 3.83 (s, 1H), 3.23 (d, J = 6.7 Hz, 3H), 3.14 (d, J = 11.1 Hz, 2H), 3.03 (d, J = 6.9 Hz, 2H), 2.97-2.95 (m, 1H), 2.47 (t, J = 12.0 Hz, 2H), 2.19-2.12 (m, 1H), 1.98-1.96 (m, 1H), 1.90-1.81 (m, 2H), 1.70 (d, J = 12.9 Hz, 2H), 1.45-1.33 (m, 4H). | formate |
| 6E | 2.40 | (MeOD); δ 8.87 (d, J = 2.1 Hz, 1H), 8.61 (d, J = 1.9 Hz, 1H), 8.54 (s, 2H), 8.41 (d, J = 9.8 Hz, 1H), 8.09-8.06 (m, 1H), 7.78 (s, 1H), 7.72-7.68 (m, 1H), 7.55-7.53 (m, 2H), 7.47-7.43 (m, 2H), 7.42-7.34 (m, 8H), 7.31 (d, J = 8.2 Hz, 1H), 7.05 (d, J = 8.2 Hz, 1H), 6.70 (d, J = 9.8 Hz, 1H), 5.44 (t, J = 6.7 Hz, 1H), 4.73 (d, J = 13.9 Hz, 1H), 4.15 (dd, J = 2.3, 6.4 Hz, 2H), 3.88 (s, 2H), 3.79 (d, J = 13.1 Hz, 1H), 3.23 (d, J = 6.5 Hz, 3H), 3.12 (d, J = 12.0 Hz, 2H), 3.06-2.99 (m, 2H), 2.97-2.92 (m, 1H), 2.45 (t, J = 12.1 Hz, 2H), 2.19-2.08 (m, 1H), 1.99 (d, J = 20.5 Hz, 1H), 1.90-1.79 (m, 2H), 1.67 (d, J = 13.1 Hz, 2H), 1.45-1.30 (m, 4H). | Formate |
| 6F | 2.44 | (DMSO-d6, 100° C.); δ 8.22 (d, J = 9.9 Hz, 1H), 8.16 (s, 2H), 8.13 (s, 1H), 7.97-7.92 (m, 2H), 7.86 (d, J = 7.9 Hz, 1H), 7.51-7.41 (m, 5H), 7.38-7.33 (m, 2H), 7.31-7.27 (m, 3H), 7.26-7.20 (m, 3H), 7.10 (d, J = 8.0 Hz, 1H), 6.96 (d, J = 8.2 Hz, 1H), 6.49 (d, J = 9.8 Hz, 1H), 5.08-5.03 (m, 1H), 4.09-4.03 (m, 2H), 3.40 (s, 2H), 2.94 (s, 2H), 2.85-2.77 (m, 2H), 2.69 (d, J = 10.4 Hz, 2H), 2.56-2.54 (m, 3H), 1.91-1.85 (m, 2H), 1.72-1.71 (m, 3H), 1.58-1.55 (m, 1H), 1.47 (d, J = 12.7 Hz, 2H), 1.29-1.13 (m, 5H). | Formate |

| Cpd. No. | Rt (min) Method 1 | NMR data (400 MHz) | Salt (2 eq unless stated) |
|---|---|---|---|
| 7 | 2.47 | (MeOD); δ 8.56 (s, 1H), 8.32 (d, J = 9.9 Hz, 1H), 7.55 (d, J = 8.0 Hz, 2H), 7.48 (d, J = 8.2 Hz, 2H), 7.43-7.37 (m, 3H), 7.37-7.29 (m, 9H), 7.27-7.23 (m, 3H), 7.02 (d, J = 8.2 Hz, 1H), 6.65 (d, J = 9.8 Hz, 1H), 5.33 (dd, J = 3.8, 9.0 Hz, 1H), 4.78 (d, J = 10.2 Hz, 1H), 4.14-4.08 (m, 4H), 3.79 (d, J = 11.3 Hz, 1H), 3.70 (s, 2H), 3.23 (s, 1H), 3.06-2.96 (m, 4H), 2.95-2.83 (m, 2H), 2.23 (t, J = 11.9 Hz, 2H), 1.93 (s, 1H), 1.76-1.58 (m, 6H), 1.35-1.24 (m, 2H). | mono-formate |
| 7A | 2.48 | (MeOD); δ 8.50 (s, 2H), 8.30 (d, J = 9.9 Hz, 1H), 7.50 (d, J = 7.7 Hz, 1H), 7.41 (s, 5H), 7.40-7.33 (m, 6H), 7.32-7.25 (m, 4H), 7.16 (s, 1H), 7.09 (d, J = 7.8 Hz, 1H), 7.04 (d, J = 8.4 Hz, 1H), 6.68 (d, | formate |

| Cpd. No. | Rt (min) Method 1 | NMR data (400 MHz) | Salt (2 eq unless stated) |
|---|---|---|---|
| | | J = 9.8 Hz, 1H), 5.41 (t, J = 7.1 Hz, 1H), 4.78 (d, J = 11.9 Hz, 1H), 4.34 (s, 2H), 4.16-4.11 (m, 2H), 3.97 (s, 5H), 3.80 (d, J = 10.5 Hz, 1H), 3.27 (d, J = 13.2 Hz, 1H), 3.20 (d, J = 7.0 Hz, 4H), 2.99-2.84 (m, 2H), 2.59 (t, J = 11.9 Hz, 2H), 1.95 (d, J = 10.9 Hz, 1H), 1.85-1.64 (m, 6H), 1.40 (q, J = 11.9 Hz, 2H). | |
| 7B | 2.47 | (MeOD); δ 8.50 (s, 2H), 8.35-8.29 (m, 1H), 7.42-7.37 (m, 7H), 7.36-7.31 (m, 5H), 7.29-7.20 (m, 5H), 7.16 (d, J = 7.6 Hz, 1H), 7.03 (d, J = 8.3 Hz, 1H), 6.66 (d, J = 9.9 Hz, 1H), 5.39 (t, J = 5.7 Hz, 1H), 4.78 (d, J = 13.1 Hz, 1H), 4.23 (s, 2H), 4.16-4.09 (m, 2H), 4.01-3.94 (m, 2H), 3.90 (d, J = 18.3 Hz, 2H), 3.77 (s, 1H), 3.53-3.46 (m, 1H), 3.23-3.13 (m, 5H), 2.96-2.80 (m, 2H), 2.64-2.53 (m, 2H), 1.92-1.81 (m, 2H), 1.70-1.49 (m, 5H), 1.42-1.34 (m, 2H). | formate |
| 7C | 2.49 | (MeOD); δ 8.56 (s, 1H), 8.38 (d, J = 9.9 Hz, 1H), 7.45-7.37 (m, 6H), 7.37-7.30 (m, 9H), 7.29-7.23 (m, 4H), 7.02 (d, J = 8.3 Hz, 1H), 6.68 (d, J = 9.9 Hz, 1H), 5.35 (dd, J = 4.5, 8.6 Hz, 1H), 4.76 (d, J = 9.8 Hz, 1H), 4.15-4.03 (m, 2H), 3.81 (d, J = 15.7 Hz, 1H), 3.62 (s, 2H), 3.26-3.17 (m, 3H), 3.16-3.11 (m, 2H), 3.07-3.00 (m, 2H), 2.97-2.81 (m, 4H), 2.12 (t, J = 12.1 Hz, 2H), 1.93 (s, 1H), 1.72-1.61 (m, 3H), 1.55 (d, J = 11.3 Hz, 3H), 1.27 (q, J = 12.0 Hz, 2H). | formate |
| 7D | 2.50 | (MeOD); δ 8.49 (s, 1H), 8.41 (d, J = 9.8 Hz, 1H), 7.43-7.38 (m, 8H), 7.36 (s, 2H), 7.35-7.33 (m, 3H), 7.31 (s, 2H), 7.28 (s, 1H), 7.25 (d, J = 7.8 Hz, 2H), 7.06 (d, J = 8.2 Hz, 1H), 6.72 (d, J = 9.8 Hz, 1H), 5.42 (dd, J = 4.9, 8.2 Hz, 1H), 4.76 (d, J = 11.8 Hz, 1H), 4.20-4.10 (m, 3H), 3.96 (s, 2H), 3.82 (s, 1H), 3.53-3.42 (m, 2H), 3.30-3.25 (m, 2H), 3.25-3.18 (m, 5H), 2.95-2.83 (m, 2H), 2.57 (t, J = 12.0 Hz, 2H), 1.94-1.81 (m, 2H), 1.71-1.67 (m, 5H), 1.43-1.32 (m, 2H). | Formate |

| Cpd. No. | Rt (min) Method 1 | NMR data (400 MHz) | Salt (2 eq unless stated) |
|---|---|---|---|
| 8 | 2.49 | (MeOD); δ 8.37 (d, J = 9.9 Hz, 1H), 7.87 (d, J = 8.3 Hz, 2H), 7.52-7.48 (m, 1H), 7.44-7.31 (m, 15H), 7.26 (d, J = 8.1 Hz, 1H), 7.02 (d, J = 8.1 Hz, 1H), 6.69 (d, J = 9.9 Hz, 1H), 6.09 (s, 1H), 5.39-5.33 (m, 1H), 4.37 (s, 1H), 4.29 (s, 1H), 4.26-4.20 (m, 2H), 4.16-4.04 (m, 2H), 3.85-3.74 (m, 2H), 3.70 (s, 2H), 3.25 (t, J = 7.1 Hz, 2H), 3.18 (t, J = 8.0 Hz, 2H), 3.10-2.98 (m, 4H), 2.63 (s, 1H), 2.57-2.53 (m, 1H), 2.23 (t, J = 12.0 Hz, 2H), 1.77-1.68 (m, 1H), 1.59 (d, J = 11.9 Hz, 2H), 1.35-1.24 (m, 2H). | mono-formate |
| 8A | 2.50 | (MeOD); δ 8.30 (d, J = 9.9 Hz, 1H), 8.11 (d, J = 7.9 Hz, 1H), 7.52-7.47 (m, 6H), 7.46-7.29 (m, 10H), 7.23 (d, J = 8.0 Hz, 1H), 7.05 (d, J = 8.2 Hz, 1H), 6.67 (d, J = 9.8 Hz, 1H), 6.13 (d, J = 3.0 Hz, 1H), 5.45 (dd, J = 5.5, 7.7 Hz, 1H), 4.43 (s, 1H), 4.39 (d, J = 7.4 Hz, 3H), 4.28-4.23 (m, 4H), 4.16-4.12 (m, 2H), 4.09 (d, J = 5.2 Hz, 3H), 3.88 (t, J = 5.4 Hz, 1H), 3.77 (t, J = 5.8 Hz, 1H), 3.46 (d, J = 12.2 Hz, 2H), 3.31 (d, J = 6.6 Hz, 2H), 2.96 (dd, J = 12.9, 12.9 Hz, 2H), 2.69-2.63 (m, 1H), 2.57 (s, 1H), 2.03-1.96 (m, 1H), 1.84 (d, J = 14.1 Hz, 2H), 1.47-1.37 (m, 2H). | TFA |
| 8B | 2.50 | (DMSO, 90° C.); δ 8.18-8.16 (m, 4H), 7.82 (d, J = 8.3 Hz, 2H), 7.48 (s, 1H), 7.39 (d, J = 7.7 Hz, 4H), 7.36-7.30 (m, 6H), 7.29-7.20 (m, 5H), 7.09 (d, J = 8.2 Hz, 1H), 6.95 (d, J = 8.2 Hz, 1H), 6.47 (d, J = 9.9 Hz, 1H), 6.11-6.07 (m, 1H), 5.09 (dd, J = 4.9, 6.9 Hz, 1H), 5.03 (t, J = 6.6 Hz, 1H), 4.20-4.20 (m, 2H), 4.05 (dd, J = 2.3, 6.4 Hz, 2H), 3.84 (s, 2H), 3.81-3.65 (m, 2H), 3.50 (s, 2H), 2.87-2.71 (m, 6H), 1.92 (t, J = 11.5 Hz, 2H), 1.61-1.55 (m, 1H), 1.49 (d, J = 13.2 Hz, 2H), 1.36 (d, J = 6.9 Hz, 3H), 1.23-1.13 (m, 2H). | Formate |
| 8C | 2.50 | (DMSO, 90° C.); δ 8.18-8.16 (m, 4H), 7.82 (d, J = 8.3 Hz, 2H), 7.48 (s, 1H), 7.39 (d, J = 7.7 Hz, 4H), 7.36-7.30 (m, 6H), 7.29-7.20 (m, 5H), 7.09 (d, J = 8.2 Hz, 1H), 6.95 (d, J = 8.2 Hz, 1H), 6.47 (d, J = 9.9 Hz, 1H), 6.11-6.07 (m, 1H), 5.09 (dd, J = 4.9, 6.9 Hz, 1H), 5.03 (t, J = 6.6 Hz, 1H), 4.20-4.20 (m, 2H), 4.05 (dd, J = 2.3, 6.4 Hz, 2H), 3.84 (s, 2H), 3.81-3.65 (m, 2H), 3.50 (s, 2H), 2.87-2.71 (m, 6H), 1.92 (t, J = 11.5 Hz, 2H), 1.61-1.55 (m, 1H), 1.49 (d, J = 13.2 Hz, 2H), 1.36 (d, J = 6.9 Hz, 3H), 1.23-1.13 (m, 2H). | Formate |
| 8D | 2.48 | (MeOD); δ 8.19 (dd, J = 2.3, 9.9 Hz, 1H), 7.87 (d, J = 8.3 Hz, 2H), 7.53 (d, J = 8.1 Hz, 2H), 7.38-7.34 (m, 6H), 7.33-7.15 (m, 9H), 6.92 (d, J = 8.1 Hz, 1H), 6.55 (dd, J = 1.5, 9.9 Hz, 1H), 5.99 (dd, J = 3.4, 3.4 Hz, 1H), 5.32 (dd, J = 6.7, 6.7 Hz, 1H), 4.27 (d, J = 5.4 Hz, 3H), 4.20 (s, 1H), 4.18-4.12 (m, 4H), 4.02-3.98 (m, 2H), 3.74-3.64 (m, 2H), 3.33 (d, J = 16.3 Hz, 2H), 3.15 (d, J = 7.5 Hz, 2H), 2.83 (dd, J = 13.0, 13.0 Hz, 2H), 2.53 (s, 1H), 2.42 (s, 1H), 1.90-1.81 (m, 1H), 1.75-1.65 (m, 2H), 1.35-1.28 (m, 2H). | TFA |
| 8E | 2.48 | (MeOD); δ 8.28 (d, J = 9.2 Hz, 1H), 7.63 (s, 1H), 7.57-7.47 (m, 8H), 7.46-7.32 (m, 8H), 7.29 (d, J = 8.2 Hz, 1H), 7.05 (d, J = 8.2 Hz, 1H), 6.68 (d, J = 9.7 Hz, 1H), 6.12 (t, J = 3.3 Hz, 1H), 5.45 (t, J = 6.5 Hz, 1H), 4.43-4.38 (m, 3H), 4.34 (s, 1H), 4.31-4.26 (m, 4H), 4.16-4.11 (m, 2H), 4.03-4.00 (m, 3H), 3.88-3.78 (m, 2H), 3.47 (d, J = 12.3 Hz, 2H), 3.26 (d, J = 6.4 Hz, 2H), 2.96 (t, J = 12.7 Hz, 2H), 2.67 (s, 1H), 2.55 (s, 1H), 1.97 (s, 1H), 1.82 (d, J = 13.7 Hz, 2H), 1.43 (d, J = 12.0 Hz, 2H). | TFA |
| 8F | 2.51 | (DMSO-d6); δ 8.17-8.15 (m, 3H), 7.47 (s, 1H), 7.40-7.37 (m, 2H), 7.36-7.30 (m, 9H), 7.29-7.21 (m, 6H), 7.09 (d, J = 8.2 Hz, 1H), 6.95 (d, J = 8.2 Hz, 1H), 6.48 (d, J = 9.8 Hz, 1H), 6.05-6.03 (m, 1H), 5.08 (dd, J = 4.6, 7.7 Hz, 1H), 4.29 (s, 2H), 4.10-3.99 (m, 4H), 3.84-3.78 (m, 2H), 3.74 (s, 2H), 3.63 (s, 2H), 2.97-2.92 (m, 3H), 2.86-2.72 (m, 4H), 2.45 (s, 2H), 1.97-1.85 (m, 2H), 1.61-1.48 (m, 3H), 1.24-1.13 (m, 2H). | Formate |

| Cpd. No. | Rt (min) Method 1 | NMR data (400 MHz) | Salt (2 eq unless stated) |
|---|---|---|---|
| 9 | 2.46 | (MeOD); δ 9.28 (s, 1H), 9.17 (s, 1H), 8.33 (d, J = 9.7 Hz, 2H), 8.30-8.26 (m, 1H), 8.00 (d, J = 8.3 Hz, 2H), 7.68 (d, J = 8.3 Hz, 2H), 7.60 (d, J = 4.6 Hz, 2H), 7.55-7.46 (m, 7H), 7.46-7.38 (m, 3H), 7.30 (d, J = 8.2 Hz, 1H), 7.05 (d, J = 8.2 Hz, 1H), 6.68 (d, J = 9.8 Hz, 1H), 5.46 (dd, J = 6.7, 6.7 Hz, 1H), 4.79-4.63 (m, 2H), 4.43 (s, 2H), 4.27 (s, 2H), 4.18 (d, J = 6.5 Hz, 2H), 3.45 (d, J = 12.3 Hz, 2H), 3.29 (d, J = 6.8 Hz, 2H), 2.96 (dd, J = 10.9, 12.7 Hz, 2H), 2.71-2.62 (m, 4H), 2.04-1.95 (m, 1H), 1.88 (d, J = 13.4 Hz, 2H), 1.52-1.41 (m, 2H). | TFA |

| Cpd. No. | Rt (min) Method 1 | NMR data (400 MHz) | Salt (2 eq unless stated) |
|---|---|---|---|
| 10 | 2.39 | (MeOD); δ 9.27 (s, 1H), 9.20 (s, 1H), 8.41 (d, J = 9.8 Hz, 1H), 8.35 (s, 1H), 8.25 (d, J = 3.4 Hz, 1H), 7.56 (d, J = 5.4 Hz, 2H), 7.52-7.47 (m, 6H), 7.46-7.31 (m, 5H), 7.05 (d, J = 8.2 Hz, 1H), 6.69 (d, J = 9.8 Hz, 1H), 5.47 (dd, J = 6.7, 6.7 Hz, 1H), 4.28 (s, 2H), 4.19-4.12 (m, 2H), 3.69-3.62 (m, 2H), 3.46 (d, J = 12.5 Hz, 2H), 3.32-3.18 (m, 4H), 2.97 (dd, J = 10.7, 13.2 Hz, 2H), 2.16-2.06 (m, 2H), 2.01-1.96 (m, 1H), 1.84 (d, J = 13.3 Hz, 2H), 1.52-1.39 (m, 2H). | TFA |

| Cpd. No. | Rt (min) Method 1 | NMR data (400 MHz) | Salt (2 eq unless stated) |
|---|---|---|---|
| 11 | 2.58 | (MeOD); δ 8.51 (s, 2H), 8.31 (d, J = 9.9 Hz, 1H), 7.66 (s, 1H), 7.62 (d, J = 7.7 Hz, 1H), 7.47-7.35 (m, 13H), 7.26-7.21 (m, 2H), 7.12 (s, 1H), 7.06-7.02 (m, 2H), 6.68 (d, J = 9.8 Hz, 1H), 5.34 (dt, J = 4.4, 4.2 Hz, 1H), 4.72 (s, 2H), 4.11-4.06 (m, 4H), 3.95 (s, 2H), 3.90 (s, 3H), 3.07-3.03 (m, 2H), 2.95-2.90 (m, 2H), 2.86-2.78 (m, 2H), 1.64-1.55 (m, 2H), 1.47-1.41 (m, 2H), 0.89 (s, 3H). | Formate |

| Cpd. No. | Rt (min) Method 1 | NMR data (400 MHz) | Salt (2 eq unless stated) |
|---|---|---|---|
| 12 | 2.62 | (MeOD); δ 8.21 (d, J = 9.8 Hz, 1H), 7.73 (s, 1H), 7.68 (d, J = 7.7 Hz, 1H), 7.62 (d, J = 7.8 Hz, 1H), 7.52 (s, 1H), 7.43 (d, J = 7.4 Hz, 1H), 7.31-7.04 (m, 14H), 6.96 (d, J = 3.6 Hz, 1H), 6.86 (d, J = 8.2 Hz, 1H), 6.50 (d, J = 9.8 Hz, 1H), 5.11 (dt, J = 4.2, 4.2 Hz, 1H), 4.86 (s, 2H), 4.01 (dd, J = 6.5, 10.8 Hz, 1H), 3.89 (dd, J = 6.5, 10.7 Hz, 1H), 3.83 (s, 2H), 3.25-3.23 (m, 2H), 2.74 (ddt, J = 6.3, 13.9, 14.7 Hz, 2H), 2.65-2.58 (m, 2H), 1.77-1.70 (m, 2H), 1.50-1.44 (m, 1H), 1.38-1.34 (m, 2H), 1.13-1.01 (m, 2H). | None |

| Cpd. No. | Rt (min) Method 1 | NMR data (400 MHz) | Salt (2 eq unless stated) |
|---|---|---|---|
| 13 | 2.48 | (MeOD); δ 8.49 (s, 2H), 8.38 (d, J = 9.9 Hz, 1H), 7.89 (d, J = 8.3 Hz, 2H), 7.46-7.39 (m, 7H), 7.39-7.33 (m, 6H), 7.31-7.27 (m, 2H), 7.26-7.22 (m, 2H), 7.04 (d, J = 8.1 Hz, 1H), 6.70 (d, J = 9.9 Hz, 1H), 5.41 (t, J = 6.7 Hz, 1H), 4.66 (d, J = 13.1 Hz, 1H), 4.32 (d, J = 17.6, 57.8 Hz, 2H), 4.16-4.05 (m, 3H), 4.00 (s, 2H), 3.39-3.34 (m, 1H), 3.29-3.18 (m, 6H), 3.16-3.08 (m, 2H), 2.89-2.74 (m, 2H), 2.62 (t, J = 11.6 Hz, 2H), 1.96-1.82 (m, 3H), 1.76-1.66 (m, 3H), 1.64-1.54 (m, 1H), 1.45-1.32 (m, 2H). | Formate |

| Cpd. No. | Rt (min) Method 1 | NMR data (400 MHz) | Salt (2 eq unless stated) |
|---|---|---|---|
| 14 | 2.48 | (MeOD); δ 8.27 (d, J = 9.9 Hz, 1H), 7.56-7.48 (m, 4H), 7.47-7.43 (m, 2H), 7.40-7.32 (m, 6H), 7.32-7.25 (m, 6H), 7.19 (d, J = 8.2 Hz, 1H), 6.98 (d, J = 8.2 Hz, 1H), 6.78 (s, 1H), 6.62 (d, J = 9.8 Hz, 1H), 5.22 (dd, J = 3.9, 8.7 Hz, 1H), 4.57 (s, 2H), 4.17-4.04 (m, 2H), 3.87 (s, 3H), 3.85-3.80 (m, 2H), 3.46 (s, 2H), 2.93-2.80 (m, 4H), 1.97-1.87 (m, 2H), 1.66-1.57 (m, 1H), 1.56-1.48 (m, 2H), 1.29-1.16 (m, 2H). | None |

| Cpd. No. | UPLC-MS | UPLC Method | ¹H NMR data | Salt (2 eq unless stated) |
|---|---|---|---|---|
| 15A | Rt 4.95 min, ES+ 893.1 | 4 | $^1$H NMR (600 MHz, DMSO-d6) δ ppm 10.15-10.40 (bs, 1 H), 9.07-9.22 (t, 1 H), 8.01-8.22 (m, 1 H), 7.56 (d, J = 8.6 Hz, 2 H), 7.42-7.48 (m, 2 H), 7.16-7.40 (m, 14 H), 7.04 (m, 1 H), 6.99-7.03 (m, 1 H), 6.91 (d, J = 8.2 Hz, 1 H), 6.54 (s, 1 H), 6.44-6.52 (m, 1 H), 5.02-5.11 (m, 1 H), 4.63 (d, 2 H), 4.00 (d, J = 6.2 Hz, 2 H), 3.82 (s, 3 H), 3.75-3.80 (m, 2 H), 3.40-3.48 (m, 2 H), 3.35-3.40 (m, 4 H), 2.65-2.81 (m, 4 H), 1.73-1.87 (m, 2 H), 1.38-1.57 (m, 2 H), 1.10 (m, 2 H) | Formate |
| 15B | Rt 4.65 min ES+ 861.1 | 4 | $^1$H NMR (600 MHz, DMSO-d6) δ ppm 10.24-10.53 (bs, 1 H), 9.12-9.31 (t, 1 H), 8.06-8.23 (m, 1 H), 7.84-8.00 (m, 2 H), 7.68-7.73 (m, 1 H), 7.61-7.66 (m, 2 H), 7.54-7.60 (m, 2 H), 7.41-7.46 (m, 1 H), 7.21-7.38 (m, 12 H), 6.89-7.14 (m, 2 H), 6.60-6.68 (m, 2 H), 6.51-6.58 (m, 1 H), 5.11-5.38 (m, 1 H), 4.59-4.71 (m, 2 H), 4.09-4.22 (m, 2 H), 3.95-4.06 (m, 2 H), 3.37-3.56 (m, 4 H), 2.64-3.04 (m, 4 H), 1.44-1.67 (m, 2 H), 1.08-1.36 (m, 4 H) | Formate |
| 15C | Rt 0.51 min, ES+ 894.46 | 3 | $^1$H NMR (400 MHz, DMSO-d6) δ ppm 10.22 (br. s., 1 H), 9.17 (t, J = 5.6 Hz, 1 H), 8.37 (s, 2 H), 7.98-8.17 (m, 1 H), 7.67-7.91 (m, 3 H), 7.09-7.49 (m, 14 H), 6.93-7.07 (m, 1 H), 6.89 (d, J = 8.2 Hz, 1 H), 6.72 (br. s., 1 H), 6.45 (d, J = 9.9 Hz, 1 H), 5.31 (br. s., 1 H), 5.01 (dd, J = 7.6, 4.3 Hz, 1 H), 4.67 (d, J = 6.0 Hz, 2 H), 4.00 (d, J = 6.2 Hz, 2 H), 3.76 (s, 3 H), 3.62 (s, 2 H), 2.50 2.60 (m, 1 H), 2.55-2.77 (m, 4 H), 1.66-1.91 (m, 2 H), 1.38-1.57 (m, 5 H), 1.02-1.30 (m, 2 H) | Formate |
| 15D | Rt 0.44 min, ES+ 858.2 | 3 | $^1$H NMR (400 MHz, DMSO-d6) δ ppm 10.10-10.40 (bs, 1 H), 9.09 (t, 1 H), 8.76-8.91 (m, 1 H), 8.19 (s, 2 H), 8.11 (d, J = 9.9 Hz, 1 H), 8.03 (dd, J = 8.3, 2.3 Hz, 1 H), 7.88 (d, J = 8.4 Hz, 2 H), 7.61-7.73 (m, 2 H), 7.16-7.49 (m, 14 H), 7.06 (d, J = 8.2 Hz, 1 H), 6.91 (d, J = 8.2 Hz, 1 H), 6.59-6.78 (bs, 1 H), 6.47 (d, J = 9.9 Hz, 1 H), 5.08 (br. s., 1 H), 4.61 (d, J = 6.0 Hz, 2 H), 4.02 (d, J = 6.4 Hz, 2 H), 3.83 (s, 2 H), 3.30-3.60 (m, 4 H), 2.60-2.78 (m, 4 H), 1.78-1.94 (m, 2 H), 1.47 (d, J = 13.7 Hz, 3 H), 1.12 (d, J = 11.7 Hz, 2 H) | Formate |
| 15E | Rt 4.42 min, ES+ 833.2 | 4 | $^1$H NMR (600 MHz, DMSO-d6) δ ppm 10.30 (br. s., 1 H), 8.10 (d, J = 9.9 Hz, 1 H), 7.16-7.56 (m, 19 H), 7.07 (d, J = 7.9 Hz, 1 H), 6.91 (d, J = 8.2 Hz, 1 H), 6.59 (br. s., 1 H), 6.47 (d, J = 9.9 Hz, 1 H), 5.97-6.35 (m, 1 H), 5.09 (dd, J = 8.1, 4.1 Hz, 1 H), 4.24 (br. s., 2 H), 4.00 (d, J = 6.2 Hz, 2 H), 3.83 (s, 2 H), 3.46-3.61 (m, 4 H), 2.60-2.84 (m, 5 H), 1.83 (br. s., 2 H), 1.45 (d, J = 11.8 Hz, 4 H), 1.02-1.22 (m, 4 H) | Formate |
| 15F | Rt 1.04 min, ES+ 893.52 | 3 | $^1$H NMR (400 MHz, METHANOL-d4) δ 8.41 (bs, 3H), 8.20-8.29 (m, 1H), 7.19-7.69 (m, 20H), 6.97-7.02 (m, 1H), 6.64 (d, J = 9.87 Hz, 1H), 5.24-5.57 (m, 1H), 4.71-4.79 (m, 2H), 4.28 (s, 2H), 4.08-4.17 (m, 2H), 3.95-4.01 (s, 3H), 3.89-3.94 (m, 2H), 3.09-3.21 (m, 4H), 2.42-2.63 (m, 2H), 1.75-1.88 (m, 1H), 1.57-1.75 (m, 2H), 1.23-1.45 (m, 2H) | Hydrochloride |

Biological Characterization

Example 17

M3 Receptor Radioligand Binding Assay

Human M3 receptor membranes (15 ug/well) from Perkin Elmer were incubated with 0.52 nM Scopolamine Methyl Chloride, [N-methyl-3H] with or without test compounds, or a saturating concentration of Atropine (5 μM) for the determination of non-specific binding. The assay was carried out in 96-well polypropylene plates in a volume of 250 ul. The assay buffer used was 50 mM Tris-HCl, 154 mM NaCl (pH 7.4). The final assay concentration of DMSO was 0.5% (v/v). The plates were sealed and incubated for 2 h at room temperature on an orbital shaker (slow speed). Membranes were harvested onto 96-well unifilter GF/C filter plates pre-treated with 0.5% polyethyleneimine (v/v), using a filter manifold, washed four times with 200 ul of assay buffer. The plates were dried before addition of 50 μl of microscint-0, sealed then read in a Trilux Microbeta scintillation counter. IC50 values are determined from competition curves using a non-linear curve fitting program. Ki values were calculated from IC50 values by the Cheng and Prusoff equation.

The M3 Ki values of the compounds according to the invention are less than 50 nM, most of them even less than 10 nM. The preferred compounds according to the invention have Ki value less than 4 nM or even less than 3 nM; for the enantiomeric mixture and/or at least for one of the enantiomeric pure form (S or R) on the stereogenic center (2).

Example 18

β2 Adrenoceptor Radioligand Binding Assay

Human β$_2$ adrenoceptor membranes (7.5 ug/well) from Perkin Elmer were incubated with 0.3 nM 125-I Cyanopindolol with or without test compounds, or a saturating concentration of s-propranolol (2 μM) for the determination of non-specific binding. The assay was carried out in 96-well polypropylene plates in a volume of 200 ul. The assay buffer used was 25 mM HEPES, 0.5% BSA (w/v), 1 mM EDTA, 0.02% ascorbic acid (v/v), (pH 7.4). The final assay concentration of DMSO was 0.5% (v/v). The plates were sealed and incubated for 1 h at room temperature on an orbital shaker (slow speed). Membranes were harvested onto 96-well unifilter GF/C filter plates pre-treated with 0.5% polyethyleneimine (v/v), using a filter manifold, washed six times with 200 ul of wash buffer containing 10 mM HEPES and 500 mM NaCl. The plates were dried before addition of 50 μl of microscint-0, sealed then read in a Trilux Microbeta scintillation counter. IC50 values are determined from competition curves using a non-linear curve fitting program. Ki values were calculated from IC50 values by the Cheng and Prusoff equation.

The β2 Ki values of the compounds according to the invention are less than 50 nM, most of them even less than 10 nM.

In the following table the compounds tested are classified in terms of binding affinity according to the following ranges

| Cpd. No. | B2 Range 8.5-9.5 | M3 Range |
|---|---|---|
| Compound 1 | +++ | ++ |
| Compound 1A | +++ | ++ |
| Compound 1B | +++ | ++ |
| Compound 1C | ++ | ++ |
| Compound 1D | +++ | ++ |
| Compound 1E | +++ | ++ |
| Compound 1F | ++ | + |
| Compound 1G | +++ | ++ |
| Compound 1H | ++ | ++ |
| Compound 1I | ++ | ++ |
| Compound 1J | +++ | ++ |
| Compound 1K | +++ | ++ |
| Compound 1L | +++ | ++ |
| Compound 1M | ++ | ++ |
| Compound 1N | ++ | ++ |
| Compound 1O | +++ | + |
| Compound 1P | ++ | ++ |
| Compound 1Q | +++ | ++ |
| Compound 1R | +++ | + |
| Compound 1S | +++ | ++ |
| Compound 1T | ++ | ++ |
| Compound 1U | +++ | ++ |
| Compound 1V | +++ | ++ |
| Compound 1W | +++ | ++ |
| Compound 1X | +++ | ++ |
| Compound 2 | +++ | ++ |
| Compound 2A | +++ | ++ |
| Compound 2B | +++ | ++ |
| Compound 2C | ++ | + |
| Compound 2D | ++ | ++ |
| Compound 2E | ++ | + |
| Compound 2F | +++ | ++ |
| Compound 2G | +++ | ++ |
| Compound 2H | +++ | + |
| Compound 3 | +++ | +++ |
| Compound 3A | ++ | ++ |
| Compound 3B | +++ | ++ |
| Compound 3C | +++ | +++ |
| Compound 3D | ++ | ++ |
| Compound 3E | +++ | +++ |
| Compound 3F | +++ | ++ |
| Compound 3G | +++ | ++ |
| Compound 3H | +++ | ++ |
| Compound 3I | ++ | ++ |
| Compound 3J | +++ | +++ |
| Compound 4 | ++ | ++ |
| Compound 4A | +++ | ++ |
| Compound 4B | ++ | +++ |
| Compound 4C | +++ | +++ |
| Compound 4D | ++ | ++ |
| Compound 4E | ++ | ++ |
| Compound 4F | ++ | ++ |
| Compound 4G | +++ | ++ |
| Compound 4H | +++ | ++ |
| Compound 5 | +++ | ++ |
| Compound 5A | +++ | ++ |
| Compound 5B | +++ | ++ |
| Compound 5C | +++ | ++ |
| Compound 5D | +++ | ++ |
| Compound 5E | +++ | ++ |
| Compound 6 | +++ | ++ |
| Compound 6A | ++ | ++ |
| Compound 6B | +++ | ++ |
| Compound 6C | +++ | +++ |
| Compound 6D | +++ | ++ |
| Compound 6E | +++ | ++ |
| Compound 6F | ++ | ++ |
| Compound 7 | ++ | ++ |
| Compound 7A | ++ | ++ |
| Compound 7B | + | ++ |
| Compound 7C | +++ | ++ |
| Compound 7D | (+++) ++ | +++ |
| Compound 8 | +++ | +++ |
| Compound 8A | +++ | ++ |
| Compound 8B | ++ | ++ |
| Compound 8C | ++ | ++ |
| Compound 8D | +++ | ++ |
| Compound 8E | +++ | ++ |
| Compound 8F | ++ | ++ |
| Compound 9 | ++ | + |
| Compound 10 | ++ | ++ |
| Compound 11 | +++ | ++ |
| Compound 12 | ++ | ++ |
| Compound 13 | +++ | ++ |
| Compound 14 | ++ | ++ |
| Compound 15 | +++ | ++ |
| Compound 15A | +++ | ++ |
| Compound 15B | ++ | + |
| Compound 15C | +++ | ++ |
| Compound 15D | +++ | ++ |
| Compound 15E | +++ | ++ |
| Compound 15F | +++ | ++ |
| Compound 16 | ++ | + |

+++: IC50 < 0.3 nM
++: IC50 in the range 0.3-3 nM
+: IC50 > 3 nM

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula I:

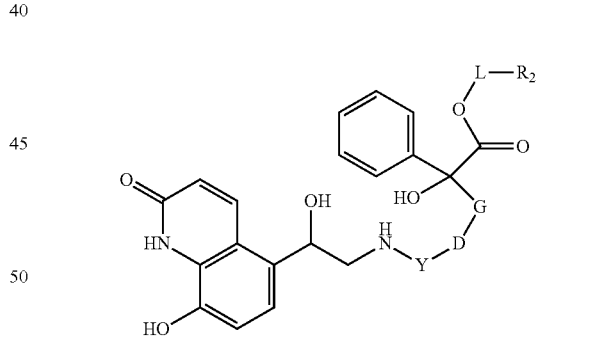

wherein:

D is a group of formula D0, D1, D2, D3, D4, D5, D6, D7, or D8:

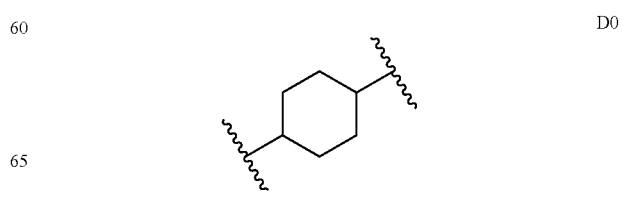

-continued

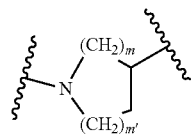
D1

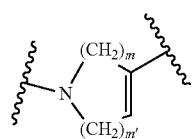
D2

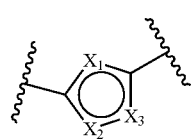
D3

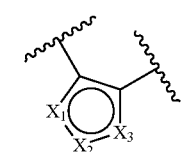
D4

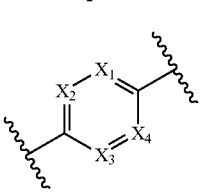
D5

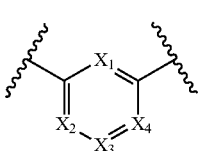
D6

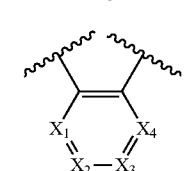
D7

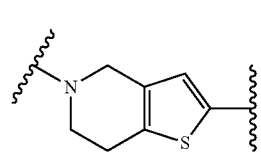
D8 wherein at least one of $X_1$, $X_2$, $X_3$, and $X_4$ is at each occurrence independently N, $NR_7$, O, or S and the others are CH groups;

Y is a divalent group of formula

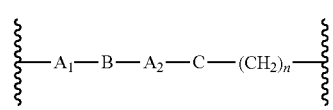

wherein

A1 and A2 are each independently absent or ($C_1$-$C_{12}$) alkylene, ($C_3$-$C_8$)cycloalkylene, or ($C_3$-$C_8$)heterocycloalkylene optionally substituted by one or more substituents selected from the group consisting of ($C_1$-$C_6$) alkyl, aryl($C_1$-$C_6$)alkyl and heteroaryl($C_1$-$C_6$)alkyl;

B is absent or is ($C_3$-$C_8$)cycloalkylene, ($C_3$-$C_8$)heterocycloalkylene, arylene, or heteroarylene optionally substituted by one or more groups selected from the group consisting of —OH, halogens, —CN, ($C_1$-$C_6$)alkyl, ($C_1$-$C_6$)alkoxy, ($C_1$-$C_6$)haloalkyl, ($C_1$-$C_6$)haloalkoxy, and aryl($C_1$-$C_6$)alkyl;

C is absent or is —O—, —C(O)—, —OC(O)—, —(O)CO—, —S—, —S(O)—, —S(O)$_2$-, or —N($R_7$)—, or is a group of formula C1, C2, C3, C4, or C5:

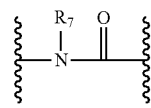
C1

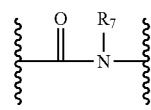
C2

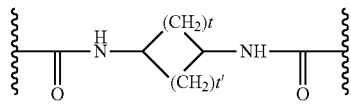
C3

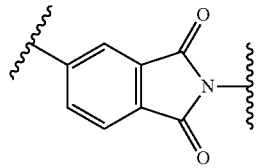
C4

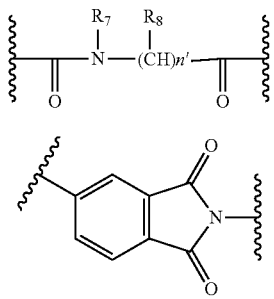
C5 wherein $R_7$ is at each occurrence independently H, linear or branched ($C_1$-$C_8$)alkyl, aryl($C_1$-$C_6$)alkyl, arylsulfanyl, arylsulfinyl, arylsulfonyl, ($C_3$-$C_8$)cycloalkyl, ($C_3$-$C_8$) hetcrocycloalkyl, aryl, or heteroaryl;

$R_8$ is at each occurrence independently H or ($C_1$-$C_8$)alkyl;

n and n' are at each occurrence independently 0 or an integer from 1 to 3;

m, m', t, t', v, and v' are at each occurrence independently an integer from 1 to 3;

G is arylene optionally substituted by one or more substituents selected from the group consisting of halogen, —OH, oxo (=O), —SH, —NO$_2$, —CN, —CON($R_6$)$_2$,—NH$_2$, —NHCOR$_6$, —CO$_2$R$_6$, ($C_1$-$C_{10}$) alkylsulfanyl, ($C_1$-$C_{10}$)alkylsulfinyl, ($C_1$-$C_{10}$)alkylsulfonyl, ($C_1$-$C_{10}$)alkyl, aryl, haloaryl, heteroaryl, and ($C_1$-$C_{10}$)alkoxy;

L is a bond or ($C_1$-$C_8$)alkylene;

$R_2$ is a group of formula J1, J2, J3, J4, J5, J6, J7, or -J8:

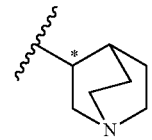
J1

-continued

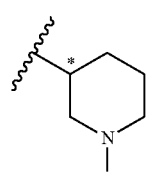
J2

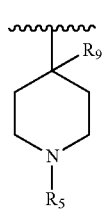
J3

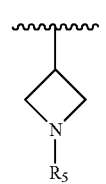
J4

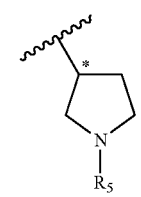
J5

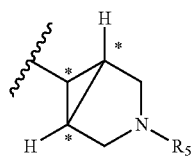
J6

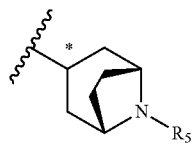
J7

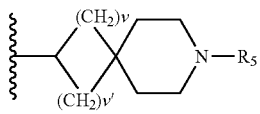
J8

$R_5$ is a group of formula K

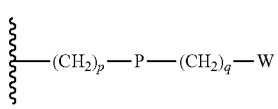
K wherein p is 0 or an integer from 1 to 4; q is 0 or an integer from 1 to 4;
P is absent or is O, S, SO, SO$_2$, CO, NR$_6$ CH═CH, N(R$_6$)SO$_2$, N(R$_6$)COO, N(R$_6$)C(O), SO$_2$N(R$_6$), OC(O)N(R$_6$), or C(O)N(R$_6$);
W is H, (C$_1$-C$_6$)alkyl, (C$_3$-C$_8$)cycloalkyl, aryl, or heteroaryl, optionally substituted by one or more substituents selected independently from the group consisting of halogen, —OH, oxo (═O), —SH, —NO$_2$, —CN, —CON(R$_6$)$_2$, —NH$_2$, —NHCOR$_6$, —CO$_2$R$_6$, (C$_1$-C$_{10}$)alkylsulfanyl, (C$_1$-C$_{10}$)alkylsulfinyl, (C$_1$-C$_{10}$)alkylsulfonyl, (C$_1$-C$_{10}$)alkyl, and (C$_1$-C$_{10}$)alkoxy;
R$_6$ is at each occurrence independently H, or selected from the group consisting of (C$_1$-C$_{10}$)alkyl, (C$_1$-C$_6$)haloalkyl, (C$_2$-C$_6$)alkynyl, (C$_2$-C$_6$)alkenyl, (C$_3$-C$_8$)cycloalkyl, heteroaryl and aryl optionally substituted by one or more substituents selected from the group consisting of halogen, —OH, oxo (═O), —SH, —NO$_2$, —CN, —CONH$_2$, —COOH, (C$_1$-C$_{10}$)alkoxycarbonyl, (C$_1$-C$_{10}$)alkylsulfanyl, (C$_1$-C$_{10}$)alkylsulfinyl, (C$_1$-C$_{10}$)alkylsulfonyl, (C$_1$-C$_{10}$)alkyl and (C$_1$-C$_{10}$)alkoxy; and
R$_9$ is in each occurrence independently H or (C$_1$-C$_8$)alkyl,
or a pharmaceutically acceptable salt thereof.

2. A compound or salt according to claim 1, wherein R$_2$ is a group of formula J3:

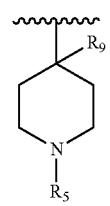
J3 wherein R$_5$ is a group of formula K, wherein p is 0 or 1, P is absent or is CO, q is absent or is 1 and W is H (C$_1$-C$_6$)alkyl, or aryl.

3. A compound or salt according to claim 1, wherein G is is p-phenylene or m-phenylene.

4. A compound or salt according to claim 1, wherein A1 and A2 are independently absent or selected from the group consisting of methylene, ethylene, propylene, butylene, pentylene, hexylene, heptylene, octylene, and nonylene.

5. A compound or salt according to claim 1, wherein:
A2 is absent or methylene and A1 is independently selected from the group consisting of methylene, ethylene, n-propylene, butylene, isobutylene, pentylene, hexylene, heptylene, and octylene;
B is absent or is selected from the group consisting of piperidinylene, indanediyl, phenylene, thiophenediyl, and pyridine-diyl; B being optionally substituted by one or more groups selected independently from the group consisting of —OH, fluorine, chlorine, bromine, methyl, methoxy, ethoxy, isopropoxy, trifluoromethyl, and trifluoromethoxy;
C is absent, —C(O)—, or a group of formula C1, C2, C3, C4, or C5; wherein R$_7$ is H or methyl and R$_8$ is H or methyl, t, t' and n' are 1;
D is absent or is cyclohexanediyl, piperidin-diyl, pyrrolidine-diyl, tetrahydropyridin-diyl, 1H-dihydropyrrolediyl furane-diyl, thiophene-diyl, pyrazolediyl, thiazole-diyl, oxazole-diyl, pyrazolediyl, pyridinediyl, pyrimidinediyl, pyrazinediyl, pyridazinediyl, pyridinediyl, pyrimidinediyl, pyrazinediyl, pyridinediyl, pyrimidinediyl, pyrazinediyl, or tetrahydrothienopyridin-diyl;
n is 0 or 1;
v and v' are at each occurrence independently 1 or 2;
G is meta-phenylene or para-phenylene;
L is a bond, —CH(CH$_3$)— or —(CH$_2$)—;
R$_2$ is a group of formula J1, J2, J3, J4, J5, J6, J7, or J8
R$_5$ is a group of formula K

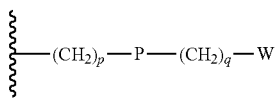

K wherein p is 0 or 1; q is 0;
P is absent
W is methyl, cyclobutyl, cyclopentyl, or phenyl optionally substituted by methoxy; and
$R_9$ is in each occurrence independently H or methyl.

6. A compound or salt according to claim 1, wherein:
A2 is absent and A1 is independently selected from the group consisting of methylene and ethylene;
B is phenylene optionally substituted by one or more groups selected independently from the group consisting of fluorine and methoxy;
C is absent, —C(O)—, or a group of formula C4; wherein $R_7$ is H and $R_8$ is H or methyl;
D is tetrahydropyridin-diyl, 1H-dihydropyrrolediyl, or pyridazinediyl;
n is 0 and n' is 1;
G is arylene which is meta-phenylene;
L is —(CH$_2$)—;
$R_2$ is a group of formula J3 wherein
$R_5$ is benzyl; and
$R_9$ is H.

7. A compound or salt according to claim 1, which is a compound selected from the group consisting of:
(1-benzylpiperidin-4-yl)methyl(S)-2-(3-(5-((2-chloro-4-((((R)-2-hydroxy-2-(8-hydroxy-2-oxo-1,2-dihydroquinolin-5-yl)ethyl)amino)methy)benzamido)methyl)-thiophen-2-yl)phenyl)-2-hydroxy-2-phenylacetate;
(1-benzylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)benzamido)-methyl)thiophen-2-yl)phenyl)-2-phenylacetate;
(1-benzylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)-3-methoxybenzamido)-methyl)thiophen-2-yl)phenyl)-2-phenylacetate;
(1-benzylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)-2-methoxybenzamido)-methyl)thiophen-2-yl)phenyl)-2-phenylacetate;
(1-benzylpiperidin-4-yl)methyl(S)-2-(3-(5-((2-chloro-4-((((R)-2-hydroxy-2-(8-hydroxy-2-oxo-1,2-dihydroquinolin-5-yl)ethyl)amino)methyl)-5-methoxybenzamido)-methyl)thiophen-2-yl)phenyl)-2-hydroxy-2-phenylacetate;
(1-benzylpiperidin-4-yl)methyl(S)-2-(3-(5-((2-fluoro-4-((((R)-2-hydroxy-2-(8-hydroxy-2-oxo-1,2-dihydroquinolin-5-yl)ethyl)amino)methyl)-5-methoxybenzamido)methyl)thiophen-2-yl)phenyl)-2-hydroxy-2-phenylacetate;
(1-benzylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)-3-(trifluoromethyl)benzamido)methyl)thiophen-2-yl)phenyl)-2-phenylacetate;
(1-benzylpiperidin-4-yl)methyl(S)-2-(3-(5-((2-fluoro-4-((((R)-2-hydroxy-2-(8-hydroxy-2-oxo-1,2-dihydroquinolin-5-yl)ethyl)amino)methyl)benzamido)-methyl)thiophen-2-yl)phenyl)-2-hydroxy-2-phenylacetate;
(1-benzylpiperidin-4-yl)methyl(S)-2-hydroxy-2-(3-(5-((4-(2-((((R)-2-hydroxy-2-(8-hydroxy-2-oxo-1,2-dihydroquinolin-5-yl)ethyl)amino)methyl)benzamido)-methyl)thiophen-2-yl)phenyl)-2-phenylacetate;
(1-benzylpiperidin-4-yl)methyl(S)-2-(3-(5-((3-ethoxy-4-((((R)-2-hydroxy-2-(8-hydroxy-2-oxo-1,2-dihydroquinolin-5-yl)ethyl)amino)methyl)benzamido)methyl)-thiophen-2-yl)phenyl)-2-hydroxy-2-phenylacetate;
(1-benzylpiperidin-4-yl)methyl(S)-2-(3-(5-((3-fluoro-4-((((R)-2-hydroxy-2-(8-hydroxy-2-oxo-1,2-dihydroquinolin-5-yl)ethyl)amino)methyl)benzamido)methyl)-thiophen-2-yl)phenyl)-2-hydroxy-2-phenylacetate;
(1-benzylpiperidin-4-yl)methyl(S)-2-(3-(5-((2-fluoro-4-((((R)-2-hydroxy-2-(8-hydroxy-2-oxo-1,2-dihydroquinolin-5-yl)ethyl)amino)methyl)-3-methoxybenzamido)-methyl)thiophen-2-yl)phenyl)-2-hydroxy-2-phenylacetate;
(1-benzylpiperidin-4-yl)methyl(S)-2-hydroxy-2-(3-(5-((6-((((R)-2-hydroxy-2-(8-hydroxy-2-oxo-1,2-dihydroquinolin-5-yl)ethyl)amino)methyl)nicotinamido)-methyl)thiophen-2-yl)phenyl)-2-phenylacetate;
(1-benzylpiperidin-4-yl)methyl(S)-2-(3-(5-((3-fluoro-4-((((R)-2-hydroxy-2-(8-hydroxy-2-oxo-1,2-dihydroquinolin-5-yl)ethyl)amino)methyl)-5-methoxybenzamido)-methyl)thioplien-2-yl)phenyl)-2-hydroxy-2-phenylacetate;
(1-benzylpiperidin-4-yl)methyl(S)-2-hydroxy-2-(3-(5-((3-((((R)-2-hydroxy-2-(8-hydroxy-2-oxo-1,2-dihydroquinolin-5-yl)ethyl)amino)methyl)benzamido) methyl)-thiophen-2-yl)phenyl)-2-phenylacetate;
(1-benzylpiperidin-4-yl)methyl(S)-2-(3-(5-((2-fluoro-4-((((R)-2-hydroxy-2-(8-hydroxy-2-oxo-1,2-dihydroquinolin-5-yl)ethyl)amino)methyl)-5-methylbenzamido)-methyl)thiophen-2-yl)phenyl)-2-hydroxy-2-phenylacetate;
(1-benzylpiperidin-4-yl)methyl(S)-2-hydroxy-2-(3-(5-((2-(4-((((R)-2-hydroxy-2-(8-hydroxy-2-oxo-1,2-dihydroquinolin-5-yl)ethyl)amino)methyl)phenyl)acetamido)-methyl)thiophen-2-yl)phenyl)-2-phenylacetate;
(1-benzylpiperidin-4-yl)methyl(S)-2-hydroxy-2-(3-(5-((5-((((R)-2-hydroxy-2-(8-hydroxy-2-oxo-1,2-dihydroquinolin-5-yl)ethyl)amino)methyl)picolinamido)-methyl)thiophen-2-yl)phenyl)-2-phenylacetate;
(1-benzylpiperidin-4-yl)methyl(S)-2-(3-(5-((3-chloro-4-((((R)-2-hydroxy-2-(8-hydroxy-2-oxo-1,2-dihydroquinolin-5-yl)ethyl)amino)methyl)benzamido)methyl)-thiophen-2-yl)phenyl)-2-hydroxy-2-phenylacetate;
(1-benzylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)-3-methylbenzamido)-methyl)thiophen-2-yl)phenyl)-2-phenylacetate;
(1-benzylpiperidin-4-yl)methyl(S)-2-hydroxy-2-(3-(5-((5-((((R)-2-hydroxy-2-(8-hydroxy-2-oxo-1,2-dihydroquinolin-5-yl)ethyl)amino)methyl)thiophene-2-carboxamido)-methyl)thiophen-2-yl)phenyl)-2-phenylacetate;
(1-benzylpiperidin-4-yl)methyl(S)-2-(3-(5-(2,5-difluoro-4-((((R)-2-hydroxy-2-(8-hydroxy-2-oxo-1,2-dihydroquinolin-5-yl)ethyl)amino)methyl)benzamido)-methyl)thiophen-2-yl)phenyl)-2-hydroxy-2-phenylacetate;
(1-benzylpiperidin-4-yl)methyl(S)-2-(3-(5-((2,3-difluoro-4-((((R)-2-hydroxy-2-(8-hydroxy-2-oxo-1,2-dihydroquinolin-5-yl)ethyl)amino)methyl)benzamido)methyl)-thiophen-2-yl)phenyl)-2-hydroxy-2-phenylacetate;

(1-benzylpiperidin-4-yl)methyl(S)-2-(3-(5-((2-chloro-6-fluoro-4-((((R)-2-hydroxy-2-(8-hydroxy-2-oxo-1,2-dihydroquinolin-5-yl)ethyl)amino)methyl)benzamido)-methyl)thiophen-2-yl)phenyl)-2-hydroxy-2-phenylacetate;

(1-benzylpiperidin-4-yl)methyl(S)-2-(3-(5-((2-fluoro-4-((((R)-2-hydroxy-2-(8-hydroxy-2-oxo-1,2-dihydroquinolin-5-yl)ethyl)amino)methyl)-6-methoxybenzamido)-methyl)thiophen-2-yl)phenyl)-2-hydroxy-2-phenylacetate;

1-methylpiperidin-4-yl(S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)thiophen-2-yl)phenyl)-2-phenylacetate;

(1-(4-methoxybenzyl)piperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)thiophen-2-yl)phenyl)-2-phenylacetate;

(1-methylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)-thiophen-2-yl)phenyl)-2-phenylacetate;

((S)-1-benzylpiperidin-3-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)-thiophen-2-yl)phenyl)-2-phenylacetate;

((1R,5S,6r)-3-benzyl-3-azabicyclo[3.1.0]hexan-6-yl)methyl(S)-2-hydroxy-2-(3-(5-((4-((((R)-2-hydroxy-2-(8-hydroxy-2-oxo-1,2-dihydroquinolin-5-yl)ethyl)amino)-methyl)benzamido)methyl)thiophen-2-yl)phenyl)-2-phenylacetate;

(1-(3-methoxybenzyl)piperidin-4-yl)methyl(S)-2-hydroxy-2-(3-(5(4-((((R)-2-hydroxy-2-(8-hydroxy-2-oxo-1,2-dihydroquinolin-5-yl)ethyl)amino)methyl)benzamido)-methyl)thiophen-2-yl)phenyl)-2-phenylacetate;

1-benzylpiperidin-4-yl(S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)thiophen-2-yl)phenyl)-2-phenylacetate;

(R)-1-(1-benzylpiperidin-4-yl)ethyl(S)-2-hydroxy-2-(3-(5-((4-((((R)-2-hydroxy-2-(8-hydroxy-2-oxo-1,2-dihydroquinolin-5-yl)ethyl)amino)methyl)benzamido)-methyl)thiophen-2-yl)phenyl)-2-phenylacetate;

3-benzyl-3-azaspiro[5.5]undecan-9-yl(S)-2-hydroxy-2-(3-(5-((4-((((R)-2-hydroxy-2-(8-hydroxy-2-oxo-1,2-dihydroquinolin-5-yl)ethyl)amino)methyl)-benzamido)methyl)thiophen-2-yl)phenyl)-2-phenylacetate;

(1-benzylpiperidin-4-yl)methyl(S)-2-hydroxy-2-(3-(1-(4-(2-(((R)-2-hydroxy-2-(8-hydroxy-2-oxo-1,2-dihydroquinolin-5-yl)ethyl)amino)methyl)benzoyl)-1,2,3,6-tetrahydropyridin-4-yl)phenyl)-2-phenylacetate;

(1-benzylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)furan-2-yl)phenyl)-2-phenylacetate;

(1-benzylpiperidin-4-yl)methyl(S)-2-hydroxy-2-(3-(1-(4-((((R)-2-hydroxy-2-(8-hydroxy-2-oxo-1,2-dihydroquinolin-5-yl)ethyl)amino)methyl)benzoyl)-1,2,3,6-tetrahydropyridin-4-yl)phenyl)-2-phenylacetate;

(1-benzylpiperidin-4-yl)methyl(S)-2-(3-(1-(4-((((R)-2-hydroxy-2-(8-hydroxy-2-oxo-1,2-dihydroquinolin-5-yl)ethyl)amino)methyl)-3-methoxybenzoyl)-1,2,3,6-tetrahydropyridin-4-yl)phenyl)-2-phenylacetate;

(1-benzylpiperidin-4-yl)methyl(S)-2-(3-(1-(2-fluoro-4-((((R)-2-hydroxy-2-(8-hydroxy-2-oxo-1,2-dihydroquinolin-5-yl)ethyl)amino)methyl)-3-methoxybenzoyl)-1,2,3,6-tetrahydropyridin-4-yl)phenyl)-2-hydroxy-2-phenylacetate;

(1-benzylpiperidin-4-yl)methyl(S)-2-hydroxy-2-(3-(1-(4-((((R)-2-hydroxy-2-(8-hydroxy-2-oxo-1,2-dihydroquinolin-5-yl)ethyl)amino)methyl)-2-methoxybenzoyl)-1,2,3,6-tetrahydropyridin-4-yl)phenyl)-2-phenylacetate;

(1-benzylpiperidin-4-yl)methyl(S)-2-hydroxy-2-(3-(1-(4-(2-(((R)-2-hydroxy-2-(8-hydroxy-2-oxo-1,2-dihydroquinolin-5-yl)ethyl)amino)ethyl)benzoyl)-2,5-dihydro-1H-pyrrol-3-yl)phenyl)-2-phenylacetate;

(1-benzylpiperidin-4-yl)methyl(S)-2-hydroxy-2-(3-(1-(4-((((R)-2-hydroxy-2-(8-hydroxy-2-oxo-1,2-dihydroquinolin-5-yl)ethyl)amino)methyl)benzoyl)-2,5-dihydro-1H-pyrrol-3-yl)phenyl)-2-phenylacetate;

(1-benzylpiperidin-4-yl)methyl(S)-2-hydroxy-2-(3-(1-(4-((((R)-2-hydroxy-2-(8-hydroxy-2-oxo-1,2-dihydroquinolin-5-yl)ethyl)amino)methyl)-3-methoxybenzoyl)-1,2,5,6-tetrahydropyridin-3-yl)phenyl)-2-phenylacetate;

(1-benzylpiperidin-4-yl)methyl(S)-2-hydroxy-2-(3-(1-(4-((((R)-2-hydroxy-2-(8-hydroxy-2-oxo-1,2-dihydroquinolin-5-yl)ethyl)amino)methyl)benzoyl)-1,2,5,6-tetrahydropyridin-3-yl)phenyl)-2-phenylacetate;

(1-benzylpiperidin-4-yl)methyl(S)-2-hydroxy-2-(3-(1-(4-((((R)-2-hydroxy-2-(8-hydroxy-2-oxo-1,2-dihydroquinolin-5-yl)ethyl)amino)methyl)-3-methoxybenzoyl)-2,5-dihydro-1H-pyrrol-3-yl)phenyl)-2-phenylacetate;

(1-benzylpiperidin-4-yl)methyl(S)-2-hydroxy-2-(3-(2-((4-((((R)-2-hydroxy-2-(8-hydroxy-2-oxo-1,2-dihydroquinolin-5-yl)ethyl)amino)methyl)benzamido)-methyl)pyrimidin-5-yl)phenyl)-2-phenylacetate;

(1-benzylpiperidin-4-yl)methyl(S)-2-hydroxy-2-(3-(4-((4-((((R)-2-hydroxy-2-(8-hydroxy-2-oxo-1,2-dihydroquinolin-5-yl)ethyl)amino)methyl)-3-methoxybenzamido)-methyl)pyrimidin-2-yl)phenyl)-2-phenylacetate;

(1-benzylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)pyrazin-2-yl)phenyl)-2-phenylacetate;

(1-benzylpiperidin-4-yl)methyl(S)-2-hydroxy-2-(3-(6-((4-((((R)-2-hydroxy-2-(8-hydroxy-2-oxo-1,2-dihydroquinolin-5-yl)ethyl)amino)methyl)-3-methoxybenzamido)-methyl)pyridazin-3-yl)phenyl)-2-phenylacetate;

(1-benzylpiperidin-4-yl)methyl(S)-2-hydroxy-2-(3-(4-((4-((((R)-2-hydroxy-2-(8-hydroxy-2-oxo-1,2-dihydroquinolin-5-yl)ethyl)amino)methyl)benzamido)-methyl)pyrimidin-2-yl)phenyl)-2-phenylacetate;

(1-benzylpiperidin-4-yl)methyl(S)-2-hydroxy-2-(3-(2-((4-((((R)-2-hydroxy-2-(8-hydroxy-2-oxo-1,2-dihydroquinolin-5-yl)ethyl)amino)methyl)-3-methoxybenzamido)-methyl)pyrimidin-5-yl)phenyl)-2-phenylacetate;

(1-benzylpiperidin-4-yl)methyl(S)-2-hydroxy-2-(3-(3-((4-((((R)-2-hydroxy-2-(8-hydroxy-2-oxo-1,2-dihydroquinolin-5-yl)ethyl)amino)methyl)-3-methoxybenzamido)-methyl)-1-methyl-1 H-pyrazol-4-yl)phenyl)-2-phenylacetate;

(1-benzylpiperidin-4-yl)methyl(S)-2-hydroxy-2-(3-(6-((4-((((R)-2-hydroxy-2-(8-hydroxy-2-oxo-1,2-dihydroquinolin-5-yl)ethyl)amino)methyl)-3-methoxybenzamido)-methyl)pyrazin-2-yl)phenyl)-2-phenylacetate;

(1-benzylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)-3-methoxybenzamido)-methyl)pyrazin-2-yl)phenyl)-2-phenylacetate;

(1-benzylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)benzamido)-methyl)thiophen-3-yl)phenyl)-2-phenylacetate;

(1-benzylpiperidin-4-yl)methyl(S)-2-hydroxy-2-(3-(4-((4-((((R)-2-hydroxy-2-(8-hydroxy-2-oxo-1,2-dihydroquinolin-5-yl)ethyl)amino)methyl)benzamido-)methyl)thiophen-2-yl)phenyl)-2-phenylacetate;

(1-benzylpiperidin-4-yl)methyl(S)-2-hydroxy-2-(3-(5-((4-((((R)-2-hydroxy-2-(8-hydroxy-2-oxo-1,2-dihydroquinolin-5-yl)ethyl)amino)methyl)benzamido)methyl)thiazol-2-yl)phenyl)-2-phenylacetate;

(1-benzylpiperidin-4-yl)methyl(S)-2-hydroxy-2-(3-(5-(4-((((R)-2-hydroxy-2-(8-hydroxy-2-oxo-1,2-dihydroquinolin-5-yl)ethyl)amino)methyl)benzoyl)-4,5,6,7-tetrahydrothieno[3,2-c]pyridin-2-yl)phenyl)-2-phenylacetate;

(1-benzylpiperidin-4-yl)methyl(S)-2-hydroxy-2-(3-(5-(2-(4-((((R)-2-hydroxy-2-(8-hydroxy-2-oxo-1,2-dihydroquinolin-5-yl)ethyl)amino)methyl)benzamido)-ethyl)thiophen-2-yl)phenyl)-2-phenylacetate;

(1-benzylpiperidin-4-yl)methyl(S)-2-hydroxy-2-(3-(3-((4-((((R)-2-hydroxy-2-(8-hydroxy-2-oxo-1,2-dihydroquinolin-5-yl)ethyl)amino)methyl)-3-methoxybenzamido)-methyl)pyrazin-2-yl)phenyl)-2-phenylacetate;

(1-benzylpiperidin-4-yl)methyl(S)-2-hydroxy-2-(3-(4-(4-((((R)-2-hydroxy-2-(8-hydroxy-2-oxo-1,2-dihydroquinotin-5-yl)ethyl)amino)methyl)piperidine-1-carbonyl)-pyridin-2-yl)phenyl)-2-phenylacetate;

(1-benzylpiperidin-4-yl)methyl(S)-2-hydroxy-2-(3-(6-(4-((((R)-2-hydroxy-2-(8-hydroxy-2-oxo-1,2-dihydroquinolin-5-yl)ethyl)amino)methyl)piperidine-1-carbonyl)-pyrazin-2-yl)phenyl)-2-phenylacetate;

(1-benzylpiperidin-4-yl)methyl(S)-2-hydroxy-2-(3-(2-(4-((((R)-2-hydroxy-2-(8-hydroxy-2-oxo-1,2-dihydroquinolin-5-yl)ethyl)amino)methyl)piperidine-1-carbonyl)-pyridin-4-yl)phenyl)-2-phenylacetate;

(1-benzylpiperidin-4-yl)methyl(S)-2-hydroxy-2-(3-(6-(4-((((R)-2-hydroxy-2-(8-hydroxy-2-oxo-1,2-dihydroquinolin-5-yl)ethyl)amino)methyl)piperidine-1-carbonyl)-pyridin-3-yl)phenyl)-2-phenylacetate;

(1-benzylpiperidin-4-yl)methyl(S)-2-hydroxy-2-(3-(5-(4-((((R)-2-hydroxy-2-(8-hydroxy-2-oxo-1,2-dihydroquinolin-5-yl)ethyl)amino)methyl)piperidine-1-carbonyl)-pyridin-2-yl)phenyl)-2-phenylacetate;

(1-benzylpiperidin-4-yl)methyl(S)-2-hydroxy-2-(3-(5-(4-((((R)-2-hydroxy-2-(8-hydroxy-2-oxo-1,2-dihydroquinolin-5-yl)ethyl)amino)methyl)piperidine-1-carbonyl)-pyridin-3-yl)phenyl)-2-phenylacetate;

(1-benzylpiperidin-4-yl)methyl(S)-2-hydroxy-2-(3-(6-(4-((((R)-2-hydroxy-2-(8-hydroxy-2-oxo-1,2-dihydroquinolin-5-yl)ethyl)amino)methyl)piperidine-1-carbonyl)-pyridin-2-yl)phenyl)-2-phenylacetate;

(1-benzylpiperidin-4-yl)methyl(S)-2-hydroxy-2-(3-(1-(4-((((R)-2-hydroxy-2-(8-hydroxy-2-oxo-1,2-dihydroquinolin-5-yl)ethyl)amino)methyl)benzoyl)piperidin-4-yl)phenyl)-2-phenylacetate;

(1-benzylpiperidin-4-yl)methyl(S)-2-hydroxy-2-(3-(1-(4-((((R)-2-hydroxy-2-(8-hydroxy-2-oxo-1,2-dihydroquinolin-5-yl)ethyl)amino)methyl)-3-methoxybenzoyl)-piperidin-4-yl)phenyl)-2-phenylacetate;

(1-benzylpiperidin-4-yl)methyl(S)-2-hydroxy-2-(3-(1-(4-((((R)-2-hydroxy-2-(8-hydroxy-2-oxo-1,2-dihydroquinolin-5-yl)ethyl)amino)methyl)-2-methoxybenzoyl)-piperidin-4-yl)phenyl)-2-phenylacetate;

(1-benzylpiperidin-4-yl)methyl(S)-2-hydroxy-2-(3-(1-(4-(2-(((R)-2-hydroxy-2-(8-hydroxy-2-oxo-1,2-dihydroquinolin-5-yl)ethyl)amino)ethyl)benzoyl)piperidin-4-yl)phenyl)-2-phenylacetate;

(1-benzylpiperidin-4-yl)methyl (2S)-2-hydroxy-2-(3-(1-(2-(((R)-2-hydroxy-2-(8-hydroxy-2-oxo-1,2-dihydroquinolin-5-yl)ethyl)amino)-2,3-dihydro-1H-indene-5-carbonyl)piperidin-4-yl)phenyl)-2-phenylacetate;

(1-benzylpiperidin-4-yl)methyl(S)-2-hydroxy-2-(3-(1-((4-(2-(((R)-2-hydroxy-2-(8-hydroxy-2-oxo-1,2-dihydroquinolin-5-yl)ethyl)amino)ethyl)benzoyl)glycyl)-1,2,3,6-tetrahydropyridin-4-yl)phenyl)-2-phenylacetate;

(1-benzylpiperidin-4-yl)methyl(S)-2-hydroxy-2-(3-(1-((4-((((R)-2-hydroxy-2-(8-hydroxy-2-oxo-1,2-dihydroquinolin-5-yl)ethyl)amino)methyl)-2-methoxybenzoyl)-glycyl)-1,2,3,6-tetrahydropyridin-4-yl)phenyl)-2-phenylacetate;

(1-benzylpiperidin-4-yl)methyl(S)-2-hydroxy-2-(3-(1-((4-((((R)-2-hydroxy-2-(8-hydroxy-2-oxo-1,2-dihydroquinolin-5-yl)ethyl)amino)methyl)benzoyl)-D-alanyl)-1,2,3,6-tetrahydropyridin-4-yl)phenyl)-2-phenylacetate;

(1-benzylpiperidin-4-yl)methyl(S)-2-hydroxy-2-(3-(1-((4-((((R)-2-hydroxy-2-(8-hydroxy-2-oxo-1,2-dihydroquinolin-5-yl)ethyl)amino)methyl)benzoyl)-L-alanyl)-1,2,3,6-tetrahydropyridin-4-yl)phenyl)-2-phenylacetate;

(1-benzylpiperidin-4-yl)methyl(S)-2-hydroxy-2-(3-(1-((4-((((R)-2-hydroxy-2-(8-hydroxy-2-oxo-1,2-dihydroquinolin-5-yl)ethyl)amino)methyl)benzoyl)glycyl)-1,2,3,6-tetrahydropyridin-4-yl)phenyl)-2-phenylacetate;

(1-benzylpiperidin-4-yl)methyl(S)-2-hydroxy-2-(3-(1-((4-((((R)-2-hydroxy-2-(8-hydroxy-2-oxo-1,2-dihydroquinolin-5-yl)ethyl)amino)methyl)-3-methoxybenzoyl)-glycyl)-1,2,3,6-tetrahydropyridin-4-yl)phenyl)-2-phenylacetate;

(1-benzylpiperidin-4-yl)methyl(S)-2-hydroxy-2-(3-(1-(N-(4-((((R)-2-hydroxy-2-(8-hydroxy-2-oxo-1,2-dihydroquinolin-5-yl)ethyl)amino)methyl)benzoyl)-N-methylglycyl)-1,2,3,6-tetrahydropyridin-4-yl)phenyl)-2-phenylacetate;

(1-benzylpiperidin-4-yl)methyl(S)-2-hydroxy-2-(3-(6-(((1R,3S)-3-(4-((((R)-2-hydroxy-2-(8-hydroxy-2-oxo-1,2-dihydroquinolin-5-yl)ethyl)amino)methyl)benzamido)-cyclobutyl)carbamoyl)pyrazin-2-yl)phenyl)-2-phenylacetate;

(1-benzylpiperidin-4-yl)methyl(S)-2-hydroxy-2-(3-(6-((3-(((R)-2-hydroxy-2-(8-hydroxy-2-oxo-1,2-dihydroquinolin-5-yl)ethyl)amino)propyl)carbamoyl)pyrazin-2-yl)phenyl)-2-phenylacetate;

(1-benzyl-4-methylpiperidin-4-yl)methyl(S)-2-(3-(5(2-chloro-4-((((R)-2-hydroxy-2-(8-hydroxy-2-oxo-1,2-dihydroquinolin-5-yl)ethyl)amino)methyl)-5-methoxybenzamido)methyl)thiophen-2-yl)phenyl)-2-hydroxy-2-phenylacetate;

(1-benzylpiperidin-4-yl)methyl(S)-2-hydroxy-2-(3-(5-((5-((((R)-2-hydroxy-2-(8-hydroxy-2-oxo-1,2-dihydroquinolin-5-yl)ethyl)amino)methyl)-1,3-dioxoisoindolin-2-yl)methyl)thiophen-2-yl)phenyl)-2-phenylacetate;

(1-benzylpiperidin-4-yl)methyl(S)-2-hydroxy-2-(3-(1-((4-(2-(((R)-2-hydroxy-2-(8-hydroxy-2-oxo-1,2-dihydroquinolin-5-yl)ethyl)amino)ethyl)benzoyl)glycyl)piperidin-4-yl)phenyl)-2-phenylacetate;

(1-benzylpiperidin-4-yl)methyl(S)-2-hydroxy-2-(3-(3-((4-((((R)-2-hydroxy-2-(8-hydroxy-2-oxo-1,2-dihydroquinolin-5-yl)ethyl)amino)methyl)benzyl)carbamoyl)-1-methyl-1H-pyrazol-5-yl)phenyl)-2-phenylacetate;
(1-benzylpiperidin-4-yl)methyl(S)-2-hydroxy-2-(4-(5-((4-((((R)-2-hydroxy-2-(8-hydroxy-2-oxo-1,2-dihydroquinolin-5-yl)ethyl)amino)methyl)benzamido)methyl)-thiophen-2-yl)phenyl)-2-phenylacetate;
(1-benzylpiperidin-4-yl)methyl(S)-2-hydroxy-2-(4-(5-((4-((((R)-2-hydroxy-2-(8-hydroxy-2-oxo-1,2-dihydroquinolin-5-yl)ethyl)amino)methyl)-3-methoxybenzamido)-methyl)thiophen-2-yl)phenyl)-2-phenylacetate;
(1-benzylpiperidin-4-yl)methyl(S)-2-hydroxy-2-(4-(5-((4-((((R)-2-hydroxy-2-(8-hydroxy-2-oxo-1,2-dihydroquinolin-5-yl)ethyl)amino)methyl)benzamido)-methyl)thiophen-3-yl)phenyl)-2-phenylacetate;
(1-benzylpiperidin-4-yl)methyl(S)-2-hydroxy-2-(4-(5-((4-((((R)-2-hydroxy-2-(8-hydroxy-2-oxo-1,2-dihydroquinolin-5-yl)ethyl)amino)methyl)benzamido)methyl)thiazol-2-yl)phenyl)-2-phenylacetate;
(1-benzylpiperidin-4-yl)methyl(S)-2-hydroxy-2-(4-(6-((4-((((R)-2-hydroxy-2-(8-hydroxy-2-oxo-1,2-dihydroquinolin-5-yl)ethyl)amino)methyl)benzamido)methyl)pyridin-3-yl)phenyl)-2-phenylacetate;
(1-benzylpiperidin-4-yl)methyl(S)-2-hydroxy-2-(4-(1-(4-((((R)-2-hydroxy-2-(8-hydroxy-2-oxo-1,2-dihydroquinolin-5-yl)ethyl)amino)methyl)benzoyl)-1,2,3,6-tetrahydropyridin-4-yl)phenyl)-2-phenylacetate;
(1-benzylpiperidin-4-yl)methyl(S)-2-hydroxy-2-(4-(5-((4-((((R)-2-hydroxy-2-(8-hydroxy-2-oxo-1,2-dihydroquinolin-5-yl)ethyl)amino)methyl)-3-methoxybenzamido)-methyl)thiophen-3-yl)phenyl)-2-phenylacetate; and
(1-benzylpiperidin-4-yl)methyl(S)-2-hydroxy-2-(4-(5-((4-(2-(((R)-2-hydroxy-2-(8-hydroxy-2-oxo-1,2-dihydroquinolin-5-yl)ethyl)amino)ethyl)benzyl)-carbamoyl)thiophen-2-yl)phenyl)-2-phenylacetate;
or a pharmaceutically acceptable salt of said compound.

8. A pharmaceutical composition, comprising a compound or salt according to claim 1 and one or more pharmaceutically acceptable carriers and/or excipients.

9. A pharmaceutical composition according to claim 8, which is in a form suitable to be administered by inhalation.

10. A pharmaceutical composition according to claim 9, which is an inhalable powder.

11. A pharmaceutical composition according to claim 9, which aerosol comprises a propellant.

12. A pharmaceutical composition according to claim 9, which is a propellant-free inhalable formulation.

13. A method for the treatment of a broncho-obstructive or inflammatory disease, comprising administering to a subject in need thereof an effective amount of a compound or salt according to claim 1,
wherein said broncho-obstructive or inflammatory disease is asthma, chronic bronchitis, or chronic obstructive pulmonary disease.

14. A combination, comprising a compound or salt according to claim 1 and one or more active ingredients selected from the group consisting of a corticosteroid, a P38 MAP kinase inhibitor, a IKK2 inhibitor, an HNE inhibitor, a PDE4 inhibitor, a leukotriene modulator, a NSAID, and a mucus regulator.

15. A device, comprising a pharmaceutical composition according to claim 9, which is a single- or multi-dose dry powder inhaler, a metered dose inhale, or a soft mist nebulizer.

16. A method according to claim 13, wherein said broncho-obstructive or inflammatory disease is asthma.

17. A method according to claim 13, wherein said broncho-obstructive or inflammatory disease is chronic bronchitis.

18. A method according to claim 13, wherein said broncho-obstructive or inflammatory disease is or chronic obstructive pulmonary disease.

19. A method for the treatment of a broncho-obstructive or inflammatory disease, comprising administering to a subject in need thereof an effective amount of a compound or salt according to claim 7,
wherein said broncho-obstructive or inflammatory disease is asthma, chronic bronchitis, or chronic obstructive pulmonary disease.

20. A method for the treatment of a broncho-obstructive or inflammatory disease, comprising administering to a subject in need thereof an effective amount of a compound or salt according to claim 2,
wherein said broncho-obstructive or inflammatory disease is asthma, chronic bronchitis, or chronic obstructive pulmonary disease.

* * * * *